United States Patent
Joung et al.

(10) Patent No.: US 10,544,433 B2
(45) Date of Patent: *Jan. 28, 2020

(54) USING RNA-GUIDED FOKI NUCLEASES (RFNS) TO INCREASE SPECIFICITY FOR RNA-GUIDED GENOME EDITING

(71) Applicant: The General Hospital Corporation, Boston, MA (US)

(72) Inventors: J. Keith Joung, Winchester, MA (US); Shengdar Tsai, Charlestown, MA (US)

(73) Assignee: The General Hospital Corporation, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/003,973

(22) Filed: Jun. 8, 2018

(65) Prior Publication Data
US 2018/0340189 A1   Nov. 29, 2018

Related U.S. Application Data

(60) Continuation of application No. 14/900,444, filed as application No. PCT/US2014/035162 on Apr. 23, 2014, now Pat. No. 10,011,850, which is a continuation-in-part of application No. PCT/US2014/028630, filed on Mar. 14, 2014, application No. 16/003,973, which is a division of application No. 15/415,431, filed on Jan. 25, 2017, now Pat. No. 10,138,476, which is a division of application No. 14/213,479, filed on Mar. 14, 2014, now Pat. No. 9,567,603.

(60) Provisional application No. 61/838,178, filed on Jun. 21, 2013, provisional application No. 61/838,148, filed on Jun. 21, 2013, provisional application No. 61/921,007, filed on Dec. 26, 2013, provisional application No. 61/799,647, filed on Mar. 15, 2013.

(51) Int. Cl.
| | | |
|---|---|---|
| C12N 15/90 | (2006.01) | |
| C12N 15/11 | (2006.01) | |
| C12N 15/10 | (2006.01) | |
| C12N 15/01 | (2006.01) | |
| C12N 9/96 | (2006.01) | |
| C12N 9/16 | (2006.01) | |
| C12N 9/10 | (2006.01) | |
| C12N 9/02 | (2006.01) | |
| C07K 14/195 | (2006.01) | |
| C07K 14/005 | (2006.01) | |
| C12N 15/85 | (2006.01) | |
| C12N 15/63 | (2006.01) | |
| C12N 9/22 | (2006.01) | |

(52) U.S. Cl.
CPC ......... *C12N 15/907* (2013.01); *C07K 14/005* (2013.01); *C07K 14/195* (2013.01); *C12N 9/0071* (2013.01); *C12N 9/1007* (2013.01); *C12N 9/16* (2013.01); *C12N 9/22* (2013.01); *C12N 9/96* (2013.01); *C12N 15/01* (2013.01); *C12N 15/102* (2013.01); *C12N 15/1031* (2013.01); *C12N 15/11* (2013.01); *C12N 15/63* (2013.01); *C12N 15/85* (2013.01); *C12Y 301/21004* (2013.01); *C07K 2319/00* (2013.01); *C07K 2319/01* (2013.01); *C07K 2319/80* (2013.01); *C12N 2310/20* (2017.05); *C12N 2710/00033* (2013.01); *C12N 2770/00033* (2013.01); *C12N 2800/80* (2013.01); *C12Y 114/11* (2013.01); *C12Y 201/01* (2013.01); *C12Y 301/00* (2013.01)

(58) Field of Classification Search
None
See application file for complete search history.

(56) References Cited

U.S. PATENT DOCUMENTS

| | | | |
|---|---|---|---|
| 4,603,044 | A | 7/1986 | Geho et al. |
| 4,957,773 | A | 9/1990 | Spencer et al. |
| 5,436,150 | A | 7/1995 | Candrasegaran |
| 6,007,988 | A | 12/1999 | Choo et al. |
| 6,013,453 | A | 1/2000 | Choo et al. |
| 6,503,717 | B2 | 1/2003 | Case et al. |
| 6,511,808 | B2 | 1/2003 | Wolffe et al. |
| 7,021,555 | B2 | 4/2006 | Bagnall |
| 7,220,719 | B2 | 5/2007 | Case |
| 7,914,796 | B2 | 3/2011 | Miller |
| 7,919,277 | B2 | 4/2011 | Russell et al. |
| 8,034,598 | B2 | 10/2011 | Miller |

(Continued)

FOREIGN PATENT DOCUMENTS

| | | |
|---|---|---|
| CN | 103224947 | 7/2013 |
| CN | 103233028 | 8/2013 |

(Continued)

OTHER PUBLICATIONS

Extended European Search Report in Application No. 18208105.9, dated Jan. 15, 2019, 10 pages.

(Continued)

*Primary Examiner* — Suzanne M Noakes
*Assistant Examiner* — Jae W Lee
(74) *Attorney, Agent, or Firm* — Fish & Richardson P.C.

(57) ABSTRACT

Many studies have shown that CRISPR-Cas nucleases can tolerate up to five mismatches and still cleave; it is hard to predict the effects of any given single or combination of mismatches on activity. Taken together, these nucleases can show significant off-target effects but it can be challenging to predict these sites. Described herein are methods for increasing the specificity of genome editing using the CRISPR/Cas system, e.g., using RNA-guided Foki Nucleases (RFNs), e.g., FokI-Cas9 or FokI-dCas9-based fusion proteins.

10 Claims, 26 Drawing Sheets

Specification includes a Sequence Listing.

(56) References Cited

U.S. PATENT DOCUMENTS

| | | |
|---|---|---|
| 8,071,370 B2 | 12/2011 | Wolfe |
| 8,252,535 B2 | 8/2012 | Biekle et al. |
| 8,282,920 B2 | 10/2012 | Heo et al. |
| 8,361,725 B2 | 1/2013 | Russell et al. |
| 8,697,359 B1 | 4/2014 | Zhang |
| 8,771,986 B2 | 7/2014 | Miller |
| 8,865,406 B2 | 10/2014 | Zhang et al. |
| 8,962,281 B2 | 2/2015 | Doyon |
| 8,993,233 B2 | 3/2015 | Zhang et al. |
| 9,023,649 B2 | 5/2015 | Mali et al. |
| 9,074,199 B1 | 7/2015 | Chavez et al. |
| 9,322,037 B2 | 4/2016 | Liu et al. |
| 9,771,601 B2 | 9/2017 | May et al. |
| 9,885,033 B2 | 2/2018 | Joung |
| 9,926,546 B2 | 3/2018 | Joung et al. |
| 2002/0160940 A1 | 10/2002 | Case et al. |
| 2002/0164575 A1 | 11/2002 | Case et al. |
| 2005/0214851 A1 | 9/2005 | Arts et al. |
| 2006/0199190 A1 | 9/2006 | Russell et al. |
| 2007/0020627 A1 | 1/2007 | Barbas, III |
| 2008/0124725 A1 | 5/2008 | Barrangou et al. |
| 2008/0193470 A1 | 8/2008 | Masignani et al. |
| 2010/0034924 A1 | 2/2010 | Fremaux et al. |
| 2010/0055793 A1 | 3/2010 | Chandrasegaran |
| 2010/0076057 A1 | 3/2010 | Sontheimer et al. |
| 2010/0093617 A1 | 4/2010 | Barrangou et al. |
| 2010/0104690 A1 | 4/2010 | Barrangou et al. |
| 2010/0120043 A1 | 5/2010 | Sood et al. |
| 2010/0183559 A1 | 7/2010 | Van Sinderen et al. |
| 2010/0184624 A1 | 7/2010 | Samuel et al. |
| 2010/0209998 A1 | 8/2010 | Attwood et al. |
| 2010/0209999 A1 | 8/2010 | Altermann et al. |
| 2010/0221185 A1 | 9/2010 | Altermann et al. |
| 2010/0311061 A1 | 12/2010 | Korlach et al. |
| 2010/0317116 A1 | 12/2010 | Flusberg et al. |
| 2011/0002889 A1 | 1/2011 | Barrangou et al. |
| 2011/0092381 A1 | 4/2011 | Sood et al. |
| 2011/0143348 A1 | 6/2011 | Tomigahara et al. |
| 2011/0150852 A1 | 6/2011 | Chambaud et al. |
| 2011/0171647 A1 | 7/2011 | Tomigahara et al. |
| 2011/0189674 A1 | 8/2011 | Tomigahara et al. |
| 2011/0189776 A1 | 8/2011 | Terns et al. |
| 2011/0201007 A1 | 8/2011 | Waller et al. |
| 2011/0201118 A1 | 8/2011 | Yang et al. |
| 2011/0217739 A1 | 9/2011 | Terns et al. |
| 2011/0217791 A1 | 9/2011 | Tomigahara et al. |
| 2011/0223638 A1 | 9/2011 | Wiedenheft et al. |
| 2011/0236530 A1 | 9/2011 | Manoury et al. |
| 2011/0236894 A1 | 9/2011 | Rao et al. |
| 2011/0269119 A1 | 11/2011 | Hutchison et al. |
| 2011/0300528 A1 | 12/2011 | Jassim et al. |
| 2011/0300538 A1 | 12/2011 | Barrangou et al. |
| 2012/0027786 A1 | 2/2012 | Gupta et al. |
| 2012/0088676 A1 | 4/2012 | Weill et al. |
| 2012/0151635 A1 | 6/2012 | Coruzzi et al. |
| 2012/0214160 A1 | 8/2012 | Deng et al. |
| 2013/0011516 A1 | 1/2013 | Griffin et al. |
| 2013/0011828 A1 | 1/2013 | Barrangou et al. |
| 2013/0130248 A1 | 5/2013 | Haurwitz et al. |
| 2013/0145497 A1 | 6/2013 | Choi et al. |
| 2013/0150240 A1 | 6/2013 | Newman et al. |
| 2013/0158245 A1 | 6/2013 | Russell et al. |
| 2013/0253040 A1 | 9/2013 | Miller et al. |
| 2013/0288251 A1 | 10/2013 | Horvath et al. |
| 2013/0326645 A1 | 12/2013 | Cost et al. |
| 2013/0326725 A1 | 12/2013 | Shukla et al. |
| 2013/0330778 A1 | 12/2013 | Zeiner et al. |
| 2013/0337454 A1 | 12/2013 | Duchateau |
| 2014/0068797 A1 | 3/2014 | Doudna et al. |
| 2014/0093941 A1 | 4/2014 | Terns et al. |
| 2014/0113376 A1 | 4/2014 | Sorek et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0199767 A1 | 7/2014 | Barrangou et al. |
| 2014/0201857 A1 | 7/2014 | Fahrenkrug et al. |
| 2014/0212869 A1 | 7/2014 | Sampas et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0242702 A1 | 8/2014 | Chen et al. |
| 2014/0248702 A1 | 9/2014 | Zhang et al. |
| 2014/0256046 A1 | 9/2014 | Zhang et al. |
| 2014/0271987 A1 | 9/2014 | Manoury et al. |
| 2014/0273037 A1 | 9/2014 | Wu |
| 2014/0273226 A1 | 9/2014 | Wu |
| 2014/0273230 A1 | 9/2014 | Chen et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0273235 A1 | 9/2014 | Voytas et al. |
| 2014/0287938 A1 | 9/2014 | Zhang et al. |
| 2014/0294773 A1 | 10/2014 | Brouns et al. |
| 2014/0295556 A1 | 10/2014 | Joung et al. |
| 2014/0295557 A1 | 10/2014 | Joung et al. |
| 2014/0298547 A1 | 10/2014 | Sastry-Dent et al. |
| 2014/0304853 A1 | 10/2014 | Ainley et al. |
| 2014/0309487 A1 | 10/2014 | Lee et al. |
| 2014/0310828 A1 | 10/2014 | Lee et al. |
| 2014/0310830 A1 | 10/2014 | Zhang et al. |
| 2014/0315985 A1 | 10/2014 | May et al. |
| 2014/0335063 A1 | 11/2014 | Cannon et al. |
| 2014/0335620 A1 | 11/2014 | Zhang et al. |
| 2014/0349400 A1 | 11/2014 | Jakimo et al. |
| 2014/0356867 A1 | 12/2014 | Peter et al. |
| 2014/0356958 A1 | 12/2014 | Mali et al. |
| 2014/0357530 A1 | 12/2014 | Zhang et al. |
| 2014/0377868 A1 | 12/2014 | Joung et al. |
| 2015/0020223 A1 | 1/2015 | Zhang et al. |
| 2015/0024499 A1 | 1/2015 | Brouns et al. |
| 2015/0024500 A1 | 1/2015 | Yu et al. |
| 2015/0031134 A1 | 1/2015 | Zhang et al. |
| 2015/0044772 A1 | 2/2015 | Zhao |
| 2015/0045546 A1 | 2/2015 | Siksnys et al. |
| 2015/0050699 A1 | 2/2015 | Siksnys et al. |
| 2015/0056629 A1 | 2/2015 | Guthrie-Honea |
| 2015/0067922 A1 | 3/2015 | Yang et al. |
| 2015/0071899 A1 | 3/2015 | Liu et al. |
| 2015/0079681 A1 | 3/2015 | Zhang |
| 2015/0093473 A1 | 4/2015 | Barrangou et al. |
| 2015/0159174 A1 | 6/2015 | Frendeway et al. |
| 2015/0159175 A1 | 6/2015 | Frendeway et al. |
| 2015/0166969 A1 | 6/2015 | Takeuchi et al. |
| 2015/0167000 A1 | 6/2015 | Voytas et al. |
| 2015/0176064 A1 | 6/2015 | Fach et al. |
| 2015/0184139 A1 | 7/2015 | Zhang et al. |
| 2015/0191744 A1 | 7/2015 | Wolfe et al. |
| 2015/0203872 A1 | 7/2015 | Zhang |
| 2015/0232882 A1 | 8/2015 | Zhang et al. |
| 2015/0232883 A1 | 8/2015 | Dahlman et al. |
| 2015/0247150 A1 | 9/2015 | Zhang et al. |
| 2015/0252358 A1 | 9/2015 | Maeder et al. |
| 2015/0291965 A1 | 10/2015 | Zhang et al. |
| 2015/0291966 A1 | 10/2015 | Zhang et al. |
| 2015/0315576 A1 | 11/2015 | Caliando et al. |
| 2015/0356239 A1 | 12/2015 | Zhang et al. |
| 2015/0376652 A1 | 12/2015 | Kuhn et al. |
| 2016/0010076 A1 | 1/2016 | Joung et al. |
| 2016/0010147 A1 | 1/2016 | Heron |
| 2016/0017301 A1 | 1/2016 | Khalili et al. |
| 2016/0017366 A1 | 1/2016 | Chen et al. |
| 2016/0024510 A1 | 1/2016 | Bikard et al. |
| 2016/0024523 A1 | 1/2016 | Joung et al. |
| 2016/0024524 A1 | 1/2016 | Joung et al. |
| 2016/0024529 A1 | 1/2016 | Carstens et al. |

(56) References Cited

U.S. PATENT DOCUMENTS

2016/0312198 A1 10/2016 Joung et al.
2016/0362688 A1 12/2016 May et al.

FOREIGN PATENT DOCUMENTS

| CN | 103343120 | 10/2013 |
|---|---|---|
| EP | 2325332 | 5/2011 |
| WO | WO 2003/072788 | 9/2003 |
| WO | WO 2004/099366 | 11/2004 |
| WO | WO 2007/014275 | 2/2007 |
| WO | WO 2007/025097 | 3/2007 |
| WO | WO 2008/108989 | 9/2008 |
| WO | WO 2010/054108 | 5/2010 |
| WO | WO 2011/017293 | 2/2011 |
| WO | WO 2011/143124 | 11/2011 |
| WO | WO 2012/093833 | 7/2012 |
| WO | WO 2012/164565 | 12/2012 |
| WO | WO 2013/012674 | 1/2013 |
| WO | WO 2013/098244 | 7/2013 |
| WO | WO 2013/141680 | 9/2013 |
| WO | WO 2013/142578 | 9/2013 |
| WO | WO 2013/169398 | 11/2013 |
| WO | WO 2013/176772 | 11/2013 |
| WO | WO 2014/059255 | 4/2014 |
| WO | WO 2014/089290 | 6/2014 |
| WO | WO 2014/093622 | 6/2014 |
| WO | WO 2014/093655 | 6/2014 |
| WO | WO 2014/099744 | 6/2014 |
| WO | WO 2014/124284 | 8/2014 |
| WO | WO 2014/127287 | 8/2014 |
| WO | WO 2014/144288 | 9/2014 |
| WO | WO 2014/144592 | 9/2014 |
| WO | WO 2014/144761 | 9/2014 |
| WO | WO 2014/152432 | 9/2014 |
| WO | WO 2014/204578 | 12/2014 |
| WO | WO 2014/204724 | 12/2014 |
| WO | WO 2015/035162 | 3/2015 |
| WO | WO 2015/089364 | 6/2015 |
| WO | WO 2015/099850 | 7/2015 |
| WO | WO 2015/153940 | 10/2015 |
| WO | WO 2016/115355 | 6/2016 |

OTHER PUBLICATIONS

Office Action in Chinese Application No. 201480076396.6, dated Feb. 19, 2019, 16 pages (with English translation).
Partial Supplementary Search report in European Application No. 16842722.7, dated Mar. 7, 2019, 13 pages.
Kim et al., Hybrid restriction enzymes: zinc finger fusions to Fok I cleavage domain, PNAS, Feb. 1996, 93: 1156-1160.
Melo et al., "eRNAs Are Required for p53-Dependent Enhancer Activity and Gene Transcription," Mol Cell, Feb. 2013, 49: 524-535.
Mino et al., "Efficient double-strand DNA cleavage by artificial zinc-finger nucleases composed of one zinc-finger protein and a single-chain FokI dimer," Journal of biotechnology, 2009, 140: 156-161.
Nielsen et al., "Interaction with members of the heterochromatin protein 1 (HP1) family and histone deacetylation are differentially involved in transcriptional silencing by members of the TIF1 family," EMBO J., 1999, 18: 6385-6395.
Office Action in Canadian Application No. 2907198, dated May 14, 2018, 3 pages.
Office Action in Australian Application No. 2017204909, dated Aug. 8, 2018, 8 pages.
Office Action in European Application No. 14875819.6, dated Jun. 19, 2018.
Office Action in Japanese Application No. 2016-502406, dated Jun. 12, 2018, 23 pages (with English translation).
Office Action in Japanese Application No. 2016-502853, dated Jun. 12, 2018, 15 pages (with English translation).
Qi et al., "Repurposing CRISPR as an RNA-Guided Platform for Sequence-Specific Control of Gene Expression," Supplemental Information, Cell, Feb. 2013, 152.
Williams et al., Tet1 and hydroxymethylcytosine in transcription and DNA methylation fidelity, Nature, May 2011, 473: 343-349.
AU Office Action in Australian Appln. No. 2014239665, dated Sep. 5, 2019, 4 pages.
BR Office Action in Brazilian Appln. No. BR112015023489-5, dated Oct. 3, 2019, 6 pages (with English abstract).
CN Action in Chinese Appln. No. 201480076396.6, dated Sep. 20, 2019, 8 pages (with English translation).
EP Extended European Search Report in European Appln. No. 16842722.7, dated Jun. 7, 2019, 13 pages.
IL Office Action in Israeli Appln. No. 241671, dated Aug. 1, 2019, 5 pages (with English translation).
JP Office Action in Japanese Appln. No. 2016-502406, dated May 31, 2019, 24 pages (with English translation).
JP Office Action in Japanese Appln. No. 2016-502853, dated May 29, 2019, 7 pages (with English translation).
JP Office Action in Japanese Appln. No. 2016-542968, dated Jul. 30, 2019, 8 pages (with English translation).
JP Office Action in Japanese Appln. No. 2016-502976, dated Apr. 2, 2019, 16 pages (with English translation).
Office Action in Chinese Application No. 201480027950.1, dated Oct. 18, 2018, 6 pages.
Office Action in European Application No. 14764117.9, dated Oct. 5, 2018, 6 pages.
Office Action in Israeli Application No. 241671, dated Sep. 13, 2018, 8 pages (with English translation).
Office Action in Japanese Application No. 2016-542968, dated Sep. 18, 2018 (with English translation).
Ui-Tei et al., "Functional dissection of siRNA sequence by systematic DNA substitution: modified siRNA with a DNA seed arm is a powerful tool for mammalian gene silencing with significantly reduced off-target effect," Nucleic Acids Research, 2008, 36: 2136-2151.
Lino et al, "Delivering CRISPR: a review of the challenges and approaches," Drug Delivery, 2018, 25: 1234-1257.
Liu et al, "Delivery strategies of the CRISPR-Cas9 gene-editing system for therapeutic applications, Journal of Controlled Release," 2017, 266: 17-26.
U.S. Appl. No. 61/610,212, Joung et al, filed Mar. 13, 2012
U.S. Appl. No. 61/799,647, Joung et al, filed Mar. 15, 2013.
U.S. Appl. No. 61/838,148, filed Jun. 21, 2013, Joung et al.
Addgene 2016; CRISPR/Cas9 Guide on the web at addgene.org/CRISPR/guide/.
Al-Attar et al., "Clustered regularly interspaced short palindromic repeats (CRISPRs): the hallmark of an ingenious antiviral defense mechanism in prokaryotes," Biol Chem., Apr. 2011, 392:277-289.
Alexopoulou et al., "The CMV early enhancer/chicken β actin (CAG) promoter can be used to drive transgene expression during the differentiation of murine embryonic stem cells into vascular progenitors," BMC Cell Biology, Jan. 2008, 9:2.
Anders et al., "Structural basis of PAM-dependent target DNA recognition by the Cas9 endonuclease," Nature, Sep. 2014, 513:569-573.
Anonymous, "2013 Runners-Up. Genetic microsurgery for the masses," Science. Dec. 2013 20;342(6165):1434-5.
Appela., "Non-natural nucleic acids for synthetic biology," Current Opinion in Chemical Biology, Dec. 2009,13(5-6): 687-696.
Arimondo et al., "Exploring the Cellular Activity of Camptothecin—Triple—Helix-Forming Oligonucleotide Conjugates," Mol. Cell. Biol., Jan. 2006, 26(1):324-33.
Arnould et al., "Engineering of large numbers of highly specific homing endonucleases that induce recombination on novel DNA targets," J Mol Biol., 355(3):443-458, Epub Nov. 15, 2005.
Arnould et al., "The I-CreI meganuclease and its engineered derivatives: applications from cell modification to gene therapy," Protein Eng Des Sel., 24(1-2):27-31, Epub Nov. 3, 2010.
Arora et al., "Residues 1-254 of anthrax toxin lethal factor are sufficient to cause cellular uptake of fused polypeptides," J. Biol. Chem., Feb. 1993, 268:3334-41.

(56) References Cited

OTHER PUBLICATIONS

Auer et al., "Highly efficient CRISPR/Case9-mediated known-in in zebrafish by homology-independent DNA repair," Genome Res., Jan. 2014, 24:142-153.
Bae et al., "Cas-OFFinder: a fast and versatile algorithm that searches for potential off-target sites of Cas9 RNA-guided endonucleases," Bioinformatics, May 2014, 30:1473-1475.
Bae et al., "Human zinc fingers as building blocks in the construction of artificial transcription factors," Nat Biotechnol., 21(3):275-280, Epub Feb. 18, 2003.
Barker et al., "Increased DNA microarray hybridization specificity using sscDNA targets," BMC Genomics, Apr. 2005, 6:57, 8 pages.
Baron-Benhamou et al., "Using the λN Peptide to Tether Proteins to RNAs," Methods Mole Biol., Jan. 2004, 257:135-153.
Barrangou & May, "Unraveling the potential of CRISPR-Cas9 for gene therapy," Expert Opin. Biol. Ther., Mar. 2015, 15:311-314.
Barrangou et al., "CRISPR Provides Acquired Resistance Against Viruses in Prokaryotes," Sci., Mar. 2007, 315:1709-1712.
Barrangou, "RNA-mediated programmable DNA cleavage," Nature Biotechnol., Sep. 2012, 30(9):836-838.
Bassett et al., "Highly efficient targeted mutagenesis of *Drosophila* with the CRISPR/Cas9 system," Cell Reports, Jul. 2013, 4:220-228.
Beerli and Barbas, "Engineering polydactyl zinc-finger transcription factors," Nat Biotechnol., Feb. 2002, 20(2):135-141.
Beerli et al., "Toward controlling gene expression at will: specific regulation of the erbB-2/HER-2 promoter by using polydactyl zinc finger proteins constructed from modular building blocks," PNAS USA, Dec. 1998, 95:14628-14633.
Belhaj et al., "Plant genome editing made easy: targeted mutagenesis in model and crop plants using the CRISPR/Cas system," Plant Methods, Oct. 2013, 9:39, 10 pages.
Bello et al., "Hypermethylation of the DNA repair gene MGMT: association with TP53 G:C to A:T transitions in a series of 469 nervous system tumors," Mutat. Res., Oct. 2004, 554:23-32.
Berg, "Proposed structure for the zinc-binding domains from transcription factor IIIA and related proteins," Proc Natl Acad Sci U S A., Jan. 1988, 85(1):99-102.
Bikard et al., "Programmable repression and activation of bacterial gene expression using an engineered CRISPR-Cas system," Nucleic Acid Res., Jun. 2013, 41(15):7429-7437.
Bitinaite et al., "FokI dimerization is required for DNA cleavage," Proc. Natl. Acad. Sci. USA, Sep. 1998, 95:10570-10575.
Blackburn et al., "The CRISPR System-Keeping Zebrafish Gene Targeting Fresh," Zebrafish, Mar. 2013, 10(1):116-118.
Blaese et al., "T lymphocyte-directed gene therapy for ADA-SCID: initial trial results after 4 years," Science, Oct. 1995, 270:475-480.
Boch et al., "Breaking the code of DNA binding specificity of TAL-type III effectors," Science, Dec. 2009,326(5959):1509-12.
Bogdanove & Voytas, "TAL Effectors: Customizable Proteins for DNA Targeting," Science, Sep. 2011, 333:1843-1846.
Bogdanove et al., "TAL effectors: finding plant genes for disease and defense," Curr. Opin. Plant Biol., Aug. 2010, 13:394-401.
Burgess, "A CRISPR genome-editing tool," Nature Reviews Genetics Feb. 2013, 14, 80-81.
Burnett et al., "Conditional macrophage ablation in transgenic mice expressing a Fas-based suicide gene," J. Leukoc. Biol., Apr. 2004, 75(4):612-623.
Butler and Kadonaga, "The RNA polymerase II core promoter: a key component in the regulation of gene expression," Genes & Dev., Oct. 2002, 16:2583-2592.
Canadian Office Action in Canadian Application No. 2907198, dated Jul. 8, 2016, 4 pages.
Carbonetti et al., "Use of pertussis toxin vaccine molecule PT19K/129G to deliver peptide epitopes for stimulation of a cytotoxic T lymphocyte response," Abstr. Annu. Meet. Am. Soc. Microbiol., 1995, 95:295.
Carroll et al., "Design, construction and in vitro testing of zinc finger nucleases," Nat Protoc., 2006, 1(3):1329-1341.
Carroll, "A CRISPR Approach to Gene Targeting," Molecular Therapy, Sep. 2012, 20(9):1658-1660.
Carroll, "Progress and prospects: zinc-finger nucleases as gene therapy agents," Gene Ther., 15(22):1463-1468, Epub Sep. 11, 2008.
Carroll, "Staying on target with CRISPR-Case," Nat Biotechnol., Sep. 2013, 31(9):807-809.
Castellano et al., "Inducible recruitment of Cdc42 or WASP to a cell-surface receptor triggers actin polymerization and filopodium formation," Curr. Biol., Apr. 1999, 9(7): 351-360.
Cathomen and Joung, "Zinc-finger nucleases: the next generation emerges," Mol. Ther., Jul. 2008, 16:1200-1207.
Cermak et al., "Efficient design and assembly of custom TALEN and other TAL effector-based constructs for DNA targeting," Nucleic Acids Res., Jul. 2011, 39:e82, p. 1-11.
Chaikind et al., "Targeted DNA Methylation Using an Artificially Bisected M.HhaI Fused to Zinc Fingers," PLoS One, 2012, 7(9):E44852 pp. 1-11.
Chang et al., "Genome editing with RNA-guided Cas9 nuclease in zebrafish embryos," Cell Res., Apr. 2013, 23:465-472.
Chen & Zhao, "A highly sensitive selection method for directed evolution of homing endonucleases," Nucleic Acids Res., Oct. 2005, 33(18):e154.
Chen et al., "Cut Site Selection by the Two Nuclease Domains of the Cas9 RNA-guided Endonuclease," J Biol Chem. May 2014; 289(19):13284-94.
Chen et al., "Dynamic imaging of genomic loci in living human cells by an optimized CRISPR/Cas system," Cell, Dec. 2013, 155(7):1479-1491.
Chen et al., "Efficient genome editing in Caenorhabditis elegans by CRISPR-targeted homologous recombination," Nucleic Acids Res., Nov. 2013, 41(20):e193, 6 pages.
Chen et al., "Induced DNA demethylation by targeting Ten-Eleven Translocation 2 to the human ICAM-1 promoter," Nucleic Acids Res., 42(3):1563-1574, Epub Nov. 4, 2013.
Cheng et al., "Multiplexed activation of endogenous genes by CRISPR-on, an RNA-guided transcriptional activator system," Cell Res., Oct. 2013 Oct, 23(10):1163-71.
Chim et al., "Methylation profiling in multiple myeloma," Leuk. Res., Apr. 2004, 28:379-85.
Chiu et al., "Transgene-free genome editing in Caenorhabditis elegans using CRISPR-Cas," Genetics, Nov. 2013, 195(3):1167-71.
Cho et al., "Analysis of off-target effects of CRISPR/Case-derived RNA-guided endonucleases and nickases," Genome Res., Jan. 2014, 24:132-141.
Cho et al., "Targeted genome engineering in human cells with the Cas9 RNA-guided endonuclease," Nat Biotechnol., Mar. 2013, 31:230-232.
Choo and Klug, "Toward a code for the interactions of zinc fingers with DNA: selection of randomized fingers displayed on phage," Proc Natl Acad Sci U S A., Nov. 1994, 91(23):11163-11167.
Christian et al., "Targeting DNA Double-Strand Breaks with TAL Effector Nucleases," Genetics, Oct. 2010, 186:757-761.
Chylinski et al., "Classification and evolution of type II CRISPR-Cas systems," Nucleic Acids Res. Jun. 2014;42(10):6091-105.
Chylinski et al., "The tracrRNA and Cas9 families of type II CRISPR-Cas immunity systems," RNA Biol., May 2013, 10(5):726-737.
Clark-Curtiss and Curtiss, "[23] Analysis of recombinant DNA using *Escherichia coli* minicells," Methods in Enzymology, 1983, 101:347-362.
Colley et al., "Conversion of a Golgi Apparatus Sialyltransferase to a Secretory Protein by Replacement of the NH2-terminall Signal Anchor with a Signal Peptide," J. Biol. Chem., Oct. 1989, 264:17619-22.
Cong et al., "Multiplex genome engineering using CRISPR/Cas systems," Science, Feb. 2013, 339:819-823 (Author Manuscript).
Conklin, "Sculpting genomes with a hammer and chisel," Nature Methods, Sep. 2013, 10(9):839-840.
Costa et al., "REELIN and schizophrenia: a disease at the interface of the genome and the epigenome," Mol. Interv., Feb. 2002, 2:47-57.
Crabtree and Schreiber, "Three-part inventions: intracellular signaling and induced proximity," Trends Biochem. Sci., Nov. 1996, 21(11):418-422.

(56) References Cited

OTHER PUBLICATIONS

Cradick et al., "CRISPR/Cas9 systems targeting beta-globin and CCR5 genes have substantial off-target activity," Nucleic Acids Res., Nov. 2013, 41(20):9584-92.
D'Avignon et al., "Site-specific experiments on folding/unfolding of Jun coiled coils: thermodynamic and kinetic parameters from spin inversion transfer nuclear magnetic resonance at leucine-18," Biopolymers, 83(3):255-267, Oct. 2006.
De Souza, "RNA-guided gene editing," Nat Methods, Mar. 2013, 10(3):189.
De Zhu, "The altered DNA methylation pattern and its implications in liver cancer," Cell. Res., Apr. 2005, 15:272-80.
Deltcheva et al., "CRISPR RNA maturation by trans-encoded small RNA and host factor Rnase III," Nature, Mar. 2011, 471(7340):602-607 (Author Manuscript).
Deveau et al., "Phage response to CRISPR-encoded resistance in *Streptococcus thermophilus*," J Bacteriol., Feb. 2008, 190(4):1390-400.
Dicarlo et al., "Genome engineering in *Saccharomyces cerevisiae* using CRISPR-Cas systems," Nucleic Acids Res., Apr. 2013, 41(7):4336-43.
Dickinson et al., "Engineering the Caenorhabditis elegans genome using Cas9-triggered homologous recombination," Nat Methods., Oct. 2013, 10(10):1028-34.
Ding et al., "Enhanced efficiency of human pluripotent stem cell genome editing through replacing TALENs with CRISPRs," Cell Stem Cell., Apr. 2013, 12(4):393-4 (Author Manuscript).
Donnelly et al., "Targeted delivery of peptide epitopes to class I major histocompatibility molecules by a modified Pseudomonas exotoxin," PNAS, Apr. 1993, 90:3530-34.
Doudna and Charpentier, "Genome editing. The new frontier of genome engineering with CRISPR-Cas9," Science, Nov. 2014, 346:1258096, 11 pages.
Doyon et al., "Directed Evolution and Substrate Specificity Profile of Homing Endonuclease I-SceI," J. Am. Chem. Soc., Feb. 2006, 128:2477-2484.
Doyon et al., "Heritable targeted gene disruption in zebrafish using designed zinc-finger nucleases," Nat Biotechnol., Jun. 2008, 26:702-708.
Dranoff et al., "A phase I study of vaccination with autologous, irradiated melanoma cells engineered to secrete human granulocyte-macrophage colony stimulating factor," Hum. Gene Ther., Jan. 1997, 8(1):111-23.
Dunbar et al., "Retrovirally Marked CD34-Enriched Peripheral Blood and Bone Marrow Cells Contribute to Long-Term Engraftment After Autologous Transplantation ," Blood, Jun. 1995, 85:3048-3057.
Eisenschmidt et al., "Developing a programmed restriction endonuclease for highly specific DNA cleavage," Nucleic Acids Res., Dec. 2005, 33(22):7039-47.
Ellem et al., "A case report: immune responses and clinical course of the first human use of granulocyte/macrophage-colony-stimulating-factor-transduced autologous melanoma cells for immunotherapy," Immunol Immunother., Mar. 1997, 44:10-20.
Elrod-Erickson et al., "High-resolution structures of variant Zif268-DNA complexes: implications for understanding zinc finger-DNA recognition," Structure, Apr. 1998, 6(4):451-464.
Esteller et al., "A Gene Hypermethylation Profile of Human Cancer," Cancer Res., Apr. 2001, 61:3225-9.
Esteller et al., "Promoter Hypermethylation and BRCA1 Inactivation in Sporadic Breast and Ovarian Tumors," J. Natl. Cancer Inst., Apr. 2000, 92:564-9.
Esvelt et al., "Orthogonal Cas9 proteins for RNA-guided gene regulation and editing," Nat Methods, Nov. 2013, 10(11):1116-21.
European Partial Supplementary Search Report in European Application No. 14764117.9, dated Aug. 11, 2016, 7 pages.
European Search Report in European Application No. 14763916.5, dated Jul. 27, 2016, 10 pages.
Extended European Search Report in European Application No. 14764159.1, dated Aug. 10, 2016.
Extended European Search Report in European Application No. 14768877.4, dated Aug. 10, 2016.
Fisher et al., "A scalable, fully automated process for construction of sequence-ready human exome targeted capture libraries," Genome Biol., 2011, 12-R1.
Fonfara et al., "Phylogeny of Cas9 determines functional exchangeability of dual-RNA and Cas9 among orthologous type II CRISPR-Cas systems," Nucleic Acids Res., Feb. 2014, 42(4):2577-90.
Freeman et al., "Inducible Prostate Intraepithelial Neoplasia with Reversible Hyperplasia in Conditional FGFR1-Expressing Mice," Cancer Res., Dec. 2003, 63(23):8256-8563.
Friedland et al., "Heritable genome editing in C. elegans via a CRISPR-Cas9 system," Nature Methods, Aug. 2013, 10(8): 741-743 (Author Manuscript).
Fu et al, "Targeted genome editing in human cells using CRISPR/Cas nucleases and truncated guide RNAs", Methods in Enzymology, Nov. 2014, 546: 21-45.
Fu et al., "High-frequency off-target mutagenesis induced by CRISPR-Cas nucleases in human cells," Nat Biotechnol., Sep. 2013, 31:822-826 (Author Manuscript).
Fu et al., "Improving CRISPR-Cas nuclease specificity using truncated guide RNAs," Nat. Biotechnol. Mar. 2014, 32:279-284.
Gabriel et al., "An unbiased genome-wide analysis of zinc-finger nuclease specificity," Nat Biotechnol., Aug. 2011, 29:816-823.
Gagnon et al., "Efficient mutagenesis by Cas9 protein-mediated oligonucleotide insertion and large-scale assessment of single-guide RNAs," PLoS One, May 2014, 9, e98186.
Gaj et al., "ZFN, TALEN, and CRISPR/Cas-based methods for genome engineering", Trends in Biotechnology, Jul. 2013, 31(7): 397-405.
Gao et al., "Hypermethylation of the RASSF1A gene in gliomas", Clin. Chim. Acta., Nov. 2004, 349:173-9.
Garcia-Bustos et al., "Nuclear protein localization," Biochim. Biophys. Acta, Mar. 1991, 1071:83-101.
Garneau et al., "The CRISPR/Cas bacterial immune system cleaves bacteriophage and plasmid DNA," Nature, Nov. 2010, 468(7320):67-71.
Gasiunas and Siksnys, "RNa-dependent DNA endonuclease Cas9 of the CRISPR system: Holy Grail of genome editing?," Trends Microbiol., Nov. 2013, 21(11):562-567.
Gasiunas, "Cas9-crRNA ribonucleoprotein complex mediates specific DNA cleavage for adaptive immunity in bacteria," Proc Natl Acad Sci U S A, Sep. 2012, 109(39):E2579-86.
Geibler et al., "Transcriptional Activators of Human Genes with Programmable DNA-Specificity," PLoS One, 2011, 6:e19509.
Gilbert et al., "CRISPR-mediated modular RNA-guided regulation of transcription in eukaryotes," Cell, Jul. 2013, 154(2):442-51.
Gossen and Bujard, "Tight control of gene expression in mammalian cells by tetracycline-responsive promoters," Proc. Natl. Acad. Sci., Jun. 1992, 89:5547-5551.
Graef et al., "Proximity and orientation underlie signaling by the non-receptor tyrosine kinase ZAP70," Embo. J., Sep. 1997, 16(18):5618-5628.
Gratz et al., "CRISPR/Cas9-mediated genome engineering and the promise of designer flies on demand," Fly (Austin), Oct.-Dec. 2013, 7(4):249-55.
Gratz et al., "Genome engineering of *Drosophila* with the CRISPR RNA-guided Cas9 nuclease," Genetics, Aug. 2013, 194(4):1029-35.
Grizot et al., "Generation of redesigned homing endonucleases comprising DNA-binding domains derived from two different scaffolds," Nucleic Acids Res., 38(6):2006-2018, Epub Dec. 21, 2009.
Gross and Garrard, "Nuclease Hypersensitive Sites in Chromatin," Annu. Rev. Biochem., Jul. 1988, 57:159-97.
Guilinger et al., "Broad specificity profiling of TALENs results in engineered nucleases with improved DNA-cleavage specificity," Nat. Methods, Apr. 2014, 11:429-435.
Guilinger et al., "Fusion of catalytically inactive Cas9 to FokI nuclease improves the specificity of genome modification," Nat Biotechnol., Apr. 2014, 32(6):577-583.
Guo et al., "Hydroxylation of 5-Methylcytosine by TET1 Promotes Active DNA Demethylation in the Adult Brain," Cell, Apr. 2011, 145:423-434.

(56) References Cited

OTHER PUBLICATIONS

Haft et al., "A Guild of 45 CRISPR-Associated (Cas) Protein Families and multiple CRISPER/cas Subtypes Exist in Prokaryotic Genomes," PLOS, Nov. 2005, 1(6):0474-0483.
Hale et al., "Essential features and rational design of CRISPR RNAs that function with the Case RAMP module complex to cleave RNAs," Mol Cell., Feb. 2012, 45(3):292-302 (Author Manuscript).
Han et al., "CTCF Is the Master Organizer of Domain-Wide Allele-Specific Chromatin at the H19/Igf2 Imprinted Region," Mol. Cell Biol., Feb. 2008, 28(3):1124-35.
Han et al., "Ligand-directed retroviral targeting of human breast cancer cells," PNAS, Oct. 1995, 92:9747-51.
Harikrishna et al., "Construction and function of fusion enzymes of the human cytochrome P450scc system," DNA Cell Biol., Jun. 1993, 12(5):371-379.
Harrison, "A structural taxonomy of DNA-binding domains," Nature, Oct. 1991, 353(6346): 715-719.
Haurwitz et al., "Sequence- and Structure-Specific RNA Processing by a CRISPR Endonuclease," Science, Sep. 2010, 329(5997):1355-8.
Haurwitz, R. "The CRISPR endoribonuclease Csy4 utilizes unusual sequence and structures pecific mechanisms to recognize and process crRNAs," Thesis. May 8, 2012 (May 8, 2012), University of California, Berkeley, pp. 1-120. Retrieved from the Internet:<http://escholarship.org/uc/item/0rh5940p> on Dec. 26, 2014 (Dec. 26, 2014). entire document.
He et al., "Tet-Mediated Formation of 5-Carboxylcytosine and Its Excision by TDG in Mammalian DNA," Science, Sep. 2011, 333:1303-1307.
Hockemeyer et al., "Genetic engineering of human ES and iPS cells using TALE nucleases," Nat Biotechnol., 2011, 29:731-734 (Author Manuscript).
Horii et al., "Generation of an ICF Syndrome Model by Efficient Genome Editing of Human Induced Pluripotent Stem Cells using the CRISPR System," Int J Mol Sci., Sep. 2013, 14:19774-19781.
Horvath and Barrangou, "CRISPR/Cas, the immune system of bacteria and archaea," Science, Jan. 2010, 327:167-170.
Horvath et al., "Diversity, activity, and evolution of CRISPR loci in *Streptococcus thermophilus*," J. Bacteriol., Feb. 2008, 190:1401-1412.
Hou et al., "Efficient genome engineering in human pluripotent stem cells using Cas9 from Neisseria meningitidis," Proc Natl Acad Sci U S A, Sep. 2013, 110(39):15644-9.
Hsu et al., "Development and Applications of CRISPR-Cas9 for Genome Engineering," Cell, Jun. 2014, 157(6):1262-1278.
Hsu et al., "DNA targeting specificity of RNA-guided Cas9 nucleases," Nat Biotechnol., Sep. 2013, 31:827-832.
Huang et al., "Heritable gene targeting in zebrafish using customized TALENs," Nat. Biotechnol., Aug. 2011, 29:699-700.
Hwang et al., "Efficient In Vivo Genome Editing Using RNA-Guided Nucleases," Nat Biotechnol., 2013, 31:227-229 (Author Manuscript).
Hwang et al., "Heritable and Precise Zebrafish Genome Editing Using a CRISPR-Cas System," PLoS One, Jul. 2013, 8(7):e68708, 9 pages.
International Preliminary Report on Patentability in International Application No. PCT/US2013/043075, dated Dec. 2, 2014, 7 pages.
International Preliminary Report on Patentability in International Application No. PCT/US2014/027335, dated Sep. 15, 2015, 10 pages.
International Preliminary Report on Patentability in International Application No. PCT/US2014/028630, dated Sep. 15, 2015, 8 pages.
International Preliminary Report on Patentability in International Application No. PCT/US2014/029068, dated Sep. 15, 2015, 10 pages.
International Preliminary Report on Patentability in International Application No. PCT/US2014/029304, dated Sep. 22, 2015, 12 pages.
International Preliminary Report on Patentability in International Application No. PCT/US2014/056416, dated Jun. 28, 2016, 7 pages.
International Search Report and Written Opinion in International Application No. PCT/US2013/043075, dated Sep. 26, 2013, 10 pages.
International Search Report and Written Opinion in International Application No. PCT/US2014/027335, dated Jul. 16, 2014, 13 pages.
International Search Report and Written Opinion in International Application No. PCT/US2014/028630, dated Jul. 24, 2014, 9 pages.
International Search Report and Written Opinion in International Application No. PCT/US2014/029068, dated Nov. 5, 2014, 15 pages.
International Search Report and Written Opinion in International Application No. PCT/US2014/029304, dated Nov. 14, 2014, 17 pages.
International Search Report and Written Opinion in International Application No. PCT/US2014/035162, dated Oct. 14, 2014, 10 pages.
International Search Report and Written Opinion in International Application No. PCT/US2014/056416, dated Apr. 3, 2015, 11 pages.
International Search Report and Written Opinion in International Application No. PCT/US2013/074736, dated Sep. 17, 2014.
International Search Report and Written Opinion in International Application No. PCT/US16/49147, dated Dec. 23, 2016, 12 pages.
International Search Report in International Application No. PCT/US2014/054291, dated Mar. 27, 2015.
Invitation to Pay Additional Fees and, Where Applicable, Protest Fee in International Application No. PCT/US2014/029068, dated Aug. 20, 2014, 3 pages.
Invitation to Pay Additional Fees and, Where Applicable, Protest Fee in International Application No. PCT/US2014/029304, dated Jul. 30, 2014, 3 pages.
Invitation to Pay Additional Fees and, Where Applicable, Protest Fee in International application No. PCT/US2016/49147, dated Oct. 31, 2016.
Isalan et al., "A rapid, generally applicable method to engineer zinc fingers illustrated by targeting the HIV-1 promoter," Nat. Biotechnol., Jul. 2001, 19(7):656-660.
Ishino et al., "Nucleotide sequence of the iap gene, responsible for alkaline phosphatase isozyme conversion in *Escherichia coli*, and identification of the gene product," J Bacteriol., Dec. 1987, 169(12):5429-33.
Ito et al., "Tet proteins can convert 5-methylcytosine to 5-formylcytosine and 5-carboxylcytosine," Science, Sep. 2011, 333(6047):1300-1303.
Iyer et al., "Prediction of novel families of enzymes involved in oxidative and other complex modifications of bases in nucleic acids," Cell Cycle, Jun. 2009, 8(11):1698-710.
Iyer et al., Supplementary Material for "Prediction of novel families of enzymes involved in oxidative and other complex modifications of bases in nucleic acids," Cell Cycle, Jun. 1, 2009, 8(11):1698-710, [retrieved on Dec. 22, 2015]. Retrieved from the Internet: URL <ftp://ftp.ncbi.nih.gov/pub/aravind/DONS/supplementary_material_DONS.html>.
Jamieson et al., "In vitro selection of zinc fingers with altered DNA-binding specificity," Biochemistry, May 1994, 33(19):5689-5695.
Jansen et al., "Identification of genes that are associated with DNA repeats in prokaryotes," Mol. Microbiol., Mar. 2002, 43(6):1565-75.
Jiang et al., "CRISPR-assisted editing of bacterial genomes," Nat Biotechnol., 2013, 31:233-239 (Author Manuscript).
Jiang et al., "Structural Biology. A Cas9-guide RNA complex preorganized for target DNA recognition," Science, Jun. 2015, 348:1477-1481.
Jinek et al., "A programmable dual-RNA-guided DNA endonuclease in adaptive bacterial immunity," Science, 2012, 337:816-821.
Jinek et al., "RNA-programmed genome editing in human cells," Elife, Jan. 2013, 2:e00471, 9 pages.

(56) References Cited

OTHER PUBLICATIONS

Jinek et al., "Structures of Cas9 Endonucleases Reveal RNA-Mediated Conformational Activation," Science, Mar. 2014; 343(6176):1247997.

Josephs et al., "Structure and specificity of the RNA-guided endonuclease Cas9 during DNA interrogation, target binding and cleavage," Nucleic Acids Res., Sep. 2015, 43:8924-8941.

Joung and Sander, "TALENs: a widely applicable technology for targeted genome editing," Nat Rev Mol Cell Biol., 14(1):49-55, Epub Nov. 21, 2012.

Joung et al., "Reply to Successful genome editing with modularly assembled zinc finger nucleases," Nat. Methods, Jan. 2010, 7:91-92.

Karkare and Bhatnagar, "Promising nucleic acid analogs and mimics. characteristic features and applications of PNA, LNA, and morpholino," Applied Microbiology and Biotechnology, May 2006, 71(5): 575-586.

Karmirantzou and Harnodrakas, "A Web-based classification system of DNA-binding protein families," Protein Eng., Jul. 2001, 14(7):465-472.

Karvelis et al., "crRNA and tracrRNA guide Cas9-mediated DNA interference in *Streptococcus thermophilus*," RNA Biol., May 2013, 10(5):841-851.

Katic and Großhans, "Targeted heritable mutation and gene conversion by Cas9-CRISPR in Caenorhabditis elegans," Genetics, Nov. 2013, 195(3):1173-6.

Kearns et al., "Recombinant adeno-associated virus (AAV-CFTR) vectors do not integrate in a site-specific fashion in an immortalized epithelial cell line," Gene Ther., Sep. 1996, 9:748-55.

Keryer-Bibens et al., "Tethering of proteins to RNAs by bacteriophage proteins," Biol. Cell, Feb. 2008, 100:125-138.

Kiani et al., "Cas9 gRNA engineering for genome editing, activation and repression," Nat. Methods, Nov. 2015, 12:1051-1054.

Kim and Kim, "A guide to genome engineering with programmable nucleases," Nature Rev Genetics May 2014, 15, 321-334.

Kim et al., "Highly efficient RNA-guided genome editing in human cells via delivery of purified Cas9 ribonucleoproteins," Genome Res., Jun. 2014, 24(6):1012-9.

Kim et al., "Targeted genome editing in human cells with zinc finger nucleases constructed via modular assembly," Genome Res., 19(7):1279-1288, Epub May 21, 2009.

Kim et al., "Genome editing with modularly assembled zinc-finger nucleases," Nat. Methods, Feb. 2010, 7(2):91-92.

Kleinstiver et al., "A unified genetic, computational and experimental framework identifies functionally relevant residues of the homing endonuclease I-BmoI," Nucleic Acids Res., Apr. 2010, 38:2411-2427.

Kleinstiver et al., "Engineered CRISPR-Cas9 nucleases with altered PAM specificities," Nature, Jul. 2015, 523(7561):481-5.

Kleinstiver et al., "High-fidelity CR1SPR-Cas9 nucleases with no detectable genome-wide offtarget effects," Nature, Jan. 2016, 529: 490-495.

Klimpel et al., "Anthrax toxin protective antigen is activated by a cell surface protease with the sequence specificity and catalytic properties of furin," PNAS, Nov. 1992, 89:10277-81.

Klug, "Co-chairman's remarks: protein designs for the specific recognition of DNA," Gene, Dec. 1993, 135(1-2):83-92.

Koike-Yusa et al., "Genome-wide recessive genetic screening in mammalian cells with a lentiviral CRISPR-guide RNA library," Nat Biotechnol., Mar. 2014, 32(3):267-73.

Kondo and Ueda, "Highly improved gene targeting by germline-specific Cas9 expression in *Drosophila*," Genetics, Nov. 2013, 195(3):715-21.

Konermann et al., "Optical control of mammalian endogenous transcription and epigenetic states," Nature, Aug. 2013, 500(7463):472-6. (Author Manuscript).

Kumar et al., "DNA-Prot: identification of DNA binding proteins from protein sequence information using random forest," J Biomol Struct Dyn., Jun. 2009, 26(6):679-686.

Kumar et al., "Identification of DNA-binding proteins using support vector machines and evolutionary profiles," BMC Bioinformatics, Nov. 2007, 8:463.

Kummerfeld and Teichmann, "DBD: a transcription factor prediction database," Nucleic Acids Res., Jan. 2006, 34 (Database issue): D74-D81.

Kurmasheva et al., "Upstream CpG island methylation of the PAX3 gene in human rhabdomyosarcomas," Pediatr. Blood Cancer, Apr. 2005, 44:328-37.

Lea et al., "Aberrant p16 methylation is a biomarker for tobacco exposure in cervical squamous cell carcinogenesis," Am. J. Obstet. Gynecol., Mar. 2004, 190:674-9.

Lee et al., "Three-dimensional solution structure of a single zinc finger DNA-binding domain," Science., Aug. 1989, 245(4918):635-637.

Li et al., "DNA methylation in prostate cancer," Biochim. Biophys. Acta., Sep. 2004, 1704:87-102.

Li et al., "Heritable gene targeting in the mouse and rat using a CRISPR-Cas system," Nat Biotechnol, Aug. 2013, 31(8):681-3.

Li et al., "Modularly assembled designer TAL effector nucleases for targeted gene knockout and gene replacement in eukaryotes," Nucleic Acids Res., 39(14):6315-6325, Epub Mar. 31, 2011.

Li et al., "Protein trans-splicing as a means for viral vector-mediated in vivo gene therapy," Hum Gene Ther., Sep. 2008, 19(9):958-964.

Li et al., "Simultaneous generation and germline transmission of multiple gene mutations in rat using CRISPR-Cas systems," Nat Biotechnol., Aug. 2013, 31(8):684-6.

Li et al., "Tal nucleases (TALNs): hybrid proteins composed of TAL effectors and FokI DNA-cleavage domain," Nucleic Acids Res., Jan. 2011, 39(1): 359-372.

Lin et al., "CRISPR/Cas9 systems have off-target activity with insertions or deletions between target DNA and guide RNA sequences," Nucleic Acids Res., Jun. 2014, 42:7473-7485.

Lin et al., "iDNA-Prot: identification of DNA binding proteins using random forest with grey model," PLoS One., 6(9):e24756, Epub Sep. 15, 2011.

Liu et al., "Regulation of an Endogenous Locus Using a Panel of Designed Zinc Finger Proteins Targeted to Accessible Chromatin Regions," J. Biol. Chem., Apr. 2001, 276(14):11323-34.

Liu et al., "Validated zinc finger protein designs for all 16 GNN DNA triplet targets," J. Biol. Chem., 277(6):3850-3856, Epub Nov. 28, 2001.

Lo et al., "Precise and Heritable Genome Editing in Evolutionarily Diverse Nematodes Using TALENs and CRISPR/Cas9 to Engineer Insertions and Deletions," Genetics, Oct. 2013, 195:331-348.

Lund et al., "DNA Methylation Polymorphisms Precede Any Histological Sign of Atherosclerosis in Mice Lacking Apolipoprotein E," J. Biol. Chem., Jul. 2004, 279:29147-54.

Mabaera et al., "Developmental- and differentiation-specific patterns of human γ- and β-globin promoter DNA methylation," Blood, Aug. 2007, 110(4):1343-52.

Maeder et al., "CRISPR RNA-guided activation of endogenous human genes," Nat Methods, Oct. 2013, 10:977-979 (Author Manuscript).

Maeder et al., "Rapid 'open-source' engineering of customized zinc-finger nucleases for highly efficient gene modification," Mol Cell, Jul. 2008, 31(2):294-301.

Maeder et al., "Robust, synergistic regulation of human gene expression using TALE activators," Nat. Methods, Mar. 2013, 10:243-245.

Maeder et al., "Targeted DNA demethylation and activation of endogenous genes using programmable TALE-TET1 fusion proteins," Nat Biotechnol., 31(12):1137-1142, [author manuscript] Epub Oct. 9, 2013.

Mahfouz et al., "De novo-engineered transcription activator-like effector (TALE) hybrid nuclease with novel DNA binding specificity creates double-strand breaks," Proc Natl Acad Sci U S A, Feb. 2011, 108:2623-2628.

Maiti and Drohat, "Thymine DNA glycosylase can rapidly excise 5-formylcytosine and 5-carboxylcytosine: potential implications for active demethylation of CpG sites," J Biol Chem., 286(41):35334-35338, Epub Aug. 23, 2011.

(56) References Cited

OTHER PUBLICATIONS

Majumdar et al., "Targeted Gene Knock In and Sequence Modulation Mediated by a Psoralen-linked Triplex-forming Oligonucleotide," J Biol Chem., Apr. 2008, 283(17):11244-52.
Makarova et al., "A putative RNA-interference-based immune system in prokaryotes: computational analysis of the predicted enzymatic machinery, functional analogies with eukaryotic RNAi, and hypothetical mechanisms of action," Biol. Direct, Mar. 2006, 1:7, 26 pages.
Makarova et al., "Evolution and classification of the CRISPR-Cas systems," Nat. Rev. Microbiol., Jun. 2011, 9(6):467-77 (Author Manuscript).
Makarova et al., "Unification of Cas protein families and a simple scenario for the origin and evolution of CRISPR-Cas systems," Biol. Direct, Jul. 2011, 6:38, 27 pages.
Malech et al., "Prolonged production of NADPH oxidase-corrected granulocytes after gene therapy of chronic granulomatous disease," PNAS, Oct. 1997, 94:12133-38.
Mali et al., "Cas9 as a versatile tool for engineering biology," Nature Methods, Oct. 2013, 10(10):957-963.
Mali et al., "CAS9 transcriptional activators for target specificity screening and paired nickases for cooperative genome engineering," Nat Biotechnol., Sep. 2013, 31:833-838.
Mali et al., "RNA-guided human genome engineering via Cas9," Science, Feb. 2013, 339:823-826 (Author Manuscript).
Mancini et al. "CpG methylation within the 5' regulatory region of the BRCA1 gene is tumor specific and includes a putative CREB binding site," Oncogene, Mar. 1998, 16:1161-9.
Mandell and Barbas et al., "Zinc Finger Tools: custom DNA-binding domains for transcription factors and nucleases," Nucleic Acids Res., 34(Web Server issue):W516-W523, Jul. 1, 2006.
Marraffini and Sontheimer, "CRISPR Interference Limits Horizontal Gene Transfer in Staphylococci by Targeting DNA," Science, Dec. 2008, 322(5909):1843-1845.
Marraffini and Sontheimer, "Self vs. non-self discrimination during CRISPR RNA-directed immunity," Nature, Jan. 2010, 463(7280):568-571 (Author Manuscript).
Mashiko et al., "Generation of mutant mice by pronuclear injection of circular plasmid expressing Cas9 and single guided RNA," Sci Reports, Nov. 2013, 3(3355):1-6.
McGarty, "CRISPRs and Cancer," White Paper No. 111, Apr. 2014, 22 pages.
Mendenhall et al., "Locus-specific editing of histone modifications at endogenous enhancers," Nat Biotechnol., 31(12):1133-1136, Epub Sep. 8, 2013.
Miller et al., "A TALE nuclease architecture for efficient genome editing," Nature Biotechnology, Feb. 2011, 29:143-148.
Miller et al., "An improved zinc-finger nuclease architecture for highly specific genome editing," Nat Biotechnol., Jul. 2007, 25:778-785.
Miller et al., "Repetitive zinc-binding domains in the protein transcription factor IIIA from Xenopus oocytes," EMBO J., Jun. 1985, 4(6):1609-1614.
Miyazaki et al., "Expression vector system based on the chicken beta-actin promoter directs efficient production of interleukin-5," Gene, Jul. 1989, 79(2):269-77.
Mojica et al., "Biological significance of a family of regularly spaced repeats in the genomes of Archaea, Bacteria and mitochondria," Mol Microbiol., Apr. 2000, 36(1):244-6.
Mojica et al., "Short motif sequences determine the targets of the prokaryotic CRISPR defense system," Microbiology, Mar. 2009, 155:733-740.
Moore et al., "Design of polyzinc finger peptides with structured linkers," Proc Natl Acad Sci USA, Feb. 2001, 98:1432-1436.
Morbitzer et al., "Regulation of selected genome loci using de novo-engineered transcription activator-like effector (TALE)-type transcription factors," Proc Natl Acad Sci U S A., 107(50):21617-21622, Epub Nov. 24, 2010.

Morbitzer et al., "Assembly of custom TALE-type DNA binding domains by modular cloning," Nucl Acids Res., Jul. 2011, 39:5790-5799.
Morrison, "Transformation in *Escherichia coli*: Cryogenic Preservation of Competent Cells," J. Bacteriol., Oct. 1977, 132:349-351.
Moscou and Bogdanove, "A simple cipher governs DNA recognition by TAL effectors," Science, Dec. 2009, 326(5959):1501.
Mussolino and Cathomen, "RNA guides genome engineering," Nat Biotechnol., Mar. 2013, 31(3):208-209.
Mussolino et al., "A novel TALE nuclease scaffold enables high genome editing activity in combination with low toxicity," Nucleic Acids Res., Nov. 2011, 39:9283-93.
Muthuswamy et al., "Controlled Dimerization of ErbB Receptors Provides Evidence for Differential Signaling by Homo- and Heterodimers," Mol. Cell. Biol., Oct. 1999, 19(10):6845-6857.
Needleman and Wunsch, "A General Method Applicable to the Search for Similarities in the Amino Acid Sequence of Two Proteins," J. Mol. Biol., 1970, 48:444-453.
Neering et al., "Transduction of Primitive Human Hematopoietic Cells With Recombinant Adenovirus Vectors," Blood, Aug. 1996, 88:1147-55.
Nishimasu et al., "Crystal structure of Cas9 in complex with guide RNA and target DNA," Cell, Feb. 2014, 156:935-949.
Nissim et al., "Multiplexed and Programmable Regulation of Gene Networks with an Integrated RNA and CRISPR/Cas Toolkit in Human Cells," Molecular Cell, May 2014, 54:698-710.
Niu et al., "Generation of gene-modified cynomolgus monkey via Cas9/RNA-mediated gene targeting in one-cell embryos," Cell, Feb. 2014, 156:836-843.
Niwa et al., "Efficient selection for high-expression transfectants with a novel eukaryotic vector," Gene, Dec. 1991, 108(2):193-9.
Novak et al., "Functional Characterization of Protease-treated Bacillus anthracis Protective Antigen," J. Biol. Chem., Aug. 1992, 267:17186-93.
Office Action in Autralian Application No. 2014227653, dated Nov. 18, 2016.
Oligino et al., "Drug inducible transgene expression in brain using a herpes simplex virus vector," Gene Ther., Apr. 1998, 5:491-496.
Palva et al., "Secretion of interferon by Bacillus subtilis," Gene, May-Jun. 1983, 22:229-235.
Pattanayak et al., "High-throughput profiling of off-target DNA cleavage reveals RNA-programmed Cas9 nuclease specificity," Nat Biotechnol., Sep. 2013, 31:839-843 (Author Manuscript).
Pattanayak et al., "Revealing off-target cleavage specificities of zinc-finger nucleases by in vitro selection," Nat Methods, Aug. 2011, 8:765-770 (Author Manuscript).
Pavletich and Pabo, "Zinc finger-DNA recognition: crystal structure of a Zif268-DNA complex at 2.1 A," Science, May 1991, 252(5007):809-817.
Perelle et al., "Characterization of Clostridium perfringens Iota-Toxin Genes and Expression in *Eschenichia coli*," Infect. Immun., Dec. 1993, 61:5147-56.
Perez et al., "Establishment of HIV-1 resistance in CD4+ T cells by genome editing using zinc-finger nucleases," Nat Biotechnol., Jul. 2008, 26:808-816 (Author Manuscript).
Perez-Pinera et al., "RNA-guided gene activation by CRISPR-Case9-based transcription factors," Nat Methods, Oct. 2013, 10(10):973-976 (Author Manuscript).
Pingoud and Silva, "Precision genome surgery," Nat Biotechnol., Jul. 2007, 25(7):743-744.
Puchta and Fauser et al., "Synthetic nucleases for genome engineering in plants: prospects for a bright future," Plant J. Jun. 2014, 78(5):727-41.
Qi et al., "Repurposing CRISPR as an RNA-Guided Platform for Sequence-Specific Control of Gene Expression," Cell, Feb. 2013, 152:1173-1183.
Ramakrishna et al., "Gene disruption by cell-penetrating peptide-mediated delivery of Cas9 protein and guide RNA," Genome Res., Jun. 2014; 24(6): 1020-1027.
Ramakrishna et al., "Surrogate reporter-based enrichment of cells containing RNA-guided Cas9 nuclease-induced mutations," Nat Commun., Feb. 2014, 5:3378.

(56) References Cited

OTHER PUBLICATIONS

Ramalingam et al., "A CRISPR way to engineer the human genome," Genome Biol., Feb. 2013, 14:107, 4 pages.
Ramirez et al., "Unexpected failure rates for modular assembly of engineered zinc fingers," Nat Methods., May 2008, 5(5):374-375.
Ran et al., "Double nicking by RNA-guided CRISPR Cas9 for enhanced genome editing specificity," Cell, Sep. 2013, 154:1380-1389.
Ran et al., "Genome engineering using the CRISPR-Cas9 system," Nature Protocols, Nov. 2013, 8(11):2281-2308.
Ran et al., "In vivo genome editing using *Staphylococcus aureus* Cas9," Nature, Apr. 2015, 520:186-191.
Rebar and Pabo, "Zinc finger phage affinity selection of fingers with new DNA-binding specificities," Science, Feb. 1994, 263(5147):671-673.
Ren et al., "Optimized gene editing technology for *Drosophila melanogaster* using germ line-specific Cas9," Proc Natl Acad Sci U S A, Nov. 2013, 110(47):19012-7.
Rendahl et al., "Regulation of gene expression in vivo following transduction by two separate rAAV vectors," Nat. Biotechnol., Aug. 1998, 16:757-761.
Reyon et al., "Flash assembly of TALENs for high-throughput genome editing," Nat Biotech, May 2012, 30:460-465 (Author Manuscript).
Ro et al., "Adenovirus-based short hairpin RNA vectors containing an EGFP marker and mouse U6, human H1, or human U6 promoter," BioTechniques, Apr. 2005, 38(4):625-627.
Rodenhiser and Mann, "Epigenetics and human disease: translating basic biology into clinical applications," CMAJ, Jan. 2006, 174(3):341-348.
Rohde et al., "BISMA—Fast and accurate bisulfite sequencing data analysis of individual clones from unique and repetitive sequences," BMC Bioinformatics, May 2010, 11:230 12 pages.
Rothman, "Mechanisms of intracellular protein transport," Nature, Nov. 1994, 372(6501):55-63.
Rusk, "CRISPRs and epigenome editing," Nature Methods, Jan. 2014, 11(1):28.
Sander and Joung et al., "CRISPR-Cas systems for editing, regulating and targeting genomes," Nat Biotechnol., Apr. 2014, 32(4):347-55.
Sander et al., "In silico abstraction of zinc finger nuclease cleavage profiles reveals an expanded landscape of off-target sites," Nucleic Acids Res., Oct. 2013, 41:e181.
Sander et al., "ZiFiT (Zinc Finger Targeter): an updated zinc finger engineering tool," Nucleic Acids Res., Jul. 2010, 38:W462-468.
Sander et al., "Zinc Finger Targeter (ZiFiT): an engineered zinc finger/target site design tool," Nucleic Acids Res., Jul. 2007, 35:W599-605.
Sander et al., "Targeted gene disruption in somatic zebrafish cells using engineered TALENs," Nat. Biotechnol., Aug. 2011, 29:697-698.
Sanjana et al., "A transcription activator-like effector toolbox for genome engineering," Nature Protocols, Jan. 2012, 7:171-192.
Sapranauskas et al., "The *Streptococcus thermophilus* CRISPR/Cas system provides immunity in *Escherichia coli*," Nucleic Acids Res., Nov. 2011, 39(21):9275-9282.
Schleifman et al., "Triplex-mediated gene modification," Methods Mol. Biol., 435:175-190, 2008.
Scholze & Boch, "TAL effectors are remote controls for gene activation," J. Curr. Opin. Microbiol., Feb. 2011, 14:47-53.
Schwank et al., "Functional repair of CFTR by CRISPR/Cas9 in intestinal stem cell organoids of cystic fibrosis patients," Cell Stem Cell, Dec. 2013, 13(6):653-8.
Sebo et al., "Cell-invasive activity of epitope-tagged adenylate cyclase of Bordetella pertussis allows in vitro presentation of a foreign epitope to CD8+ cytotoxic T cells," Infect. Immun., Oct. 1995, 63:3851-57.
Segal et al., "Evaluation of a modular strategy for the construction of novel polydactyl zinc finger DNA-binding proteins," Biochemistry, Feb. 2003, 42(7):2137-2148.

Shah et al., "Protospacer recognition motifs," RNA Biol., May 2013, 10:891-899.
Sharma, "Schizophrenia, epigenetics and ligand-activated nuclear receptors: a framework for chromatin therapeutics," Schizophr. Res., Jan. 2005, 72:79-90.
Shen et al., "Efficient genome modification by CRISPR-Cas9 nickase with minimal off-target effects," Nat Methods, Apr. 2014, 11(4):399-402.
Shen et al., "Generation of gene-modified mice via Cas9/RNA-mediated gene targeting," Cell Res., May 2013, 23(5):720-3.
Shmakov et al., "Discovery and Functional Characterization of Diverse Class 2 CRISPR-Cas Systems," Molecular Cell, Nov. 2015 60:385-397.
Silva et al., "Meganucleases and other tools for targeted genome engineering: perspectives and challenges for gene therapy," Curr Gene Ther., Feb. 2011, 11(1):11-27.
Silver, "How Proteins Enter the Nucleus," Cell, Feb. 1991, 64(3):489-497.
Simon et al., "Sequence-specific DNA cleavage mediated by bipyridine polyamide conjugates," Nucl. Acids Res., Jun. 2008, 36(11):3531-8.
Slaymaker et al., "Rationally engineered Cas9 nucleases with improved specificity," Science, Jan. 2016, 351(6268): 84-88.
Stenmark et al., "Peptides fused to the amino-terminal end of diphtheria toxin are translocated to the cytosol," J. Cell Biol., Jun. 1991, 113:1025-32.
Sterman et al., "Adenovirus-mediated herpes simplex virus thymidine kinase/ganciclovir gene therapy in patients with localized malignancy: results of a phase I clinical trial in malignant mesothelioma," Hum. Gene Ther., May 1998, 7:1083-89.
Sternberg et al., "Conformational control of DNA target cleavage by CRISPR-Cas9," Nature, Nov. 2015, 527:110-113.
Sternberg et al., "DNA interrogation by the CRISPR RNA-guided endonuclease Cas9," Nature, Mar. 2014, 507:62-67.
Sternberg et al., "Mechanism of substrate selection by a highly specific CRISPR endoribonuclease," RNA, Apr. 2012, 18:661-672.
Stoddard, "Homing endonuclease structure and function," Q. Rev. Biophys., 38(1): 49-95, Epub Dec. 9, 2005.
Storrs, "A CRISPR Fore-Cas-t: A newcomer's guide to the hottest gene-editing tool on the block," Scientist Magazine, Mar. 2014, 4 pages.
Sugimoto et al., "Thermodynamic parameters to predict stability of RNA/DNA hybrid duplexes," Biochemistry, Sep. 1995, 34:11211-11216.
Sugimoto et al., "Thermodynamics-structure relationship of single mismatches in RNA/DNA duplexes," Biochemistry, Sep. 2000, 39(37):11270-81.
Swarts el al., "CRISPR Interference Directed Strand Specific Spacer Acquisition," PLOS, 2012, 7(4):1-7.
Szczepek et al., "Structure-based redesign of the dimerization interface reduces the toxicity of zinc-finger nucleases," Nat Biotechnol., Jul. 2007, 25:786-793.
Szyf et al., "DNA methylation and breast cancer," Biochem. Pharmacol., Sep. 2004, 68:1187-97.
Tahiliani et al., "Conversion of 5-Methylcytosine to 5-Hydroxymethylcytosine in Mammalian DNA by MLL Partner TET1," Science, May 2009, 324:930-935.
Tan et al., "Efficient nonmeiotic allele introgression in livestock using custom endonucleases," Proc Natl Acad Sci U S A, Oct. 2013, 110(41):16526-31.
Tan et al., "Zinc-finger protein-targeted gene regulation: genomewide single-gene specificity," Proc Natl Acad Sci U S A., 100(21):11997-2002, Epub Sep. 26, 2003.
Terns and Terns, "CRISPR-based adaptive immune systems," Curr Opin Microbiol., Jun. 2011, 14:321-327.
Tesson et al., "Knockout rats generated by embryo microinjection of TALENs," Nat. Biotechnol., Aug. 2011, 29:695-696.
Tjong and Zhou, "DISPLAR: an accurate method for predicting DNA-binding sites on protein surfaces," Nucleic Acids Res., 35(5):1465-1477, Epub Feb. 6, 2007.
Tsai et al., "Dimeric CRISPR RNA-guided Fok1 nucleases for highly specific genome editing," Nat Biotechnol., Apr. 2014, 32(6):569-576.

(56) References Cited

OTHER PUBLICATIONS

Tsai et al., "GUIDE-Seq enables genome-wide profiling of off-target cleavage by CRISPR-Cas nucleases," Nat Biotechnol, Feb. 2015, 33:187-197.
Tzur et al., "Heritable Custom Genomic Modifications in Caenorhabditis elegans via a CRISPR-Cas9 System," Genetics, Nov. 2013, 195:1181-1185.
Uhlmann et al., "Distinct methylation profiles of glioma subtypes," Int. J. Cancer, Aug. 2003, 106:52-9.
U.S. Final Office Action in U.S. Appl. No. 13/838,520, dated Jul. 15, 2015, 35 pages.
U.S. Final Office Action in U.S. Appl. No. 14/211,117, dated Jun. 30, 2016, 26 pages.
U.S. Non-Final Office Action in U.S. Appl. No. 14/211,117, dated Sep. 8, 2015, 20 pages.
U.S. Non-Final Office Action in U.S. Appl. No. 14/213,479, dated Dec. 9, 2015, 39 pages.
U.S. Non-Final Office Action in U.S. Appl. No. 14/213,723, dated Mar. 2, 2016, 39 pages.
U.S. Non-Final Office Action in U.S. Appl. No. 13/838,520, dated Oct. 6, 2014, 38 pages.
Van der Oost et al., "Unravelling the Structural and Mechanistic Basis of CRISPR-Cas Systems," Nature Reviews Microbiology, Jul. 2014, 12:479-492.
Ventura et al., "Cre-lox-regulated conditional RNA interference from transgenes," PNAS, Jul. 2004, 101:10380-10385.
Waaijers et al., "CRISPR/Cas9-Targeted Mutagenesis in Caenorhabditis elegans," Genetics, Nov. 2013, 195:1187-1191.
Wagner et al., "Efficient and persistent gene transfer of AAV-CFTR in maxillary sinus," Lancet, Jun. 1998, 351:1702-1703.
Wang et al., "One-Step Generation of Mice Carrying Mutations in Multiple Genes by CRISPR/Cas-Mediated Genome Engineering," Cell, May 2013, 153:910-918.
Wang et al., "Positive and negative regulation of gene expression in eukaryotic cells with an inducible transcriptional regulator," Gene Ther., May 1997, 4:432-441.
Wang et al., "The CRISPR/Cas system mediates efficient genome engineering in Bombyx mori," Cell Res., Dec. 2013, 23(12):1414-6.
Weber et al., "Assembly of Designer TAL Effectors by Golden Gate Cloning," PLoS One, 2011, 6:e19722.
Widschwendter and Jones, "DNA methylation and breast carcinogenesis," Oncogene, Aug. 2002, 21:5462-82.
Wiedenheft, "RNA-guided genetic silencing systems in bacteria and archaea," Nature, Feb. 2012, 482:331-338.
Wolfe et al., "DNA recognition by Cys2His2 zinc finger proteins," Annu Rev Biophys Biomol Struct. 2000, 29:183-212.
Wong et al., "Detection of aberrant p16 methylation in the plasma and serum of liver cancer patients," Cancer Res., Jan. 1999, 59(1):71-73.
Wood et al., "Targeted Genome Editing Across Species Using ZFNs and TALENs," Science, Jul. 2011, 333:307.
Wright et al., "Standardized reagents and protocols for engineering zinc finger nucleases by modular assembly," Nat Protoc., 2006, 1(3):1637-1652.
Wu et al., "Building zinc fingers by selection: toward a therapeutic application," Proc Natl Acad Sci U S A., Jan. 1995, 92(2):344-348.
Wu et al., "Correction of a genetic disease in mouse via use of CRISPR-Cas9," Cell Stem Cell., Dec. 2013, 13(6):659-62.
Wu et al., "Custom-designed zinc finger nucleases: what is next?," Cell Mol Life Sci., Nov. 2007, 64(22):2933-2944.
Wu et al., "Genome-wide binding of the CRISPR endonuclease Cas9 in mammalian cells," Nat Biotechnol. Jul. 2014; 32(7):670-6.
Xu et al., "Optimization of transcriptional regulatory elements for constructing plasmid vectors," Gene. Jul. 2001, 272(1-2):149-56.
Xu et al., "Genome-wide regulation of 5hmC, 5mC, and gene expression by Tet1 hydroxylase in mouse embryonic stem cells," Mol Cell., 42(4):451-464, Epub Apr. 21, 2011.
Yang et al., "One-step generation of mice carrying reporter and conditional alleles by CRISPR/Cas-mediated genome engineering," Cell, Sep. 2013; 154(6):1370-9.
Yang et al., "Optimization of scarless human stem cell genome editing," Nucleic Acids Res., Oct. 2013, 41:9049-9061.
Yin et al., "Genome editing with Cas9 in adult mice corrects a disease mutation and phenotype," Nature Biotechnology Jun. 2014, 32, 551-553.
Zetsche et al., "Cpf1 Is a Single RNA-Guided Endonuclease of a Class 2 CRISPR-Cas System," Cell, Oct. 2015, 163:759-771.
Zhang et al., "Efficient construction of sequence-specific TAL effectors for modulating mammalian transcription," Nat Biotechnol., 29(2):149-153, Epub Jan. 19, 2011.
Zhang et al., "TET1 is a DNA-binding protein that modulates DNA methylation and gene transcription via hydroxylation of 5-methylcytosine," Cell Res., 20(12):1390-1393, Epub Nov. 16, 2010.
Zhou et al., "High-throughput screening of a CRISPR/Cas9 library for functional genomics in human cells," Nature, May 2014; 509(7501):487-91.
Zitzewitz et al., "Probing the folding mechanism of a leucine zipper peptide by stopped-flA4:A48ism spectroscopy," Biochemistry, Oct. 1995, 34(39):12812-12819.
Chinese Office Action in Application No. 2014800261133.4, dated May 31, 2017, 21 pages (with English abstract).
Extended European Search Report in Application No. 14875819.6, dated Jun. 8, 2017, 11 pages.
Jinek et al., "Supplementary Materials for a Programmable Dual-RNA-Guided DNA Endonuclease in Adaptive Bacterial Immunity," Science Express, pp. 1-37, Jun. 2012.
Office Action in European Application No. 14763916.5, dated Mar. 27, 2017, 6 pages.
Office Action in U.S. Appl. No. 14/775,930, dated Feb. 27, 2017, 55 pages.
Office Action in U.S. Appl. No. 14/776,620, dated Mar. 31, 2017, 45 pages.
Office Action in Canadian Application No. 2907198, dated Aug. 24, 2017, 10 pages.
Office Action in European Application No. 14763916.5, dated Oct. 26, 2017, 5 pages.
Office Action in European Application No. 14764117.9, dated Jul. 6, 2017, 4 pages.
Office Action in European Application No. 14764159.1, dated Jun. 16, 2017, 4 pages.
Office Action in European Application No. 14768877.4, dated Jul. 14, 2017, 4 pages.
Office Action in U.S. Appl. No. 14/775,930, dated Sep. 21, 2017, 23 pages.
Office Action in U.S. Appl. No. 14/776,620, dated Sep. 28, 2017, 8 pages.
Office Action in U.S. Appl. No. 14/775,869, dated Sep. 11, 2017, 43 pages.
Office Action in U.S. Appl. No. 14/211,117, dated Nov. 3, 2017, 11 pages.
Office Action in European Application No. 14764159.1, dated Nov. 21, 2017, 3 pages.
Office Action in European Application No. 14764117.9, dated Jan. 4, 2018, 4 pages.
Office Action in European Application No. 14768877.4, dated Jan. 8, 2018, 4 pages.
Office Action in U.S. Appl. No. 14/211,117, dated Jan. 9, 2017, 12 pages.
Office Action in Chinese Application No. 201480026133.4, dated Feb. 12, 2018, 22 pages (with English translation).
Office Action in U.S. Appl. No. 15/107,550, dated Mar. 9, 2018, 21 pages.
Blast sequence alignment: Query = Applicants SEQ ID No. 26 and Subject = Jinek et al.'s SEQ ID No. 8 from W02013176772 (Retrieved from the Internet <https://blast.nchi.nlm.nih.gov/Blast.cgi>, retrieved on Feb. 1, 2018, 3 pages.
Sequence Alignment instant SEQ ID No. 1 with SEQ ID No. 103. Search conducted on Feb. 15, 2018, 1 page.
Farboud and Meyer, "Dramatic Enhancement of Genome Editing by CRISPR/Cas9 Through Improved Guide RNA Design," Genetics, Apr. 2015, 199:959-971.

(56) References Cited

OTHER PUBLICATIONS

International Preliminary Report on Patentability in International Application No. PCT/US2016/49147, dated Mar. 6, 2018, 8 pages.
Jiang et al., "RNA-guided editing of bacterial genomes using CRISPR-Cas systems," Nature Biotechnology, Mar. 2013, 31: 233-239.
Ma et al., "A Guide RNA Sequence Design Platform for the CRISPR/Cas9 System for Model Organism Genomes," BioMed Research International, Oct. 2013, 2013: 270805, 4 pages.
Office Action in Chinese Application No. 201480026276.5, dated Apr. 17, 2018, 12 pages (with English translation).
Office Action in Chinese Application No. 201480027950.1, dated Mar. 23, 2018, 13 pages (with English translation).
Office Action in Japanese Application No. 2016-502976, dated May 8, 2018, 16 pages (with English translation).
Sequence Alignment of SEQ ID No. 1 of U.S. Appl. No. 15/107,550 with SEQ ID No. 103 of US2013/0130248A1. Search conducted on Feb. 15, 2018, 1 page as part of Office Action in U.S. Appl. No. 15/107,550.

```
EMX1 truncated gRNA
GAAGCTGGAGGAGGAAGGGCCTGAGTCCGAGCAGAAGAAGAAgGGCTCCCATCACATCAACCGGTGG  wild-type x24
GAAGCTGGAGGAGGA-------------------------------------------------    Δ365
--------------------------------------------------TCAACCGGTGG       Δ181
GAAGCTGGAGGAGGAAGG----------------------------------------------    Δ138
----------------------------------------------------------------    Δ126
---------------------------------GGGCTCCCATCACATCAACCGGTGG          Δ114
GAAGCTGGAGGAGGAAGGGCCTGA----------------------------------------    Δ101
GAAGCTGGAGGA--------------------------------------------------GG    Δ53
GAAGCTGGAGGAGGAAGGG-------------------------CCCATCACATCAACCGGTGG    Δ29
GAAGCTGGAGGAGGAAGGGC------------------------TCGCACACATCAACCGGTGG    Δ27
GAAGCTGGAGGAGGAAGGGC-------------------------CTTCCATCACATCAACCGGTGG Δ25
GAAGCTGGAGGAGGAAGGGCCTGAG---------------------TCCCATCACATCAACCGGTGG Δ21 x2
GAAGCTGGAGGAGGAAGGGCCTGAGTCCGAG-----------------TCCCATCACATCAACCGGTGG Δ15
GAAGCTGGAGGAGGAAGGGCCTGAGTCCGAGCAGAAG-----------TCCCATCACATCAACCGGTGG Δ9
GAAGCTGGAGGAGGAAGGGCCTGAGTCCTGCCGTTTGTAG--------CCATCACATCAACCGGTGG  Δ8
GAAGCTGGAGGAGGAAGGGCCTGAGTCCGAGCAGAAGA---------GCTCCCATCACATCAACCGGTGG Δ6
GAAGCTGGAGGAGGAAGGGCCTGAGTCCGAGCAGAAGAA--------CTCCCATCACATCAACCGGTGG Δ6
GAAGCTGGAGGAGGAAGGGCTGAGTCCGAGC----AGAAGAAGGGCTCCCATCACATCAACCGGTGG  Δ3 x3
GAAGCTGGAGGAGGAAGGGCCTGAGTCCGAGCAGAAGA--AAGGGCTCCCATCACATCAACCGGTGG  Δ2
GAAGCTGGAGGAGGAAGGGCCTGAGTCCGAGCAGAAGAxAGAAGGGCTCCCATCACATCAACCGGT  +2

EMX1 full-length gRNA
GAAGCTGGAGGAGGAAGGGCCTGAGTCCGAGCAGAAGAAGAAgGGCTCCCATCACATCAACCGGTGG  wild-type x35
GAAGCTGGAGGAGGAAGGGCCTGAGTCCGAG---------------------------------    Δ202
---------------------------------------------------------------    Δ115
GAA------------------------------------------------------------>   Δ94
---------------------------------------------------------------    Δ78
GAAGCTGGAGG----------------------------------------------------    Δ72
GAAGCTGGA---------------------------------------------------GG     Δ56
GAAGCTGGAGGAGGAAGGGCCTGA----------------------------------GTGG     Δ39
GAAGCTGGAGGAG-----------------GAAGGGCTCCCATCACATCAACCGGTGG          Δ26 x2
GAAGCTGGAGGAGGAAGGGCCTGAGT----------------CCATCACATCAACCGGTGG       Δ22
GAAGCTGGAGGAGGAAGGGCCTGAG-------------------TCCCATCACATCAACCGGTGG   Δ21 x3
GAAGCTGGAGGAGGAAGGGCCTGAGTCCGAG-----------------CATCACATCAACCGGTGG  Δ19
GAAGCTGGAGGAGGAAGGGCCTGAGTCCGA-----------------GCTCCCATCACATCAACCGGTGG Δ14
GAAGCTGGAGGAGGAAGGGCCTGAGTCCGAGC---------AGAAGGGCTCCCATCACATCAACCGGTGG Δ6 x3
GAAGCTGGAGGAGGAAGGGCCTGAGTCCGAGC----AGAAGAAGGGCTCCCATCACATCAACCGGTGG  Δ3 x3
GAAGCTGGAGGAGGAAGGGCCTGAGTCCGAGCAGA--AAGAAGGGCTCCCATCACATCAACCGGTGG   Δ2 x2
GAAGCTGGAGGAGGAAGGGCCTGAGTCCGAGCAGAAGAxAGAAGGGCTCCCATCACATCAACCGGT   +2
```

FIG. 3C

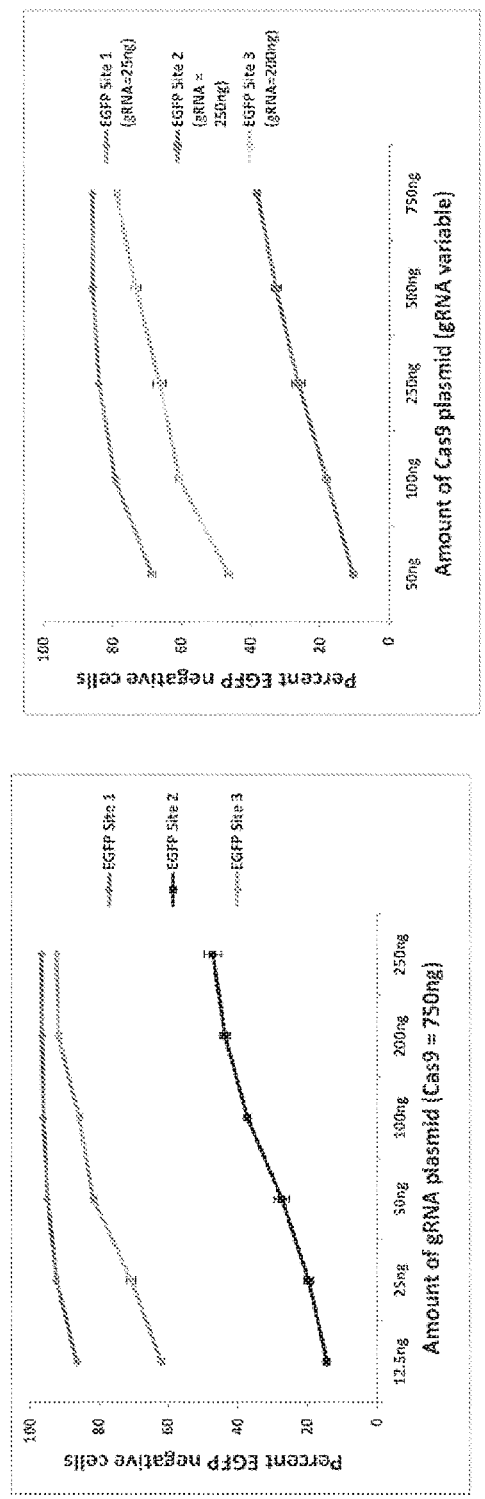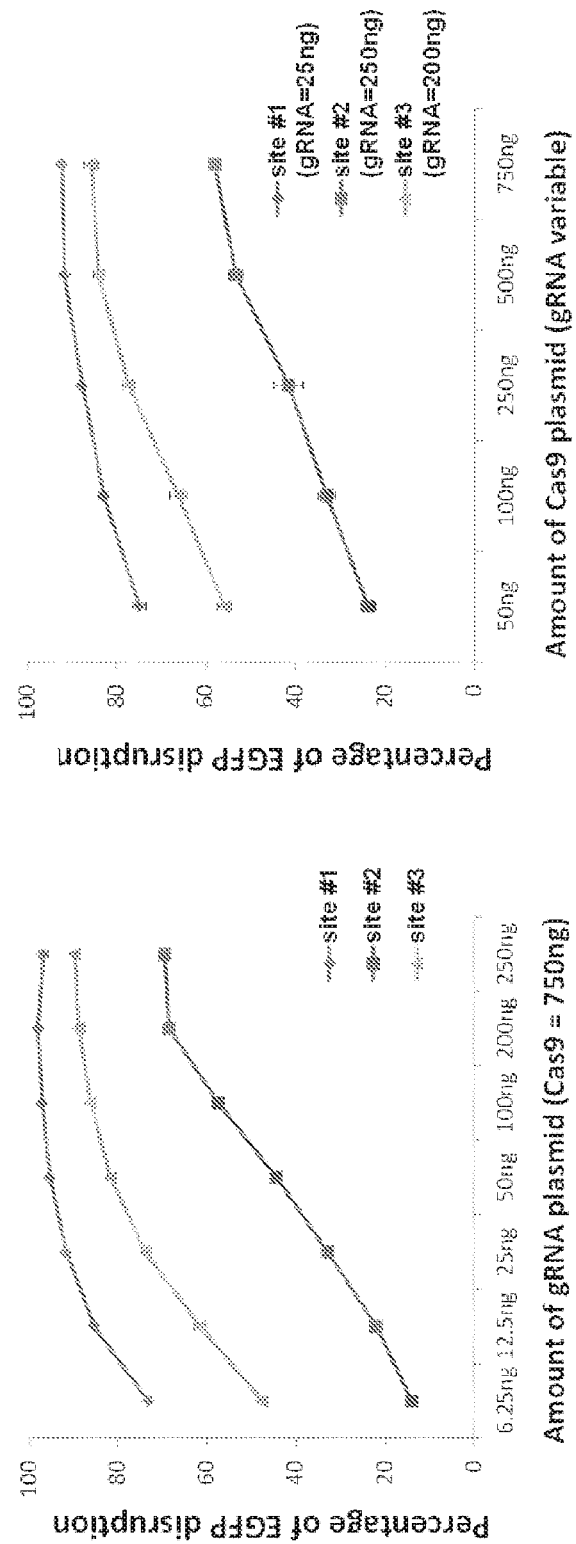
Figure 3E
Figure 3F

```
TCGTGACCACCCTGACCTACGGCGTGCAGTGCTTCAGCCGCTACCCCGACCACACATGAAGCAGCACGACTTCTTCAAGTCCGCCATGCCC  GTGAACCGC WT
TCGTGACCACCCTGACCTACG------TGCAGTGCTTCAGCCGCTACCCCGACCACACATGAAGCAGCACGACTTCTTCAAGTCCGCCATGCCC  GTGAACCGC Δ3/0
TCGTGACCACCCTGACCT------------CAGCCGCTACCCCGACCACACATGAAGCAGCACGACTTCTTCAAGTCCGCCATGCCC  GTGAACCGC Δ16/Δ13
TCGTGACCACCCTGACCTACGGCGTGCAGTGCTTCAGCCGCTACCCCGACCACACATGAAGCAGCACGACTTCTTCAAGTCCGCCATGCCC  GTGAACCGC 0/Δ33
TCGTGACCACCCTGACC-------GTGCAGTGCTTCAGCCGCTACCCCGACCACACATGAAGCAGCACGACTTCTTCAAGTCCGCCATGCCC  GGTGAACCG Δ6/+18
TCGTGACCACCCTGACCG--------------------------------------  GTGAACCCG Δ135 (x3)
TCGTGACCACCCTGACCTACGCcctcggcgcgggtcttgtagttgcgtcgtcctgaagaagatggtgcgtcctgaagaagatggtgcgtcctggacgtagccttcg  GTGAACCGC +135
TCGgcgcgggtcttgtagttgcgtc--gtccttgaagaagatggtgcgtcctggacgtagcctcgggcatgccttgggcatgccttgggcatgccttgggcatgccttggga  GTGAACCGC Δ168 (Δ40+128)
TCGTGACCACCCTG------------------  GTGAACCGC Δ147

GAAGGCTACGTCCAGGAGCGCCACCATCTTTCTTCAAGGAGACGGCAACTACAAGACCCGCCGAGGTGAAGTTCGAGGGCGACACCCTG
GAAGGCTACGTCCAGGAGCGCCACCATCTTTCTTCAAGGAGACGGCAACTACAAGACCCGCCGAGGTGAAGTTCGAGGGCGACACCCTG
GAAGGCTACGTCCAGGAGCGCCACCATCTTTCTTCAAGGAGACGGCAACTACAAGACCCGCCGAGG-----------CGACACCCTG
GAAGGCTACGTCCAGGAGCGCCACCATCTTTCTTCAAGGAGACGGCAACTACA----------------------------CCCCT
GAAGGCTACGTCCAGGAGCGCCACCATCTTTCTTCAAGGAGACGGCAACTACAAGACCCGCCGAGGtcttgttcgagggacACCCT
------------------------------------------------TGAAGTTCGAGGGCGACACCCTG
ggcatggcggacttgaagaagtcgtgcttcatgtgtcggggtagccggctgaagcactgcacgcTGAAGTTCGAAGTTCGAGGGCGACACCCTG
tcgtgctgcttcatgtgtcggggtagccggctgaagcactgc--------------------------ACACCCTG
---------------------------------------TTCGAGGGCGACACCCTG
```

FIG. 4C

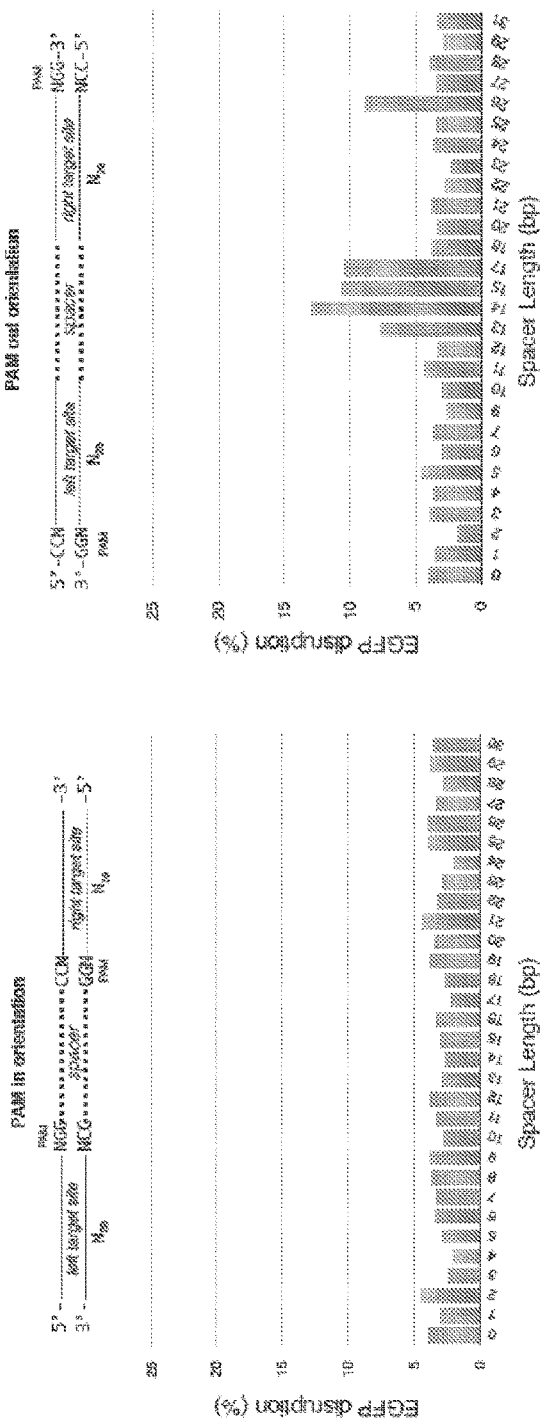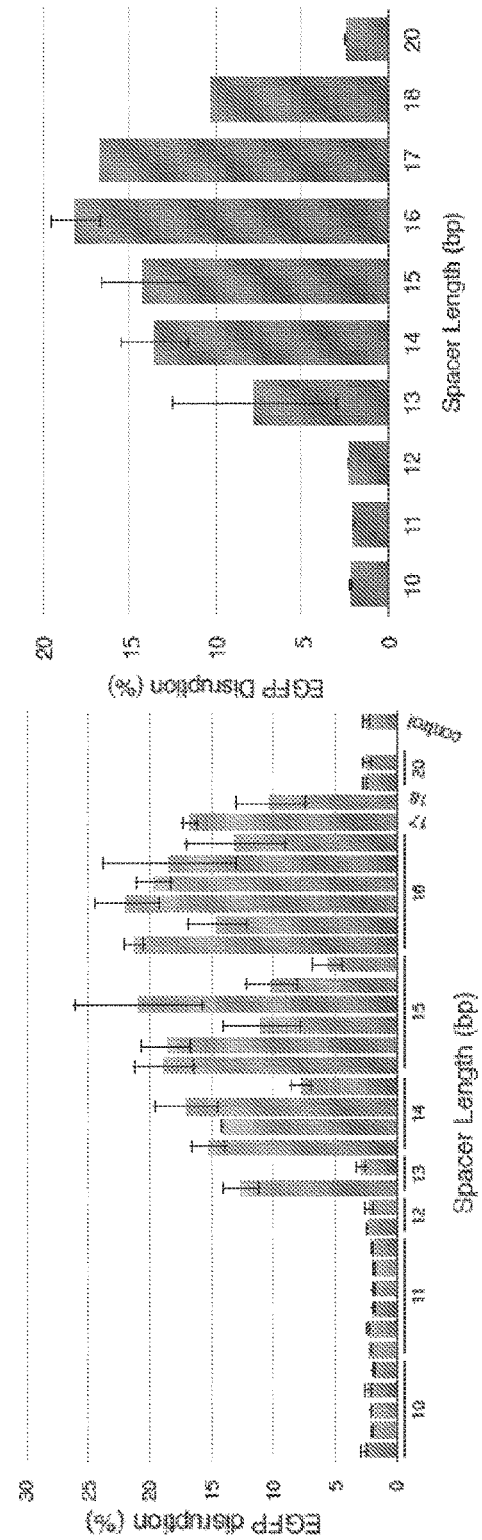
FIG. 5B
FIG. 5C
FIG. 5D

FIG. 5F

APC
Mutations in 9 of 23 sequences ≈ 39.1% (SEQ ID NOS 354-363, respectively, in order of appearance)

```
CAGGAGACGAAGAGCCCGGGCGCCTTCGTACTTTCTGGCCACTGGGCGAGCGTCTGGCCAGTGAGTGAGGCTTGCAGGCATTGACGTCTCCTC WT
CAGGAGACGAAGAGCCCGGGGCGCTCGCTCGTCGTACTTCTGGCCACTGGGCGaGCGTCTGGCCAGTGAGTGAGGCTTGCAGGCATTGACGTCTCCTC Δ0  (Δ3 +3)
CAGGAGACGAAGAGCCCGGGGCGCTCGCTCGTCGTACTTCTGGCC------------TCTGGCCAGTGAGTGAGTGAGGCTTGCAGGCATTGACGTCTCCTC Δ12
CAGGAGACGAAGAGCCCGGGGCGCTCGCTCGTCGTACTTCT------------AGCGTCTGGCCAGTGAGTGAGTGAGGCTTGCAGGCATTGACGTCTCCTC Δ12
CAGGAGACGAAGAGCCCGGGGCGCTCGCTCGTCGTACTTC------------GTCTGGCCAGTGAGTGAGTGAGGCTTGCAGGCATTGACGTCTCCTC Δ16
CAGGAGACGAAGAGCCCGGGGCGCTCGCTCGTCGTACTTC--------------TGGTGAGTGAGTGAGGCTTGCAGGCATTGACGTCTCCTC Δ17
CAGGAGACGAAGAGCCCGGGGCGCTCGCTCGTCGTACTTCTGGC----------AGTGAGTGAGTGAGGCTTGCAGGCATTGACGTCTCCTC Δ19
CAGGAGACGAAGAGCCCGGGGCGCTCGCTCGTCGT--------------CTGGCCAGTGAGTGAGTGAGGCTTGCAGGCATTGACGTCTCCTC Δ23
ACCGCGGGCAGCAGCC-------------------TGAGTGAGGCTGAGTGAGGCTTGCAGGCATTGACGTCTCCTC Δ34
CAGGAGACGAAGAGCC---------------------------//-------------------------TGAGTGAGGCTGAGTGAGGCTTGCAGGCATTGACGTCTCCTC Δ73
```

BRCA1
Mutations in 7 of 86 sequences ≈ 8.1% (SEQ ID NOS 364-370, respectively, in order of appearance)

```
TGGGAGAGTGGATTTCCGAGCTGACAGATGGGTATTCTTTGAGGGGGGTAGGGCGGATCCTAGAGCCCGTTAGGCGTTGTGAACCCTGG WT
TGGGAGAGTGGATTTCCGAGCTGACAGATGGGTATTCTTTGA-----GTAGGGGCGGAACCTGAGAGGCGTTGTGAACCCTGG Δ6
TGGGAGAGTGGATTTCCGAGCTGACAGATGGGTAT-------GGGGGGTAGGGCGGAACCTGAGAGGCGTTGTGAACCCTGG Δ8
TGGGAGAGTGGATTTCCGAGCTGACAGATGGGTATTCTT--------GGTAGGGCGGAACCTGAGAGGCGTTGTGAACCCTGG Δ8
TGGGAGAGTGGATTTCCGAGCTGACAGATGGGTATTCTTTGAGGGGG--------GAACCTGAGAGGCGTTGTGAACCCTGG Δ10
TGGGAGAGTGGATTTCCGAGCTGACAGATGGGTATTCTTTG---------GGCCGGAACCTGAGAGGCGTTGTGAACCCTGG Δ12
TGGGAGAGTGGATTTCCGAGCTGACAGATGGGT-----------------GCGGAACCTGAGAGGCGTTGTGAACCCTGG Δ22 (2x)
```

EMX1
Mutations in 2 of 91 sequences ≈ 2.2% (SEQ ID NOS 371-372, respectively, in order of appearance)

```
CAAGCTGGACTCTGCCCACTCCCTGGCCTTTGGGGAGGCCTGAGTCATGCCTTCCAGCTTGAAGCCTGGGGCCGCCATTGAC WT
CAAGCTGGACTCTGGCCACTCCCTGGCCAGGCTTT-----ATGCCCCACAGGGCTTGAAGCCCGGGGGCCGCCATTGAC Δ16 (2x)
```

FANCF site 1
Name/name  Mutations in 9 of 29 sequences ≈ 31% (SEQ ID NOS 373-382, respectively, in order of appearance)

```
AGAGAGTCGCCGTCTCCAAGGTGAAAGCGGAAGTAGGGCCTTCGCGCACCTCATGGAATCCTTTCTGCAGCACCTGGATCGCTTTTCCGAGC WT
AGAGAGTCGCCGTCTCCAAGGTGAAAGCGGAAGTAG---------CGCACCTCATGGAATCCTTCTGCAGCACCTGGATCGCTTTTCCGAGC Δ8
AGAGAGTCGCCGTCTCCAAGGTGAAAGCGGAAGTAGGGCC-----CTCACCTCATGGAATCCTTCTGCAGCACCTGGATCGCTTTTCCGAGC Δ9
AGAGAGTCGCCGTCTCCAAGGTGAAAGCGGAAGTAGGGCC--------CATGGAATCCTTCTGCAGCACCTGGATCGCTTTTCCGAGC Δ10
AGAGAGTCGCCGTCTCCAAGGTGAAAGCGGAAGTAGGCCT--------CATGGAATCCTTCTGCAGCACCTGGATCGCTTTTCCGAGC Δ10
AGAGAGTCGCCGTCTCCAAGGTGAAAGCGGAAGTAGG--------------CATGGAATCCTTCTGCAGCACCTGGATCGCTTTTCCGAGC Δ10
AGAGAGTCGCCGTCTCCAAGGTGAAAGCGGAAGTAG------------CACCTCACCTCATGGAATCCTTCTGCAGCACCTGGATCGCTTTTCCGAGC Δ10 (Δ12 +1)
AGAGAGTCGCCGTCTCCAAGGTGAAAGCGGAAGTAGGCCGAA----CGCACCTCATGGAATCCTTCTGCAGCACCTGGATCGCTTTTCCGAGC Δ11
AGAGAGTCGCCGTCTCCAAGGTGAAAGCGGAAGTAGGGCCGCA---------TTCTGCAGCACCTGGATCGCTTTTCCGAGC Δ14
AGAGAGTCGCCGTCTCCAAGGTGAAAGCGGAAGTAGGGCCGCA-----CCTCATGAATCCTTCTGCAGCACCTGGATCGCTTTTCCGAGC Δ15
AGAGAGTCGCCGTCTCCAAG--------------------------CATGAATCCCTTCTGCAGCACCTGGATCGCTTTTCCGAGC Δ31
```

FIG. 5G

```
FANCF site 2
Mutations in 13 of 71 sequences ≈ 18.3% (SEQ ID NOS 383-396, respectively, in order of appearance)
TTTGGTCGGCATGGCCATTCGCACGGCTCTGGAGCGCGGCTGCACAACAGTGGAGGCAAGAGGGCGGCTTTGGGCGGGTCCAGTTCC  WT
TTTGGTCGGCATGGCCCCATTCGCACGGCTCTGGAGCGCGGCG----CAACCAGTGGAGGCAAGAGGGCGGCTTTGGGCGGGTCCAGTTCC  Δ3
TTTGGTCGGCATGGCCCCCATTCGCACGGCTCTGGAGCGCGGCT-----AACCAGTGGAGGCAAGAGGGCGGCTTTGGGCGGGTCCAGTTCC  Δ4
TTTGGTCGGCATGGCCCCCATTCGCACGGCTCTGGAGCGCGGCGC------CAGTGGAGGCAAGAGGGCGGCTTTGGGCGGGTCCAGTTCC  Δ8
TTTGGTCGGCATGGCCCCCATTCGCACGGCTCTGGAGCGCGGCTG-------CAGTGGAGGCAAGAGGGCGGCTTTGGGCGGGTCCAGTTCC  Δ9
TTTGGTCGGCATGGCCCCCATTCGCACGGCTCTGGAGCGCGGCTG----------TGGAGGCAAGAGGGCGGCTTTGGGCGGGTCCAGTTCC  Δ11
TTTGGTCGGCATGGCCCCCATTCGCACGGCTCTGGAGCGCGGCTG----------GAGGCAAGAGGGCGGCTTTGGGCGGGTCCAGTTCC  Δ12
TTTGGTCGGCATGGCCCCCATTCGCACGGCTCTGGAGCGCGGCGGga-----------GAGGCAAGAGGGCGGCTTTGGGCGGGTCCAGTTCC  Δ12 (Δ14 +2)
TTTGGTCGGCATGGCCCCCATTCGCACGGCTCTGGAGCGCGGCGC-------------GAGGCAAGAGGGCGGCTTTGGGCGGGTCCAGTTCC  Δ13
TTTGGTCGGCATGGCCCCCATTCGCACGGCTCTGGAGCGCGGCGTG-------------GCAAGAGAGGGCGGCTTTGGGCGGGTCCAGTTCC  Δ14
TTTGGTCGGCATGGCCCCCATTCGCACGGCTCTGGAGCGCGGCG----------------GCAAGAGAGGGCGGCTTTGGGCGGGTCCAGTTCC  Δ15
TTTGGTCGGCATGGCCCCCATTCGCACGGCTCTGGAGCGCGGCG-------------------TGGAGGCAAGAGAGGCGGCTTTGGGCGGGTCCAGTTCC  Δ18
TTTGGTCGGCATGGCCCCCATTCGCACGGCTCTGGAG-----------------------GCAAGAGAGGGCGGCTTTGGGCGGGTCCAGTTCC  Δ23
TTTGGTCGGCATGGCCCCC----------------------//------------------------GTCACTGT  Δ97

TTTGGTCGGCATGGCCCCATTCGCACGGCTCTGGAGCGCGGCacactattgcaatgaaaataaattccttttattagctagaagtgagatc  +168(Δ9 +177)
tgaagggcttcatgatgtcccccataattttttgcagaggggaaaaagatctcagtggtattgtgagcagggcattggccacaccagcaac
cacctttgataggcagcctgcacctgagagtgcgAGTGGAGCAAGAGGGCGGCTTTGGGCGGGGTCCAGTTCC GLI1
Mutations in 4 of 66 sequences ≈ 6.1% (SEQ ID NOS 397-401, respectively, in order of appearance)
GTTCAACTCGATGACCACCACCAATCAGTAGCTATGGCGAGCCCTGCTGTCTCCGGCCCCTCCCCAGTCAGCGGGCCCCAGTGTGGGA  WT
GTTCAACTCGATGACCACCACCAATCAGTAGCTAT---------CCTGCTGTCTCCGGCCCCTCCCCAGTCAGCAGGGCCCCCAGTGTGGGA  Δ7
GTTCAACTCGATGACCACCACCAATCAGTAGCTATG------------TCTCCGGCCCCTCCCCAGTCAGCAGGGCCCCAGTGTGGGA  Δ13
GTTCAACTCGATGACCACCACCAATCAGTAGCTATG-----------------CCTGCTGTCTCCGGCCCCTCCCCAGTCAGCAGGGCCCCAGTGTGGGA  Δ17
GTTCAACTCGATGACCACCACCACCACCAA----------------CCTGCTGTCTCCGGCCCCTCCCCAGTCAGCAGGGCCCCAGTGTGGGA  Δ18

MLH1
Mutations in 4 of 20 sequences ≈ 20% (SEQ ID NOS 402-406, respectively, in order of appearance)
TGGCTGAAGGCACTTCCGTTGAGCATCTAGACGTTTCCTTGGCTCTTCTTCCTCTTCGGCGCCAAATGTCGTTCGTTGGCAGGGTTATTCGGCGGCTGG  WT
TGGCTGAAGGCACTTCCGTTGAGCATCTAGACGTTTCCT--------TGGCGCCAAATGTCGTTCGTTGCAGGGGTTATTCGGCGGCTGG  Δ9
TGGCTGAAGGCACTTCCGTTGAGCATCTA----------------TTCTGGCGCCAAATGTCGTTCGTTGCAGGGGTTATTCGGCGGCTGG  Δ16
TGGCTGAAGGCACTTCCGTTGAGCATCTAGACGTTTCCTTGG-----------ATGTCGTTCGTTGCAGGGGTTATTCGGCGGCTGG  Δ16
TGGCTGAAGGCACTTCCGTTGAGCATCTAGACGTTT-----------------GTCGTTCGTTGCAGGGGTTATTCGGCGGCTGG  Δ24
```

FIG. 5H

RARA
Mutations in 4 of 86 sequences ≈ 4.7% (SEQ ID NOS 407-411, respectively, in order of appearance)
CCCTTCTGACTGTGGCCGCTTGCATGGCCAGCAACAGCAGCTTCCTGCCGACACCTGGGGTGGGCACCTCATGGGTACCCGTGCCTCC WT
CCCTTCTGACTGTGGCCGCTTGGCCGCTTGGCCATGGCCAGCAACA------CCTGCCCGACACCTGGGGCGGGCACCTCAATGGTACCCGTGCCTCC Δ6
CCCTTCTGACTGTGGCCGCTTGGCCGCTTGGCCATGGCCAGCAACA-------CTGCCCGACACCTGGGGCGGGCACCTCAATGGTACCCGTGCCTCC Δ7
CCCTTCTGACTGTGGCCGCTTGGCCGCTTGGCCATGGCCAGCA-------------GCCCGACACCTGGGGCGGGCACCTCAATGGTACCCGTGCCTCC Δ12
CCCTTCTGACTGTGGCCGCTTGGCCGCTTGGCCATGGCCAG-----------------GCCCGACACCTGGGGCGGGCACCTCAATGGTACCCGTGCCTCC Δ14

VEGFA site 1
Mutations in 19 of 74 sequences ≈ 25.7% (SEQ ID NOS 412-426, respectively, in order of appearance)
TCAGAAATAGGGGGTCCAGGAGCAAATCCCCCCACCCCCTTTCCAAAGCCCATTCCCTCTTTAGCCAGAGCCGGGTGTGCAGACGGCAGT WT
TCAGAAATAGGGGGTCCAGGAGCAAATCCCCCCACCCCCTTTCCAAAaGCCCATTCCCTCTTTAGCCAGAGCCGGGTGTGCAGACGGCA +2
TCAGAAATAGGGGGTCCAGGAGCAAATCCCCCCACCCCCTTTCC----GCCCATTCCCTCTTTAGCCAGAGCCGGGTGTGCAGACGGCAGT Δ3
TCAGAAATAGGGGGTCCAGGAGCAAATCCCCCCACCCCCTTTCCT-----AGCCCATTCCCTCTTTAGCCAGAGCCGGGTGTGCAGACGGCAGT Δ5
TCAGAAATAGGGGGTCCAGGAGCAAATCCCCCCACCCCCTTT-------AAAGCCCATTCCCTCTTTAGCCAGAGCCGGGTGTGCAGACGGCAGT Δ5
TCAGAAATAGGGGGTCCAGGAGCAAATCCCCCCACCCCC--------AAAGCCCATTCCCTCTTTAGCCAGAGCCGGGTGTGCAGACGGCAGT Δ6 (2x)
TCAGAAATAGGGGGTCCAGGAGCAAATCCCCCCACCCCCTTTCCA-------TTCCCTCTTTAGCCAGAGCCGGGTGTGCAGACGGCAGT Δ7
TCAGAAATAGGGGGTCCAGGAGCAAATCCCCCCACCCCCTTTC--------ATTCCCTCTTTAGCCAGAGCCGGGTGTGCAGACGGCAGT Δ8
TCAGAAATAGGGGGTCCAGGAGCAAATCCCCCCACCCCCAC---------AAAGCCCATTCCCTCTTTAGCCAGAGCCGGGTGTGCAGACGGCAGT Δ9 (2x)
TCAGAAATAGGGGGTCCAGGAGCAAATCCCCCCACCCCC------------ATTCCCTCTTTAGCCAGAGCCGGGTGTGCAGACGGCAGT Δ14 (3x)
TCAGAAATAGGGGGTCCAGGAGCAAATCCCCCCACCC--------------CAAAGCCCATTCCCTCTTTAGCCAGAGCCGGGTGTGCAGACGGCAGT Δ17 (2x)
TCAGAAATAGGGGGTCCAGGAGCAAATCCCCCCACCCCCC------------------CTTTAGCCAGAGCCGGGTGTGCAGACGGCAGT Δ18
TCAGAAATAGGGGGTCCAGGAGCAAATCCCCCCACCCCCCCCCC---------AGCCAGAGCCGGGTGTGCAGACGGCAGT Δ20
TCAGAAATAGGGGGTCCAGGAGCAAATCCCCCCACCCCCCT-------CAAAGCCCATTCCCTCTTTAGCCAGAGCCGGGTGTGCAGACGGCAGT Δ24
TCAGAAATAGGGGGTCCAGG------------------------------TCTTTAGCCAGAGCCGGGTGTGCAGACGGCAGT Δ35

VEGF site 2
Mutations in 26 of 80 sequences ≈ 32.5% (SEQ ID NOS 427-439, respectively, in order of appearance)
CCCCAGCCCCAGCTACACTTCCTCCCCGGCGCGCGGCGGACAGTGGAGCGCGCGGCGAGCCCGGGCAGGGCCGGAGCCCGCGCCCGGAG WT
CCCCAGCCCCAGCTACACCTCCTCCCCGGCGCG---------TGGACGCGGCGGACAGTGGA-------AGCCCGGGCAGGGCCGGAGCCCGCGCCCGGAG Δ8 (2x)
CCCCAGCCCCAGCTACACCTCCTCCCCGGCGCG----------ACGCGGCGGACAGTGGA-------AGCCCGGGCAGGGCCGGAGCCCGCGCCCGGAG Δ13
CCCCAGCCCCAGCTACACCTCCTCCCCGGCGC-----------TGGACGCGGCGGACAG------AGCCCGGGCAGGGCCGGAGCCCGCGCCCGGAG Δ13
CCCCAGCCCCAGCTACACCTCCTCCCCGGCG----------------CCGCGGCGGACAGCGGGGAGCCCGGGCAGGGCCGGAGCCCGCGCCCGGAG Δ16
CCCCAGCCCCAGCTACACCTCCTCCCCGGCG--------------------ACGCGGCGGACAG-----AGCCCGGGCAGGGCCGGAGCCCGCGCCCGGAG Δ17
CCCCAGCCCCAGCTACACCTCCTCCCCGGCG-------------------------AGCCCGGGCAGGGCCGGAGCCCGCGCCCGGAG Δ43
---------------------AGCCCGGGCAGGGCCGGAAG Δ54 (3x)
-----------------GGGGGTCGGGGCTCG--AG Δ56 (2x)
------AG Δ56 (2x)
-----------------GGTGGAGGGGTCGG Δ56 (2x)
------CaCGCGGCGTCGCAC Δ69 (Δ71 +2)
CCCCAGCCCCAGCTACACCTCCTCCCCGGCGCG---------------------GGAG Δ87 (2x)
C----------------------CTGAAACTTTTCGTC Δ89 (7x)
CCGAGCGCGGCGTG--------------------GAGGGGTCGGGGCT Δ165 (2x)

FIG. 5I

```
VEGFA site 3
Mutations in 31 of 77 sequences ≈ 40.3% (SEQ ID NOS 440-466, respectively, in order of appearance)
CCATTCCCTCTTTAGCCAGACCGGGGGCTTGCCACGGGCAGTCACTAGGGGGCGTGGGCCAGCCAGCGAAGCTGGGTGAATGGAGCGAGC    WT
CCATTCCCTCTTTAGCCAGCCAGAGCCGGGGTGTGCAGACGGCACT---TAGGGGGCGCTCGGCCACCACAGGAAGCTGGGTGAATGGAGCGAGC    Δ3
CCATTCCCTCTTTAGCCAGCCAGAGCCGGGGTGTGCAGACGGCGCA---CTAGGGGGCGCTCGGCCACCACAGGAAGCTGGGTGAATGGAGCGAGC    Δ4
CCATTCCCTCTTTAGCCAGCCAGAGCCGGGGTGTGCAGACGGCAGTCA-----GGGCGGGGCGCTCGGCCACCACAGGAAGCTGGGTGAATGGAGCGAGC    Δ5
CCATTCCCTCTTTAGCCAGCCAGAGCCGGGGTGTGCAGACGGCGCA-----TAGGGGGGCGCTCGGCCACCACAGGAAGCTGGGTGAATGGAGCGAGC    Δ5
CCATTCCCTCTTTAGCCAGCCAGAGCCGGGGTGTGCAGACGGCAGAC-------CTAGGGGGCGCTCGGCCACCACAGGAAGCTGGGTGAATGGAGCGAGC    Δ8  (2x)
CCATTCCCTCTTTAGCCAGCCAGAGCCGGGGTGTGCAGACGGCAG--------GGCGCTCGGCCACCACAGGAAGCTGGGTGAATGGAGCGAGC    Δ9
CCATTCCCTCTTTAGCCAGCCAGAGCCGGGGTGTGCAGACGGCAG----TAGGGGGGCGCTCGGCCACCACAGGAAGCTGGGTGAATGGAGCGAGC    Δ9  (2x)
CCATTCCCTCTTTAGCCAGCCAGAGCCGGGGTGTGCAGACGGCAG--------AGGGGGGCGCTCGGCCACCACAGGAAGCTGGGTGAATGGAGCGAGC    Δ10
CCATTCCCTCTTTAGCCAGCCAGAGCCGGGGTGTGCAGACGGTGTGCA---------CTAGGGGCGCTCGGCCACCACAGGAAGCTGGGTGAATGGAGCGAGC    Δ11
CCATTCCCTCTTTAGCCAGCCAGAGCCGGGGTGTGCAGACGGCAGT-----TCGGCCGCTCGGCCACCACAGGAAGCTGGGTGAATGGAGCGAGC    Δ11
CCATTCCCTCTTTAGCCAGCCAGAGCCGGGGTGTGCAGACGGCAGT-----CTAGGGGCGCTCGGCCACCACAGGAAGCTGGGTGAATGGAGCGAGC    Δ13
CCATTCCCTCTTTAGCCAGCCAGAGCCGGGGTGTGCAGACGGCAG-----GGGCGCTCGGCCACCACAGGAAGCTGGGTGAATGGAGCGAGC    Δ14
CCATTCCCTCTTTAGCCAGCCAGAGCCGGGGTGTGCAGACGGCAG-----GGGCGCTCGGCCACCACAGGAAGCTGGGTGAATGGAGCGAGC    Δ15
CCATTCCCTCTTTAGCCAGCCAGAGCCGGGGTGTGCAGACGGCAG-----GGGCGCTCGGCCACCACAGGAAGCTGGGTGAATGGAGCGAGC    Δ16  (2x)
CCATTCCCTCTTTAGCCAGCCAGAGCCGGGGTGTGCAGACGGCAGCGC----------CACAGGCCACCACAGGAAGCTGGGTGAATGGAGCGAGC    Δ16
CCATTCCCTCTTTAGCCAGCCAGAGCCGGGGTGTGCAGACGGCAGCGC-----TCGGCCGCTCGGCCACCACAGGAAGCTGGGTGAATGGAGCGAGC    Δ16
CCATTCCCTCTTTAGCCAGCCAGAGCCGGGGTGTGCAGACGG-----------CTCGGCCGCTCGGCCACCACAGGAAGCTGGGTGAATGGAGCGAGC    Δ17
CCATTCCCTCTTTAGCCAGCCAGAGCCGGGGTGTG---------GGGGCGCTCGGCCACCACAGGAAGCTGGGTGAATGGAGCGAGC    Δ19
CCATTCCCTCTTTAGCCAGCCAGAGCCGGGGTGTGC----------GCTCGGCCGCTCGGCCACCACAGGAAGCTGGGTGAATGGAGCGAGC    Δ21
CCATTCCCTCTTTAGCCAGCCAGAGCCGGGGTGTGCAGACGGCAGTCAC--------AGGAAGGAAGCTGGGTGAATGGAGCGAGC    Δ21
CCATTCCCTCTTTAGCCAGCCAGAGCCGGGGTGTGCAGACGGCAGC----------CACCACAGGAAGCTGGGTGAATGGAGCGAGC    Δ21  (2x)
CCATTCCCTCTTTAGCCAGCCAGAGCCGGGGTGTGCAGACGGCAGTCA-----------GGAAGGAAGCTGGGTGAATGGAGCGAGC    Δ23
CCATTCCCTCTTTAGCCAGCCAGAGCCGGGGTGTGCAGACGGCAG-----GCCACCACAGGAAGCTGGGTGAATGGAGCGAGC    Δ24
CCATTCCCTCTTTAGCCAGCCAGAGCCGGGGTGTGCAGAC----------CACCACAGGAAGCTGGGTGAATGGAGCGAGC    Δ24
CCATTCCCTCTTTAGCCAGCCAGAGCCGGGGTGTGCAGAC------------CACAGGAAGCTGGGTGAATGGAGCGAGC    Δ27
CCATTCCCTCTT-----------------------AGTGACTGCTCGGCCACCACAGGAAGCTGGGTGAATGGAGCGAGC    Δ34  (2x)
```

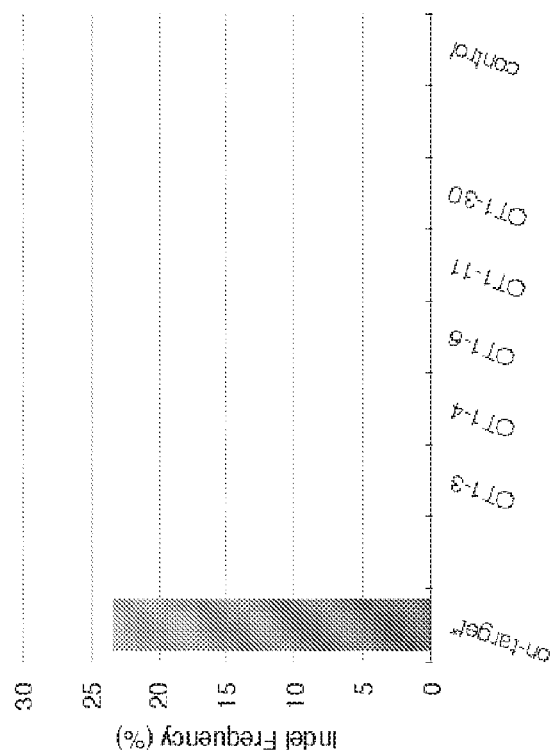
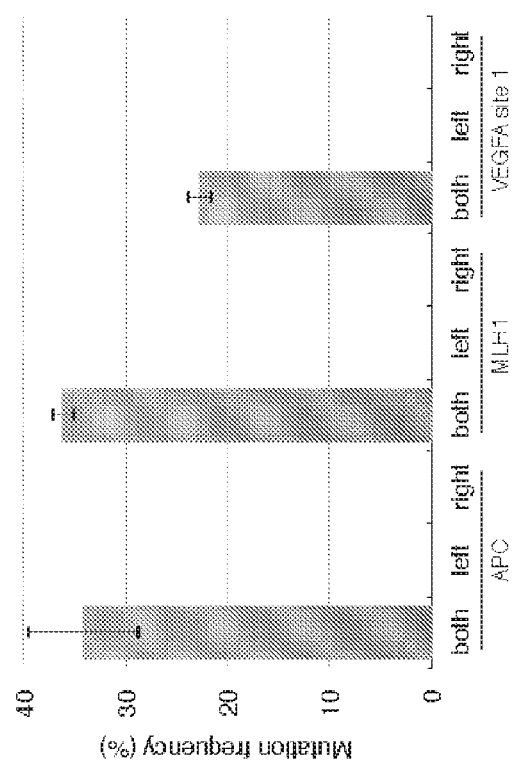
FIG. 6C
FIG. 6D

USING RNA-GUIDED FOKI NUCLEASES (RFNS) TO INCREASE SPECIFICITY FOR RNA-GUIDED GENOME EDITING

CLAIM OF PRIORITY

This application claims priority under 35 USC § 119(e) to U.S. Patent Application Ser. No. 61/838,178, filed on Jun. 21, 2013; 61/838,148, filed on Jun. 21, 2013; 61/921,007, filed on Dec. 26, 2013; and PCT/US2014/028630, filed Mar. 14, 2014. The entire contents of the foregoing are hereby incorporated by reference.

FEDERALLY SPONSORED RESEARCH OR DEVELOPMENT

This invention was made with Government support under Grant Nos. DP1 GM105378 awarded by the National Institutes of Health. The Government has certain rights in the invention.

TECHNICAL FIELD

Methods for increasing specificity of RNA-guided genome editing, e.g., editing using CRISPR/Cas9 systems, using RNA-guided FokI Nucleases (RFNs), e.g., FokI-dCas9 fusion proteins.

BACKGROUND

Recent work has demonstrated that clustered, regularly interspaced, short palindromic repeats (CRISPR)/CRISPR-associated (Cas) systems (Wiedenheft et al., Nature 482, 331-338 (2012); Horvath et al., Science 327, 167-170 (2010); Terns et al., Curr Opin Microbiol 14, 321-327 (2011)) can serve as the basis genome editing in bacteria, yeast and human cells, as well as in vivo in whole organisms such as fruit flies, zebrafish and mice (Wang et al., Cell 153, 910-918 (2013); Shen et al., Cell Res (2013); Dicarlo et al., Nucleic Acids Res (2013); Jiang et al., Nat Biotechnol 31, 233-239 (2013); Jinek et al., Elife 2, e00471 (2013); Hwang et al., Nat Biotechnol 31, 227-229 (2013); Cong et al., Science 339, 819-823 (2013); Mali et al., Science 339, 823-826 (2013c); Cho et al., Nat Biotechnol 31, 230-232 (2013); Gratz et al., Genetics 194(4):1029-35 (2013)). The Cas9 nuclease from *S. pyogenes* (hereafter simply Cas9) can be guided via base pair complementarity between the first 20 nucleotides of an engineered gRNA and the complementary strand of a target genomic DNA sequence of interest that lies next to a protospacer adjacent motif (PAM), e.g., a PAM matching the sequence NGG or NAG (Shen et al., Cell Res (2013); Dicarlo et al., Nucleic Acids Res (2013); Jiang et al., Nat Biotechnol 31, 233-239 (2013); Jinek et al., Elife 2, e00471 (2013); Hwang et al., Nat Biotechnol 31, 227-229 (2013); Cong et al., Science 339, 819-823 (2013); Mali et al., Science 339, 823-826 (2013c); Cho et al., Nat Biotechnol 31, 230-232 (2013); Jinek et al., Science 337, 816-821 (2012)). Previous studies performed in vitro (Jinek et al., Science 337, 816-821 (2012)), in bacteria (Jiang et al., Nat Biotechnol 31, 233-239 (2013)) and in human cells (Cong et al., Science 339, 819-823 (2013)) have shown that Cas9-mediated cleavage can, in some cases, be abolished by single mismatches at the gRNA/target site interface, particularly in the last 10-12 nucleotides (nts) located in the 3' end of the 20 nucleotide (nt) gRNA complementarity region.

SUMMARY

Many studies have shown that CRISPR-Cas nucleases can tolerate up to five mismatches and still cleave; it is hard to predict the effects of any given single or combination of mismatches on activity. Taken together, these nucleases can show significant off-target effects but it can be challenging to predict these sites. Described herein are methods for increasing the specificity of genome editing using the CRISPR/Cas system, e.g., using RNA-guided FokI Nucleases (RFNs), e.g., FokI-Cas9 or FokI-dCas9-based fusion proteins.

In a first aspect, the invention provides FokI-dCas9 fusion proteins, comprising a FokI catalytic domain sequence fused to the terminus, e.g., the N terminus, of dCas9, optionally with an intervening linker, e.g., a linker of from 2-30 amino acids, e.g., 4-12 amino acids, e.g., Gly$_4$Ser. In some embodiments, the FokI catalytic domain comprises amino acids 388-583 or 408-583 of SEQ ID NO:4. In some embodiments, the dCas9 comprises mutations at the dCas9 comprises mutations at D10, E762, H983, or D986; and at H840 or N863; e.g., at: (i) D10A or D10N; and (ii) H840A, H840Y or H840N.

In another aspect, the invention provides nucleic acids encoding these fusion proteins, vector comprising the nucleic acids, and host cells harboring or expressing the nucleic acids, vectors, or fusion proteins.

In another aspect, the invention provides methods for inducing a sequence-specific break in a double-stranded DNA molecule, e.g., in a genomic sequence in a cell, the method comprising expressing in the cell, or contacting the cell with, the FokI-dCas9 fusion protein described herein, and:

(a) two single guide RNAs, wherein each of the two single guide RNAs include sequences that are each complementary to one strand of the target sequence such that using both guide RNAs results in targeting both strands (i.e., one single guide RNA targets a first strand, and the other guide RNA targets the complementary strand), and FokI cuts each strand resulting in a pair of nicks on opposite DNA strands, thereby creating a double-stranded break, or (b) a tracrRNA and two crRNAs wherein each of the two crRNAs include sequences that are complementary to one strand of the target sequence such that using both crRNAs results in targeting both strands (i.e., one crRNA targets a first strand, and the other crRNA targets the complementary strand), and FokI cuts each strand resulting in a pair of nicks on opposite DNA strands, thereby creating a double-stranded break.

In another aspect, the invention provides methods for increasing specificity of RNA-guided genome editing in a cell, the method comprising contacting the cell with an RNA-guided FokI Nuclease (RFN) fusion protein described herein.

The method may further comprise expressing in the cell, or contacting the cell with, (a) two single guide RNAs, wherein each of the two single guide RNAs include sequences that are each complementary to one strand of the target sequence such that using both guide RNAs results in targeting both strands (i.e., one single guide RNA targets a first strand, and the other guide RNA targets the complementary strand), and FokI cuts each strand resulting in a pair of nicks on opposite DNA strands, thereby creating a double-stranded break, or (b) a tracrRNA and two crRNAs wherein each of the two crRNAs include sequences that are complementary to one strand of the target sequence such that using both crRNAs results in targeting both strands (i.e., one crRNA targets a first strand, and the other crRNA targets the complementary strand), and FokI cuts each strand resulting in a pair of nicks on opposite DNA strands, thereby creating a double-stranded break.

In some embodiments, the two target genomic sequences (i.e., the sequences to which the target complementarity regions of the crRNA or single guide RNAs are complementary) are spaced 10-20 base pairs apart, preferably 13-17 base pairs apart.

In some embodiments, an indel mutation is induced between the two target sequences.

In some embodiments, the specificity of RNA-guided genome editing in a cell is increased.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

```
EGFP Site 1
                                    (SEQ ID NO: 1)
GGGCACGGGCAGCTTGCCGGTGG EGFP Site 2
                                    (SEQ ID NO: 2)
GATGCCGTTCTTCTGCTTGTCGG
```

-continued
```
EGFP Site 3
                                    (SEQ ID NO: 3)
GGTGGTGCAGATGAACTTCAGGG
```

Figure 2A:
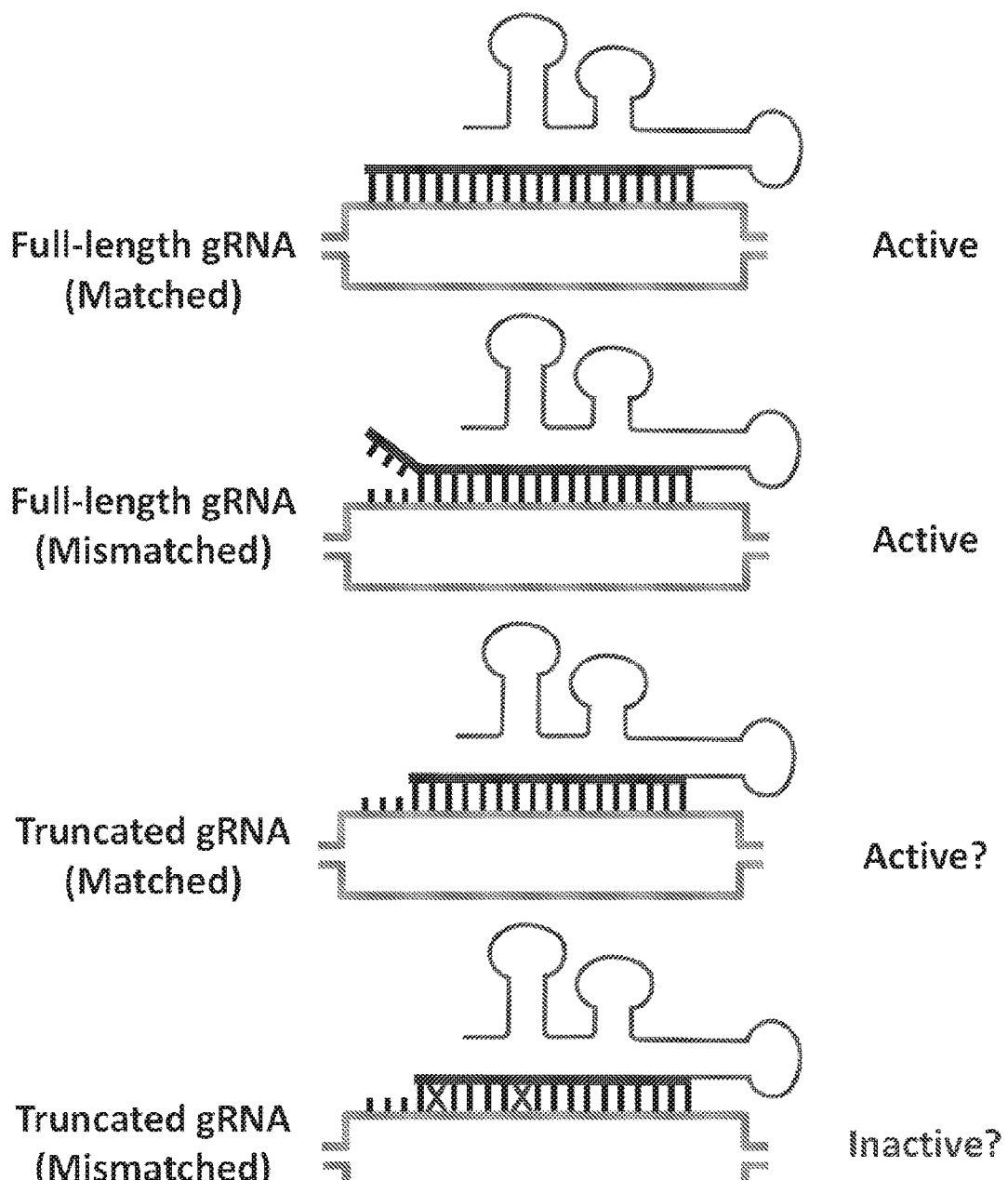
FIG. 2A: Schematic illustrating the rationale for truncating the 5' complementarity region of a gRNA. Thick grey lines=target DNA site, thin dark grey line structure=gRNA, grey oval=Cas9 nuclease, black lines indicate base pairing between gRNA and target DNA site.
Figure 2B:
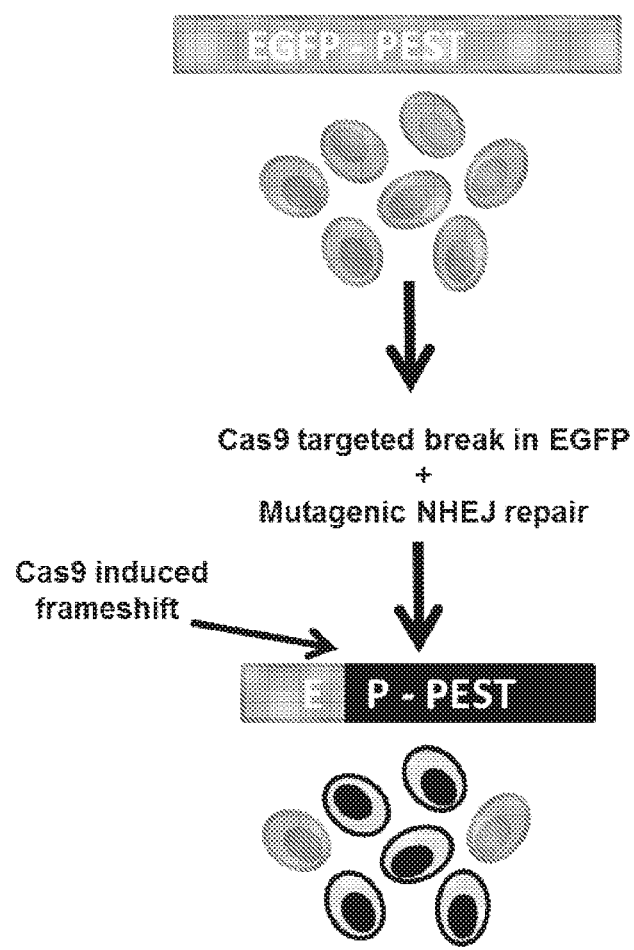
FIG. 2B: Schematic overview of the EGFP disruption assay. Repair of targeted Cas9-mediated double-stranded breaks in a single integrated EGFP-PEST reporter gene by error-prone NHEJ-mediated repair leads to frame-shift mutations that disrupt the coding sequence and associated loss of fluorescence in cells.
Figure 2C:
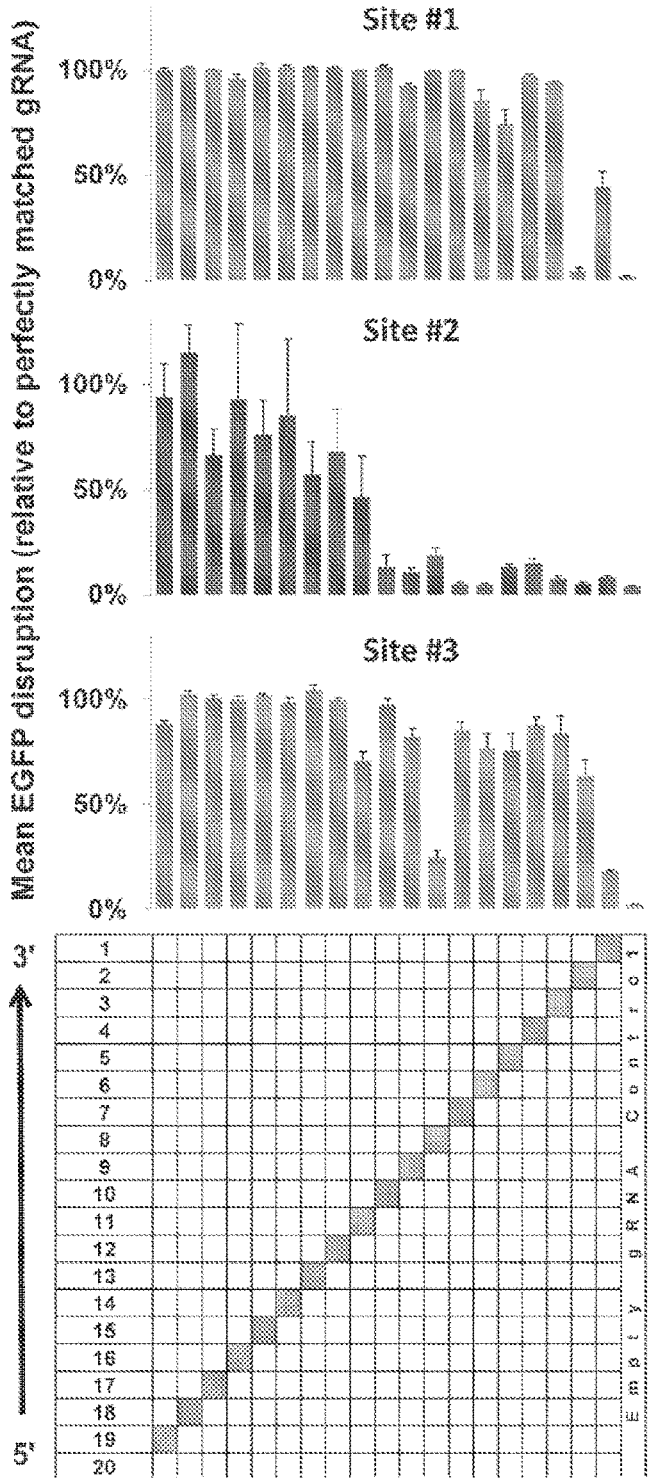
FIGS. 2C-F: Activities of RGNs harboring sgRNAs bearing (C) single mismatches, (D) adjacent double mismatches, (E) variably spaced double mismatches, and (F) increasing numbers of adjacent mismatches assayed on three different target sites in the EGFP reporter gene sequence. Mean activities of replicates (see Online Methods) are shown, normalized to the activity of a perfectly matched gRNA. Error bars indicate standard errors of the mean. Positions mismatched in each gRNA are highlighted in grey in the grid below. Sequences of the three EGFP target sites were as follows.
Figure 2D:
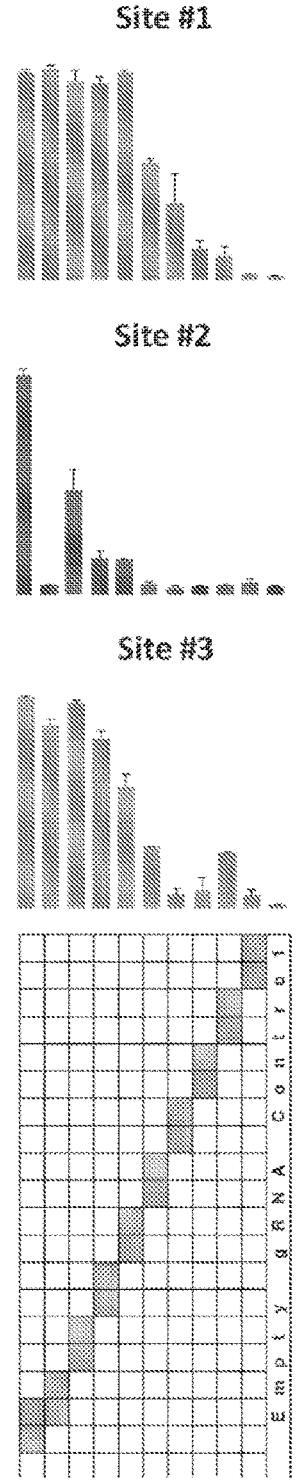
Figure 2E:
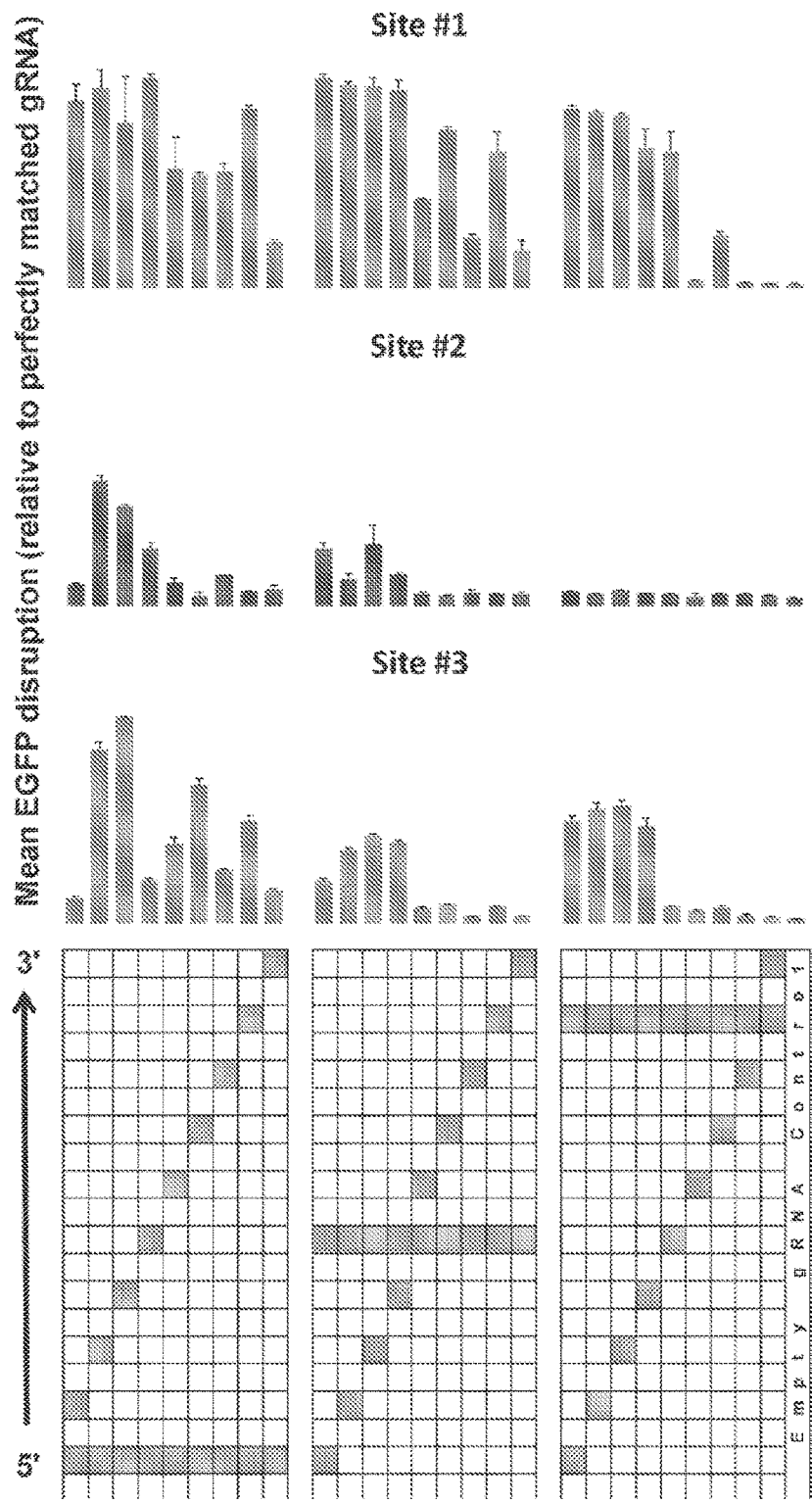
Figure 2F:
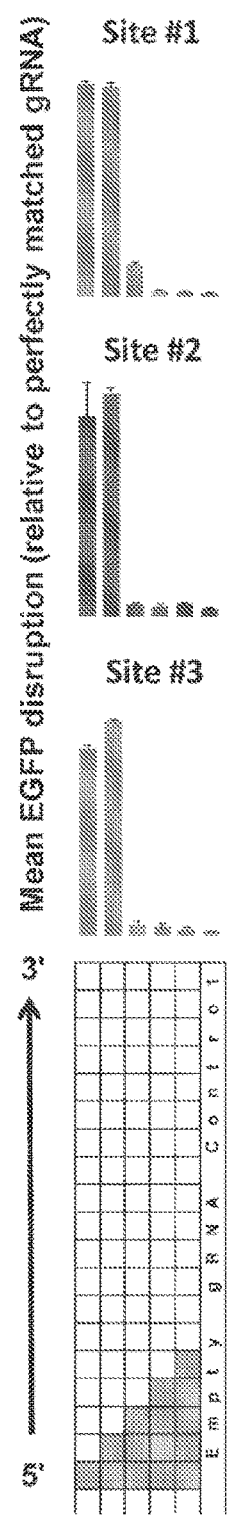
Figure 2G:
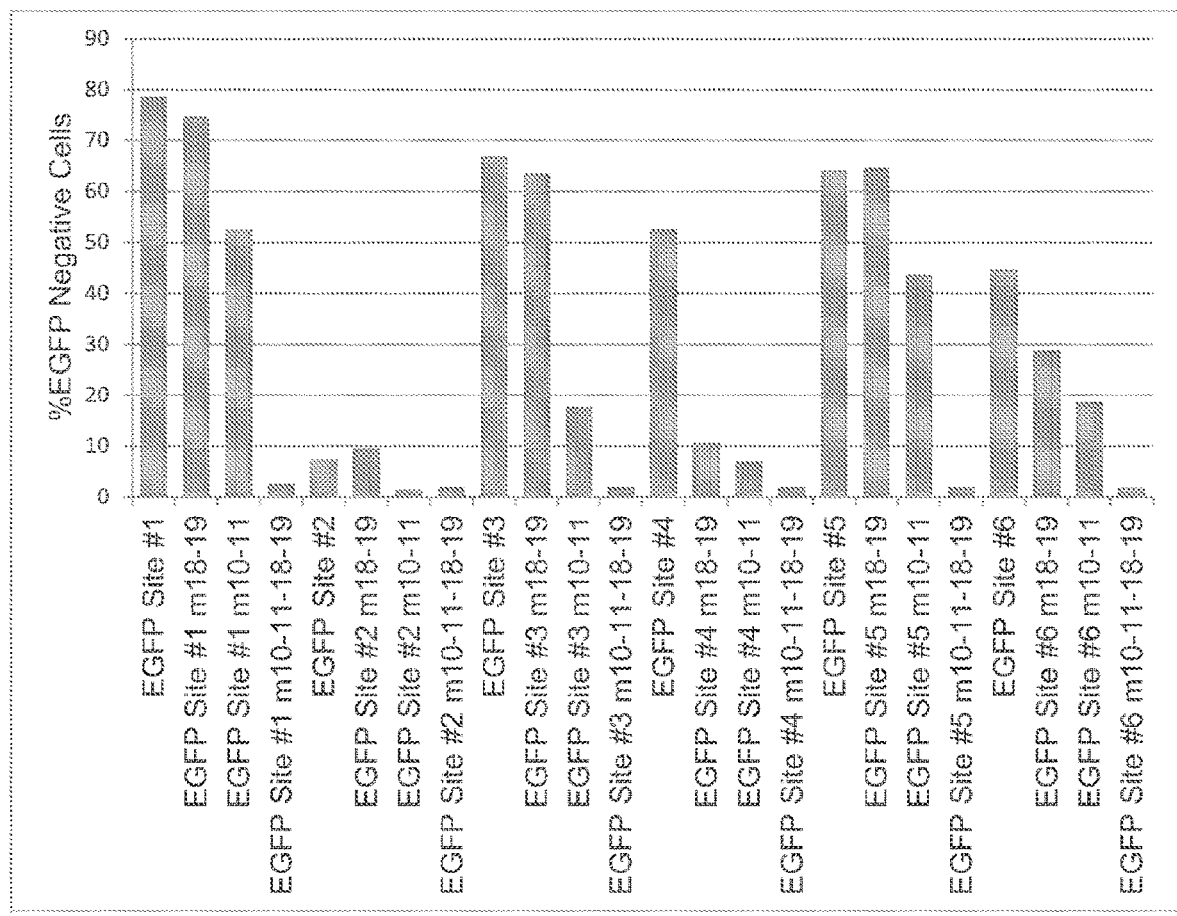

FIG. 2G: Mismatches at the 5' end of the gRNA make CRISPR/Cas more sensitive more 3' mismatches. The gRNAs Watson-Crick base pair between the RNA&DNA with the exception of positions indicated with an "m" which are mismatched using the Watson-Crick transversion (i.e. EGFP Site #2 M18-19 is mismatched by changing the gRNA to its Watson-Crick partner at positions 18 & 19. Although positions near the 5' of the gRNA are generally very well tolerated, matches in these positions are important for nuclease activity when other residues are mismatched. When all four positions are mismatched, nuclease activity is no longer detectable. This further demonstrates that matches at these 5' position can help compensate for mismatches at other more 3' positions. Note these experiments were performed with a non-codon optimized version of Cas9 which can show lower absolute levels of nuclease activity as compared to the codon optimized version.

Figure 2H:
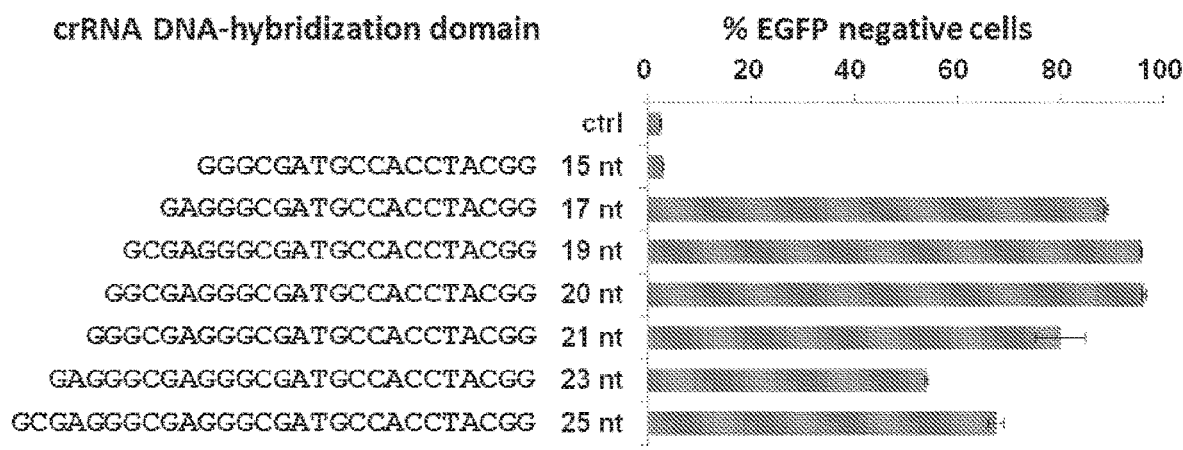

FIG. 2H: Efficiency of Cas9 nuclease activities directed by gRNAs bearing variable length complementarity regions ranging from 15 to 25 nts in a human cell-based U2OS EGFP disruption assay. Expression of a gRNA from the U6 promoter requires the presence of a 5' G and therefore it was only possible to evaluate gRNAs harboring certain lengths of complementarity to the target DNA site (15, 17, 19, 20, 21, 23, and 25 nts).

Figure 3A:
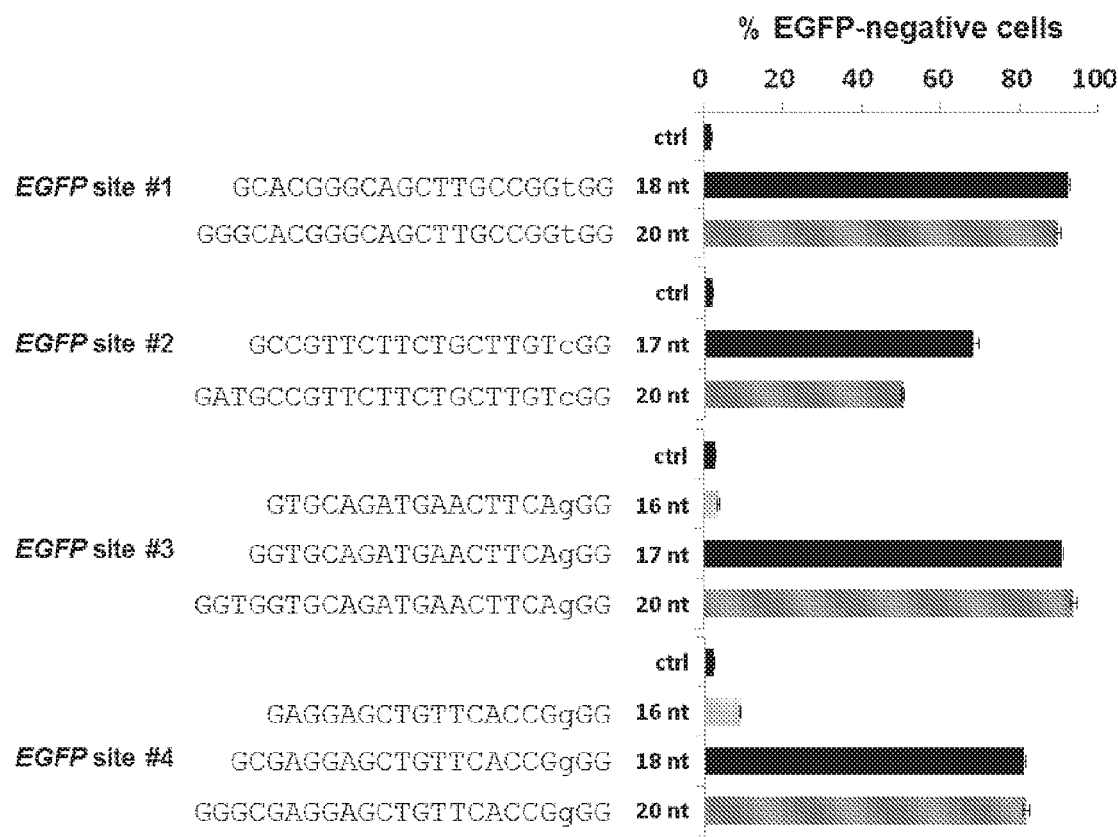

FIG. 3A: Efficiencies of EGFP disruption in human cells mediated by Cas9 and full-length or shortened gRNAs for four target sites in the EGFP reporter gene. Lengths of complementarity regions and corresponding target DNA sites are shown. Ctrl=control gRNA lacking a complementarity region.

Figure 3B:
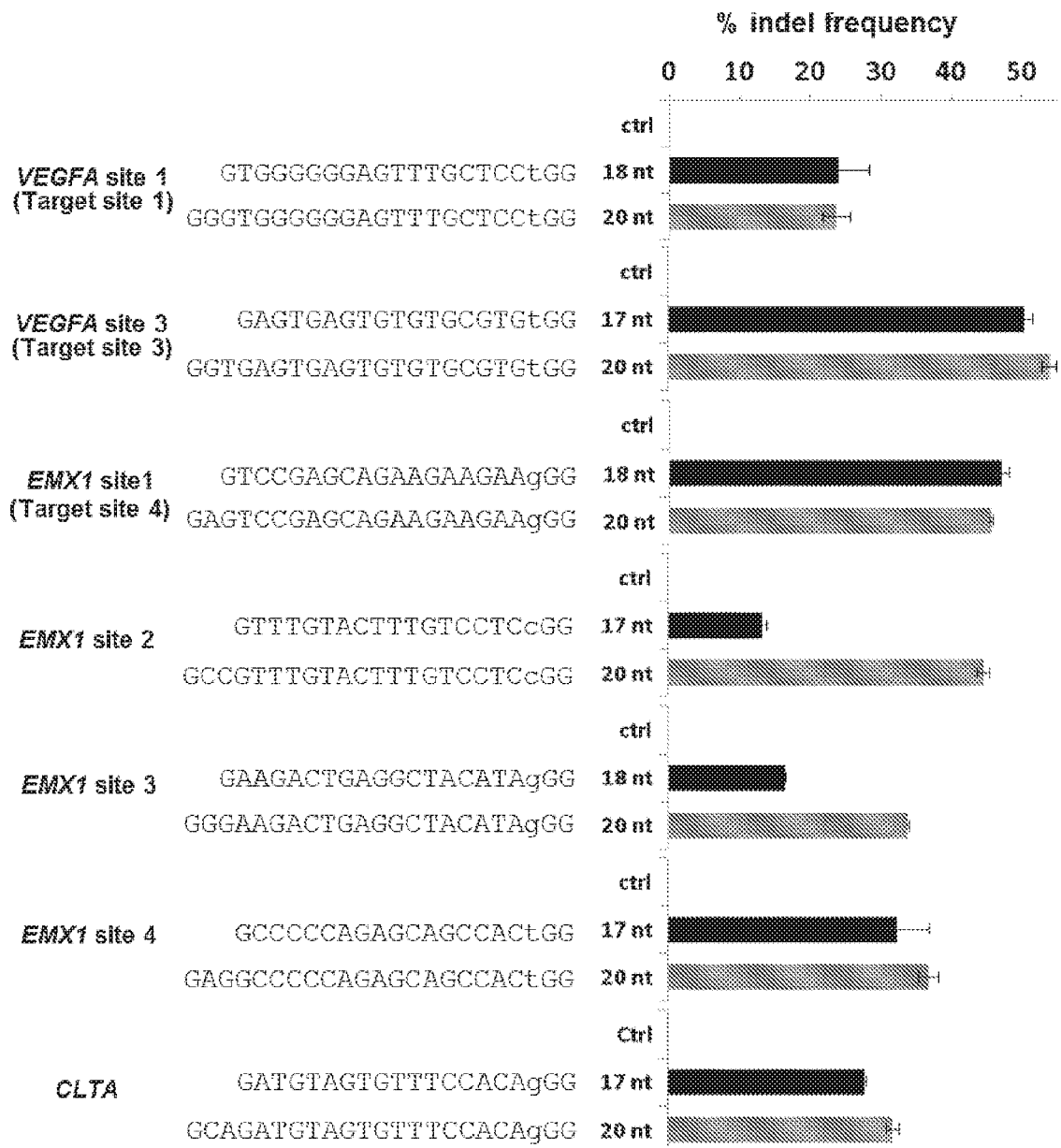

FIG. 3B: Efficiencies of targeted indel mutations introduced at seven different human endogenous gene targets by matched standard and tru-RGNs. Lengths of complementarity regions and corresponding target DNA sites are shown. Indel frequencies were measured by T7EI assay. Ctrl=control gRNA lacking a complementarity region.

FIG. 3C: DNA sequences of indel mutations induced by RGNs using a tru-gRNA or a matched full-length gRNA targeted to the EMX1 site. The portion of the target DNA site that interacts with the gRNA complementarity region is highlighted in grey with the first base of the PAM sequence shown in lowercase. Deletions are indicated by dashes highlighted in grey and insertions by italicized letters highlighted in grey. The net number of bases deleted or inserted and the number of times each sequence was isolated are shown to the right.

Figure 3D:
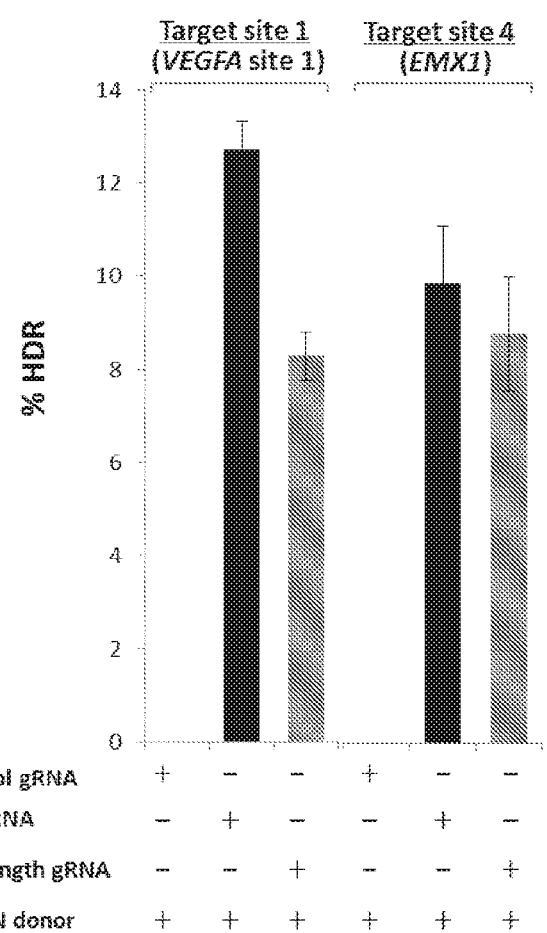

FIG. 3D: Efficiencies of precise HDR/ssODN-mediated alterations introduced at two endogenous human genes by matched standard and tru-RGNs. % HDR was measured using a BamHI restriction digest assay (see the Experimental Procedures for Example 2). Control gRNA=empty U6 promoter vector.

FIG. 3E: U2OS.EGFP cells were transfected with variable amounts of full-length gRNA expression plasmids (top) or tru-gRNA expression plasmids (bottom) together with a fixed amount of Cas9 expression plasmid and then assayed for percentage of cells with decreased EGFP expression. Mean values from duplicate experiments are shown with standard errors of the mean. Note that the data obtained with tru-gRNA matches closely with data from experiments performed with full-length gRNA expression plasmids instead of tru-gRNA plasmids for these three EGFP target sites.

FIG. 3F: U2OS.EGFP cells were transfected with variable amount of Cas9 expression plasmid together with variable amounts of full-length gRNA expression plasmids (top) or tru-gRNA expression plasmids (bottom) (amounts determined for each tru-gRNA from the experiments of FIG. 3E). Mean values from duplicate experiments are shown with standard errors of the mean. Note that the data obtained with tru-gRNA matches closely with data from experiments performed with full-length gRNA expression plasmids instead of tru-gRNA plasmids for these three EGFP target sites. The results of these titrations determined the concentrations of plasmids used in the EGFP disruption assays performed in Examples 1 and 2.

Figure 4A:
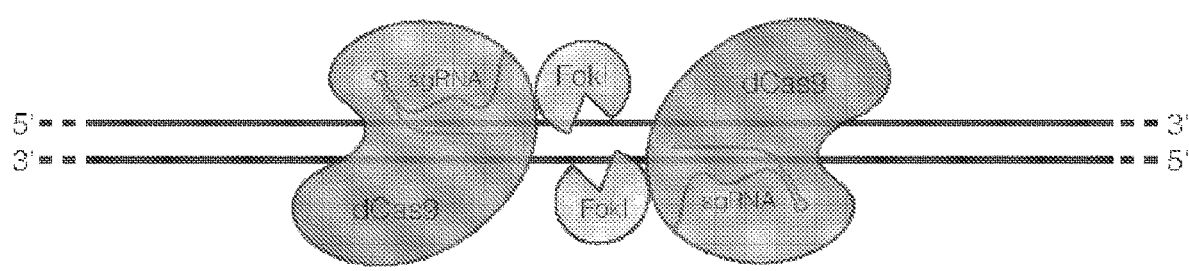
Figure 4B:
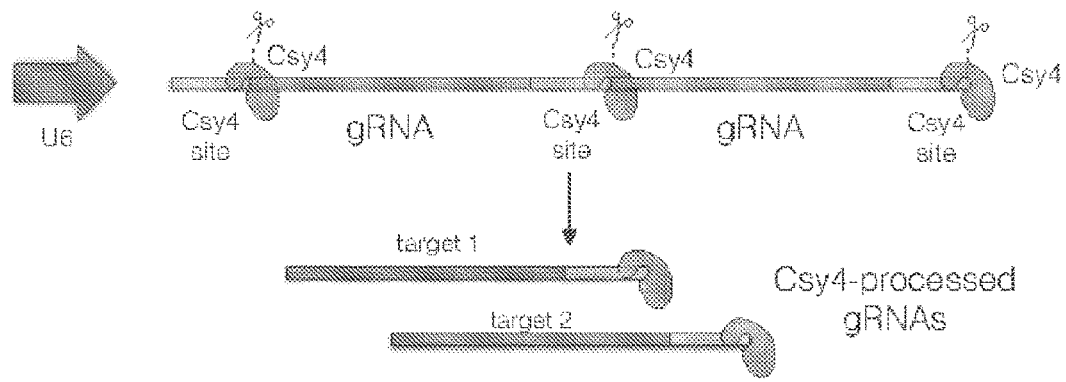

FIGS. 4A-C. RNA-guided FokI nucleases and a CRISPR/Cas Subtype Ypest protein 4 (Csy4)-based multiplex gRNA expression system.

(a) Schematic overview of RNA-guided FokI nucleases. Two FokI-dCas9 fusion proteins are recruited to adjacent target sites by two different gRNAs in order to facilitate FokI dimerization and DNA cleavage.

(b) Schematic overview of a Csy4-based multiplex gRNA expression system. Two gRNAs (with any 5' end nucleotide) are co-expressed in a single transcript from a U6 promoter with each gRNA flanked by Csy4 recognition sites. Csy4 cleaves and releases gRNAs from the transcript. The Csy4 recognition site remains at the 3' end of the gRNA with a Csy4 nuclease bound to that site.

(c) Validation of the multiplex, Csy4-based system. Two gRNAs targeted to adjacent sites in EGFP were expressed in a single RNA transcript using the Csy4-based system in human U2OS.EGFP cells together with Csy4 and Cas9 nucleases. Sequences of indel mutations induced in these cells are shown. The wild-type sequence is shown in the top with both target sites highlighted in grey and PAM sequences shown as underlined text. Deletions are indicated by dashes against gray background and insertions by lowercase letters against a grey background. To the right of each sequence, the sizes of insertions (+) or deletions (Δ) are specified.

FIGS. 5A-F. Design and optimization of RNA-guided FokI nucleases.

(a) Schematic illustrations of a ZFN, TALEN, FokI-dCas9 fusion, and dCas9-FokI fusion.

(b) Screening the EGFP disruption activities of FokI-dCas9 fusion with gRNA pairs targeted to half-sites in one of two orientations: PAMs in (left panel) and PAMs out (right panel). Half-sites were separated by spacer sequences of variable lengths ranging from 0 to 31 bps. EGFP disruption was quantified by flow cytometry, n=1. Corresponding data for the dCas9-FokI fusion and the same gRNA pairs is shown in FIG. 5E.

(c) Additional assessment of FokI-dCas9-mediated EGFP disruption activities on target sites with half-sites oriented with their PAMs out and with spacer lengths ranging from 10 to 20 bp. EGFP disruption was quantified by flow cytometry. Error bars indicate standard errors of the mean (s.e.m.), n=2.

(d) Mean EGFP disruption values of the data from (c) grouped according to spacer length. Error bars represent s.e.m.

(e) These plots show the results of a screen for dCas9-FokI activity in EGFP disruption assay in the U2OS.EGFP cells with 60 gRNA pairs with spacings of 0-31 bp and PAM in and PAM out orientations.

(f) Sequences of FokI-dCas9 induced mutations in U2OS cells are shown. The 23-nt target sequence bound by Cas9 or FokI-dCas9 is labeled in grey. The protospacer adjacent motif or PAM sequence is labeled in boldface with underlining. Deletions are marked with dashes on a light grey background. Insertions are highlighted in grey. The net number of bases inserted or deleted are indicated in a column directly to the right of the sequences.

FIGS. 6A-D. Dimerization of FokI-dCas9 RFNs is required for efficient genome editing activity.

(a) EGFP disruption activities of two RFN pairs assessed in the presence of correctly targeted gRNA pairs (to EGFP sites 47 and 81) and pairs in which one or the other of the gRNAs has been replaced with another gRNA targeted to a non-EGFP sequence (in the VEGFA gene). EGFP disruption was quantified by flow cytometry. EGFP, Enhanced Green Fluorescent Protein; VEGFA, Vascular Endothelial Growth Factor A. Error bars represent standard errors of the mean (s.e.m.), n=3.

(b) Quantification of mutagenesis frequencies by T7EI assay performed with genomic DNA from the same cells used in the EGFP disruption assay of (a). Error bars represent s.e.m., n=3.

(c) Activities of RFNs targeted to sites in the APC, MLH1 and VEGFA genes. For each target, we co-expressed FokI-dCas9 with a pair of cognate gRNAs, only one gRNA for the "left" half-site, or only one gRNA for the "right" half-site. Rates of mutagenesis were measured by T7E1 assay. APC, Adenomatous polyposis coli; MLH1, mutL homolog 1; VEGFA, Vascular Endothelial Growth Factor A. Error bars represent s.e.m., n=3.

(d) Mutagenesis frequencies of RFNs targeted to VEGFA site 1 at the on-target site and at five previously known off-target (OT) sites for one of the gRNAs used to target VEGFA site 1. Frequencies of mutation were determined by deep sequencing. Each value reported was determined from a single deep sequencing library prepared from genomic DNA pooled from three independent transfection experiments. The value shown for the on-target VEGFA site 1 (marked with an asterisk) is the same as the one shown in FIG. 4a below and is only shown here for ease of comparison with the values presented in this figure.

Figure 7A:
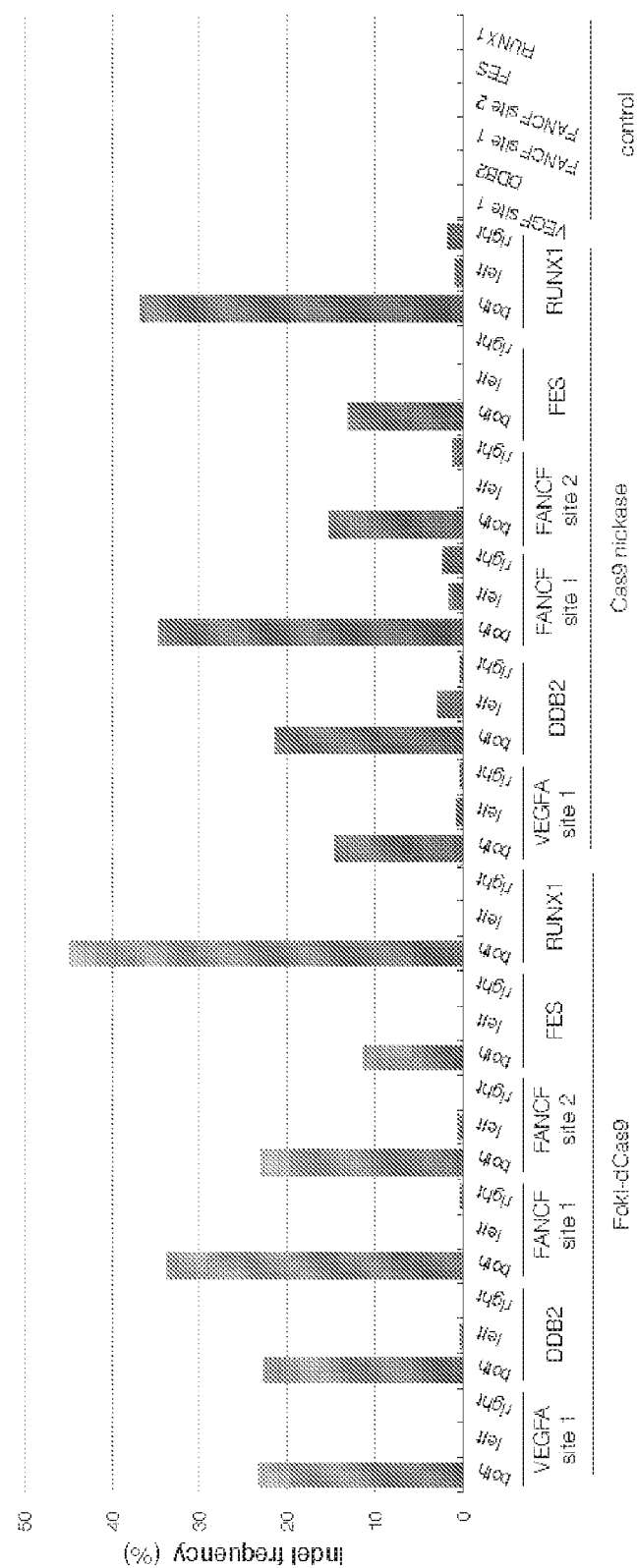
Figure 7B:
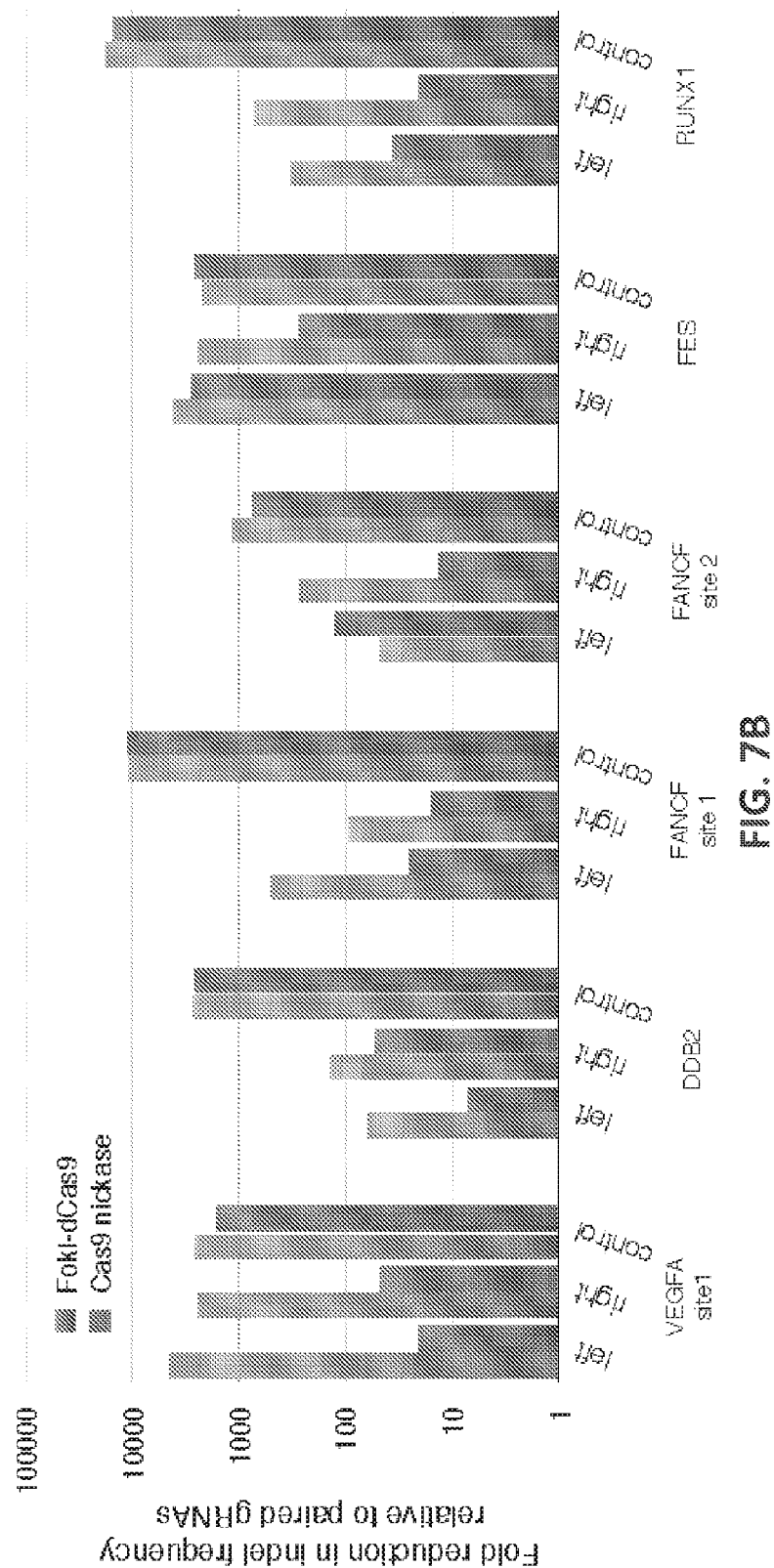

FIGS. 7A-B. Mutagenic activities of a Cas9 nickase or FokI-dCas9 co-expressed with a single gRNA.

(a) Indel mutation frequencies induced by FokI-dCas9 (left bars) or Cas9 nickase (middle bars) in the presence of one or two gRNAs targeted to six different human gene sites. For each gene target, we assessed indel frequencies with both gRNAs, only one gRNA for the "left" half-site, or only the other gRNA for the "right" half-site. Mutation frequencies were determined by deep sequencing. Each indel frequency value reported was determined from a single deep sequencing library prepared from genomic DNA pooled from three independent transfection experiments. VEGFA, Vascular Endothelial Growth Factor A; DDB2, Damage-Specific DNA Binding Protein 2; FANCF, Fanconi Anemia, Complementation Group F; FES, Feline Sarcoma Oncogene; RUNX 1, Runt-Related Transcription Factor 1.

(b) Data from (a) presented as a fold-reduction in the indel frequency comparing values obtained for each target site with a gRNA pair to each of the single gRNA experiments or to the control experiment (no gRNA and no Cas9 nickase or FokI-dCas9). This fold-reduction was calculated for both FokI-dCas9 (left bars in each pair, lighter grey) and Cas9 nickase (right bars in each pair, darker grey).

Figures 8A, 8B, 8C:

FIGS. 8A-C: Single Cas9 nickases can introduce point mutations with high efficiencies into their target sites.

Frequencies of different point mutations found at each position in half-sites targeted by single gRNAs for (a) VEGFA, (b) FANCF, and (c) RUNX1 gene targets in the presence of FokI-dCas9, Cas9 nickase, or a tdTomato control. Mutation frequencies were determined by deep sequencing. Each point mutation value reported was determined from a single deep sequencing library prepared from genomic DNA pooled from three independent transfection experiments. Note that the genomic DNA used for these experiments was isolated from the same cells analyzed for indel mutations in FIGS. 7A-B. VEGFA, Vascular Endothelial Growth Factor A; FANCF, Fanconi Anemia, Complementation Group F; RUNX 1, Runt-Related Transcription Factor 1.

DETAILED DESCRIPTION

CRISPR RNA-guided nucleases (RGNs) have rapidly emerged as a facile and efficient platform for genome editing. Although Marraffini and colleagues (Jiang et al., Nat Biotechnol 31, 233-239 (2013)) recently performed a systematic investigation of Cas9 RGN specificity in bacteria, the specificities of RGNs in human cells have not been extensively defined. Understanding the scope of RGN-mediated off-target effects in human and other eukaryotic cells will be critically essential if these nucleases are to be used widely for research and therapeutic applications. The present inventors have used a human cell-based reporter assay to characterize off-target cleavage of Cas9-based RGNs. Single and double mismatches were tolerated to varying degrees depending on their position along the guide RNA (gRNA)-DNA interface. Off-target alterations induced by four out of six RGNs targeted to endogenous loci in human cells were readily detected by examination of partially mismatched sites. The off-target sites identified harbor up to five mismatches and many are mutagenized with frequencies comparable to (or higher than) those observed at the intended on-target site. Thus RGNs are highly active even with imperfectly matched RNA-DNA interfaces in human cells, a finding that might confound their use in research and therapeutic applications.

The results described herein reveal that predicting the specificity profile of any given RGN is neither simple nor straightforward. The EGFP reporter assay experiments show that single and double mismatches can have variable effects on RGN activity in human cells that do not strictly depend upon their position(s) within the target site. For example, consistent with previously published reports, alterations in the 3' half of the gRNA/DNA interface generally have greater effects than those in the 5' half (Jiang et al., Nat Biotechnol 31, 233-239 (2013); Cong et al., Science 339, 819-823 (2013); Jinek et al., Science 337, 816-821 (2012)); however, single and double mutations in the 3' end sometimes also appear to be well tolerated whereas double mutations in the 5' end can greatly diminish activities. In addition, the magnitude of these effects for mismatches at any given position(s) appears to be site-dependent. Comprehensive profiling of a large series of RGNs with testing of all possible nucleotide substitutions (beyond the Watson-Crick transversions used in our EGFP reporter experiments) may help provide additional insights into the range of potential off-targets. In this regard, the recently described bacterial cell-based method of Marraffini and colleagues (Jiang et al., Nat Biotechnol 31, 233-239 (2013)) or the in vitro, combinatorial library-based cleavage site-selection methodologies previously applied to ZFNs by Liu and colleagues (Pattanayak et al., Nat Methods 8, 765-770 (2011)) might be useful for generating larger sets of RGN specificity profiles.

Despite these challenges in comprehensively predicting RGN specificities, it was possible to identify bona fide off-targets of RGNs by examining a subset of genomic sites that differed from the on-target site by one to five mismatches. Notably, under conditions of these experiments, the frequencies of RGN-induced mutations at many of these off-target sites were similar to (or higher than) those observed at the intended on-target site, enabling the detection of mutations at these sites using the T7EI assay (which, as performed in our laboratory, has a reliable detection limit of ~2 to 5% mutation frequency). Because these mutation rates were very high, it was possible to avoid using deep sequencing methods previously required to detect much lower frequency ZFN- and TALEN-induced off-target alterations (Pattanayak et al., Nat Methods 8, 765-770 (2011); Perez et al., Nat Biotechnol 26, 808-816 (2008); Gabriel et al., Nat Biotechnol 29, 816-823 (2011); Hockemeyer et al., Nat Biotechnol 29, 731-734 (2011)). Analysis of RGN off-target mutagenesis in human cells also confirmed the difficulties of predicting RGN specificities—not all single and double mismatched off-target sites show evidence of mutation whereas some sites with as many as five mismatches can also show alterations. Furthermore, the bona fide off-target sites identified do not exhibit any obvious bias toward transition or transversion differences relative to the intended target sequence.

Although off-target sites were seen for a number of RGNs, identification of these sites was neither comprehensive nor genome-wide in scale. For the six RGNs studied, only a very small subset of the much larger total number of potential off-target sequences in the human genome was examined. Although examining such large numbers of loci for off-target mutations by T7EI assay is neither a practical nor a cost-effective strategy, the use of high-throughput sequencing in future studies might enable the interrogation of larger numbers of candidate off-target sites and provide a more sensitive method for detecting bona fide off-target mutations. For example, such an approach might enable the unveiling of additional off-target sites for the two RGNs for which we failed to uncover any off-target mutations. In addition, an improved understanding both of RGN specificities and of any epigenetic factors (e.g., DNA methylation and chromatin status) that may influence RGN activities in cells might also reduce the number of potential sites that need to be examined and thereby make genome-wide assessments of RGN off-targets more practical and affordable.

A number of strategies can be used to minimize the frequencies of genomic off-target mutations. For example, the specific choice of RGN target site can be optimized; given that off-target sites that differ at up to five positions from the intended target site can be efficiently mutated by RGNs, choosing target sites with minimal numbers of off-target sites as judged by mismatch counting seems unlikely to be effective; thousands of potential off-target sites that differ by four or five positions within the 20 bp RNA:DNA complementarity region will typically exist for any given RGN targeted to a sequence in the human genome. It is also possible that the nucleotide content of the gRNA complementarity region might influence the range of potential off-target effects. For example, high GC-content has been shown to stabilize RNA:DNA hybrids (Sugimoto et al., Biochemistry 34, 11211-11216 (1995)) and therefore might also be expected to make gRNA/genomic DNA hybridization more stable and more tolerant to mismatches. Additional experiments with larger numbers of gRNAs will be needed to assess if and how these two parameters (numbers of mismatched sites in the genome and stability of the RNA:DNA hybrid) influence the genome-wide specificities of RGNs. However, it is important to note that even if such predictive parameters can be defined, the effect of implementing such guidelines would be to further restrict the targeting range of RGNs.

One potential general strategy for reducing RGN-induced off-target effects might be to reduce the concentrations of gRNA and Cas9 nuclease expressed in the cell. This idea was tested using the RGNs for VEGFA target sites 2 and 3 in U2OS.EGFP cells; transfecting less gRNA- and Cas9-expressing plasmid decreased the mutation rate at the on-target site but did not appreciably change the relative rates of off-target mutations. Consistent with this, high-level off-target mutagenesis rates were also observed in two other human cell types (HEK293 and K562 cells) even though the absolute rates of on-target mutagenesis are lower than in U2OS.EGFP cells. Thus, reducing expression levels of gRNA and Cas9 in cells is not likely to provide a solution for reducing off-target effects. Furthermore, these results also suggest that the high rates of off-target mutagenesis observed in human cells are not caused by overexpression of gRNA and/or Cas9.

The finding that significant off-target mutagenesis can be induced by RGNs in three different human cell types has important implications for broader use of this genome-editing platform. For research applications, the potentially confounding effects of high frequency off-target mutations will need to be considered, particularly for experiments involving either cultured cells or organisms with slow generation times for which the outcrossing of undesired alterations would be challenging. One way to control for such effects might be to utilize multiple RGNs targeted to different DNA sequences to induce the same genomic alteration because off-target effects are not random but instead related to the targeted site. However, for therapeutic applications, these findings clearly indicate that the specificities of RGNs will need to be carefully defined and/or improved if these nucleases are to be used safely in the longer term for treatment of human diseases.

Methods for Improving Specificity

As shown herein, CRISPR-Cas RNA-guided nucleases based on the *S. pyogenes* Cas9 protein can have significant off-target mutagenic effects that are comparable to or higher than the intended on-target activity (Example 1). Such off-target effects can be problematic for research and in particular for potential therapeutic applications. Therefore, methods for improving the specificity of CRISPR-Cas RNA guided nucleases (RGNs) are needed.

As described in Example 1, Cas9 RGNs can induce high-frequency indel mutations at off-target sites in human cells (see also Cradick et al., 2013; Fu et al., 2013; Hsu et al., 2013; Pattanayak et al., 2013). These undesired alterations can occur at genomic sequences that differ by as many as five mismatches from the intended on-target site (see Example 1). In addition, although mismatches at the 5' end of the gRNA complementarity region are generally better tolerated than those at the 3' end, these associations are not absolute and show site-to-site-dependence (see Example 1 and Fu et al., 2013; Hsu et al., 2013; Pattanayak et al., 2013). As a result, computational methods that rely on the number and/or positions of mismatches currently have limited predictive value for identifying bona fide off-target sites. Therefore, methods for reducing the frequencies of off-target mutations remain an important priority if RNA-guided nucleases are to be used for research and therapeutic applications.

Dimerization is an attractive potential strategy for improving the specificity of Cas9 nucleases. This is distinct from a paired Cas9 nickase approach, which is not a true dimeric system. Paired nickases work by co-localizing two Cas9 nickases on a segment of DNA, thereby inducing high efficiency genome editing via an undefined mechanism. Because dimerization is not required for enzymatic activity, single Cas9 nickases can also induce indels with high efficiencies at certain sites (via an unknown mechanism) and can therefore potentially cause unwanted off-target mutations in the genome.

Thus, one strategy to improve the specificity of RGNs is fusing a FokI endonuclease domain to a catalytically inactive form of Cas9 bearing the D10A and H840A mutations (also known as dCas9). FokI nuclease domain functions as a dimer and therefore two subunits must be recruited to the same local piece of DNA in order to induce a double-stranded break. In this configuration (FIG. 9A and Example 2), two FokI-dCas9 fusions are recruited in an appropriate configuration using two different gRNAs to yield a double-stranded break. Thus, in this system, the FokI-dCas9 fusions would bind to a site that is twice as long as that of a single RGN and therefore this system would be expected to be more specific.

Therefore provided herein are FokI-dCas9 fusion proteins, wherein the FokI sequence is fused to dCas9 (preferably to the amino-terminal end of dCas9, but also optionally to the carboxy terminus), optionally with an intervening linker, e.g., a linker of from 2-30 amino acids, e.g., 4-12 amino acids, e.g., Gly$_4$Ser (SEQ ID NO:23) or (Gly$_4$Ser)$_3$. In some embodiments, the fusion proteins include a linker between the dCas9 and the FokI domains. Linkers that can be used in these fusion proteins (or between fusion proteins in a concatenated structure) can include any sequence that does not interfere with the function of the fusion proteins. In preferred embodiments, the linkers are short, e.g., 2-20 amino acids, and are typically flexible (i.e., comprising amino acids with a high degree of freedom such as glycine, alanine, and serine). In some embodiments, the linker comprises one or more units consisting of GGGS (SEQ ID NO:22) or GGGGS (SEQ ID NO:23), e.g., two, three, four, or more repeats of the GGGS (SEQ ID NO:22) or GGGGS (SEQ ID NO:23) unit. Other linker sequences can also be used.

Also described herein is a RNA-guided FokI nuclease platform in which dimerization, rather than just co-localization, is required for efficient genome editing activity. These nucleases can robustly mediate highly efficient genome editing in human cells and can reduce off-target mutations to undetectable levels as judged by sensitive deep sequencing methods. Also described is an efficient system for expressing pairs of gRNAs with any 5' end nucleotide, a method that confers a wider targeting range on the RFN platform. Finally, monomeric Cas9 nickases generally introduce more undesirable indels and point mutations than the nucleases described herein in the presence of a single gRNA. These results define a robust, user-friendly nuclease platform with the specificity advantages of a well-characterized dimeric architecture and an improved mutagenesis profile relative to paired Cas9 nickases, features that will be important for research or therapeutic applications requiring the highest possible genome editing precision.

Thus a new RNA-guided FokI Nuclease (RFN) platform is described herein for performing robust and highly specific genome editing in human cells. RFNs require two gRNAs for activity and function as dimers. Surprisingly, the engineering of an active RFN required fusion of the FokI nuclease domain to the amino-terminal end of the dCas9 protein, an architecture different from ZFNs and TALENs in which the FokI domain is fused to the carboxy-terminal end of engineered zinc finger or transcription activator-like effector repeat arrays. RFNs also require that the half-sites bound by each Fok-dCas9/gRNA complex have a particular relative orientation (PAMs out) with a relatively restricted intervening spacer length of 14 to 17 bps (although activity may be possible at additional spacings but with less consistent success).

The dimeric nature of RFNs provides important specificity advantages relative to standard monomeric Cas9 nucleases. In an ideal dimeric system, little to no activity will be observed with monomers on half-sites. The present data demonstrate that FokI-dCas9 directed by a single gRNA induces very little or no mutagenesis at RFN half-sites. 12 single gRNAs (for six RFN target sites) were tested with co-expressed FokI-dCas9 and indels were observed at very low frequencies (range of 0.0045% to 0.47%), in some cases at levels as low as background rates observed in control cells in which there was no expression of gRNA or nuclease. Given that the FokI nuclease domain functions as a dimer, it is presumed that any indels observed with a single gRNA are likely due to recruitment of a FokI-dCas9 dimer to the DNA. Regardless of mechanism, given that only very low level mutagenesis was observed when FokI-dCas9 was tested with single gRNAs at 12 on-target half-sites, it is very unlikely that any mutagenesis will be induced at partially mismatched, off-target half-sites. Indeed, an RFN targeted to VEGFA did not induce detectable mutations at known off-target sites of one of the gRNAs as judged by deep sequencing.

Because RFNs are a true dimeric system, they possess a number of important advantages over paired nickase technology, which depends on co-localization but does not require dimerization. First, the direct comparisons herein show that single Cas9 nickases generally induce indel mutations with greater efficiencies than do FokI-dCas9 fusion proteins directed by the same individual gRNAs. Second, monomeric Cas9 nickases can also induce base pair substitutions in their target half-sites with high efficiencies, a previously unknown mutagenic side-effect that we uncovered in this study. Again, the direct comparisons show that monomeric Cas9 nickases induce these unwanted point mutations at substantially higher rates than FokI-dCas9 fusions guided by the same single gRNAs. Third, paired Cas9 nickases show greater promiscuity in the orientation and spacing of target half-sites than dimeric RFNs and therefore have a greater potential range of sites at which off-target mutations might be induced. Paired nickase half-sites can be oriented with their PAMs in or PAMs out and with spacer sequences ranging in length from 0 to 1000 bps (Ran et al., Cell 154, 1380-1389 (2013); Mali et al., Nat Biotechnol 31, 833-838 (2013); Cho et al., Genome Res (2013)). This promiscuity exists because the genome editing activities of Cas9 nickases do not depend on dimerization of the enzyme but rather just co-localization of the two nicks. By contrast, RFNs are much more stringent in their specificities—half-sites must have their PAMs out and must be spaced apart by 14 to 17 bps, due to the requirement for two appropriately positioned FokI cleavage domains for efficient cleavage.

FokI

FokI is a type IIs restriction endonuclease that includes a DNA recognition domain and a catalytic (endonuclease) domain. The fusion proteins described herein can include all of FokI or just the catalytic endonuclease domain, e.g., amino acids 388-583 or 408-583 of GenBank Acc. No. AAA24927.1, e.g., as described in Li et al., Nucleic Acids Res. 39(1): 359-372 (2011); Cathomen and Joung, Mol. Ther. 16: 1200-1207 (2008), or a mutated form of FokI as described in Miller et al. Nat Biotechnol 25: 778-785 (2007); Szczepek et al., Nat Biotechnol 25: 786-793 (2007); or Bitinaite et al., Proc. Natl. Acad. Sci. USA. 95:10570-10575 (1998).

An exemplary amino acid sequence of FokI is as follows:

```
                                              (SEQ ID NO: 4)
          10         20         30         40
    MFLSMVSKIR TFGWVQNPGK FENLKRVVQV FDRNSKVHNE 50         60         70         80
    VKNIKIPTLV KESKIQKELV AIMNQHDLIY TYKELVGTGT 90        100        110        120
    SIRSEAPCDA IIQATIADQG NKKGYIDNWS SDGFLRWAHA 130        140        150        160
    LGFIEYINKS DSFVITDVGL AYSKSADGSA IEKEILIEAI 170        180        190        200
    SSYPPAIRIL TLLEDGQHLT KFDLGKNLGF SGESGFTSLP 210        220       230 240
    EGILLDTLAN AMPKDKGEIR NNWEGSSDKY ARMIGGWLDK 250        260        270        280
    LGLVKQGKKE FIIPTLGKPD NKEFISHAFK ITGEGLKVLR 290        300        310        320
    RAKGSTKFTR VPKRVYWEML ATNLTDKEYV RTRRALILEI 330        340        350        360
    LIKAGSLKIE QIQDNLKKLG FDEVIETIEN DIKGLINTGI 370        380        390        400
    FIEIKGRFYQ LKDHILQFVI PNRGVTKQLV KSELEEKKSE 410        420        430        440
    LRHKLKYVPH EYIELIEIAR NSTQDRILEM KVMEFFMKVY 450        460        470        480
    GYRGKHLGGS RKPDGAIYTV GSPIDYGVIV DTKAYSGGYN 490        500        510        520
    LPIGQADEMQ RYVEENQTRN KHINPNEWWK VYPSSVTEFK 530        540        550        560
    FLFVSGHFKG NYKAQLTRLN HITNCNGAVL SVEELLIGGE 570        580
    MIKAGTLTLE EVRRKFNNGE INF
```

An exemplary nucleic acid sequence encoding FokI is as follows:

```
                                            (SEQ ID NO: 285)
ATGTTTTTGAGTATGGTTTCTAAAATAAGAACTTTCGGTTGGGTTCAA

ATCCAGGTAAATTTGAGAATTTAAAACGAGTAGTTCAAGTATTTGATAG

AAATTCTAAAGTACATAATGAAGTGAAAAATATAAAGATACCAACCCTA

GTCAAAGAAAGTAAGATCCAAAAAGAACTAGTTGCTATTATGAATCAAC

ATGATTTGATTTATACATATAAAGAGTTAGTAGGAACAGGAACTTCAAT
```

```
-continued
ACGTTCAGAAGCACCATGCGATGCAATTATTCAAGCAACAATAGCAGAT

CAAGGAAATAAAAAAGGCTATATCGATAATTGGTCATCTGACGGTTTTT

TGCGTTGGGCACATGCTTTAGGATTTATTGAATATATAAATAAAAGTGA

TTCTTTTGTAATAACTGATGTTGGACTTGCTTACTCTAAATCAGCTGAC

GGCAGCGCCATTGAAAAGAGATTTTGATTGAAGCGATATCATCTTATC

CTCCAGCGATTCGTATTTTAACTTTGCTAGAAGATGGACAACATTTGAC

AAAGTTTGATCTTGGCAAGAATTTAGGTTTTAGTGGAGAAAGTGGATTT

ACTTCTCTACCGGAAGGAATTCTTTTAGATACTCTAGCTAATGCTATGC

CTAAAGATAAAGGCGAAATTCGTAATAATTGGGAAGGATCTTCAGATAA

GTACGCAAGAATGATAGGTGGTTGGCTGGATAAACTAGGATTAGTAAAG

CAAGGAAAAAAAGAATTTATCATTCCTACTTTGGGTAAGCCGGACAATA

AAGAGTTTATATCCCACGCTTTTAAAATTACTGGAGAAGGTTTGAAAGT

ACTGCGTCGAGCAAAAGGCTCTACAAAATTTACACGTGTACCTAAAAGA

GTATATTGGGAAATGCTTGCTACAAACCTAACCGATAAAGAGTATGTAA

GAACAAGAAGAGCTTTGATTTTAGAAATATTAATCAAAGCTGGATCATT

AAAAATAGAACAAATACAAGACAACTTGAAGAAATTAGGATTTGATGAA

GTTATAGAAACTATTGAAAATGATATCAAAGGCTTAATTAACACAGGTA

TATTTATAGAAATCAAAGGGCGATTTTATCAATTGAAAGACCATATTCT

TCAATTTGTAATACCTAATCGTGGTGTGACTAAGCAACTAGTCAAAAGT

GAACTGGAGGAGAAGAAATCTGAACTTCGTCATAAATTGAAATATGTGC

CTCATGAATATATTGAATTAATTGAAATTGCCAGAAATTCCACTCAGGA

TAGAATTCTTGAAATGAAGGTAATGGAATTTTTTATGAAAGTTTATGGA

TATAGAGGTAAACATTTGGGTGGATCAAGGAAACCGGACGGAGCAATTT

ATACTGTCGGATCTCCTATTGATTACGGTGTGATCGTGGATACTAAAGC

TTATAGCGGAGGTTATAATCTGCCAATTGGCCAAGCAGATGAAATGCAA

CGATATGTCGAAGAAAATCAAACACGAAACAAACATATCAACCCTAATG

AATGGTGGAAAGTCTATCCATCTTCTGTAACGGAATTTAAGTTTTTATT

TGTGAGTGGTCACTTTAAAGGAAACTACAAAGCTCAGCTTACACGATTA

AATCATATCACTAATTGTAATGGAGCTGTTCTTAGTGTAGAAGAGCTTT

TAATTGGTGGAGAAATGATTAAAGCCGGCACATTAACCTTAGAGGAAGT

GAGACGGAAATTTAATAACGGCGAGATAAACTTTTAA
```

In some embodiments, the FokI nuclease used herein is at least about 50% identical SEQ ID NO:4, e.g., to amino acids 388-583 or 408-583 of SEQ ID NO:4. These variant nucleases must retain the ability to cleave DNA. In some embodiments, the nucleotide sequences are about 50%, 55%, 60%, 65%, 70%, 75%, 80%, 85%, 90%, 95%, 99% or 100% identical to amino acids 388-583 or 408-583 of SEQ ID NO:4. In some embodiments, any differences from amino acids 388-583 or 408-583 of SEQ ID NO:4 are in non-conserved regions.

To determine the percent identity of two sequences, the sequences are aligned for optimal comparison purposes (gaps are introduced in one or both of a first and a second amino acid or nucleic acid sequence as required for optimal alignment, and non-homologous sequences can be disregarded for comparison purposes). The length of a reference sequence aligned for comparison purposes is at least 50% (in some embodiments, about 50%, 55%, 60%, 65%, 70%, 75%, 85%, 90%, 95%, or 100% of the length of the reference sequence is aligned). The nucleotides or residues at corresponding positions are then compared. When a position in the first sequence is occupied by the same nucleotide or residue as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For purposes of the present application, the percent identity between two amino acid sequences is determined using the Needleman and Wunsch ((1970) J. Mol. Biol. 48:444-453) algorithm which has been incorporated into the GAP program in the GCG software package, using a Blossum 62 scoring matrix with a gap penalty of 12, a gap extend penalty of 4, and a frameshift gap penalty of 5.

Cas9

Figure 1:
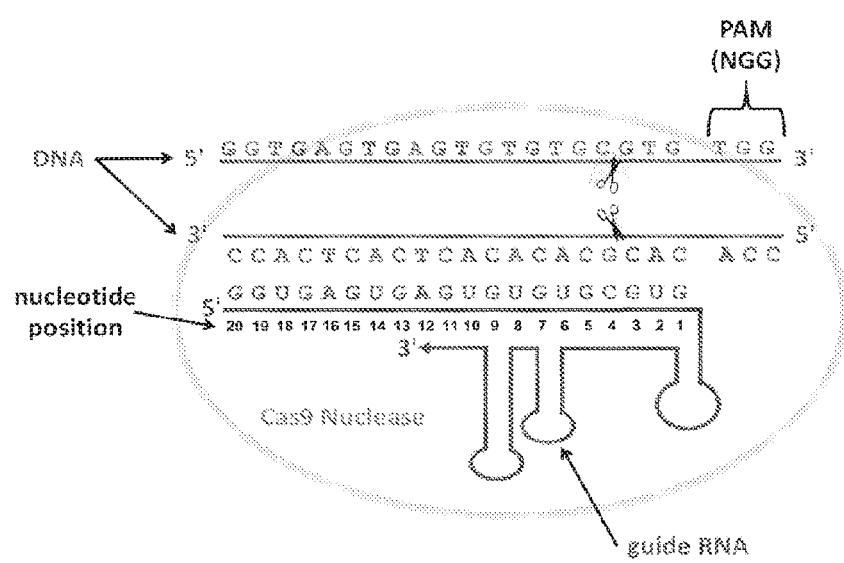
FIG. 1: Schematic illustrating a gRNA/Cas9 nuclease complex bound to its target DNA site. Scissors indicate approximate cleavage points of the Cas9 nuclease on the genomic DNA target site. Note the numbering of nucleotides on the guide RNA proceeds in an inverse fashion from 5' to 3'.

A number of bacteria express Cas9 protein variants. The Cas9 from *Streptococcus pyogenes* is presently the most commonly used; some of the other Cas9 proteins have high levels of sequence identity with the *S. pyogenes* Cas9 and use the same guide RNAs. Others are more diverse, use different gRNAs, and recognize different PAM sequences as well (the 2-5 nucleotide sequence specified by the protein which is adjacent to the sequence specified by the RNA). Chylinski et al. classified Cas9 proteins from a large group of bacteria (RNA Biology 10:5, 1-12; 2013), and a large number of Cas9 proteins are listed in supplementary FIG. 1 and supplementary table 1 thereof, which are incorporated by reference herein. Additional Cas9 proteins are described in Esvelt et al., Nat Methods. 2013 November; 10(11):1116-21 and Fonfara et al., "Phylogeny of Cas9 determines functional exchangeability of dual-RNA and Cas9 among orthologous type II CRISPR-Cas systems." Nucleic Acids Res. 2013 Nov. 22. [Epub ahead of print] doi:10.1093/nar/gkt1074.

Cas9 molecules of a variety of species can be used in the methods and compositions described herein. While the *S. pyogenes* and *S. thermophilus* Cas9 molecules are the subject of much of the disclosure herein, Cas9 molecules of, derived from, or based on the Cas9 proteins of other species listed herein can be used as well. In other words, while the much of the description herein uses *S. pyogenes* and *S. thermophilus* Cas9 molecules, Cas9 molecules from the other species can replace them. Such species include those set forth in the following table, which was created based on supplementary FIG. 1 of Chylinski et al., 2013.

| Alternative Cas9 proteins | |
|---|---|
| GenBank Acc No. | Bacterium |
| 303229466 | *Veillonella atypica* ACS-134-V-Col7a |
| 34762592 | *Fusobacterium nucleatum* subsp. *vincentii* |
| 374307738 | *Filifactor alocis* ATCC 35896 |
| 320528778 | *Solobacterium moorei* F0204 |
| 291520705 | *Coprococcus catus* GD-7 |
| 42525843 | *Treponema denticola* ATCC 35405 |
| 304438954 | *Peptoniphilus duerdenii* ATCC BAA-1640 |
| 224543312 | *Catenibacterium mitsuokai* DSM 15897 |

| Alternative Cas9 proteins | |
|---|---|
| GenBank Acc No. | Bacterium |
| 24379809 | Streptococcus mutans UA159 |
| 15675041 | Streptococcus pyogenes SF370 |
| 16801805 | Listeria innocua Clip11262 |
| 116628213 | Streptococcus thermophilus LMD-9 |
| 323463801 | Staphylococcus pseudintermedius ED99 |
| 352684361 | Acidaminococcus intestini RyC-MR95 |
| 302336020 | Olsenella uli DSM 7084 |
| 366983953 | Oenococcus kitaharae DSM 17330 |
| 310286728 | Bifidobacterium bifidum S17 |
| 258509199 | Lactobacillus rhamnosus GG |
| 300361537 | Lactobacillus gasseri JV-V03 |
| 169823755 | Finegoldia magna ATCC 29328 |
| 47458868 | Mycoplasma mobile 163K |
| 284931710 | Mycoplasma gallisepticum str. F |
| 363542550 | Mycoplasma ovipneumoniae SC01 |
| 384393286 | Mycoplasma canis PG 14 |
| 71894592 | Mycoplasma synoviae 53 |
| 238924075 | Eubacterium rectale ATCC 33656 |
| 116627542 | Streptococcus thermophilus LMD-9 |
| 315149830 | Enterococcus faecalis TX0012 |
| 315659848 | Staphylococcus lugdunensis M23590 |
| 160915782 | Eubacterium dolichum DSM 3991 |
| 336393381 | Lactobacillus coryniformis subsp. torquens |
| 310780384 | Ilyobacter polytropus DSM 2926 |
| 325677756 | Ruminococcus albus 8 |
| 187736489 | Akkermansia muciniphila ATCC BAA-835 |
| 117929158 | Acidothermus cellulolyticus 11B |
| 189440764 | Bifidobacterium longum DJO10A |
| 283456135 | Bifidobacterium dentium Bd1 |
| 38232678 | Corynebacterium diphtheriae NCTC 13129 |
| 187250660 | Elusimicrobium minutum Pei191 |
| 319957206 | Nitratifractor salsuginis DSM 16511 |
| 325972003 | Sphaerochaeta globus str. Buddy |
| 261414553 | Fibrobacter succinogenes subsp. succinogenes |
| 60683389 | Bacteroides fragilis NCTC 9343 |
| 256819408 | Capnocytophaga ochracea DSM 7271 |
| 90425961 | Rhodopseudomonas palustris BisB18 |
| 373501184 | Prevotella micans F0438 |
| 294674019 | Prevotella ruminicola 23 |
| 365959402 | Flavobacterium columnare ATCC 49512 |
| 312879015 | Aminomonas paucivorans DSM 12260 |
| 83591793 | Rhodospirillum rubrum ATCC 11170 |
| 294086111 | Candidatus Puniceispirillum marinum IMCC1322 |
| 121608211 | Verminephrobacter eiseniae EF01-2 |
| 344171927 | Ralstonia syzygii R24 |
| 159042956 | Dinoroseobacter shibae DFL 12 |
| 288957741 | Azospirillum sp- B510 |
| 92109262 | Nitrobacter hamburgensis X14 |
| 148255343 | Bradyrhizobium sp- BTAi1 |
| 34557790 | Wolinella succinogenes DSM 1740 |
| 218563121 | Campylobacter jejuni subsp. jejuni |
| 291276265 | Helicobacter mustelae 12198 |
| 229113166 | Bacillus cereus Rock1-15 |
| 222109285 | Acidovorax ebreus TPSY |
| 189485225 | uncultured Termite group 1 |
| 182624245 | Clostridium perfringens D str. |
| 220930482 | Clostridium cellulolyticum H10 |
| 154250555 | Parvibaculum lavamentivorans DS-1 |
| 257413184 | Roseburia intestinalis L1-82 |
| 218767588 | Neisseria meningitidis Z2491 |
| 15602992 | Pasteurella multocida subsp. multocida |
| 319941583 | Sutterella wadsworthensis 3 1 |
| 254447899 | gamma proteobacterium HTCC5015 |
| 54296138 | Legionella pneumophila str. Paris |
| 331001027 | Parasutterella excrementihominis YIT 11859 |
| 34557932 | Wolinella succinogenes DSM 1740 |
| 118497352 | Francisella novicida U112 |

The constructs and methods described herein can include the use of any of those Cas9 proteins, and their corresponding guide RNAs or other guide RNAs that are compatible. The Cas9 from *Streptococcus thermophilus* LMD-9 CRISPR1 system has also been shown to function in human cells in Cong et al (Science 339, 819 (2013)). Cas9 orthologs from *N. meningitides* are described in Hou et al., Proc Natl Acad Sci USA. 2013 Sep. 24; 110(39):15644-9 and Esvelt et al., Nat Methods. 2013 November; 10(11):1116-21. Additionally, Jinek et al. showed in vitro that Cas9 orthologs from *S. thermophilus* and *L. innocua*, (but not from *N. meningitidis* or *C. jejuni*, which likely use a different guide RNA), can be guided by a dual *S. pyogenes* gRNA to cleave target plasmid DNA, albeit with slightly decreased efficiency.

In some embodiments, the present system utilizes the Cas9 protein from *S. pyogenes*, either as encoded in bacteria or codon-optimized for expression in mammalian cells, containing mutations at D10, E762, H983, or D986 and H840 or N863, e.g., D10A/D10N and H840A/H840N/H840Y, to render the nuclease portion of the protein catalytically inactive; substitutions at these positions could be alanine (as they are in Nishimasu al., Cell 156, 935-949 (2014)) or they could be other residues, e.g., glutamine, asparagine, tyrosine, serine, or aspartate, e.g., E762Q, H983N, H983Y, D986N, N863D, N863S, or N863H (FIG. 1C). The sequence of the catalytically inactive *S. pyogenes* Cas9 that can be used in the methods and compositions described herein is as follows; the exemplary mutations of D10A and H840A are in bold and underlined.

```
                                        (SEQ ID NO: 5)
         10         20         30         40
MDKKYSIGLA IGTNSVGWAV ITDEYKVPSK KFKVLGNTDR 50         60         70         80
HSIKKNLIGA LLFDSGETAE ATRLKRTARR RYTRRKNRIC 90        100        110        120
YLQEIFSNEM AKVDDSFFHR LEESFLVEED KKHERHPIFG 130        140        150        160
NIVDEVAYHE KYPTIYHLRK KLVDSTDKAD LRLIYLALAH 170        180        190        200
MIKFRGHFLI EGDLNPDNSD VDKLFIQLVQ TYNQLFEENP 210        220        230        240
INASGVDAKA ILSARLSKSR RLENLIAQLP GEKKNGLFGN 250        260        270        280
LIALSLGLTP NFKSNFDLAE DAKLQLSKDT YDDDLDNLLA 290        300        310        320
QIGDQYADLF LAAKNLSDAI LLSDILRVNT EITKAPLSAS 330        340        350        360
MIKRYDEHHQ DLTLLKALVR QQLPEKYKEI FFDQSKNGYA 370        380        390        400
GYIDGGASQE EFYKFIKPIL EKMDGTEELL VKLNREDLLR 410        420        430        440
KQRTFDNGSI PHQIHLGELH AILRRQEDFY PFLKDNREKI 450        460        470        480
EKILTFRIPY YVGPLARGNS RFAWMTRKSE ETITPWNFEE 490        500        510        520
VVDKGASAQS FIERMTNFDK NLPNEKVLPK HSLLYEYFTV 530        540        550        560
YNELTKVKYV TEGMRKPAFL SGEQKKAIVD LLFKTNRKVT 570        580        590        600
VKQLKEDYFK KIECFDSVEI SGVEDRFNAS LGTYHDLLKI 610        620        630        640
IKDKDFLDNE ENEDILEDIV LTLTLFEDRE MIEERLKTYA 650        660        670        680
HLFDDKVMKQ LKRRRYTGWG RLSRKLINGI RDKQSGKTIL
```

-continued

```
          690         700         710         720
    DFLKSDGFAN  RNFMQLIHDD  SLTFKEDIQK  AQVSGQGDSL 730         740         750         760
    HEHIANLAGS  PAIKKGILQT  VKVVDELVKV  MGRHKPENIV 770         780         790         800
    IEMARENQTT  QKGQKNSRER  MKRIEEGIKE  LGSQILKEHP 810         820         830         840
    VENTQLQNEK  LYLYYLQNGR  DMYVDQELDI  NRLSDYDVDA 850         860         870         880
    IVPQSFLKDD  SIDNKVLTRS  DKNRGKSDNV  PSEEVVKKMK 890         900         910         920
    NYWRQLLNAK  LITQRKFDNL  TKAERGGLSE  LDKAGFIKRQ 930         940         950         960
    LVETRQITKH  VAQILDSRMN  TKYDENDKLI  REVKVITLKS 970         980         990        1000
    KLVSDFRKDF  QFYKVREINN  YHHAHDAYLN  AVVGTALIKK 1010        1020        1030        1040
    YPKLESEFVY  GDYKVYDVRK  MIAKSEQEIG  KATAKYFFYS 1050        1060        1070        1080
    NIMNFFKTEI  TLANGEIRKR  PLIETNGETG  EIVWDKGRDF 1090        1100        1110        1120
    ATVRKVLSMP  QVNIVKKTEV  QTGGFSKESI  LPKRNSDKLI 1130        1140        1150        1160
    ARKKDWDPKK  YGGFDSPTVA  YSVLVVAKVE  KGKSKKLKSV 1170        1180        1190        1200
    KELLGITIME  RSSFEKNPID  FLEAKGYKEV  KKDLIIKLPK 1210        1220        1230        1240
    YSLFELENGR  KRMLASAGEL  QKGNELALPS  KYVNFLYLAS 1250        1260        1270        1280
    HYEKLKGSPE  DNEQKQLFVE  QHKHYLDEII  EQISEFSKRV 1290        1300        1310        1320
    ILADANLDKV  LSAYNKHRDK  PIREQAENII  HLFTLTNLGA 1330        1340        1350        1360
    PAAFKYFDTT  IDRKRYTSTK  EVLDATLIHQ  SITGLYETRI

DLSQLGGD
```

In some embodiments, the Cas9 nuclease used herein is at least about 50% identical to the sequence of S. pyogenes Cas9, i.e., at least 50% identical to SEQ ID NO:5. In some embodiments, the nucleotide sequences are about 50%, 55%, 60%, 65%, 70%, 75%, 80%, 85%, 90%, 95%, 99% or 100% identical to SEQ ID NO:5. In some embodiments, any differences from SEQ ID NO:5 are in non-conserved regions, as identified by sequence alignment of sequences set forth in Chylinski et al., RNA Biology 10:5, 1-12; 2013 (e.g., in supplementary FIG. 1 and supplementary table 1 thereof); Esvelt et al., Nat Methods. 2013 November; 10(11):1116-21 and Fonfara et al., Nucl. Acids Res. (2014) 42 (4): 2577-2590. [Epub ahead of print 2013 Nov. 22] doi:10.1093/nar/gkt1074. Identity is determined as set forth above.

Guide RNAs (gRNAs)

Guide RNAs generally speaking come in two different systems: System 1, which uses separate crRNA and tracr-RNAs that function together to guide cleavage by Cas9, and System 2, which uses a chimeric crRNA-tracrRNA hybrid that combines the two separate guide RNAs in a single system (referred to as a single guide RNA or sgRNA, see also Jinek et al., Science 2012; 337:816-821). The tracrRNA can be variably truncated and a range of lengths has been shown to function in both the separate system (system 1) and the chimeric gRNA system (system 2). For example, in some embodiments, tracrRNA may be truncated from its 3' end by at least 1, 2, 3, 4, 5, 6, 7, 8, 9, 10, 15, 20, 25, 30, 35 or 40 nts. In some embodiments, the tracrRNA molecule may be truncated from its 5' end by at least 1, 2, 3, 4, 5, 6, 7, 8, 9, 10, 15, 20, 25, 30, 35 or 40 nts. Alternatively, the tracrRNA molecule may be truncated from both the 5' and 3' end, e.g., by at least 1, 2, 3, 4, 5, 6, 7, 8, 9, 10, 15 or 20 nts on the 5' end and at least 1, 2, 3, 4, 5, 6, 7, 8, 9, 10, 15, 20, 25, 30, 35 or 40 nts on the 3' end. See, e.g., Jinek et al., Science 2012; 337:816-821; Mali et al., Science. 2013 Feb. 15; 339(6121):823-6; Cong et al., Science. 2013 Feb. 15; 339 (6121):819-23; and Hwang and Fu et al., Nat Biotechnol. 2013 March; 31(3):227-9; Jinek et al., Elife 2, e00471 (2013)). For System 2, generally the longer length chimeric gRNAs have shown greater on-target activity but the relative specificities of the various length gRNAs currently remain undefined and therefore it may be desirable in certain instances to use shorter gRNAs. In some embodiments, the gRNAs are complementary to a region that is within about 100-800 bp upstream of the transcription start site, e.g., is within about 500 bp upstream of the transcription start site, includes the transcription start site, or within about 100-800 bp, e.g., within about 500 bp, downstream of the transcription start site. In some embodiments, vectors (e.g., plasmids) encoding more than one gRNA are used, e.g., plasmids encoding, 2, 3, 4, 5, or more gRNAs directed to different sites in the same region of the target gene.

Cas9 nuclease can be guided to specific 17-20 nt genomic targets bearing an additional proximal protospacer adjacent motif (PAM), e.g., of sequence NGG, using a guide RNA, e.g., a single gRNA or a tracrRNA/crRNA, bearing 17-20 nts at its 5' end that are complementary to the complementary strand of the genomic DNA target site. Thus, the present methods can include the use of a single guide RNA comprising a crRNA fused to a normally trans-encoded tracr-RNA, e.g., a single Cas9 guide RNA as described in Mali et al., Science 2013 Feb. 15; 339(6121):823-6, with a sequence at the 5' end that is complementary to the target sequence, e.g., of 25-17, optionally 20 or fewer nucleotides (nts), e.g., 20, 19, 18, or 17 nts, preferably 17 or 18 nts, of the complementary strand to a target sequence immediately 5' of a protospacer adjacent motif (PAM), e.g., NGG NAG, or NNGG. In some embodiments, the single Cas9 guide RNA consists of the sequence:

```
                                           (SEQ ID NO: 6)
(X17-20) GUUUUAGAGCUAGAAAUAGCAAGUUAAAAUAAGGCUAGUC
CG (XN);

(SEQ ID NO: 7)
(X17-20) GUUUUAGAGCUAUGCUGAAAAGCAUAGCAAGUUAAAAUAA
GGCUAGUCCGUUAUC (XN);

(SEQ ID NO: 8)
(X17-20) GUUUUAGAGCUAUGCUGUUUUGGAAACAAAACAGCAUAGC
AAGUUAAAAUAAGGCUAGUCCGUUAUC (XN);

(SEQ ID NO: 9)
(X17-20) GUUUUAGAGCUAGAAAUAGCAAGUUAAAAUAAGGCUAGUC
CGUUAUCAACUUGAAAAAGUGGCACCGAGUCGGUGC (XN), (SEQ ID NO: 10)
(X17-20) GUUUAAGAGCUAGAAAUAGCAAGUUUAAAUAAGGCUAGUC
CGUUAUCAACUUGAAAAAGUGGCACCGAGUCGGUGC;
```

-continued (SEQ ID NO: 11)
(X$_{17-20}$) GUUUUAGAGCUAUGCUGGAAACAGCAUAGCAAGUUUAAAU
AAGGCUAGUCCGUUAUCAACUUGAAAAAGUGGCACCGAGUCGGUGC;
or (SEQ ID NO: 12)
(X$_{17-20}$) GUUUAAGAGCUAUGCUGGAAACAGCAUAGCAAGUUUAAAU
AAGGCUAGUCCGUUAUCAACUUGAAAAAGUGGCACCGAGUCGGUGC;

wherein X$_{17-20}$ is the nucleotide sequence complementary to 17-20 consecutive nucleotides of the target sequence. DNAs encoding the single guide RNAs have been described previously in the literature (Jinek et al., Science. 337(6096): 816-21 (2012) and Jinek et al., Elife. 2:e00471 (2013)).

The guide RNAs can include X$_N$ which can be any sequence, wherein N (in the RNA) can be 0-200, e.g., 0-100, 0-50, or 0-20, that does not interfere with the binding of the ribonucleic acid to Cas9.

In some embodiments, the guide RNA includes one or more Adenine (A) or Uracil (U) nucleotides on the 3' end. In some embodiments the RNA includes one or more U, e.g., 1 to 8 or more Us (e.g., U, UU, UUU, UUUU, UUUUU, UUUUUU, UUUUUUU, UUUUUUUU) at the 3' end of the molecule, as a result of the optional presence of one or more Ts used as a termination signal to terminate RNA PolIII transcription.

Although some of the examples described herein utilize a single gRNA, the methods can also be used with dual gRNAs (e.g., the crRNA and tracrRNA found in naturally occurring systems). In this case, a single tracrRNA would be used in conjunction with multiple different crRNAs expressed using the present system, e.g., the following:
(X$_{17-20}$)GUUUUAGAGCUA (SEQ ID NO:13);
(X$_{17-20}$)GUUUUAGAGCUAUGCUGUUUUG (SEQ ID NO:14); or
(X$_{17-20}$)GUUUUAGAGCUAUGCU (SEQ ID NO:15); and
a tracrRNA sequence. In this case, the crRNA is used as the guide RNA in the methods and molecules described herein, and the tracrRNA can be expressed from the same or a different DNA molecule. In some embodiments, the methods include contacting the cell with a tracrRNA comprising or consisting of the sequence GGAACCAUUCAAAACAG-CAUAGCAAGUUAAAAUAAGGCUAGUCCGUUA UCAACUUGAAAAAGUGGCACCGAGUCGGUGC (SEQ ID NO:16) or an active portion thereof (an active portion is one that retains the ability to form complexes with Cas9 or dCas9). In some embodiments, the tracrRNA molecule may be truncated from its 3' end by at least 1, 2, 3, 4, 5, 6, 7, 8, 9, 10, 15, 20, 25, 30, 35 or 40 nts. In another embodiment, the tracrRNA molecule may be truncated from its 5' end by at least 1, 2, 3, 4, 5, 6, 7, 8, 9, 10, 15, 20, 25, 30, 35 or 40 nts. Alternatively, the tracrRNA molecule may be truncated from both the 5' and 3' end, e.g., by at least 1, 2, 3, 4, 5, 6, 7, 8, 9, 10, 15 or 20 nts on the 5' end and at least 1, 2, 3, 4, 5, 6, 7, 8, 9, 10, 15, 20, 25, 30, 35 or 40 nts on the 3' end. Exemplary tracrRNA sequences in addition to SEQ ID NO:8 include the following: UAG-CAAGUUAAAAUAAGGCUAGUCCGUUAUCAAC-UUGAAAAAGUGGCA CCGAGUCGGUGC (SEQ ID NO:17) or an active portion thereof; or AGCAUAG-CAAGUUAAAAUAAGGCUAGUCCGUUAUCAAC-UUGAAAAAGU GGCACCGAGUCGGUGC (SEQ ID NO:18) or an active portion thereof.

In some embodiments wherein (X$_{17-20}$)GUUUUA-GAGCUAUGCUGUUUUG (SEQ ID NO:14) is used as a crRNA, the following tracrRNA is used: GGAACCAUU-CAAAACAGCAUAGCAAGUUAAAAUAAGGCUAGU-CCGUUA UCAACUUGAAAAAGUGGCACCGAGUCG-GUGC (SEQ ID NO:16) or an active portion thereof. In some embodiments wherein (X$_{17-20}$)GUUUUAGAGCUA (SEQ ID NO:13) is used as a crRNA, the following tracr-RNA is used: UAGCAAGUUAAAAUAAGGCUAGUC-CGUUAUCAACUUGAAAAAGUGGCA CCGAGUCG-GUGC (SEQ ID NO:17) or an active portion thereof. In some embodiments wherein (X$_{17-20}$)GUUUUAGAGC-UAUGCU (SEQ ID NO:15) is used as a crRNA, the following tracrRNA is used: AGCAUAG-CAAGUUAAAAUAAGGCUAGUCCGUUAUCAAC-UUGAAAAAGU GGCACCGAGUCGGUGC (SEQ ID NO:18) or an active portion thereof.

In some embodiments, the gRNA is targeted to a site that is at least three or more mismatches different from any sequence in the rest of the genome in order to minimize off-target effects.

Modified RNA oligonucleotides such as locked nucleic acids (LNAs) have been demonstrated to increase the specificity of RNA-DNA hybridization by locking the modified oligonucleotides in a more favorable (stable) conformation. For example, 2'-O-methyl RNA is a modified base where there is an additional covalent linkage between the 2' oxygen and 4' carbon which when incorporated into oligonucleotides can improve overall thermal stability and selectivity (Formula I).

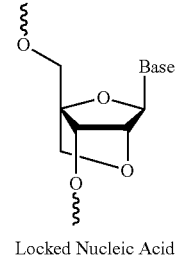

Formula I

Locked Nucleic Acid

Thus in some embodiments, the tru-gRNAs disclosed herein may comprise one or more modified RNA oligonucleotides. For example, the truncated guide RNAs molecules described herein can have one, some or all of the 17-18 or 17-19 nts 5' region of the guideRNA complementary to the target sequence are modified, e.g., locked (2'-O-4'-C methylene bridge), 5'-methylcytidine, 2'-O-methyl-pseudouridine, or in which the ribose phosphate backbone has been replaced by a polyamide chain (peptide nucleic acid), e.g., a synthetic ribonucleic acid.

In other embodiments, one, some or all of the nucleotides of the tru-gRNA sequence may be modified, e.g., locked (2'-O-4'-C methylene bridge), 5'-methylcytidine, 2'-O-methyl-pseudouridine, or in which the ribose phosphate backbone has been replaced by a polyamide chain (peptide nucleic acid), e.g., a synthetic ribonucleic acid.

In some embodiments, the single guide RNAs and/or crRNAs and/or tracrRNAs can include one or more Adenine (A) or Uracil (U) nucleotides on the 3' end.

Existing Cas9-based RGNs use gRNA-DNA heteroduplex formation to guide targeting to genomic sites of interest. However, RNA-DNA heteroduplexes can form a more promiscuous range of structures than their DNA-DNA counterparts. In effect, DNA-DNA duplexes are more sensitive to mismatches, suggesting that a DNA-guided nuclease may not bind as readily to off-target sequences, making them comparatively more specific than RNA-guided nucleases. Thus, the guide RNAs usable in the methods described herein can be hybrids, i.e., wherein one or more deoxyribonucleotides, e.g., a short DNA oligonucleotide, replaces all or part of the gRNA, e.g., all or part of the complementarity region of a gRNA. This DNA-based molecule could replace either all or part of the gRNA in a single gRNA system or alternatively might replace all of part of the crRNA and/or tracrRNA in a dual crRNA/tracrRNA system. Such a system that incorporates DNA into the complementarity region should more reliably target the intended genomic DNA sequences due to the general intolerance of DNA-DNA duplexes to mismatching compared to RNA-DNA duplexes. Methods for making such duplexes are known in the art, See, e.g., Barker et al., BMC Genomics. 2005 Apr. 22; 6:57; and Sugimoto et al., Biochemistry. 2000 Sep. 19; 39(37):11270-81.

In addition, in a system that uses separate crRNA and tracrRNA, one or both can be synthetic and include one or more modified (e.g., locked) nucleotides or deoxyribonucleotides.

In a cellular context, complexes of Cas9 with these synthetic gRNAs could be used to improve the genome-wide specificity of the CRISPR/Cas9 nuclease system. The methods described can include expressing in a cell, or contacting the cell with, a Cas9 gRNA plus a fusion protein as described herein.

Expression Systems

In order to use the fusion proteins described, it may be desirable to express them from a nucleic acid that encodes them. This can be performed in a variety of ways. For example, the nucleic acid encoding the guide RNA can be cloned into an intermediate vector for transformation into prokaryotic or eukaryotic cells for replication and/or expression. Intermediate vectors are typically prokaryote vectors, e.g., plasmids, or shuttle vectors, or insect vectors, for storage or manipulation of the nucleic acid encoding the fusion proteins for production of the fusion proteins. The nucleic acid encoding the fusion proteins can also be cloned into an expression vector, for administration to a plant cell, animal cell, preferably a mammalian cell or a human cell, fungal cell, bacterial cell, or protozoan cell.

To obtain expression, a sequence encoding a fusion protein is typically subcloned into an expression vector that contains a promoter to direct transcription. Suitable bacterial and eukaryotic promoters are well known in the art and described, e.g., in Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 2010). Bacterial expression systems for expressing the engineered protein are available in, e.g., *E. coli, Bacillus* sp., and *Salmonella* (Palva et al., 1983, Gene 22:229-235). Kits for such expression systems are commercially available. Eukaryotic expression systems for mammalian cells, yeast, and insect cells are well known in the art and are also commercially available.

The promoter used to direct expression of a nucleic acid depends on the particular application. For example, a strong constitutive promoter is typically used for expression and purification of fusion proteins. In contrast, when the guide RNA is to be administered in vivo for gene regulation, either a constitutive or an inducible promoter can be used, depending on the particular use of the guide RNA. In addition, a preferred promoter for administration of the guide RNA can be a weak promoter, such as HSV TK or a promoter having similar activity. The promoter can also include elements that are responsive to transactivation, e.g., hypoxia response elements, Gal4 response elements, lac repressor response element, and small molecule control systems such as tetracycline-regulated systems and the RU-486 system (see, e.g., Gossen & Bujard, 1992, Proc. Natl. Acad. Sci. USA, 89:5547; Oligino et al., 1998, Gene Ther., 5:491-496; Wang et al., 1997, Gene Ther., 4:432-441; Neering et al., 1996, Blood, 88:1147-55; and Rendahl et al., 1998, Nat. Biotechnol., 16:757-761).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the gRNA, and any signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use of the gRNA, e.g., expression in plants, animals, bacteria, fungus, protozoa, etc. Standard bacterial expression vectors include plasmids such as pBR322 based plasmids, pSKF, pET23D, and commercially available tag-fusion expression systems such as GST and LacZ.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

The vectors for expressing the guide RNAs can include RNA Pol III promoters to drive expression of the guide RNAs, e.g., the H1, U6 or 7SK promoters. These human promoters allow for expression of gRNAs in mammalian cells following plasmid transfection. Alternatively, a T7 promoter may be used, e.g., for in vitro transcription, and the RNA can be transcribed in vitro and purified. Vectors suitable for the expression of short RNAs, e.g., siRNAs, shRNAs, or other small RNAs, can be used. With the Cys4-based multiplex system described in FIG. 4B, multiple gRNAs can be expressed in a single transcript (driven by a RNA Pol II or Pol III promoter) and then cleaved out from that larger transcript.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with the gRNA encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., 1989, J. Biol. Chem., 264:17619-22; Guide to Protein Purification, in Methods in Enzymology, vol. 182 (Deutscher, ed., 1990)). Transformation of eukaryotic and prokaryotic cells are performed according to standard techniques (see, e.g., Morrison, 1977, J. Bacteriol. 132:349-351; Clark-Curtiss & Curtiss, Methods in Enzymology 101:347-362 (Wu et al., eds, 1983).

Any of the known procedures for introducing foreign nucleotide sequences into host cells may be used. These include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the gRNA.

The present invention includes the vectors and cells comprising the vectors.

EXAMPLES

The invention is further described in the following examples, which do not limit the scope of the invention described in the claims.

Example 1. Assessing Specificity of RNA-Guided Endonucleases

CRISPR RNA-guided nucleases (RGNs) have rapidly emerged as a facile and efficient platform for genome editing. This example describes the use of a human cell-based reporter assay to characterize off-target cleavage of Cas9-based RGNs.
Materials and Methods
The following materials and methods were used in Example 1.
Construction of Guide RNAs
DNA oligonucleotides harboring variable 20 nt sequences for Cas9 targeting were annealed to generate short double-strand DNA fragments with 4 bp overhangs compatible with ligation into BsmBI-digested plasmid pMLM3636. Cloning of these annealed oligonucleotides generates plasmids encoding a chimeric+103 single-chain guide RNA with 20 variable 5' nucleotides under expression of a U6 promoter (Hwang et al., Nat Biotechnol 31, 227-229 (2013); Mali et al., Science 339, 823-826 (2013)). pMLM3636 and the expression plasmid pJDS246 (encoding a codon optimized version of Cas9 used in this study are both available through the non-profit plasmid distribution service Addgene (addgene.org/crispr-cas).
EGFP Activity Assays
U2OS.EGFP cells harboring a single integrated copy of an EGFP-PEST fusion gene were cultured as previously described (Reyon et al., Nat Biotech 30, 460-465 (2012)). For transfections, 200,000 cells were Nucleofected with the indicated amounts of gRNA expression plasmid and pJDS246 together with 30 ng of a Td-tomato-encoding plasmid using the SE Cell Line 4D-Nucleofector™ X Kit (Lonza) according to the manufacturer's protocol. Cells were analyzed 2 days post-transfection using a BD LSRII flow cytometer. Transfections for optimizing gRNA/Cas9 plasmid concentration were performed in triplicate and all other transfections were performed in duplicate.

PCR Amplification and Sequence Verification of Endogenous Human Genomic Sites
PCR reactions were performed using Phusion Hot Start II high-fidelity DNA polymerase (NEB). Most loci amplified successfully using touchdown PCR (98° C., 10 s; 72-62° C., −1° C./cycle, 15 s; 72° C., 30 s]10 cycles, [98° C., 10 s; 62° C., 15 s; 72° C., 30 s]25 cycles). PCR for the remaining targets were performed with 35 cycles at a constant annealing temperature of 68° C. or 72° C. and 3% DMSO or 1M betaine, if necessary. PCR products were analyzed on a QIAXCEL capillary electrophoresis system to verify both size and purity. Validated products were treated with ExoSap-IT (Affymetrix) and sequenced by the Sanger method (MGH DNA Sequencing Core) to verify each target site.
Determination of RGN-Induced On- and Off-Target Mutation Frequencies in Human Cells
For U2OS.EGFP and K562 cells, $2 \times 10^5$ cells were transfected with 250 ng of gRNA expression plasmid or an empty U6 promoter plasmid (for negative controls), 750 ng of Cas9 expression plasmid, and 30 ng of td-Tomato expression plasmid using the 4D Nucleofector System according to the manufacturer's instructions (Lonza). For HEK293 cells, $1.65 \times 10^5$ cells were transfected with 125 ng of gRNA expression plasmid or an empty U6 promoter plasmid (for the negative control), 375 ng of Cas9 expression plasmid, and 30 ng of a td-Tomato expression plasmid using Lipofectamine LTX reagent according to the manufacturer's instructions (Life Technologies). Genomic DNA was harvested from transfected U2OS.EGFP, HEK293, or K562 cells using the QIAamp DNA Blood Mini Kit (QIAGEN), according to the manufacturer's instructions. To generate enough genomic DNA to amplify the off-target candidate sites, DNA from three Nucleofections (for U2OS.EGFP cells), two Nucleofections (for K562 cells), or two Lipofectamine LTX transfections was pooled together before performing T7EI. This was done twice for each condition tested, thereby generating duplicate pools of genomic DNA representing a total of four or six individual transfections. PCR was then performed using these genomic DNAs as templates as described above and purified using Ampure XP beads (Agencourt) according to the manufacturer's instructions. T7EI assays were performed as previously described (Reyon et al., 2012, supra).
DNA Sequencing of NHEJ-Mediated Indel Mutations
Purified PCR products used for the T7EI assay were cloned into Zero Blunt TOPO vector (Life Technologies) and plasmid DNAs were isolated using an alkaline lysis miniprep method by the MGH DNA Automation Core. Plasmids were sequenced using an M13 forward primer (5'-GTAAAACGACGGCCAG-3' (SEQ ID NO:19)) by the Sanger method (MGH DNA Sequencing Core).

Example 1a. Single Nucleotide Mismatches

To begin to define the specificity determinants of RGNs in human cells, a large-scale test was performed to assess the effects of systematically mismatching various positions within multiple gRNA/target DNA interfaces. To do this, a quantitative human cell-based enhanced green fluorescent protein (EGFP) disruption assay previously described (see Methods above and Reyon et al., 2012, supra) that enables rapid quantitation of targeted nuclease activities (FIG. 2B) was used. In this assay, the activities of nucleases targeted to a single integrated EGFP reporter gene can be quantified by assessing loss of fluorescence signal in human U2OS.EGFP cells caused by inactivating frameshift insertion/deletion (indel) mutations introduced by error prone non-homologous end-joining (NHEJ) repair of nuclease-induced double-stranded breaks (DSBs) (FIG. 2B). For the studies described here, three ~100 nt single gRNAs (sgRNAs) targeted to different sequences within EGFP were used, as follows:

```
EGFP Site 1
                                      (SEQ ID NO: 1)
GGGCACGGGCAGCTTGCCGGTGG EGFP Site 2
                                      (SEQ ID NO: 2)
GATGCCGTTCTTCTGCTTGTCGG EGFP Site 3
                                      (SEQ ID NO: 3)
GGTGGTGCAGATGAACTTCAGGG
```

Each of these sgRNAs can efficiently direct Cas9-mediated disruption of EGFP expression (see Example 1e and 2a, and FIGS. 3E (top) and 3F (top)).

In initial experiments, the effects of single nucleotide mismatches at 19 of 20 nucleotides in the complementary targeting region of three EGFP-targeted sgRNAs were tested. To do this, variant sgRNAs were generated for each of the three target sites harboring Watson-Crick transversion mismatches at positions 1 through 19 (numbered 1 to 20 in the 3' to 5' direction; see FIG. 1) and the abilities of these various sgRNAs to direct Cas9-mediated EGFP disruption in human cells tested (variant sgRNAs bearing a substitution at position 20 were not generated because this nucleotide is part of the U6 promoter sequence and therefore must remain a guanine to avoid affecting expression.)

For EGFP target site #2, single mismatches in positions 1-10 of the gRNA have dramatic effects on associated Cas9 activity (FIG. 2C, middle panel), consistent with previous studies that suggest mismatches at the 5' end of gRNAs are better tolerated than those at the 3' end (Jiang et al., Nat Biotechnol 31, 233-239 (2013); Cong et al., Science 339, 819-823 (2013); Jinek et al., Science 337, 816-821 (2012)). However, with EGFP target sites #1 and #3, single mismatches at all but a few positions in the gRNA appear to be well tolerated, even within the 3' end of the sequence. Furthermore, the specific positions that were sensitive to mismatch differed for these two targets (FIG. 2C, compare top and bottom panels)—for example, target site #1 was particularly sensitive to a mismatch at position 2 whereas target site #3 was most sensitive to mismatches at positions 1 and 8.

Example 1b. Multiple Mismatches

To test the effects of more than one mismatch at the gRNA/DNA interface, a series of variant sgRNAs bearing double Watson-Crick transversion mismatches in adjacent and separated positions were created and the abilities of these sgRNAs to direct Cas9 nuclease activity were tested in human cells using the EGFP disruption assay. All three target sites generally showed greater sensitivity to double alterations in which one or both mismatches occur within the 3' half of the gRNA targeting region. However, the magnitude of these effects exhibited site-specific variation, with target site #2 showing the greatest sensitivity to these double mismatches and target site #1 generally showing the least. To test the number of adjacent mismatches that can be tolerated, variant sgRNAs were constructed bearing increasing numbers of mismatched positions ranging from positions 19 to 15 in the 5' end of the gRNA targeting region (where single and double mismatches appeared to be better tolerated).

Testing of these increasingly mismatched sgRNAs revealed that for all three target sites, the introduction of three or more adjacent mismatches results in significant loss of RGN activity. A sudden drop off in activity occurred for three different EGFP-targeted gRNAs as one makes progressive mismatches starting from position 19 in the 5' end and adding more mismatches moving toward the 3' end. Specifically, gRNAs containing mismatches at positions 19 and 19+18 show essentially full activity whereas those with mismatches at positions 19+18+17, 19+18+17+16, and 19+18+17+16+15 show essentially no difference relative to a negative control (FIG. 2F). (Note that we did not mismatch position 20 in these variant gRNAs because this position needs to remain as a G because it is part of the U6 promoter that drives expression of the gRNA.)

Additional proof of that shortening gRNA complementarity might lead to RGNs with greater specificities was obtained in the following experiment: for four different EGFP-targeted gRNAs (FIG. 2H), introduction of a double mismatch at positions 18 and 19 did not significantly impact activity. However, introduction of another double mismatch at positions 10 and 11 then into these gRNAs results in near complete loss of activity. Interestingly introduction of only the 10/11 double mismatches does not generally have as great an impact on activity.

Taken together, these results in human cells confirm that the activities of RGNs can be more sensitive to mismatches in the 3' half of the gRNA targeting sequence. However, the data also clearly reveal that the specificity of RGNs is complex and target site-dependent, with single and double mismatches often well tolerated even when one or more mismatches occur in the 3' half of the gRNA targeting region. Furthermore, these data also suggest that not all mismatches in the 5' half of the gRNA/DNA interface are necessarily well tolerated.

In addition, these results strongly suggest that gRNAs bearing shorter regions of complementarity (specifically ~17 nts) will be more specific in their activities. We note that 17 nts of specificity combined with the 2 nts of specificity conferred by the PAM sequence results in specification of a 19 bp sequence, one of sufficient length to be unique in large complex genomes such as those found in human cells.

Example 1c. Off-Target Mutations

To determine whether off-target mutations for RGNs targeted to endogenous human genes could be identified, six sgRNAs that target three different sites in the VEGFA gene, one in the EMX1 gene, one in the RNF2 gene, and one in the FANCF gene were used. These six sgRNAs efficiently directed Cas9-mediated indels at their respective endogenous loci in human U2OS.EGFP cells as detected by T7 Endonuclease I (T7EI) assay (Methods above). For each of these six RGNs, we then examined dozens of potential off-target sites (ranging in number from 46 to as many as 64) for evidence of nuclease-induced NHEJ-mediated indel mutations in U2OS.EGFP cells. The loci assessed included all genomic sites that differ by one or two nucleotides as well as subsets of genomic sites that differ by three to six nucleotides and with a bias toward those that had one or more of these mismatches in the 5' half of the gRNA targeting sequence. Using the T7EI assay, four off-target sites (out of 53 candidate sites examined) for VEGFA site 1, twelve (out of 46 examined) for VEGFA site 2, seven (out of 64 examined) for VEGFA site 3 and one (out of 46 examined) for the EMX1 site were readily identified. No off-target mutations were detected among the 43 and 50 potential sites examined for the RNF2 or FANCF genes, respectively. The rates of mutation at verified off-target sites were very high, ranging from 5.6% to 125% (mean of 40%) of the rate observed at the intended target site. These bona fide off-targets included sequences with mismatches in the 3' end of the target site and with as many as a total of five mismatches, with most off-target sites occurring within protein coding genes. DNA sequencing of a subset of off-target sites provided additional molecular confirmation that indel mutations occur at the expected RGN cleavage site (FIGS. 8A-C).

Example 1d. Off-Target Mutations in Other Cell Types

Having established that RGNs can induce off-target mutations with high frequencies in U2OS.EGFP cells, it was next sought to determine whether these nucleases would also have these effects in other types of human cells. U2OS.EGFP cells had been chosen for initial experiments because these cells were previously used to evaluate the activities of TALENs[15] but human HEK293 and K562 cells have been more widely used to test the activities of targeted nucleases. Therefore, the activities of the four RGNs targeted to VEGFA sites 1, 2, and 3 and the EMX1 site were also assessed in HEK293 and K562 cells. Each of these four RGNs efficiently induced NHEJ-mediated indel mutations at their intended on-target site in these two additional human cell lines (as assessed by T7EI assay), albeit with somewhat lower mutation frequencies than those observed in U2OS.EGFP cells. Assessment of the 24 off-target sites for these four RGNs originally identified in U2OS.EGFP cells revealed that many were again mutated in HEK293 and K562 cells with frequencies similar to those at their corresponding on-target site. As expected, DNA sequencing of a subset of these off-target sites from HEK293 cells provided additional molecular evidence that alterations are occurring at the expected genomic loci. It is not known for certain why in HEK293 cells four and in K562 cells eleven of the off-target sites identified in U2OS.EGFP cells did not show detectable mutations. However, many of these off-target sites also showed relatively lower mutation frequencies in U2OS.EGFP cells. Therefore, mutation rates of these sites in HEK293 and K562 cells may be falling below the reliable detection limit of our T7EI assay (~2-5%) because RGNs generally appear to have lower activities in HEK293 and K562 cells compared with U2OS.EGFP cells in our experiments. Taken together, the results in HEK293 and K562 cells provide evidence that the high-frequency off-target mutations we observe with RGNs will be a general phenomenon seen in multiple human cell types.

Example 1e. Titration of gRNA- and Cas9-Expressing Plasmid Amounts Used for the EGFP Disruption Assay Single guide RNAs (sgRNAs) were generated for three different sequences (EGFP SITES 1-3, shown above) located upstream of EGFP nucleotide 502, a position at which the introduction of frameshift mutations via non-homologous end-joining can robustly disrupt expression of EGFP (Maeder, M. L. et al., Mol Cell 31, 294-301 (2008); Reyon, D. et al., Nat Biotech 30, 460-465 (2012)).

For each of the three target sites, a range of gRNA-expressing plasmid amounts (12.5 to 250 ng) was initially transfected together with 750 ng of a plasmid expressing a codon-optimized version of the Cas9 nuclease into our U2OS.EGFP reporter cells bearing a single copy, constitutively expressed EGFP-PEST reporter gene. All three RGNs efficiently disrupted EGFP expression at the highest concentration of gRNA plasmid (250 ng) (FIG. 3E (top)). However, RGNs for target sites #1 and #3 exhibited equivalent levels of disruption when lower amounts of gRNA-expressing plasmid were transfected whereas RGN activity at target site #2 dropped immediately when the amount of gRNA-expressing plasmid transfected was decreased (FIG. 3E (top)).

The amount of Cas9-encoding plasmid (range from 50 ng to 750 ng) transfected into our U2OS.EGFP reporter cells was titrated EGFP disruption assayed. As shown in FIG. 3F (top), target site #1 tolerated a three-fold decrease in the amount of Cas9-encoding plasmid transfected without substantial loss of EGFP disruption activity. However, the activities of RGNs targeting target sites #2 and #3 decreased immediately with a three-fold reduction in the amount of Cas9 plasmid transfected (FIG. 3F (top)). Based on these results, 25 ng/250 ng, 250 ng/750 ng, and 200 ng/750 ng of gRNA-/Cas9-expressing plasmids were used for EGFP target sites #1, #2, and #3, respectively, for the experiments described in Examples 1a-1d.

The reasons why some gRNA/Cas9 combinations work better than others in disrupting EGFP expression is not understood, nor is why some of these combinations are more or less sensitive to the amount of plasmids used for transfection. Although it is possible that the range of off-target sites present in the genome for these three sgRNAs might influence each of their activities, no differences were seen in the numbers of genomic sites that differ by one to six bps for each of these particular target sites (Table 1) that would account for the differential behavior of the three sgRNAs.

TABLE 1

Numbers of off-target sites in the human genome for six RGNs targeted to endogenous human genes and three RGNs targeted to the EGFP reporter gene

| Target Site | Number of mismatches to on-target site | | | | | | |
|---|---|---|---|---|---|---|---|
| | 0 | 1 | 2 | 3 | 4 | 5 | 6 |
| Target 1 (VEGFA Site 1) | 1 | 1 | 4 | 32 | 280 | 2175 | 13873 |
| Target 2 (VEGFA Site 2) | 1 | 0 | 2 | 35 | 443 | 3889 | 17398 |
| Target 3 (VEGFA Site 3) | 1 | 1 | 17 | 377 | 6028 | 13398 | 35517 |
| Target 4 (EMX) | 1 | 0 | 1 | 18 | 276 | 2309 | 15731 |
| Target 5 (RNF2) | 1 | 0 | 0 | 6 | 116 | 976 | 7443 |
| Target 6 (FANCF) | 1 | 0 | 1 | 18 | 271 | 1467 | 9551 |
| EGFP Target Site #1 | 0 | 0 | 3 | 10 | 156 | 1365 | 9755 |
| EGFP Target Site #2 | 0 | 0 | 0 | 11 | 96 | 974 | 7353 |
| EGFP Target Site #3 | 0 | 0 | 1 | 14 | 165 | 1439 | 10361 |

Off-target sites for each of the six RGNs targeted to the VEGFA, RNF2, FANCF, and EMX1 genes and the three RGNs targeted to EGFP Target Sites #1, #2 and #3 were identified in human genome sequence build GRCh37. Mismatches were only allowed for the 20 nt region to which the gRNA anneals and not to the PAM sequence.

Example 2: Using Pairs of GuideRNAs with FokI-dCas9 Fusion Proteins

Monomeric CRISPR-Cas9 nucleases are widely used for targeted genome editing but can induce unwanted off-target mutations with high frequencies. This example describes new dimeric RNA-guided FokI Nucleases (RFNs) that recognize an extended, double-length sequence and that strictly depend on two single guide RNAs (gRNAs) for cleavage activity. RFNs can robustly edit DNA sequences in endogenous human genes with high efficiencies. Additionally, a method for expressing gRNAs bearing any 5' end nucleotide is described, a critical advance that gives dimeric RFNs a useful targeting range. In direct comparisons, monomeric Cas9 nickases generally induce unwanted indels and unexpected focal point mutations with higher frequencies than RFNs directed by a matched single gRNA. RFNs combine the ease of CRISPR RNA-based targeting with the specificity enhancements of dimerization and provide an important new platform for research and therapeutic applications that require highly precise genome editing.

Materials and Methods

The following materials and methods were used in Example 2.

Single and Multiplex gRNA Expression Plasmids

Plasmids encoding single or multiplex gRNAs were assembled in a single-step ligation of annealed target site oligosduplexes (Integrated DNA Technologies) and a constant region oligoduplex (for multiplex gRNAs) with BsmBI-digested Csy4-flanked gRNA backbone (pSQT1313; Addgene).

Multiplex gRNA encoding plasmids were constructed by ligating: 1) annealed oligos encoding the first target site, 2) phosphorylated annealed oligos encoding crRNA, tracrRNA, and Csy4-binding site, and 3) annealed oligos encoding the second target site, into a U6-Csy4site-gRNA plasmid backbone digested with BsmBI Type IIs restriction enzyme. Csy4 RNA binding sites were attached to the 3' and 5' ends of a gRNA sequence and expressed with Cas9 in cells. The Csy4 RNA binding site sequence 'GUUCACUGC-CGUAUAGGCAGCUAAGAAA' (SEQ ID NO:20) was fused to the 5' and 3' end of the standard gRNA sequence.

(SEQ ID NO: 21)
GUUCACUGCCGUAUAGGCAGNNNNNNNNNNNNNNNNNNNNGUUUUAGAG

CUAGAAAUAGCAAGUUAAAAUAAGGCUAGUCCGUUAUCAACUUGAAAAA

GUGGCACCGAGUCGGUGCGUUCACUGCCGUAUAGGCAGNNNNNNNNNNN

NNNNNNNNNNGUUUUAGAGCUAGAAAUAGCAAGUUAAAAUAAGGCUAGUC

CGUUAUCAACUUGAAAAGUGGCACCGAGUCGGUGCGUUCACUGCCGUA

UAGGCAG

This sequence is a multiplex gRNA sequence flanked by Csy4 sites (underlined). Functionally, encoding these in multiplex on one transcript should have the same result as encoding them separately. Although all pairs of Csy4-flanked sgRNAs were expressed in a multiplex context in the experiments described herein, the sgRNAs can be encoded in multiplex sgRNAs separated by Csy4 sites encoded on one transcript as well as individual sgRNAs that have an additional Csy4 sequence. In this sequence, the first N20 sequence represents the sequence complementary to one strand of the target genomic sequence, and the second N20 sequence represents the sequence complementary to the other strand of the target genomic sequence.

A plasmid encoding the Csy4 recognition site containing gRNA was co-transfected with plasmid encoding Cas9 and Csy4 proteins separated by a '2A' peptide linkage. The results showed that gRNAs with Csy4 sites fused to the 5' and 3' ends remained capable of directing Cas9-mediated cleavage in human cells using the U2OS-EGFP disruption assay previously described. Thus, Csy4 RNA binding sites can be attached to 3' end of a gRNA sequence and complexes of these Csy4 site-containing gRNAs with Cas9 remain functional in the cell.

In some experiments, a construct encoding Csy4-T2A-FokI-dCas9 was used. The sequences of the FokI-dCas9 fusions are shown below, and include a GGGGS (SEQ ID NO:23) linker (underlined) between the FokI and dCas9 and a nuclear localization sequence.

FokI-dCas9 amino acid sequence (FokI-G4S-dCas9-nls-3XFLAG)
(SEQ ID NO: 24)
MQLVKSELEEKKSELRHKLKYVPHEYIELIEIARNSTQDRILEMKVMEF

FMKVYGYRGKHLGGSRKPDGAIYTVGSPIDYGVIVDTKAYSGGYNLPIG

QADEMQRYVEENQTRNKHINPNEWWKVYPSSVTEFKFLFVSGHFKGNYK

AQLTRLNHITNCNGAVLSVEELLIGGEMIKAGTLTLEEVRRKFNNGEIN

FGGGGSDKKYSIGLAIGTNSVGWAVITDEYKVPSKKFKVLGNTDRHSIK

KNLIGALLFDSGETAEATRLKRTARRRYTRRKNRICYLQEIFSNEMAKV

DDSFFHRLEESFLVEEDKKHERHPIFGNIVDEVAYHEKYPTIYHLRKKL

VDSTDKADLRLIYLALAHMIKFRGHFLIEGDLNPDNSDVDKLFIQLVQT

YNQLFEENPINASGVDAKAILSARLSKSRRLENLIAQLPGEKKNGLFGN

LIALSLGLTPNFKSNFDLAEDAKLQLSKDTYDDDLDNLLAQIGDQYADL

FLAAKNLSDAILLSDILRVNTEITKAPLSASMIKRYDEHHQDLTLLKAL

VRQQLPEKYKEIFFDQSKNGYAGYIDGGASQEEFYKFIKPILEKMDGTE

ELLVKLNREDLLRKQRTFDNGSIPHQIHLGELHAILRRQEDFYPFLKDN

REKIEKILTFRIPYYVGPLARGNSRFAWMTRKSEETITPWNFEEVVDKG

ASAQSFIERMTNFDKNLPNEKVLPKHSLLYEYFTVYNELTKVKYVTEGM

RKPAFLSGEQKKAIVDLLFKINRKVIVKQLKEDYFKKIECFDSVEISGV

EDRFNASLGTYHDLLKIIKDKDFLDNEENEDILEDIVLTLTLFEDREMI

EERLKTYAHLFDDKVMKQLKRRRYTGWGRLSRKLINGIRDKQSGKTILD

FLKSDGFANRNFMQLIHDDSLTFKEDIQKAQVSGQGDSLHEHIANLAGS

PAIKKGILQTVKVVDELVKVMGRHKPENIVIEMARENQTTQKGQKNSRE

RMKRIEEGIKELGSQILKEHPVENTQLQNEKLYLYYLQNGRDMYVDQEL

DINRLSDYDVDAIVPQSFLKDDSIDNKVLTRSDKNRGKSDNVPSEEVVK

KMKNYWRQLLNAKLITQRKFDNLTKAERGGLSELDKAGFIKRQLVETRQ

ITKHVAQILDSRMNTKYDENDKLIREVKVITLKSKLVSDFRKDFQFYKV

REINNYHHAHDAYLNAVVGTALIKKYPKLESEFVYGDYKVYDVRKMIAK

SEQEIGKATAKYFFYSNIMNFFKTEITLANGEIRKRPLIETNGETGEIV

WDKGRDFATVRKVLSMPQVNIVKKTEVQTGGFSKESILPKRNSDKLIAR

KKDWDPKKYGGFDSPTVAYSVLVVAKVEKGKSKKLKSVKELLGITIMER

SSFEKNPIDFLEAKGYKEVKKDLIIKLPKYSLFELENGRKRMLASAGEL

QKGNELALPSKYVNFLYLASHYEKLKGSPEDNEQKQLFVEQHKHYLDEI

IEQISEFSKRVILADANLDKVLSAYNKHRDKPIREQAENIIHLFTLTNL

GAPAAFKYFDTTIDRKRYTSTKEVLDATLIHQSITGLYETRIDLSQLGG

DGSPKKKRKVSSDYKDHDGDYKDHDIDYKDDDDK

FokI-dCas9 nucleotide sequence (FokI-G4S-dCas9-nls-3XFLAG)

(SEQ ID NO: 25)

ATGCAACTAGTCAAAAGTGAACTGGAGGAGAAGAAATCTGAACTTCGTC
ATAAATTGAAATATGTGCCTCATGAATATATTGAATTAATTGAAATTGC
CAGAAATTCCACTCAGGATAGAATTCTTGAAATGAAGGTAATGGAATTT
TTTATGAAAGTTTATGGATATAGAGGTAAACATTTGGGTGGATCAAGGA
AACCGGACGGAGCAATTTATACTGTCGGATCTCCTATTGATTACGGTGT
GATCGTGGATACTAAAGCTTATAGCGGAGGTTATAATCTGCCAATTGGC
CAAGCAGATGAAATGCAACGATATGTCGAAGAAAATCAAACACGAAACA
AACATATCAACCCTAATGAATGGTGGAAAGTCTATCCATCTTCTGTAAC
GGAATTTAAGTTTTTATTTGTGAGTGGTCACTTTAAAGGAAACTACAAA
GCTCAGCTTACACGATTAAATCATATCACTAATTGTAATGGAGCTGTTC
TTAGTGTAGAAGAGCTTTTAATTGGTGGAGAAATGATTAAAGCCGGCAC
ATTAACCTTAGAGGAAGTCAGACGGAAATTTAATAACGGCGAGATAAAC
TTTGGTGGCGGTGGATCCGATAAAAAGTATTCTATTGGTTTAGCCATCG
GCACTAATTCCGTTGGATGGGCTGTCATAACCGATGAATACAAAGTACC
TTCAAAGAAATTTAAGGTGTTGGGGAACACAGACCGTCATTCGATTAAA
AAGAATCTTATCGGTGCCCTCCTATTCGATAGTGGCGAAACGGCAGAGG
CGACTCGCCTGAAACGAACCGCTCGGAGAAGGTATACACGTCGCAAGAA
CCGAATATGTTACTTACAAGAAATTTTTAGCAATGAGATGGCCAAAGTT
GACGATTCTTTCTTTCACCGTTTGGAAGAGTCCTTCCTTGTCGAAGAGG
ACAAGAAACATGAACGGCACCCCATCTTTGGAAACATAGTAGATGAGGT
GGCATATCATGAAAAGTACCCAACGATTTATCACCTCAGAAAAAAGCTA
GTTGACTCAACTGATAAAGCGGACCTGAGGTTAATCTACTTGGCTCTTG
CCCATATGATAAAGTTCCGTGGGCACTTTCTCATTGAGGGTGATCTAAA
TCCGGACAACTCGGATGTCGACAAACTGTTCATCCAGTTAGTACAAACC
TATAATCAGTTGTTTGAAGAGAACCCTATAAATGCAAGTGGCGTGGATG
CGAAGGCTATTCTTAGCGCCCGCCTCTCTAAATCCCGACGGCTAGAAAA
CCTGATCGCACAATTACCCGGAGAGAAGAAAAATGGGTTGTTCGGTAAC
CTTATAGCGCTCTCACTAGGCCTGACACCAAATTTTAAGTCGAACTTCG
ACTTAGCTGAAGATGCCAAATTGCAGCTTAGTAAGGACACGTACGATGA
CGATCTCGACAATCTACTGGCACAAATTGGAGATCAGTATGCGGACTTA
TTTTTGGCTGCCAAAAACCTTAGCGATGCAATCCTCCTATCTGACATAC
TGAGAGTTAATACTGAGATTACCAAGGCGCCGTTATCCGCTTCAATGAT
CAAAAGGTACGATGAACATCACCAAGACTTGACACTTCTCAAGGCCCTA
GTCCGTCAGCAACTGCCTGAGAAATATAAGGAAATATTCTTTGATCAGT
CGAAAAACGGGTACGCAGGTTATATTGACGGCGGAGCGAGTCAAGAGGA
ATTCTACAAGTTTATCAAACCCATATTAGAGAAGATGGATGGGACGGAA
GAGTTGCTTGTAAAACTCAATCGCGAAGATCTACTGCGAAAGCAGCGGA
CTTTCGACAACGGTAGCATTCCACATCAAATCCACTTAGGCGAATTGCA
TGCTATACTTAGAAGGCAGGAGGATTTTTATCCGTTCCTCAAAGACAAT

CGTGAAAAGATTGAGAAAATCCTAACCTTTCGCATACCTTACTATGTGG
GACCCCTGGCCCGAGGGAACTCTCGGTTCGCATGGATGACAAGAAAGTC
CGAAGAAACGATTACTCCATGGAATTTTGAGGAAGTTGTCGATAAAGGT
GCGTCAGCTCAATCGTTCATCGAGAGGATGACCAACTTTGACAAGAATT
TACCGAACGAAAAAGTATTGCCTAAGCACAGTTTACTTTACGAGTATTT
CACAGTGTACAATGAACTCACGAAAGTTAAGTATGTCACTGAGGGCATG
CGTAAACCCGCCTTTCTAAGCGGAGAACAGAAGAAAGCAATAGTAGATC
TGTTATTCAAGACCAACCGCAAAGTGACAGTTAAGCAATTGAAAGAGGA
CTACTTTAAGAAAATTGAATGCTTCGATTCTGTCGAGATCTCCGGGGTA
GAAGATCGATTTAATGCGTCACTTGGTACGTATCATGACCTCCTAAAGA
TAATTAAAGATAAGGACTTCCTGGATAACGAAGAGAATGAAGATATCTT
AGAAGATATAGTGTTGACTCTTACCCTCTTTGAAGATCGGGAAATGATT
GAGGAAAGACTAAAAACATACGCTCACCTGTTCGACGATAAGGTTATGA
AACAGTTAAAGAGGCGTCGCTATACGGGCTGGGGACGATTGTCGCGGAA
ACTTATCAACGGGATAAGAGACAAGCAAAGTGGTAAAACTATTCTCGAT
TTTCTAAAGAGCGACGGCTTCGCCAATAGGAACTTTATGCAGCTGATCC
ATGATGACTCTTTAACCTTCAAAGAGGATATACAAAAGGCACAGGTTTC
CGGACAAGGGGACTCATTGCACGAACATATTGCGAATCTTGCTGGTTCG
CCAGCCATCAAAAAGGGCATACTCCAGACAGTCAAAGTAGTGGATGAGC
TAGTTAAGGTCATGGGACGTCACAAACCGGAAAACATTGTAATCGAGAT
GGCACGCGAAAATCAAACGACTCAGAAGGGGCAAAAAAACAGTCGAGAG
CGGATGAAGAGAATAGAAGAGGGTATTAAAGAACTGGGCAGCCAGATCT
TAAAGGAGCATCCTGTGGAAAATACCCAATTGCAGAACGAGAAACTTTA
CCTCTATTACCTACAAAATGGAAGGGACATGTATGTTGATCAGGAACTG
GACATAAACCGTTTATCTGATTACGACGTCGATGCCATTGTACCCCAAT
CCTTTTTGAAGGACGATTCAATCGACAATAAAGTGCTTACACGCTCGGA
TAAGAACCGAGGGAAAAGTGACAATGTTCCAAGCGAGGAAGTCGTAAAG
AAAATGAAGAACTATTGGCGGCAGCTCCTAAATGCGAAACTGATAACGC
AAAGAAAGTTCGATAACTTAACTAAAGCTGAGAGGGGTGGCTTGTCTGA
ACTTGACAAGGCCGGATTTATTAAACGTCAGCTCGTGGAAACCCGCCAA
ATCACAAAGCATGTTGCACAGATACTAGATTCCCGAATGAATACGAAAT
ACGACGAGAACGATAAGCTGATTCGGGAAGTCAAAGTAATCACTTTAAA
GTCAAAATTGGTGTCGGACTTCAGAAAGGATTTTCAATTCTATAAAGTT
AGGGAGATAAATAACTACCACCATGCGCACGACGCTTATCTTAATGCCG
TCGTAGGGACCGCACTCATTAAGAAATACCCGAAGCTAGAAAGTGAGTT
TGTGTATGGTGATTACAAAGTTTATGACGTCCGTAAGATGATCGCGAAA
AGCGAACAGGAGATAGGCAAGGCTACAGCCAAATACTTCTTTTATTCTA
ACATTATGAATTTCTTTAAGACGGAAATCACTCTGGCAAACGGAGAGAT
ACGCAAACGACCTTTAATTGAAACCAATGGGGAGACAGGTGAAATCGTA
TGGGATAAGGGCCGGGACTTCGCGACGGTGAGAAAAGTTTTGTCCATGC
CCCAAGTCAACATAGTAAAGAAAACTGAGGTGCAGACCGGAGGGTTTTC

-continued

```
AAAGGAATCGATTCTTCCAAAAAGGAATAGTGATAAGCTCATCGCTCGT
AAAAAGGACTGGGACCCGAAAAAGTACGGTGGCTTCGATAGCCCTACAG
TTGCCTATTCTGTCCTAGTAGTGGCAAAAGTTGAGAAGGGAAAATCCAA
GAAACTGAAGTCAGTCAAAGAATTATTGGGGATAACGATTATGGAGCGC
TCGTCTTTTGAAAAGAACCCCATCGACTTCCTTGAGGCGAAAGGTTACA
AGGAAGTAAAAAAGGATCTCATAATTAAACTACCAAAGTATAGTCTGTT
TGAGTTAGAAAATGGCCGAAAACGGATGTTGGCTAGCGCCGGAGAGCTT
CAAAAGGGGAACGAACTCGCACTACCGTCTAAATACGTGAATTTCCTGT
ATTTAGCGTCCCATTACGAGAAGTTGAAAGGTTCACCTGAAGATAACGA
ACAGAAGCAACTTTTTGTTGAGCAGCACAAACATTATCTCGACGAAATC
ATAGAGCAAATTTCGGAATTCAGTAAGAGAGTCATCCTAGCTGATGCCA
ATCTGGACAAAGTATTAAGCGCATACAACAAGCACAGGGATAAACCCAT
ACGTGAGCAGGCGGAAAATATTATCCATTTGTTTACTCTTACCAACCTC
GGCGCTCCAGCCGCATTCAAGTATTTTGACACAACGATAGATCGCAAAC
GATACACTTCTACCAAGGAGGTGCTAGACGCGACACTGATTCACCAATC
CATCACGGGATTATATGAAACTCGGATAGATTTGTCACAGCTTGGGGGT
GACGGATCCCCAAGAAGAAGAGGAAAGTCTCGAGCGACTACAAAGACC
ATGACGGTGATTATAAAGATCATGACATCGATTACAAGGATGACGATGA
CAAGTGA
```

Alternatively, a human codon optimized version of the construct was used, which contained both N- and C-terminal nuclear localization signals, as shown below.

Nls-FokI-dCas9-nls amino acid sequence
(SEQ ID NO: 26)
```
MPKKKRKVSSQLVKSELEEKKSELRHKLKYVPHEYIELIEIARNSTQDR
ILEMKVMEFFMKVYGYRGKHLGGSRKPDGAIYTVGSPIDYGVIVDTKAY
SGGYNLPIGQADEMQRYVEENQTRNKHINPNEWWKVYPSSVIEFKFLFV
SGHFKGNYKAQLTRLNHITNCNGAVLSVEELLIGGEMIKAGTLTLEEVR
RKFNNGEINFGGGGSDKKYSIGLAIGTNSVGWAVITDEYKVPSKKFKVL
GNTDRHSIKKNLIGALLFDSGETAEATRLKRTARRRYTRRKNRICYLQE
IFSNEMAKVDDSFFHRLEESFLVEEDKKHERHPIFGNIVDEAVAYHEKYP
TIYHLRKKLVDSTDKADLRLIYLALAHMIKFRGHFLIEGDLNPDNSDVD
KLFIQLVQTYNQLFEENPINASGVDAKAILSARLSKSRRLENLIAQLPG
EKKNGLFGNLIALSLGLTPNFKSNFDLAEDAKLQLSKDTYDDDLDNLLA
QIGDQYADLFLAAKNLSDAILLSDILRVNTEITKAPLSASMIKRYDEHH
QDLILLKALVRQQLPEKYKEIFFDQSKNGYAGYIDGGASQEEFYKFIKP
ILEKMDGTEELLVKLNREDLLRKQRTFDNGSIPHQIHLGELHAILRRQE
DFYPFLKDNREKIEKILTFRIPYYVGPLARGNSRFAWMTRKSEETITPW
NFEEVVDKGASAQSFIERMTNFDKNLPNEKVLPKHSLLYEYFTVYNELT
KVKYVTEGMRKPAFLSGEQKKAIVDLLFKTNRKVTVKQLKEDYFKKIEC
FDSVEISGVEDRFNASLGTYHDLLKIIKDKDFLDNEENEDILEDIVLTL
TLFEDREMIEERLKTYAHLFDDKVMKQLKRRRYTGWGRLSRKLINGIRD
KQSGKTILDFLKSDGFANRNFMQLIHDDSLTFKEDIQKAQVSGQGDSLH
EHIANLAGSPAIKKGILQTVKVVDELVKVMGRHKPENIVIEMARENQTT
QKGQKNSRERMKRIEEGIKELGSQILKEHPVENTQLQNEKLYLYYLQNG
RDMYVDQELDINRLSDYDVDAIVPQSFLKDDSIDNKVLTRSDKNRGKSD
NVPSEEVVKKMKNYWRQLLNAKLITQRKFDNLTKAERGGLSELDKAGFI
KRQLVETRQITKHVAQILDSRMNTKYDENDKLIREVKVITLKSKLVSDF
RKDFQFYKVREINNYHHAHDAYLNAVVGTALIKKYPKLESEFVYGDYKV
YDVRKMIAKSEQEIGKATAKYFFYSNIMNFFKTEITLANGEIRKRPLIE
TNGETGEIVWDKGRDFATVRKVLSMPQVNIVKKTEVQTGGFSKESILPK
RNSDKLIARKKDWDPKKYGGFDSPTVAYSVLVVAKVEKGKSKKLKSVKE
LLGITIMERSSFEKNPIDFLEAKGYKEVKKDLIIKLPKYSLFELENGRK
RMLASAGELQKGNELALPSKYVNFLYLASHYEKLKGSPEDNEQKQLFVE
QHKHYLDEIIEQISEFSKRVILADANLDKVLSAYNKHRDKPIREQAENI
IHLFTLTNLGAPAAFKYFDTTIDRKRYTSTKEVLDATLIHQSITGLYET
RIDLSQLGGDGSPKKKRKVSSDYKDHDGDYKDHDIDYKDDDDK
```

Nls-FokI-dCas9-nls nucleotide sequence
(SEQ ID NO: 27)
```
ATGCCTAAGAAGAAGCGGAAGGTGAGCAGCCAACTTGTGAAGTCTGAAC
TCGAGGAGAAAAAATCAGAGTTGAGACACAAGTTGAAGTACGTGCCACA
CGAATACATCGAGCTTATCGAGATCGCCAGAAACAGTACCCAGGATAGG
ATCCTTGAGATGAAAGTCATGGAGTTCTTTATGAAGGTCTACGGTTATA
GAGGAAAGCACCTTGGCGGTAGCAGAAAGCCCGATGGCGCCATCTATAC
TGTCGGATCTCCTATCGATTATGGGGTGATCGTGGATACCAAAGCTTAC
TCAGGCGGGTACAACTTGCCCATAGGACAAGCCGACGAGATGCAGCGGT
ATGTCGAAGAGAACCAGACGCGCAACAAGCACATCAACCCCAATGAATG
GTGGAAAGTGTACCCAAGTAGTGTGACTGAGTTCAAGTTCCTGTTTGTC
TCCGGCCACTTTAAGGGCAATTATAAAGCTCAGCTCACTAGACTCAATC
ACATCACAAACTGCAACGGAGCTGTGTTGTCAGTGGAGGAGCTCCTGAT
TGGAGGCGAGATGATCAAAGCCGGCACCCTTACACTGGAGGAGGTGCGG
CGGAAGTTCAACAATGGAGAGATCAACTTCGGTGGCGGTGGATCCGATA
AAAAGTATTCTATTGGTTTAGCCATCGGCACTAATTCCGTTGGATGGGC
TGTCATAACCGATGAATACAAAGTACCTTCAAAGAAATTTAAGGTGTTG
GGGAACACAGACCGTCATTCGATTAAAAAGAATCTTATCGGTGCCCTCC
TATTCGATAGTGGCGAAACGGCAGAGGCGACTCGCCTGAAACGAACCGC
TCGGAGAAGGTATACACGTCGCAAGAACCGAATATGTTACTTACAAGAA
ATTTTTAGCAATGAGATGGCCAAAGTTGACGATTCTTTCTTTCACCGTT
TGGAAGAGTCCTTCCTTGTCGAAGAGGACAAGAAACATGAACGGCACCC
CATCTTTGGAAACATAGTAGATGAGGTGGCATATCATGAAAGTACCCA
ACGATTTATCACCTCAGAAAAAGCTAGTTGACTCAACTGATAAAGCGG
ACCTGAGGTTAATCTACTTGGCTCTTGCCCATATGATAAAGTTCCGTGG
GCACTTTCTCATTGAGGGTGATCTAAATCCGGACAACTCGGATGTCGAC
```

-continued

```
AAACTGTTCATCCAGTTAGTACAAACCTATAATCAGTTGTTTGAAGAGA
ACCCTATAAATGCAAGTGGCGTGGATGCGAAGGCTATTCTTAGCGCCCG
CCTCTCTAAATCCCGACGGCTAGAAAACCTGATCGCACAATTACCCGGA
GAGAAGAAAAATGGGTTGTTCGGTAACCTTATAGCGCTCTCACTAGGCC
TGACACCAAATTTTAAGTCGAACTTCGACTTAGCTGAAGATGCCAAATT
GCAGCTTAGTAAGGACACGTACGATGACGATCTCGACAATCTACTGGCA
CAAATTGGAGATCAGTATGCGGACTTATTTTTGGCTGCCAAAAACCTTA
GCGATGCAATCCTCCTATCTGACATACTGAGAGTTAATACTGAGATTAC
CAAGGCGCCGTTATCCGCTTCAATGATCAAAAGGTACGATGAACATCAC
CAAGACTTGACACTTCTCAAGGCCCTAGTCCGTCAGCAACTGCCTGAGA
AATATAAGGAAATATTCTTTGATCAGTCGAAAAACGGGTACGCAGGTTA
TATTGACGGCGGAGCGAGTCAAGAGGAATTCTACAAGTTTATCAAACCC
ATATTAGAGAAGATGGATGGGACGGAAGAGTTGCTTGTAAAACTCAATC
GCGAAGATCTACTGCGAAAGCAGCGGACTTTCGACAACGGTAGCATTCC
ACATCAAATCCACTTAGGCGAATTGCATGCTATACTTAGAAGGCAGGAG
GATTTTTATCCGTTCCTCAAAGACAATCGTGAAAAGATTGAGAAAATCC
TAACCTTTCGCATACCTTACTATGTGGGACCCCTGGCCCGAGGGAACTC
TCGGTTCGCATGGATGACAAGAAAGTCCGAAGAAACGATTACTCCATGG
AATTTTGAGGAAGTTGTCGATAAAGGTGCGTCAGCTCAATCGTTCATCG
AGAGGATGACCAACTTTGACAAGAATTTACCGAACGAAAAAGTATTGCC
TAAGCACAGTTTACTTTACGAGTATTTCACAGTGTACAATGAACTCACG
AAAGTTAAGTATGTCACTGAGGGCATGCGTAAACCCGCCTTTCTAAGCG
GAGAACAGAAGAAAGCAATAGTAGATCTGTTATTCAAGACCAACCGCAA
AGTGACAGTTAAGCAATTGAAAGAGGACTACTTTAAGAAAATTGAATGC
TTCGATTCTGTCGAGATCTCCGGGGTAGAAGATCGATTTAATGCGTCAC
TTGGTACGTATCATGACCTCCTAAAGATAATTAAAGATAAGGACTTCCT
GGATAACGAAGAGAATGAAGATATCTTAGAAGATATAGTGTTGACTCTT
ACCCTCTTTGAAGATCGGGAAATGATTGAGGAAAGACTAAAAACATACG
CTCACCTGTTCGACGATAAGGTTATGAAACAGTTAAAGAGGCGTCGCTA
TACGGGCTGGGGACGATTGTCGCGGAAACTTATCAACGGGATAAGAGAC
AAGCAAAGTGGTAAAACTATTCTCGATTTTCTAAAGAGCGACGGCTTCG
CCAATAGGAACTTTATGCAGCTGATCCATGATGACTCTTTAACCTTCAA
AGAGGATATACAAAAGGCACAGGTTTCCGGACAAGGGGACTCATTGCAC
GAACATATTGCGAATCTTGCTGGTTCGCCAGCCATCAAAAAGGGCATAC
TCCAGACAGTCAAAGTAGTGGATGAGCTAGTTAAGGTCATGGGACGTCA
CAAACCGGAAAACATTGTAATCGAGATGGCACGCGAAAATCAAACGACT
CAGAAGGGGCAAAAAAACAGTCGAGAGCGGATGAAGAGAATAGAAGAGG
GTATTAAAGAACTGGGCAGCCAGATCTTAAAGGAGCATCCTGTGGAAAA
TACCCAATTGCAGAACGAGAAACTTTACCTCTATTACCTACAAAATGGA
AGGGACATGTATGTTGATCAGGAACTGGACATAAACCGTTTATCTGATT
```

-continued

```
ACGACGTCGATGCCATTGTACCCCAATCCTTTTTGAAGGACGATTCAAT
CGACAATAAAGTGCTTACACGCTCGGATAAGAACCGAGGGAAAAGTGAC
AATGTTCCAAGCGAGGAAGTCGTAAAGAAAATGAAGAACTATTGGCGGC
AGCTCCTAAATGCGAAACTGATAACGCAAAGAAAGTTCGATAACTTAAC
TAAAGCTGAGAGGGGTGGCTTGTCTGAACTTGACAAGGCCGGATTTATT
AAACGTCAGCTCGTGGAAACCCGCCAAATCACAAAGCATGTTGCACAGA
TACTAGATTCCCGAATGAATACGAAATACGACGAGAACGATAAGCTGAT
TCGGGAAGTCAAAGTAATCACTTTAAAGTCAAAATTGGTGTCGGACTTC
AGAAAGGATTTTCAATTCTATAAAGTTAGGGAGATAAATAACTACCACC
ATGCGCACGACGCTTATCTTAATGCCGTCGTAGGGACCGCACTCATTAA
GAAATACCCGAAGCTAGAAAGTGAGTTTGTGTATGGTGATTACAAAGTT
TATGACGTCCGTAAGATGATCGCGAAAAGCGAACAGGAGATAGGCAAGG
CTACAGCCAAATACTTCTTTTATTCTAACATTATGAATTTCTTTAAGAC
GGAAATCACTCTGGCAAACGGAGAGATACGCAAACGACCTTTAATTGAA
ACCAATGGGGAGACAGGTGAAATCGTATGGGATAAGGGCCGGGACTTCG
CGACGGTGAGAAAAGTTTTGTCCATGCCCCAAGTCAACATAGTAAAGAA
AACTGAGGTGCAGACCGGAGGGTTTTCAAAGGAATCGATTCTTCCAAAA
AGGAATAGTGATAAGCTCATCGCTCGTAAAAAGGACTGGGACCCGAAAA
AGTACGGTGGCTTCGATAGCCCTACAGTTGCCTATTCTGTCCTAGTAGT
GGCAAAAGTTGAGAAGGGAAAATCCAAGAAACTGAAGTCAGTCAAAGAA
TTATTGGGGATAACGATTATGGAGCGCTCGTCTTTTGAAAAGAACCCCA
TCGACTTCCTTGAGGCGAAAGGTTACAAGGAAGTAAAAAAGGATCTCAT
AATTAAACTACCAAAGTATAGTCTGTTTGAGTTAGAAAATGGCCGAAAA
CGGATGTTGGCTAGCGCCGGAGAGCTTCAAAAGGGGAACGAACTCGCAC
TACCGTCTAAATACGTGAATTTCCTGTATTTAGCGTCCCATTACGAGAA
GTTGAAAGGTTCACCTGAAGATAACGAACAGAAGCAACTTTTTGTTGAG
CAGCACAAACATTATCTCGACGAAATCATAGAGCAAATTTCGGAATTCA
GTAAGAGAGTCATCCTAGCTGATGCCAATCTGGACAAAGTATTAAGCGC
ATACAACAAGCACAGGGATAAACCCATACGTGAGCAGGCGGAAAATATT
ATCCATTTGTTTACTCTTACCAACCTCGGCGCTCCAGCCGCATTCAAGT
ATTTTGACACAACGATAGATCGCAAACGATACACTTCTACCAAGGAGGT
GCTAGACGCGACACTGATTCACCAATCCATCACGGGATTATATGAAACT
CGGATAGATTTGTCACAGCTTGGGGGTGACGGATCCCCCAAGAAGAAGA
GGAAAGTCTCGAGCGACTACAAAGACCATGACGGTGATTATAAAGATCA
TGACATCGATTACAAGGATGACGATGACAAGTGA
```

Tissue Culture and Transfections

All cell culture experiments were carried out in HEK 293 cells, U2OS cells, or in U2OS cells harboring a stably integrated, single-copy, destabilized EGFP gene (U2OS.EGFP cells). Cell lines were cultured in Advanced DMEM (Life Technologies) supplemented with 10% FBS, 2 mM GlutaMax (Life Technologies) and penicillin/streptomycin at 37 C with 5% CO2. Additionally, U2OS.EGFP cells were cultured in the presence of 400 μg/ml of G418.

U2OS cells and U2OS.EGFP cells were transfected using the DN-100 program of a Lonza 4D-Nucleofector according to the manufacturer's instructions. In initial FokI-dCas9 activity screens and focused spacer length analysis experiments, 750 ng of pCAG-Csy4-FokI-dCas9-nls nuclease plasmid and 250 ng of gRNA encoding plasmids were transfected together with 50 ng tdTomato expression plasmid (Clontech) as a transfection control. In all other experiments in U2OS and U2OS.EGFP cells, 975 ng of human codon optimized pCAG-Csy4-T2A-nls-hFokI-dCas9-nls (SQT1601) or pCAG-Cas9-D10A nickase (NW3) were transfected along with 325 ng of gRNA vector and 10 ng of Td tomato expression plasmid and analyzed 3 days after transfection. HEK293 cells were transfected with 750 ng of nuclease plasmid, 250 ng of gRNA expression plasmid and 10 ng of Td tomato, using Lipofectamine (Life Technologies) according to the manufacturer's instructions and analyzed for NHEJ-mediated mutagenesis 3 days after transfection.

Single transfections were performed for the initial spacer activity screen, and duplicate transfections for the focused spacer length analysis. All other transfections were performed in triplicate.

EGFP Disruption Assay

The EGFP disruption assay was performed as previously described (see Example 1 and Reyon et al., Nat Biotech 30, 460-465 (2012)) using U2OS.EGFP reporter cells. Cells were assayed for EGFP and tdTomato expression using an BD Biosciences LSR II or Fortessa FACS analyzer.

Quantification of Nuclease- or Nickase-Induced Mutation Rates by T7EI Assay

T7E1 assays were performed as previously described (Reyon et al., Nat Biotech 30, 460-465 (2012)). Briefly, genomic DNA was isolated 72 hours post transfection using the Agencourt DNAdvance Genomic DNA Isolation kit (Beckman Coulter Genomics) according to the manufacturer's instructions with a Sciclone G3 liquid-handling workstation (Caliper). PCR reactions to amplify genomic loci were performed using Phusion Hot-start Flex DNA polymerase (New England Biolabs). Samples were amplified using a two-step protocol (98° C., 30 sec; (98° C., 7 sec; 72° C., 30 sec)×35; 72° C., 5 min) or a touchdown PCR protocol ((98° C., 10 s; 72-62° C., −1° C./cycle, 15 s; 72° C., 30 s)×10 cycles, (98° C., 10 s; 62° C., 15 s; 72° C., 30 s)×25 cycles). 200 ng of purified PCR amplicons were denatured, hybridized, and treated with T7 Endonuclease I (New England Biolabs). Mutation frequency was quantified using a Qiaxcel capillary electrophoresis instrument (Qiagen) as previously described (Reyon et al., Nat Biotech 30, 460-465 (2012)).

Sanger Sequencing of Mutagenized Genomic DNA

The same purified PCR products used for T7EI assay were Topo-cloned (Life Technologies) and plasmid DNA of individual clones was isolated and sequenced using an M13 reverse primer (5'-GTAAAACGACGGCCAG-3; SEQ ID NO:19).

Illumina Library Preparation and Analysis

Short 200-350 bp PCR products were amplified using Phusion Hot-start FLEX DNA polymerase. PCR products were purified using Ampure XP beads (Beckman Coulter Genomics) according to manufacturer's instructions. Dual-indexed TruSeq Illumina deep sequencing libraries were prepared using a high-throughput library preparation system (Kapa Biosystems) on a Sciclone G3 liquid-handling workstation. Final adapter-ligated libraries were quantified using a Qiaxcel capillary electrophoresis instrument (Qiagen). 150 bp paired end sequencing was performed on an Illumina MiSeq Sequencer by the Dana-Farber Cancer Institute Molecular Biology Core.

MiSeq paired-end reads were mapped to human genome reference GChr37 using bwa. Reads with an average quality score>30 were analyzed for insertion or deletion mutations that overlapped the intended target or candidate off-target nuclease binding site. Mutation analyses were conducted using the Genome Analysis Toolkit (GATK) and Python.

Off-Target Search Algorithm:

A target-site matching algorithm was implemented that looks for matches with less than a specified number of mismatches in a sliding window across the human genome.

Example 2a. Rationale for Designing Dimeric RNA-Guided Nucleases

It was hypothesized that a single platform combining the specificity advantages of dimerization with the ease of Cas9 targeting could be developed. To do this, the well-characterized, dimerization-dependent FokI nuclease domain was fused to a RNA-guided catalytically inactive Cas9 (dCas9) protein. It was hoped that, like FokI-containing ZFNs and TALENs, dimers of these fusions might mediate sequence-specific DNA cleavage when bound to target sites composed of two "half-sites" with a certain length "spacer" sequence between them (FIG. 4A). Such fusions were hypothesized to have enhanced specificity because they should require two gRNAs for activity (FIG. 4A) and because a single gRNA would presumably be too inefficient or unable to recruit the two FokI-containing fusion proteins required for DNA cleavage. It was hypothesized that such a dimeric system would show improved specificity relative to standard monomeric Cas9 nucleases and also would potentially possess important specificity advantages over the paired nickase system in which single nickases can still exert unwanted mutagenic effects.

Example 2b. Multiplex Expression of gRNAs without 5'-End Nucleotide Limitations

The targeting range for a dimeric RNA-guided nuclease would be low using existing gRNA expression methods. Two sequence requirements typically restrict the targeting range of a dCas9 monomer: the requirement for a PAM sequence of 5'-NGG that is specified by the dCas9 and a requirement for a G nucleotide at the 5' end of the gRNA imposed by the use of a U6 promoter in most expression vectors. If, however, the requirement for the 5' G in the gRNA could be relieved, then the targeting range would improve by 16-fold.

To develop a multiplex system that would allow for the expression of gRNAs with any 5' nucleotide, a plasmid was constructed from which two gRNAs, each flanked by cleavage sites for the Csy4 ribonuclease (Haurwitz et al., Science 329, 1355-1358 (2010)), can be expressed within a single RNA transcribed from a U6 promoter (FIG. 4B). Csy4 would be expected to process this transcript thereby releasing the two gRNAs. Based on the known mechanism of Csy4-mediated cleavage ((Haurwitz et al., Science 329, 1355-1358 (2010); Sternberg et al., RNA 18, 661-672 (2012)), each processed gRNA should retain a Csy4 recognition site on its 3' end with a Csy4 protein bound to that site (FIG. 4B). In this configuration, it should be possible to express gRNAs with any 5' nucleotide. This system was tested by using it to express two gRNAs targeted to sites within the EGFP reporter gene. Co-expression of this transcript together with Csy4 and Cas9 nucleases in human cells led to the introduction of indel mutations at both EGFP target sites as well as of deletion of the sequence between these sites (FIG. 4C). These experiments suggest that both gRNAs are being processed from the single parental RNA transcript and both are capable of directing Cas9 nuclease activities in human cells.

Example 2c. Construction and Optimization of Dimeric RNA-Guided Nucleases

Figure 5A:
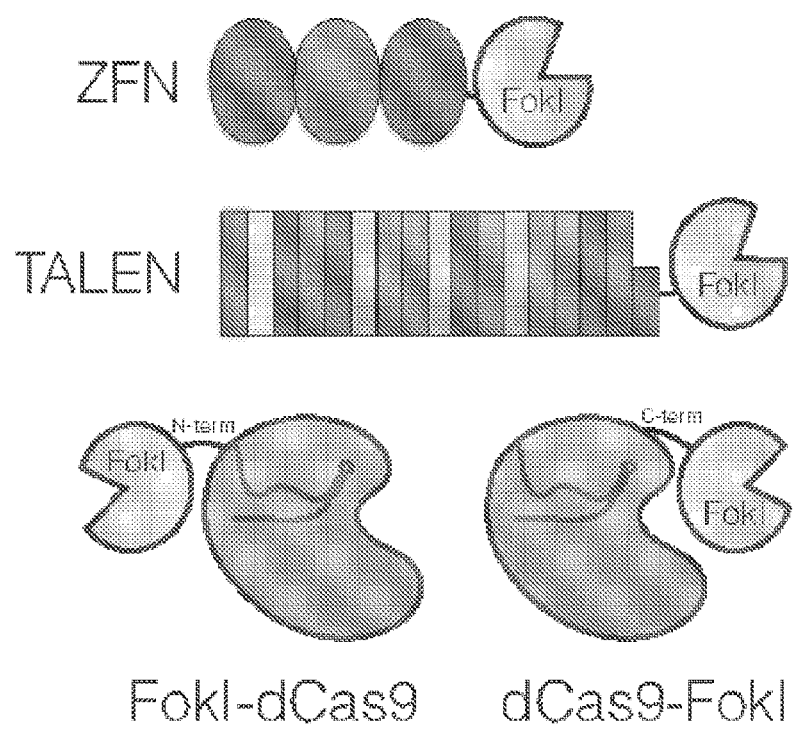
Figure 5E:
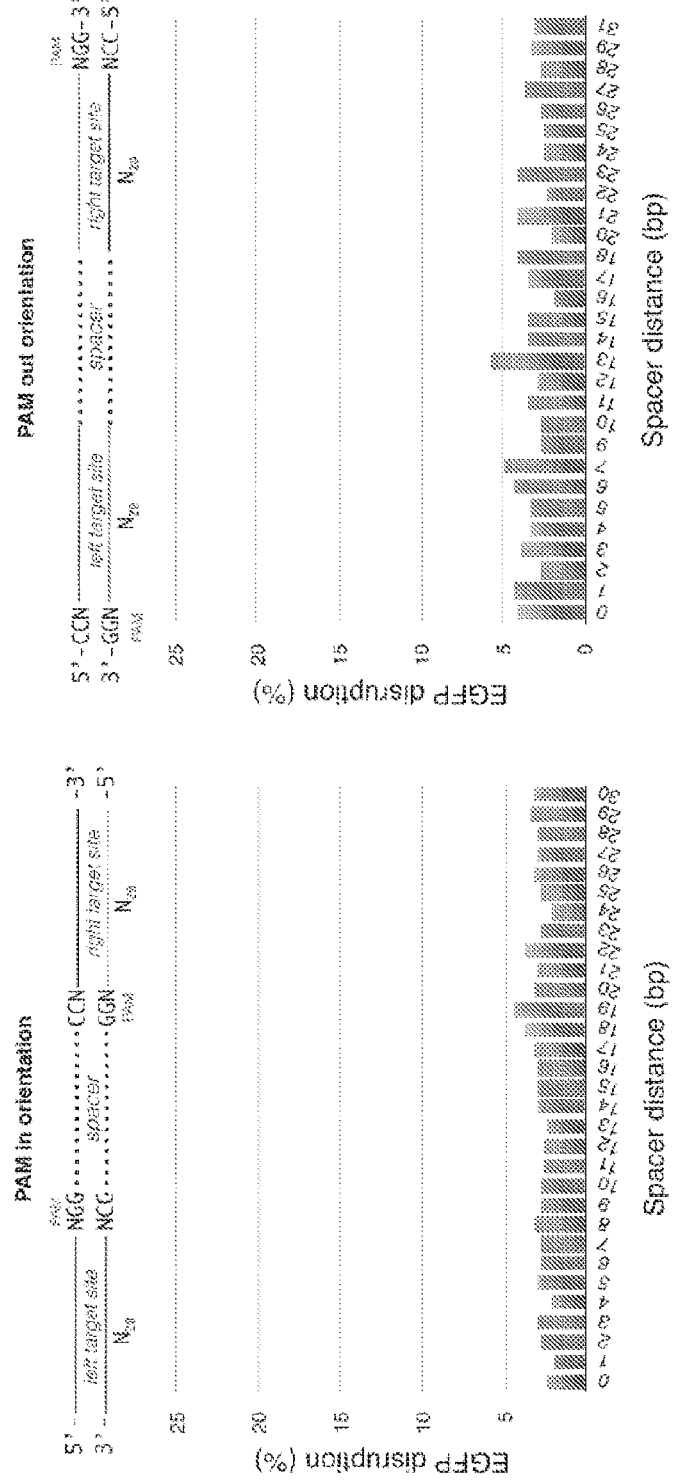

Two different hybrid proteins harboring the FokI nuclease domain and the dCas9 protein were constructed: one in which the FokI nuclease domain is fused to the carboxy-terminus of dCas9 (dCas9-FokI) and the other in which it is fused to the amino-terminus (FokI-dCas9) (FIG. 5A). The dCas9-FokI protein is analogous in architecture to ZFNs and TALENs (FIG. 5A). To ascertain whether either or both of these fusions could mediate site-specific cleavage of DNA, a well-established human cell-based assay that can rapidly and easily quantify the introduction of NHEJ-mediated indels into an EGFP reporter gene was used (the EGFP disruption assay described above in Example 1). Because the geometry of the half-sites required for efficient cleavage was not known, 60 pairs of gRNAs targeted to various sites in EGFP were designed. The two half-sites targeted by each of these gRNA pairs were oriented such that both of their PAM sequences are either directly adjacent to the spacer sequence (the "PAM in" orientation) or positioned at the outer boundaries of the full-length target site (the "PAM out" orientation) (FIG. 5B). In addition, the spacer sequence was also varied in length from 0 to 31 bps (FIG. 5B and Table 2).

TABLE 2

| FokI-dCas9 EGFP Pair # | Name | Target Start Position (+) | Sequence (+) sites | SEQ ID NO: | Sequence (-) sites | SEQ ID NO: | Edge-to-edge 'spacer' distance | PAM |
|---|---|---|---|---|---|---|---|---|
| 1 | EGFP site 1 | 74 | GAGCTGGACGGCGACGTAAACGG | 28. | CGCCGGACACGCTGAACTTGTGG | 29. | 0 | in |
| 2 | EGFP site 2 | 174 | CCGGCAAGCTGCCCGTGCCCTGG | 30. | GGTCAGGGTGGTCACGAGGGTGG | 31. | 1 | in |
| 3 | EGFP site 3 | 37 | CGAGGAGCTGTTCACCGGGGTGG | 32. | CCGTCCAGCTCGACCAGGATGGG | 33. | 2 | in |
| 4 | EGFP site 4 | 37 | CGAGGAGCTGTTCACCGGGGTGG | 34. | GCCGTCCAGCTCGACCAGGATGG | 35. | 3 | in |
| 5 | EGFP site 5 | 174 | CCGGCAAGCTGCCCGTGCCCTGG | 36. | GTAGGTCAGGGTGGTCACGAGGG | 37. | 4 | in |
| 6 | EGFP site 6 | 34 | GGGCGAGGAGCTGTTCACCGGGG | 38. | CCGTCCAGCTCGACCAGGATGGG | 39. | 5 | in |
| 7 | EGFP site 7 | 33 | AGGGCGAGGAGCTGTTCACCGGG | 40. | CCGTCCAGCTCGACCAGGATGGG | 41. | 6 | in |
| 8 | EGFP site 8 | 32 | AAGGGCGAGGAGCTGTTCACCGG | 42. | CCGTCCAGCTCGACCAGGATGGG | 43. | 7 | in |
| 9 | EGFP site 9 | 32 | AAGGGCGAGGAGCTGTTCACCGG | 44. | GCCGTCCAGCTCGACCAGGATGG | 45. | 8 | in |
| 10 | EGFP site 10 | 106 | CAGCGTGTCCGGCGAGGGCGAGG | 46. | CTTCAGGGTCAGCTTGCCGTAGG | 47. | 9 | in |
| 11 | EGFP site 11 | 34 | GGGCGAGGAGCTGTTCACCGGGG | 48. | CGTCGCCGTCCAGCTCGACCAGG | 49. | 10 | in |
| 12 | EGFP site 12 | 33 | AGGGCGAGGAGCTGTTCACCGGG | 50. | CGTCGCCGTCCAGCTCGACCAGG | 51. | 11 | in |
| 13 | EGFP site 13 | 32 | AAGGGCGAGGAGCTGTTCACCGG | 52. | CGTCGCCGTCCAGCTCGACCAGG | 53. | 12 | in |
| 14 | EGFP site 14 | 155 | CTGAAGTTCATCTGCACCACCGG | 54. | GTGGTCACGAGGGTGGGCCAGGG | 55. | 13 | in |
| 15 | EGFP site 15 | 101 | AAGTTCAGCGTGTCCGGCGAGGG | 56. | CTTCAGGGTCAGCTTGCCGTAGG | 57. | 14 | in |
| 16 | EGFP site 16 | 100 | CAAGTTCAGCGTGTCCGGCGAGG | 58. | CTTCAGGGTCAGCTTGCCGTAGG | 59. | 15 | in |
| 17 | EGFP site 17 | 58 | GGTGCCCATCCTGGTCGAGCTGG | 60. | CGCCGGACACGCTGAACTTGTGG | 61. | 16 | in |
| 18 | EGFP site 18 | 74 | GAGCTGGACGGCGACGTAAACGG | 62. | GGCATCGCCCTCGCCCTCGCCGG | 63. | 17 | in |
| 19 | EGFP site 19 | 307 | GGAGCGCACCATCTTCTTCAAGG | 64. | CTCGAACTTCACCTCGGCGCGGG | 65. | 18 | in |
| 20 | EGFP site 20 | 155 | CTGAAGTTCATCTGCACCACCGG | 66. | GTCAGGGTGGTCACGAGGGTGGG | 67. | 19 | in |
| 21 | EGFP site 21 | 95 | GGCCACAAGTTCAGCGTGTCCGG | 68. | CTTCAGGGTCAGCTTGCCGTAGG | 69. | 20 | in |
| 22 | EGFP site 22 | 203 | CTCGTGACCACCCTGACCTACGG | 70. | CGTGCTGCTTCATGTGGTCGGGG | 71. | 21 | in |
| 23 | EGFP site 23 | 174 | CCGGCAAGCTGCCCGTGCCCTGG | 72. | GCTGAAGCACTGCACGCCGTAGG | 73. | 22 | in |
| 24 | EGFP site 24 | 107 | AGCGTGTCCGGCGAGGGCGAGGG | 74. | GGTGGTGCAGATGAACTTCAGGG | 75. | 23 | in |
| 25 | EGFP site 25 | 106 | CAGCGTGTCCGGCGAGGGCGAGG | 76. | GGTGGTGCAGATGAACTTCAGGG | 77. | 24 | in |
| 26 | EGFP site 26 | 49 | CACCGGGGTGGTGCCCATCCTGG | 78. | CGCCGGACACGCTGAACTTGTGG | 79. | 25 | in |

TABLE 2-continued

| FokI-dCas9 EGFP Pair # | Name | Target Start Position (+) | Sequence (+) sites | SEQ ID NO: | Sequence (−) sites | SEQ ID NO: | Edge-to-edge 'spacer' distance | PAM |
|---|---|---|---|---|---|---|---|---|
| 27 | EGFP site 27 | 122 | GGCGAGGGCGATGCCACCTACGG | 80. | GGGCACGGGCAGCTTGCCGGTGG | 81. | 26 | in |
| 28 | EGFP site 28 | 203 | CTCGTGACCACCCTGACCTACGG | 82. | AGAAGTCGTGCTGCTTCATGTGG | 83. | 27 | in |
| 29 | EGFP site 29 | 337 | CAACTACAAGACCCGCGCCGAGG | 84. | CGATGCCCTTCAGCTCGATGCGG | 85. | 28 | in |
| 30 | EGFP site 30 | 62 | CCCATCCTGGTCGAGCTGGACGG | 86. | GGCATCGCCCTCGCCCTCGCCGG | 87. | 29 | in |
| 31 | EGFP site 31 | 100 | CAAGTTCAGCGTGTCCGGCGAGG | 88. | GGTGGTGCAGATGAACTTCAGGG | 89. | 30 | in |
| 32 | EGFP site 32 | 74 | GAGCTGGACGGCGACGTAAACGG | 90. | GACCAGGATGGGCACCACCCCGG | 91. | 0 | out |
| 33 | EGFP site 33 | 314 | ACCATCTTCTTCAAGGACGACGG | 92. | CGCTCCTGGACGTAGCCTTCGGG | 93. | 1 | out |
| 34 | EGFP site 34 | 122 | GGCGAGGGCGATGCCACCTACGG | 94. | CGCCGGACACGCTGAACTTGTGG | 95. | 2 | out |
| 35 | EGFP site 35 | 275 | TTCAAGTCCGCCATGCCCGAAGG | 96. | GTCGTGCTGCTTCATGTGGTCGG | 97. | 3 | out |
| 36 | EGFP site 36 | 275 | TTCAAGTCCGCCATGCCCGAAGG | 98. | TCGTGCTGCTTCATGTGGTCGGG | 99. | 4 | out |
| 37 | EGFP site 37 | 95 | GGCCACAAGTTCAGCGTGTCCGG | 100. | CGTCGCCGTCCAGCTCGACCAGG | 101. | 5 | out |
| 38 | EGFP site 38 | 203 | CTCGTGACCACCCTGACCTACGG | 102. | CCAGGGCACGGGCAGCTTGCCGG | 103. | 6 | out |
| 39 | EGFP site 39 | 463 | CAGCCACAACGTCTATATCATGG | 104. | TGTACTCCAGCTTGTGCCCCAGG | 105. | 7 | out |
| 40 | EGFP site 40 | 95 | GGCCACAAGTTCAGCGTGTCCGG | 106. | GCCGTCCAGCTCGACCAGGATGG | 107. | 9 | out |
| 41 | EGFP site 41 | 95 | GGCCACAAGTTCAGCGTGTCCGG | 108. | CCGTCCAGCTCGACCAGGATGGG | 109. | 10 | out |
| 42 | EGFP site 42 | 101 | AAGTTCAGCGTGTCCGGCGAGGG | 110. | CGTCGCCGTCCAGCTCGACCAGG | 111. | 11 | out |
| 43 | EGFP site 43 | 350 | CGCGCCGAGGTGAAGTTCGAGGG | 112. | GCCGTCGTCCTTGAAGAAGATGG | 113. | 12 | out |
| 44 | EGFP site 44 | 174 | CCGGCAAGCTGCCCGTGCCCTGG | 114. | CTTCAGGGTCAGCTTGCCGTAGG | 115. | 13 | out |
| 45 | EGFP site 45 | 100 | CAAGTTCAGCGTGTCCGGCGAGG | 116. | GCCGTCCAGCTCGACCAGGATGG | 117. | 14 | out |
| 46 | EGFP site 46 | 100 | CAAGTTCAGCGTGTCCGGCGAGG | 118. | CCGTCCAGCTCGACCAGGATGGG | 119. | 15 | out |
| 47 | EGFP site 47 | 101 | AAGTTCAGCGTGTCCGGCGAGGG | 120. | CCGTCCAGCTCGACCAGGATGGG | 121. | 16 | out |
| 48 | EGFP site 48 | 107 | AGCGTGTCCGGCGAGGGCGAGGG | 122. | CGTCGCCGTCCAGCTCGACCAGG | 123. | 17 | out |
| 49 | EGFP site 49 | 155 | CTGAAGTTCATCTGCACCACCGG | 124. | GGCATCGCCCTCGCCCTCGCCGG | 125. | 18 | out |
| 50 | EGFP site 50 | 106 | CAGCGTGTCCGGCGAGGGCGAGG | 126. | GCCGTCCAGCTCGACCAGGATGG | 127. | 20 | out |
| 51 | EGFP site 51 | 95 | GGCCACAAGTTCAGCGTGTCCGG | 128. | GACCAGGATGGGCACCACCCCGG | 129. | 21 | out |
| 52 | EGFP site 52 | 107 | AGCGTGTCCGGCGAGGGCGAGGG | 130. | CCGTCCAGCTCGACCAGGATGGG | 131. | 22 | out |
| 53 | EGFP site 53 | 337 | CAACTACAAGACCCGCGCCGAGG | 132. | GCGCTCCTGGACGTAGCCTTCGG | 133. | 23 | out |
| 54 | EGFP site 54 | 337 | CAACTACAAGACCCGCGCCGAGG | 134. | CGCTCCTGGACGTAGCCTTCGGG | 135. | 24 | out |
| 55 | EGFP site 55 | 397 | GCTGAAGGGCATCGACTTCAAGG | 136. | CCTCGAACTTCACCTCGGCGCGG | 137. | 25 | out |
| 56 | EGFP site 56 | 100 | CAAGTTCAGCGTGTCCGGCGAGG | 138. | GACCAGGATGGGCACCACCCCGG | 139. | 26 | out |
| 57 | EGFP site 57 | 101 | AAGTTCAGCGTGTCCGGCGAGGG | 140. | GACCAGGATGGGCACCACCCCGG | 141. | 27 | out |
| 58 | EGFP site 58 | 400 | GAAGGGCATCGACTTCAAGGAGG | 142. | CCTCGAACTTCACCTCGGCGCGG | 143. | 28 | out |
| 59 | EGFP site 59 | 337 | CAACTACAAGACCCGCGCCGAGG | 144. | CTGGACGTAGCCTTCGGGCATGG | 145. | 29 | out |
| 60 | EGFP site 60 | 307 | GGAGCGCACCATCTTCTTCAAGG | 146. | AGAAGTCGTGCTGCTTCATGTGG | 147. | 31 | out |
| 61 | EGFP site 61 | 100 | CAAGTTCAGCGTGTCCGGCGAGG | 148. | CGTCGCCGTCCAGCTCGACCAGG | 149. | 10 | out |
| 62 | EGFP site 62 | 286 | CATGCCCGAAGGCTACGTCCAGG | 150. | AGAAGTCGTGCTGCTTCATGTGG | 151. | 10 | out |
| 63 | EGFP site 63 | 337 | CAACTACAAGACCCGCGCCGAGG | 152. | TGAAGAAGATGGTGCGCTCCTGG | 153. | 10 | out |

TABLE 2-continued

| FokI-dCas9 EGFP Pair # | Name | Target Start Position (+) | Sequence (+) sites | SEQ ID NO: | Sequence (−) sites | SEQ ID NO: | Edge-to-edge 'spacer' distance | PAM |
|---|---|---|---|---|---|---|---|---|
| 64 | EGFP site 64 | 382 | GGTGAACCGCATCGAGCTGAAGG | 154. | CCTCGAACTTCACCTCGGCGCGG | 155. | 10 | out |
| 65 | EGFP site 65 | 275 | TTCAAGTCCGCCATGCCCGAAGG | 156. | GCTTCATGTGGTCGGGGTAGCGG | 157. | 11 | out |
| 66 | EGFP site 66 | 349 | CCGCGCCGAGGTGAAGTTCGAGG | 158. | GCCGTCGTCCTTGAAGAAGATGG | 159. | 11 | out |
| 67 | EGFP site 67 | 382 | GGTGAACCGCATCGAGCTGAAGG | 160. | CTCGAACTTCACCTCGGCGCGGG | 161. | 11 | out |
| 68 | EGFP site 68 | 383 | GTGAACCGCATCGAGCTGAAGGG | 162. | CCTCGAACTTCACCTCGGCGCGG | 163. | 11 | out |
| 69 | EGFP site 69 | 520 | CAAGATCCGCCACAACATCGAGG | 164. | GATGCCGTTCTTCTGCTTGTCGG | 165. | 11 | out |
| 70 | EGFP site 70 | 383 | GTGAACCGCATCGAGCTGAAGGG | 166. | CTCGAACTTCACCTCGGCGCGGG | 167. | 12 | out |
| 71 | EGFP site 71 | 415 | CAAGGAGGACGGCAACATCCTGG | 168. | TCAGCTCGATGCGGTTCACCAGG | 169. | 13 | out |
| 72 | EGFP site 72 | 286 | CATGCCCGAAGGCTACGTCCAGG | 170. | GTCGTGCTGCTTCATGTGGTCGG | 171. | 14 | out |
| 73 | EGFP site 73 | 415 | CAAGGAGGACGGCAACATCCTGG | 172. | CAGCTCGATGCGGTTCACCAGGG | 173. | 14 | out |
| 74 | EGFP site 74 | 416 | AAGGAGGACGGCAACATCCTGGG | 174. | TCAGCTCGATGCGGTTCACCAGG | 175. | 14 | out |
| 75 | EGFP site 75 | 101 | AAGTTCAGCGTGTCCGGCGAGGG | 176. | GCCGTCCAGCTCGACCAGGATGG | 177. | 15 | out |
| 76 | EGFP site 76 | 286 | CATGCCCGAAGGCTACGTCCAGG | 178. | TCGTGCTGCTTCATGTGGTCGGG | 179. | 15 | out |
| 77 | EGFP site 77 | 416 | AAGGAGGACGGCAACATCCTGGG | 180. | CAGCTCGATGCGGTTCACCAGGG | 181. | 15 | out |
| 78 | EGFP site 78 | 417 | AGGAGGACGGCAACATCCTGGGG | 182. | TCAGCTCGATGCGGTTCACCAGG | 183. | 15 | out |
| 79 | EGFP site 79 | 524 | ATCCGCCACAACATCGAGGACGG | 184. | GATGCCGTTCTTCTGCTTGTCGG | 185. | 15 | out |
| 80 | EGFP site 80 | 106 | CAGCGTGTCCGGCGAGGGCGAGG | 186. | CGTCGCCGTCCAGCTCGACCAGG | 187. | 16 | out |
| 81 | EGFP site 81 | 174 | CCGGCAAGCTGCCCGTGCCCTGG | 188. | CAGGGTCAGCTTGCCGTAGGTGG | 189. | 16 | out |
| 82 | EGFP site 82 | 286 | CATGCCCGAAGGCTACGTCCAGG | 190. | CGTGCTGCTTCATGTGGTCGGGG | 191. | 16 | out |
| 83 | EGFP site 83 | 417 | AGGAGGACGGCAACATCCTGGGG | 192. | CAGCTCGATGCGGTTCACCAGGG | 193. | 16 | out |
| 84 | EGFP site 84 | 427 | CAACATCCTGGGGCACAAGCTGG | 194. | CGATGCCCTTCAGCTCGATGCGG | 195. | 16 | out |
| 85 | EGFP site 85 | 397 | GCTGAAGGGCATCGACTTCAAGG | 196. | GTCGCCCTCGAACTTCACCTCGG | 197. | 20 | out |

Surprisingly, the dCas9-FokI protein did not show detectable EGFP disruption activity when co-expressed with any of the 60 gRNA pairs in human U2OS.EGFP cells (FIG. 5E). However, screening of the FokI-dCas9 protein with the same 60 gRNA pairs did reveal EGFP disruption activity on target sites composed of half-sites in the PAM out orientation and with spacer lengths of 13 to 17 bps and of 26 bps (approximately one turn of the DNA helix more than the 13-17 bp spacer lengths) (FIG. 5B). Testing of FokI-dCas9 on an additional 25 target DNA sites with spacer lengths ranging from 10 to 20 bps and with half-sites in the PAM out orientation demonstrated efficient cleavage on targets with spacer lengths of 13 to 18 bps (FIGS. 5C-D). In these experiments, one site each was tested for spacer lengths of 17 or 18 bps and not all sites with a 13 bp spacer length showed activity. Analysis of a subset of successfully targeted sites by T7EI analysis and Sanger sequencing further confirmed the presence of indels at the intended location. Thus FokI-dCas9 can be directed by two appropriately positioned gRNAs to efficiently cleave a full-length target site of interest. For simplicity, the complex of two FokI-dCas9 fusions and two gRNAs are referred to herein as RNA-guided FokI Nucleases (RFNs).

To extend the initial findings with the EGFP reporter gene and to ascertain whether RFNs could be used to perform routine genome editing of endogenous human genes, gRNA pairs were designed for 12 different target sites in nine different human genes (Table 2). Eleven of the 12 RFNs tested introduced indels with high efficiencies (range of 3 to 40%) at their intended target sites in human U2OS.EGFP cells as judged by T7EI assay (Table 2). Similar results were obtained with these same 12 RFN pairs in HEK293 cells (Table 2). Sanger sequencing of successfully targeted alleles from U2OS.EGFP cells revealed the introduction of a range of indels (primarily deletions) at the expected cleavage site (FIG. 5F). The high success rate and high efficiencies of modifications observed in two different human cell lines demonstrate the robustness of RFNs for modifying endogenous human genes.

Example 2d. RFNs Possess Extended Specificities for their Cleavage Sites

Figure 6B:
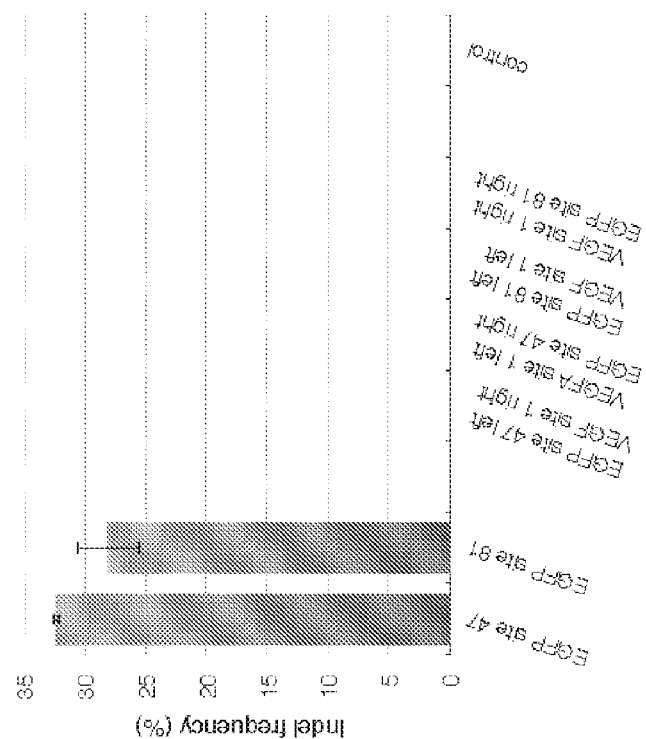
Figure 6A:
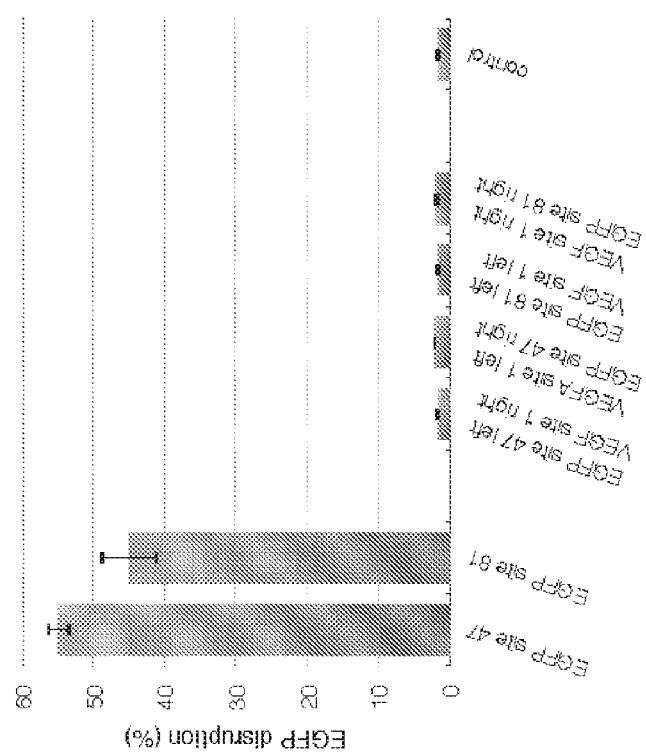

To test whether RFNs possess enhanced recognition specificities associated with dimerization, whether these nucleases strictly depend upon the presence of both gRNAs in a pair was examined. In an ideal dimeric system, single gRNAs should not be able to efficiently direct FokI-dCas9-induced indels. To perform an initial test, two pairs of gRNAs directed to two target sites in EGFP were used that had been shown to efficiently direct FokI-dCas9-induced indels to their target sites (EGFP sites 47 and 81) in human U2OS.EGFP cells (FIG. 5C). Replacement of one or the other gRNA in each of these two pairs with a gRNA targeted to an unrelated site in VEGFA resulted in reduction of EGFP disruption activity (FIG. 6A) and reduction of targeted mutations to undetectable levels as judged by T7EI assays (FIG. 6B). Similarly, the effects of using only one of each of the two gRNAs were tested using pairs that efficiently introduce FokI-dCas9-mediated indels in the human APC, MLH1, and VEGFA genes (Table 2) and again observed loss of detectable RFN-induced indels by T7EI assay (FIG. 6C). These results demonstrate that efficient induction of genome editing by an RFN requires two gRNAs with appropriate complementarity to the full-length target site.

Given that the activities of our RFNs depend on the expression of two gRNAs, it was hoped that their mutagenic effects on known off-target sites of one of the single gRNAs in the pair should be negligible. Performing these direct comparisons requires knowing the off-target sites for a monomeric Cas9 nuclease guided by a single gRNA that itself can also serve one of the two gRNAs needed to target a dimeric RFN. Although very few monomeric Cas9 nuclease off-target sites have been defined in the literature, five off-target sites had been previously identified for one of the gRNAs we used to target the dimeric RFN site in the human VEGFA gene (Example 1). Deep sequencing was used to ascertain whether these five off-target sites showed evidence of mutations in cells in which the VEGFA-targeted RFNs had been expressed (these are the same cells we used for the T7EI assay shown in FIG. 6C). The frequency of indel mutations at all five off-target sites was indistinguishable from background (FIG. 6D and Table 3). These results demonstrate that the use of RFNs can essentially eliminate the off-target effects originally induced by Cas9 nuclease and a single gRNA and are consistent with our observation that a single gRNA expressed with FokI-dCas9 does not efficiently induce indels. Although, at present, it is not possible to perform these direct comparisons on additional sites—such experiments will have to await the identification of off-target sites for more single gRNA sites that can also target a half-site for a dimeric RFN, it was concluded that dimeric RFNs have enhanced specificities relative to standard monomeric Cas9 nucleases.

TABLE 3

| Gene name | left target sequence | SEQ ID NO: | right target sequence | SEQ ID NO: | Endogenous Sequence of RFN target sites in U2OS or 293 cells (spacer sequence in lowercase) | SEQ ID NO: |
|---|---|---|---|---|---|---|
| APC1 | CCAGAAGTACGA GCGCCGCCCGG | 198. | TGGCAGGTGAGT GAGGCTGCAGG | 199. | CCGGGCGGCGCTCGTACTTCTGGccactggg cgagcgtcTGGCAGGTGAGTGAGGCTGCAGG | 200. |
| BRCA1 | GAATACCCATCT GTCAGCTTCGG | 201. | GGCGGAACCTGA GAGGCGTAAGG | 202. | CCGAAGCTGACAGATGGGTATTCtttgacgg ggggtaggGGCGGAACCTGAGAGGCGTAAGG | 203. |
| DDB2 | AATATTCAAGCA GCAGGCACAGG | 204. | CTCGCGCAGGAG GCTGCAGCGGG | 205. | CCTGTGCCTGCTGCTTGAATATTtccgcctt ttagggtgCTCGCGCAGGAGGCTGCAGCGGG | 206. |
| EMX1 | CCCAAAGCCTGG CCAGGGAGTGG | 207. | GCCCCACAGGGC TTGAAGCCCGG | 208. | CCACTCCCTGGCCAGGCTTTGGGgaggcctg gagtcatgGCCCCACAGGGCTTGAAGCCCGG | 209. |
| FANCF-site 1 | CCCTACTTCCGC TTTCACCTTGG | 210. | GGAATCCCTTCT GCAGCACCTGG | 211. | CCAAGGTGAAAGCGGAAGTAGGGccttcgcg cacctcatGGAATCCCTTCTGCAGCACCTGG | 212. |
| FANCF-site 2 | CGCTCCAGAGCC GTGCGAATGGG | 213. | TGGAGGCAAGAG GGCGGCTTTGG | 214. | CCCATTCGCACGGCTCTGGAGCGgcggctgc acaaccagTGGAGGCAAGAGGGCGGCTTTGG | 215. |
| FES | CGAGGAGACTGG GGACTGTAGGG | 216. | CCAGCTGCTGCC TTGCCTCCAGG | 217. | CCCTACAGTCCCCAGCCTCCTCGtcccatgc ctccgtctCCAGCTGCTGCCTTGCCTCCAGG | 218. |
| GLI1 | CATAGCTACTGA TTGGTGGTGGG | 219. | CCGGCCCCTCCC CAGTCAGGGGG | 220. | CCCACCACCAATCAGTAGCTATGgcgagccc tgctgtctCCGGCCCCTCCCCAGTCAGGGGG | 221. |
| MLH1 | GGAAACGTCTAG ATGCTCAACGG | 222. | CAAAATGTCGTT CGTGGCAGTGG | 223. | CCGTTGAGCATCTAGACGTTTCCttggctct tctggcgcCAAAATGTCGTTCGTGGCAGGGG | 224. |
| RARA1 | CTGTTGCTGGCC ATGCCAAGCGG | 225. | CCTGGGGCGGG CACCTCAATGG | 226. | CCGCTTGGCATGGCCAGCAACAGcagctcct gcccgacaCCTGGGGCGGGCACCTCAATGG | 227. |
| RUNX | TTCGGAGCGAAA ACCAAGACAGG | 228. | GAGTCCCCGCC TTCAGAAGAGG | 229. | CCTGTCTTGGTTTTCGCTCCGAAggtaaaag aaatcattGAGTCCCCCGCCTTCAGAAGAGG | 230. |
| SS18 | GGCCCGGTCGAC TCCGGGCCCGG | 231. | TGCTGGGAATCA GCAGTGTTTGG | 232. | CCGGGCCCGGAGTCGACCGGGCCgaggcgga ggcgggccTGCTGGGAATCAGCAGTGTTTGG | 233. |
| VEGFA-site 1 | GGGTGGGGGGAG TTTGCTCCTGG | 234. | TCCCTCTTTAGC CAGAGCCGGG | 235. | CCAGGAGCAAACTCCCCCCACCCcctttcca aagcccatTCCCTCTTTAGCCAGAGCCGGG | 236. |

TABLE 3-continued

| Gene name | | | | | | | |
|---|---|---|---|---|---|---|---|
| VEGFA-site 2 | GCCGCCGGCCGG GGAGGAGGTGG | 237. | GGCGAGCCGCGG GCAGGGGCCGG | 238. | CCACCTCCTCCCCGGCCGGCGGCggacagtg gacgcggcGGCGAGCCGCGGGCAGGGGCCGG | | 239. |
| VEGFA-site 3 | CCGTCTGCACAC CCCGGCTCTGG | 240. | CTCGGCCACCAC AGGGAAGCTGG | 241. | CCAGAGCCGGGGTGTGCAGACGGcagtcact aggggcgCTCGGCCACCACAGGGAAGCTGG | | 242. |

| Gene name | primer 1 used for T7E1 assay | SEQ ID NO: | primer 2 used for T7E1 assay | SEQ ID NO: | DMSO added (yes/no) | Thermo-cycler protocol | amplicon size (bp) | sizes of cleavage products in T7E1 (bp) |
|---|---|---|---|---|---|---|---|---|
| APC1 | GGCTGTGGGAAGCC AGCAAC | 243. | AAGCCAGGGGCCA ACTGGAG | 244. | no | touchdown | 634 | 447/187 |
| BRCA1 | GCGCGGGAATTACA GATAAATTAAAA | 245. | AGGTCCCATCCTC TCATACATACCA | 246. | no | touchdown | 751 | 454/297 |
| DDB2 | ACCGCCCCTTGGCA CCAC | 247. | CGGAGCTCATCTG CTTCCTGT | 248. | no | touchdown | 627 | 456/171 |
| EMX1 | GGAGCAGCTGGTCA GAGGGG | 249. | GGGAAGGGGGAC ACTGGGGA | 250. | yes | two-step | 729 | 480/249 |
| FANCF-site 1 | GCCCTACATCTGCT CTCCCTCCA | 251. | GGGCCGGGAAAG AGTTGCTG | 252. | no | touchdown | 634 | 361/273 |
| FANCF-site 2 | GCCCTACATCTGCT CTCCCTCCA | 253. | GGGCCGGGAAAG AGTTGCTG | 254. | no | touchdown | 634 | 466/168 |
| FES | GGGGAGGGAGGCTC CAGGTT | 255. | GGCACAATGGCTC CCAAGCA | 256. | no | touchdown | 633 | 395/238 |
| GLI1 | CCTTACCCCTCCCC TCACTCA | 257. | AGAAGGGCGGGC CAGACAGT | 258. | no | touchdown | 869 | 590/279 |
| MLH1 | ATATCCTTCTAGGT AGCGGGCAGTAGCC | 259. | TCTCGGGGGAGAG CGGTAAA | 260. | no | touchdown | 610 | 332/278 |
| RARA1 | CCCAGGAAAAGTGC CAGCTCA | 261. | TGATGGTCACCCC AACTGGA | 262. | no | touchdown | 632 | 335/297 |
| RUNX | AAGGCGGCGCTGGC TTTTT | 263. | CCAGCACAACTTA CTCGCACTTGA | 264. | no | touchdown | 626 | 389/237 |
| SS18 | GGGATGCAGGGACG GTCAAG | 265. | GCCGCCCCATCCC TAGAGAAA | 266. | no | touchdown | 629 | 455/174 |
| VEGFA-site 1 | TCCAGATGGCACAT TGTCAG | 267. | AGGGAGCAGGAA AGTGAGGT | 268. | no | touchdown | 531 | 338/193 |
| VEGFA-site 2 | AGAGAAGTCGAGGA AGAGAGAG | 269. | CAGCAGAAAGTTC ATGGTTTCG | 270. | yes | touchdown | 756 | 482/274 |
| VEGFA-site 3 | TCCAGATGGCACAT TGTCAG | 271. | AGGGAGCAGGAA AGTGAGGT | 272. | no | touchdown | 531 | 288/243 |

| Gene name | primer 1 used for deep sequencing | SEQ ID NO: | primer 2 used for deep sequencing | SEQ ID NO: |
|---|---|---|---|---|
| APC1 | | | | |
| BRCA1 | | | | |
| DDB2 | CGATGGCTCCCAAGAAACGC | 273. | GCAGGTAGAATGCACAGCCG | 274. |
| EMX1 | | | | |
| FANCF-site 1 | GCCCAGAGTCAAGGAACACG | 275. | AGGTAGTGCTTGAGACCGCC | 276. |
| FANCF-site 2 | CATCCATCGGCGCTTTGGTC | 277. | CCGGGAAAGAGTTGCTGCAC | 278. |

TABLE 3-continued

| | | | | |
|---|---|---|---|---|
| FES | CTCCCCGTCTGCAGTCCATC | 279. | CCTGCAGGGACATGTGGTGA | 280. |
| GLI1 | | | | |
| MLH1 | | | | |
| RARA1 | | | | |
| RUNX | TAGGGCTAGAGGGGTGAGGC | 281. | CCGAGGTGAAACAAGCTGCC | 282. |
| SS18 | | | | |
| VEGFA-site 1 | ATGAGGGCTCCAGATGGCAC | 283. | TTCACCCAGCTTCCCTGTGG | 284. |
| VEGFA-site 2 | | | | |
| VEGFA-site 3 | | | | |

Example 2e. Monomeric Cas9 Nickases Induce Higher Rates of Mutagenesis than Single gRNA/FokI-dCas9 Complexes As noted above, an important weakness of the paired Cas9 nickase approach is that single monomeric nickases can introduce indel mutations with high frequencies at certain target sites (See Example 1 and Ran et al., Cell 154, 1380-1389 (2013); Mali et al., Nat Biotechnol 31, 833-838 (2013); Cho et al., Genome Res (2013); and Mali et al., Science 339, 823-826 (2013)). This lack of dimerization-dependence in the paired Cas9 nickase system is a potential source of off-target effects because the two monomeric nickases can each create unwanted indel mutations elsewhere in the genome. It was hypothesized that because RFNs introduce alterations using a dimerization-dependent FokI nuclease, these fusions should generally show less undesirable indel activity in the presence of only one gRNA compared to what is observed with monomeric Cas9 nickases.

To test this hypothesis, the activities of FokI-dCas9 and Cas9 nickase were compared in the presence of a single gRNA at six dimeric human gene target sites (a total of 12 half-sites; Table 4). These particular sites were chosen because monomeric Cas9 nickases directed by just one and/or the other gRNA in a pair could induce indel mutations at these targets. Using deep sequencing, the genome editing activities of FokI-dCas9 or Cas9 nickase were assessed in the presence of both or only one or the other gRNAs. Both FokI-dCas9 and Cas9 nickase induced indels at all six target sites with high efficiencies in the presence of two gRNAs (Table 5). As hypothesized, monomeric Cas9 nickases directed by the 12 single gRNAs induced indels with frequencies ranging from 0.0048% to 3.04% (FIG. 7A and Table 5). By contrast, FokI-dCas9 directed by the same 12 single gRNAs induced indels at lower frequencies ranging from 0.0045% to 0.473% (FIG. 7A and Table 5). Comparing these data directly, FokI-dCas9 induced indels with lower frequencies than Cas9 nickase for 10 of the 12 single gRNAs (FIG. 7A and Table 5). In addition, FokI-dCas9 showed greater fold-reductions in indel frequencies than Cas9 nickase at 11 of the 12 half-sites when comparing paired gRNA rates to single gRNA rates (FIG. 7B).

TABLE 4

| Chromosome | Position | Site | FokI-dCas9 Indels | FokI-dCas9 Total | FokI-dCas9 Indel Frequency (%) | tdTomato control indels | tdTomato Total | tdTomato Indel Frequency (%) |
|---|---|---|---|---|---|---|---|---|
| 6 | 43737290 | VEGFA site 1 | 35000 | 150158 | 23.30878 | 10 | 258108 | 0.00387 |
| 15 | 65637531 | OT1-3 | 1 | 169681 | 0.00058 | 1 | 139847 | 0.00071 |
| 12 | 131690182 | OT1-4 | 4 | 190111 | 0.00210 | 5 | 139762 | 0.00357 |
| 12 | 1988060 | OT1-6 | 3 | 258976 | 0.00115 | 2 | 178162 | 0.00112 |
| 1 | 99347645 | OT1-11 | 4 | 235853 | 0.00169 | 4 | 186287 | 0.00214 |
| 17 | 39796322 | OT1-30 | 1 | 261605 | 0.00038 | 1 | 286850 | 0.00034 |

TABLE 5

Deep sequencing of FokI-dCas9, Cas9n, and tdTomato controls at 6 sites, with single and pairs of gRNAs (same data as presented in FIG. 7).

| Nuclease Type or Control | Site | guideRNA | Chromosome | Position | Indel | Totals | Percentages |
|---|---|---|---|---|---|---|---|
| FokI-dCas9 | VEGFA site 1 | both | 6 | 43737290 | 35000 | 150158 | 23.3088 |
| FokI-dCas9 | VEGFA site 1 | left | 6 | 43737290 | 5 | 95476 | 0.0052 |
| FokI-dCas9 | VEGFA site 1 | right | 6 | 43737290 | 9 | 91962 | 0.0098 |

TABLE 5-continued

Deep sequencing of FokI-dCas9, Cas9n, and tdTomato controls at 6 sites, with single and pairs of gRNAs (same data as presented in FIG. 7).

| Nuclease Type or Control | Site | guideRNA | Chromosome | Position | Indel | Totals | Percentages |
|---|---|---|---|---|---|---|---|
| FokI-dCas9 | DDB2 | both | 11 | 47236820 | 11303 | 50062 | 22.5780 |
| FokI-dCas9 | DDB2 | left | 11 | 47236820 | 311 | 85726 | 0.3628 |
| FokI-dCas9 | DDB2 | right | 11 | 47236820 | 153 | 95050 | 0.1610 |
| FokI-dCas9 | FANCF site 1 | both | 11 | 22647331 | 65846 | 195311 | 33.7134 |
| FokI-dCas9 | FANCF site 1 | left | 11 | 22647331 | 19 | 27487 | 0.0691 |
| FokI-dCas9 | FANCF site 1 | right | 11 | 22647331 | 845 | 225154 | 0.3753 |
| FokI-dCas9 | FANCF site 2 | both | 11 | 22647138 | 27743 | 120314 | 23.0588 |
| FokI-dCas9 | FANCF site 2 | left | 11 | 22647138 | 989 | 205832 | 0.4805 |
| FokI-dCas9 | FANCF site 2 | right | 11 | 22647138 | 142 | 165130 | 0.0860 |
| FokI-dCas9 | FES | both | 15 | 91428181 | 14260 | 125912 | 11.3254 |
| FokI-dCas9 | FES | left | 15 | 91428181 | 4 | 143877 | 0.0028 |
| FokI-dCas9 | FES | right | 15 | 91428181 | 7 | 145495 | 0.0048 |
| FokI-dCas9 | RUNX1 | both | 21 | 36421217 | 61057 | 136164 | 44.8408 |
| FokI-dCas9 | RUNX1 | left | 21 | 36421217 | 222 | 162636 | 0.1365 |
| FokI-dCas9 | RUNX1 | right | 21 | 36421217 | 109 | 169122 | 0.0645 |
| Cas9n | VEGFA site 1 | both | 6 | 43737290 | 14294 | 99036 | 14.4331 |
| Cas9n | VEGFA site 1 | left | 6 | 43737290 | 573 | 82316 | 0.6961 |
| Cas9n | VEGFA site 1 | right | 6 | 43737290 | 315 | 101957 | 0.3090 |
| Cas9n | DDB2 | both | 11 | 47236820 | 6673 | 31168 | 21.4098 |
| Cas9n | DDB2 | left | 11 | 47236820 | 1680 | 56019 | 2.9990 |
| Cas9n | DDB2 | right | 11 | 47236820 | 172 | 42424 | 0.4054 |
| Cas9n | FANCF site 1 | both | 11 | 22647331 | 66827 | 193111 | 34.6055 |
| Cas9n | FANCF site 1 | left | 11 | 22647331 | 1565 | 109029 | 1.4354 |
| Cas9n | FANCF site 1 | right | 11 | 22647331 | 2457 | 109289 | 2.2482 |
| Cas9n | FANCF site 2 | both | 11 | 22647138 | 17007 | 111468 | 15.2573 |
| Cas9n | FANCF site 2 | left | 11 | 22647138 | 120 | 100591 | 0.1193 |
| Cas9n | FANCF site 2 | right | 11 | 22647138 | 1063 | 93162 | 1.1410 |
| Cas9n | FES | both | 15 | 91428181 | 16529 | 126597 | 13.0564 |
| Cas9n | FES | left | 15 | 91428181 | 6 | 125196 | 0.0048 |
| Cas9n | FES | right | 15 | 91428181 | 23 | 46102 | 0.0499 |
| Cas9n | RUNX1 | both | 21 | 36421217 | 80029 | 216800 | 36.9137 |
| Cas9n | RUNX1 | left | 21 | 36421217 | 1106 | 108670 | 1.0178 |
| Cas9n | RUNX1 | right | 21 | 36421217 | 2169 | 121413 | 1.7865 |
| tdTomato controls (—) | VEGF site 1 | none | 6 | 43737290 | 29 | 313517 | 0.0092 |
| tdTomato controls (—) | FANCF site 1 | none | 11 | 22647331 | 18 | 578378 | 0.0031 |
| tdTomato controls (—) | FANCF site 2 | none | 11 | 22647138 | 81 | 393821 | 0.0206 |
| tdTomato controls (—) | FES | none | 15 | 91428181 | 21 | 410620 | 0.0051 |
| tdTomato controls (—) | DDB2 | none | 11 | 47236820 | 14 | 165314 | 0.0085 |
| tdTomato controls (—) | RUNX1 | none | 21 | 36421217 | 13 | 511977 | 0.0025 |

The deep sequencing experiments also uncovered a previously undescribed and unexpected side-effect of certain monomeric Cas9 nickases: the introduction of point mutations at particular positions within their target sites. Cas9 nickase co-expressed with a single gRNA for the "right" half-site of the VEGFA target induced base substitutions at position 15 of the recognition site at a frequency of 10.5% (FIG. 8A). Similar results were observed with Cas9 nickase and single gRNAs directed to the "right" half-site of FANCF target site 1 (mutation frequency of 16.3% at position 16) (FIG. 8B) or to the "right" half-site of the RUNX1 target site (mutation frequency of 2% at position 17) (FIG. 8C). Point mutations at these positions were not observed above background levels in control samples in which no Cas9 nickase or gRNA are expressed in the cell (FIGS. 8A-8C). Interestingly, for two of the three sites at which this hypermutation was observed, most of the substitutions observed are C to G transversions on the non-target DNA strand. The positions at which these point mutations fell within a strand-separated region of the target site that has been observed to be susceptible to P1 nuclease in vitro in a dCas9/gRNA/target DNA complex. Importantly, these point mutations occur at much lower frequencies (five to 100-fold lower) in cells that express FokI-dCas9 protein and the same gRNAs (FIG. 8A-C). Overall, it was concluded that FokI-dCas9 nucleases directed by a single gRNA generally induce mutagenic indel and point mutations with lower frequencies than matched single Cas9 nickases.

Example 2f Dimeric RFNs Possess a High Degree of Specificity

Dimeric RFNs directed by two gRNAs are not expected to induce appreciable off-target mutations in human cells. RFNs, directed by a pair of gRNAs to cleave a full-length sequence composed of two half-sites, would be expected to specify up to 44 bps of DNA in the target site. A sequence of this length will, by chance, almost always be unique (except in certain circumstances where the target might lie in duplicated genome sequence). In addition, the most closely matched sites in the genome to this full-length site should, in most cases, possess a large number of mismatches, which in turn would be expected to minimize or abolish cleavage activity by an RFN dimer. Indeed, all sites in the human genome that bear 0 to 16 mismatches (and that allow for spacers of length 14 to 17 bps) for the 15 full-length sequences successfully targeted with RFNs in this study were identified. This analysis showed that all 15 full-length sequences were unique and that the most closely matched sites in the genome ranged from 7 to 12 mismatches (Table 6). Sites containing this number of mismatches should not be efficiently mutagenized by RFNs and it will be interesting in future studies to confirm this hypothesis. Overall, dimeric RFNs should possess a high degree of specificity in human cells but the ultimate characterization of specificity will await the development of unbiased methods that can comprehensively define RFN specificity across the entire genome.

TABLE 6

Frequencies of candidate FokI-dCas9 off-target sites in the human genome that bear a defined number of mismatches

| Gene | 0 | 7 | 8 | 9 | 10 | 11 | 12 | 13 | 14 | 15 | 16 |
|---|---|---|---|---|---|---|---|---|---|---|---|
| APC | 1 | | | | | 1 | 2 | 16 | 74 | 414 | 2254 |
| BRCA1 | 1 | 1 | | | | | | 5 | 20 | 164 | 983 |
| DDB2 | 1 | | | | | | 2 | 7 | 58 | 267 | 1335 |
| EMX1 | 1 | | | 1 | | 2 | 8 | 40 | 175 | 828 | 3494 |
| FANCF | 1 | | | | | | 2 | 4 | 44 | 298 | 1639 |
| FANCF | 1 | | | | | | 2 | 12 | 79 | 358 | 1718 |
| FES | 1 | | | | | 3 | 8 | 32 | 191 | 939 | 4505 |
| GLI1 | 1 | | | | | 2 | 1 | 7 | 69 | 343 | 1711 |
| MLH1 | 1 | | | | | | 2 | 5 | 22 | 96 | 643 |
| RARA | 1 | | | | 1 | 2 | 8 | 39 | 187 | 698 | 2849 |
| RUNX1 | 1 | | | | | | | 3 | 25 | 145 | 800 |
| SS18 | 1 | | | | | 1 | 2 | 6 | 39 | 280 | 1207 |
| VEGFA-1 | 1 | | | | 1 | 2 | 3 | 22 | 103 | 543 | 2676 |
| VEGFA-2 | 1 | | | | 4 | 9 | 99 | 447 | 1675 | 5608 | 18599 |
| VEGFA-3 | 1 | | | | | | 3 | 20 | 120 | 623 | 2783 |

REFERENCES

Cheng, A. W., Wang, H., Yang, H., Shi, L., Katz, Y., Theunissen, T. W., Rangarajan, S., Shivalila, C. S., Dadon, D. B., and Jaenisch, R. Multiplexed activation of endogenous genes by CRISPR-on, an RNA-guided transcriptional activator system. Cell Res 23, 1163-1171. (2013).

Cho, S. W., Kim, S., Kim, J. M. & Kim, J. S. Targeted genome engineering in human cells with the Cas9 RNA-guided endonuclease. Nat Biotechnol 31, 230-232 (2013).

Cong, L. et al. Multiplex genome engineering using CRISPR/Cas systems. Science 339, 819-823 (2013).

Cradick, T. J., Fine, E. J., Antico, C. J., and Bao, G. CRISPR/Cas9 systems targeting beta-globin and CCR5 genes have substantial off-target activity. Nucleic Acids Res. (2013).

Dicarlo, J. E. et al. Genome engineering in *Saccharomyces cerevisiae* using CRISPR-Cas systems. Nucleic Acids Res (2013).

Ding, Q., Regan, S. N., Xia, Y., Oostrom, L. A., Cowan, C. A., and Musunuru, K. Enhanced efficiency of human pluripotent stem cell genome editing through replacing TALENs with CRISPRs. Cell Stem Cell 12, 393-394. (2013).

Fisher, S., Barry, A., Abreu, J., Minie, B., Nolan, J., Delorey, T. M., Young, G., Fennell, T. J., Allen, A., Ambrogio, L., et al. A scalable, fully automated process for construction of sequence-ready human exome targeted capture libraries. Genome Biol 12, R1. (2011).

Friedland, A. E., Tzur, Y. B., Esvelt, K. M., Colaiacovo, M. P., Church, G. M., and Calarco, J. A. Heritable genome editing in *C. elegans* via a CRISPR-Cas9 system. Nat Methods 10, 741-743. (2013).

Fu, Y., Foden, J. A., Khayter, C., Maeder, M. L., Reyon, D., Joung, J. K., and Sander, J. D. High-frequency off-target mutagenesis induced by CRISPR-Cas nucleases in human cells. Nat Biotechnol 31, 822-826. (2013).

Gabriel, R. et al. An unbiased genome-wide analysis of zinc-finger nuclease specificity. Nat Biotechnol 29, 816-823 (2011).

Gilbert, L. A., Larson, M. H., Morsut, L., Liu, Z., Brar, G. A., Torres, S. E., Stern-Ginossar, N., Brandman, O., Whitehead, E. H., Doudna, J. A., et al. (2013). CRISPR-Mediated Modular RNA-Guided Regulation of Transcription in Eukaryotes. Cell 154, 442-451.

Gratz, S. J. et al. Genome engineering of *Drosophila* with the CRISPR RNA-guided Cas9 nuclease. Genetics (2013).

Hockemeyer, D. et al. Genetic engineering of human pluripotent cells using TALE nucleases. Nat Biotechnol 29, 731-734 (2011).

Horvath, P. & Barrangou, R. CRISPR/Cas, the immune system of bacteria and archaea. Science 327, 167-170 (2010).

Hsu, P. D., Scott, D. A., Weinstein, J. A., Ran, F. A., Konermann, S., Agarwala, V., Li, Y., Fine, E. J., Wu, X., Shalem, O., et al. DNA targeting specificity of RNA-guided Cas9 nucleases. Nat Biotechnol 31, 827-832. (2013).

Hwang, W. Y. et al. Efficient genome editing in zebrafish using a CRISPR-Cas system. Nat Biotechnol 31, 227-229 (2013).

Hwang, W. Y., Fu, Y., Reyon, D., Maeder, M. L., Kaini, P., Sander, J. D., Joung, J. K., Peterson, R. T., and Yeh, J. R. Heritable and Precise Zebrafish Genome Editing Using a CRISPR-Cas System. PLoS One 8, e68708. (2013a).

Jiang, W., Bikard, D., Cox, D., Zhang, F. & Marraffini, L. A. RNA-guided editing of bacterial genomes using CRISPR-Cas systems. Nat Biotechnol 31, 233-239 (2013).

Jinek, M. et al. A programmable dual-RNA-guided DNA endonuclease in adaptive bacterial immunity. Science 337, 816-821 (2012).

Jinek, M. et al. RNA-programmed genome editing in human cells. Elife 2, e00471 (2013).

Li, D., Qiu, Z., Shao, Y., Chen, Y., Guan, Y., Liu, M., Li, Y., Gao, N., Wang, L., Lu, X., et al. Heritable gene targeting in the mouse and rat using a CRISPR-Cas system. Nat Biotechnol 31, 681-683. (2013a).

Li, W., Teng, F., Li, T., and Zhou, Q. Simultaneous generation and germline transmission of multiple gene mutations in rat using CRISPR-Cas systems. Nat Biotechnol 31, 684-686. (2013b).

Maeder, M. L., Linder, S. J., Cascio, V. M., Fu, Y., Ho, Q. H., and Joung, J. K. CRISPR RNA-guided activation of endogenous human genes. Nat Methods 10, 977-979. (2013).

Mali, P., Aach, J., Stranges, P. B., Esvelt, K. M., Moosburner, M., Kosuri, S., Yang, L., and Church, G. M. CAS9 transcriptional activators for target specificity screening and paired nickases for cooperative genome engineering. Nat Biotechnol 31, 833-838. (2013a).

Mali, P., Esvelt, K. M., and Church, G. M. Cas9 as a versatile tool for engineering biology. Nat Methods 10, 957-963. (2013b).

Mali, P. et al. RNA-guided human genome engineering via Cas9. Science 339, 823-826 (2013c).

Pattanayak, V., Lin, S., Guilinger, J. P., Ma, E., Doudna, J. A., and Liu, D. R. High-throughput profiling of off-target DNA cleavage reveals RNA-programmed Cas9 nuclease specificity. Nat Biotechnol 31, 839-843. (2013).

Pattanayak, V., Ramirez, C. L., Joung, J. K. & Liu, D. R. Revealing off-target cleavage specificities of zinc-finger nucleases by in vitro selection. Nat Methods 8, 765-770 (2011).

Perez, E. E. et al. Establishment of HIV-1 resistance in CD4+ T cells by genome editing using zinc-finger nucleases. Nat Biotechnol 26, 808-816 (2008).

Perez-Pinera, P., Kocak, D. D., Vockley, C. M., Adler, A. F., Kabadi, A. M., Polstein, L. R., Thakore, P. I., Glass, K. A., Ousterout, D. G., Leong, K. W., et al. RNA-guided gene activation by CRISPR-Cas9-based transcription factors. Nat Methods 10, 973-976. (2013).

Qi, L. S., Larson, M. H., Gilbert, L. A., Doudna, J. A., Weissman, J. S., Arkin, A. P., and Lim, W. A. Repurposing CRISPR as an RNA-guided platform for sequence-specific control of gene expression. Cell 152, 1173-1183. (2013).

Ran, F. A., Hsu, P. D., Lin, C. Y., Gootenberg, J. S., Konermann, S., Trevino, A. E., Scott, D. A., Inoue, A., Matoba, S., Zhang, Y., et al. Double nicking by RNA-guided CRISPR Cas9 for enhanced genome editing specificity. Cell 154, 1380-1389. (2013).

Reyon, D. et al. FLASH assembly of TALENs for high-throughput genome editing. Nat Biotech 30, 460-465 (2012).

Sander, J. D., Maeder, M. L., Reyon, D., Voytas, D. F., Joung, J. K., and Dobbs, D. ZiFiT (Zinc Finger Targeter): an updated zinc finger engineering tool. Nucleic Acids Res 38, W462-468. (2010).

Sander, J. D., Ramirez, C. L., Linder, S. J., Pattanayak, V., Shoresh, N., Ku, M., Foden, J. A., Reyon, D., Bernstein, B. E., Liu, D. R., et al. In silico abstraction of zinc finger nuclease cleavage profiles reveals an expanded landscape of off-target sites. Nucleic Acids Res. (2013).

Sander, J. D., Zaback, P., Joung, J. K., Voytas, D. F., and Dobbs, D. Zinc Finger Targeter (ZiFiT): an engineered zinc finger/target site design tool. Nucleic Acids Res 35, W599-605. (2007).

Shen, B. et al. Generation of gene-modified mice via Cas9/RNA-mediated gene targeting. Cell Res (2013).

Sugimoto, N. et al. Thermodynamic parameters to predict stability of RNA/DNA hybrid duplexes. Biochemistry 34, 11211-11216 (1995).

Terns, M. P. & Terns, R. M. CRISPR-based adaptive immune systems. Curr Opin Microbiol 14, 321-327 (2011).

Wang, H. et al. One-Step Generation of Mice Carrying Mutations in Multiple Genes by CRISPR/Cas-Mediated Genome Engineering. Cell 153, 910-918 (2013).

Wiedenheft, B., Sternberg, S. H. & Doudna, J. A. RNA-guided genetic silencing systems in bacteria and archaea. Nature 482, 331-338 (2012).

Yang, L., Guell, M., Byrne, S., Yang, J. L., De Los Angeles, A., Mali, P., Aach, J., Kim-Kiselak, C., Briggs, A. W., Rios, X., et al. (2013). Optimization of scarless human stem cell genome editing. Nucleic Acids Res 41, 9049-9061.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for increasing specificity of RNA-guided genome editing in a cell, the method comprising expressing in said cell, or contacting said cell with an RNA-guided FokI Nuclease (RFN) fusion protein comprising a FokI catalytic domain sequence fused to the amino terminus of a catalytically inactive *Streptococcus pyogenes* CRISPR-associated 9 (dCas9) protein comprising an amino acid sequence that is at least 95% identical to the amino acid sequence of SEQ ID NO: 5, wherein said catalytically inactive *S. pyogenes* Cas9 has point mutations at amino acid residues corresponding to positions (i) D10, E762, H983, or D986, and (ii) H840 or N863 of *S. pyogenes* Cas9, an intervening linker from 2 to 30 amino acids, and two guide RNAs that direct said RFN fusion protein to a first target genomic sequence and a second target genomic sequence, wherein said two guide RNAs that direct said RFN fusion protein to said first target genomic sequence and said second target genomic sequence are spaced 10 to 20 nucleotides apart, and said first target genomic sequence comprises a PAM recognition sequence positioned upstream of said first target genomic sequence and said second target genomic sequence comprises a PAM recognition sequence positioned downstream of said second target genomic sequence.

2. The method of claim 1, wherein said guide RNAs are:
(a) two single guide RNAs, wherein one single guide RNA targets a first strand, and a second guide RNA targets a complementary strand, and FokI cuts each strand resulting in a pair of nicks on opposite DNA strands, thereby creating a double-stranded break, or (b) a tracrRNA and two crRNAs, wherein one crRNA targets a first strand, and a second crRNA targets a complementary strand, and FokI cuts each strand resulting in a pair of nicks on opposite DNA strands, thereby creating a double-stranded break.

3. The method of claim 1, wherein each of said two guide RNAs include a complementarity region that is complementary to 17-20 nucleotides of said first target genomic sequence and said second target genomic sequence.

4. The method of claim 1, wherein an indel mutation is induced between said first target genomic sequence and said second target genomic sequence.

5. The method of claim 1, wherein the specificity of RNA-guided genome editing in a cell is increased as compared to genome editing with a native Cas9.

6. The method of claim 1, wherein said first target genomic sequence and said second target genomic sequence are spaced 13-17 nucleotides apart.

7. The method of claim 1, wherein said intervening linker comprises $Gly_4Ser$.

8. The method of claim 1, wherein said FokI catalytic domain comprises amino acid residues 388-583 or amino acid residues 408-583 of the amino acid sequence of SEQ ID NO: 4.

9. The method of claim 1, wherein said point mutations are: (i) D10A or D10N; and (ii) H840A, H840Y or H840N.

10. The method of claim 1, wherein said RNA-guided FokI Nuclease fusion protein comprises the amino acid sequence of SEQ ID NO: 26.

* * * * *

SEQUENCE LISTING

```
<160> NUMBER OF SEQ ID NOS: 466

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      binding site oligonucleotide

<400> SEQUENCE: 1
gggcacgggc agcttgccgg tgg                                              23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
``` binding site oligonucleotide

<400> SEQUENCE: 2
gatgccgttc ttctgcttgt cgg          23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      binding site oligonucleotide

<400> SEQUENCE: 3
ggtggtgcag atgaacttca ggg          23

<210> SEQ ID NO 4
<211> LENGTH: 583
<212> TYPE: PRT
<213> ORGANISM: Planomicrobium okeanokoites

<400> SEQUENCE: 4

```
Met Phe Leu Ser Met Val Ser Lys Ile Arg Thr Phe Gly Trp Val Gln
1               5                   10                  15

Asn Pro Gly Lys Phe Glu Asn Leu Lys Arg Val Val Gln Val Phe Asp
            20                  25                  30

Arg Asn Ser Lys Val His Asn Glu Val Lys Asn Ile Lys Ile Pro Thr
        35                  40                  45

Leu Val Lys Glu Ser Lys Ile Gln Lys Glu Leu Val Ala Ile Met Asn
    50                  55                  60

Gln His Asp Leu Ile Tyr Thr Tyr Lys Glu Leu Val Gly Thr Gly Thr
65                  70                  75                  80

Ser Ile Arg Ser Glu Ala Pro Cys Asp Ala Ile Ile Gln Ala Thr Ile
                85                  90                  95

Ala Asp Gln Gly Asn Lys Lys Gly Tyr Ile Asp Asn Trp Ser Ser Asp
            100                 105                 110

Gly Phe Leu Arg Trp Ala His Ala Leu Gly Phe Ile Glu Tyr Ile Asn
        115                 120                 125

Lys Ser Asp Ser Phe Val Ile Thr Asp Val Gly Leu Ala Tyr Ser Lys
    130                 135                 140

Ser Ala Asp Gly Ser Ala Ile Glu Lys Glu Ile Leu Ile Glu Ala Ile
145                 150                 155                 160

Ser Ser Tyr Pro Pro Ala Ile Arg Ile Leu Thr Leu Leu Glu Asp Gly
                165                 170                 175

Gln His Leu Thr Lys Phe Asp Leu Gly Lys Asn Leu Gly Phe Ser Gly
            180                 185                 190

Glu Ser Gly Phe Thr Ser Leu Pro Glu Gly Ile Leu Leu Asp Thr Leu
        195                 200                 205

Ala Asn Ala Met Pro Lys Asp Lys Gly Glu Ile Arg Asn Asn Trp Glu
    210                 215                 220

Gly Ser Ser Asp Lys Tyr Ala Arg Met Ile Gly Gly Trp Leu Asp Lys
225                 230                 235                 240

Leu Gly Leu Val Lys Gln Gly Lys Lys Glu Phe Ile Ile Pro Thr Leu
                245                 250                 255

Gly Lys Pro Asp Asn Lys Glu Phe Ile Ser His Ala Phe Lys Ile Thr
            260                 265                 270

Gly Glu Gly Leu Lys Val Leu Arg Arg Ala Lys Gly Ser Thr Lys Phe
```

```
                    275                 280                 285
Thr Arg Val Pro Lys Arg Val Tyr Trp Glu Met Leu Ala Thr Asn Leu
    290                 295                 300
Thr Asp Lys Glu Tyr Val Arg Thr Arg Arg Ala Leu Ile Leu Glu Ile
305                 310                 315                 320
Leu Ile Lys Ala Gly Ser Leu Lys Ile Glu Gln Ile Gln Asp Asn Leu
                325                 330                 335
Lys Lys Leu Gly Phe Asp Glu Val Ile Glu Thr Ile Glu Asn Asp Ile
                340                 345                 350
Lys Gly Leu Ile Asn Thr Gly Ile Phe Ile Glu Ile Lys Gly Arg Phe
                355                 360                 365
Tyr Gln Leu Lys Asp His Ile Leu Gln Phe Val Ile Pro Asn Arg Gly
    370                 375                 380
Val Thr Lys Gln Leu Val Lys Ser Glu Leu Glu Glu Lys Lys Ser Glu
385                 390                 395                 400
Leu Arg His Lys Leu Lys Tyr Val Pro His Glu Tyr Ile Glu Leu Ile
                405                 410                 415
Glu Ile Ala Arg Asn Ser Thr Gln Asp Arg Ile Leu Glu Met Lys Val
            420                 425                 430
Met Glu Phe Phe Met Lys Val Tyr Gly Tyr Arg Gly Lys His Leu Gly
            435                 440                 445
Gly Ser Arg Lys Pro Asp Gly Ala Ile Tyr Thr Val Gly Ser Pro Ile
    450                 455                 460
Asp Tyr Gly Val Ile Val Asp Thr Lys Ala Tyr Ser Gly Gly Tyr Asn
465                 470                 475                 480
Leu Pro Ile Gly Gln Ala Asp Glu Met Gln Arg Tyr Val Glu Glu Asn
                485                 490                 495
Gln Thr Arg Asn Lys His Ile Asn Pro Asn Glu Trp Trp Lys Val Tyr
                500                 505                 510
Pro Ser Ser Val Thr Glu Phe Lys Phe Leu Phe Val Ser Gly His Phe
            515                 520                 525
Lys Gly Asn Tyr Lys Ala Gln Leu Thr Arg Leu Asn His Ile Thr Asn
        530                 535                 540
Cys Asn Gly Ala Val Leu Ser Val Glu Glu Leu Leu Ile Gly Gly Glu
545                 550                 555                 560
Met Ile Lys Ala Gly Thr Leu Thr Leu Glu Glu Val Arg Arg Lys Phe
                565                 570                 575
Asn Asn Gly Glu Ile Asn Phe
            580

<210> SEQ ID NO 5
<211> LENGTH: 1368
<212> TYPE: PRT
<213> ORGANISM: Streptococcus pyogenes

<400> SEQUENCE: 5

Met Asp Lys Lys Tyr Ser Ile Gly Leu Ala Ile Gly Thr Asn Ser Val
1               5                   10                  15
Gly Trp Ala Val Ile Thr Asp Glu Tyr Lys Val Pro Ser Lys Lys Phe
            20                  25                  30
Lys Val Leu Gly Asn Thr Asp Arg His Ser Ile Lys Lys Asn Leu Ile
        35                  40                  45
Gly Ala Leu Leu Phe Asp Ser Gly Glu Thr Ala Glu Ala Thr Arg Leu
    50                  55                  60
```

```
Lys Arg Thr Ala Arg Arg Tyr Thr Arg Lys Asn Arg Ile Cys
 65                  70                  75                  80

Tyr Leu Gln Glu Ile Phe Ser Asn Glu Met Ala Lys Val Asp Asp Ser
             85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
            130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
            290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
```

```
              485                 490                 495
Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
                530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
                610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
                690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
                770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp Ala Ile Val Pro Gln Ser Phe Leu Lys
                835                 840                 845

Asp Asp Ser Ile Asp Asn Lys Val Leu Thr Arg Ser Asp Lys Asn Arg
                850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910
```

-continued

```
Lys Ala Gly Phe Ile Lys Arg Gln Leu Val Glu Thr Arg Gln Ile Thr
            915                 920                 925
Lys His Val Ala Gln Ile Leu Asp Ser Arg Met Asn Thr Lys Tyr Asp
    930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                    980                 985                 990
Val Gly Thr Ala Leu Ile Lys Lys Tyr Pro Lys Leu Glu Ser Glu Phe
            995                 1000                1005
Val Tyr Gly Asp Tyr Lys Val Tyr Asp Val Arg Lys Met Ile Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Asp Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Leu Gly Ile Thr Ile Met Glu Arg Ser Ser
    1160                1165                1170
Phe Glu Lys Asn Pro Ile Asp Phe Leu Glu Ala Lys Gly Tyr Lys
    1175                1180                1185
Glu Val Lys Lys Asp Leu Ile Ile Lys Leu Pro Lys Tyr Ser Leu
    1190                1195                1200
Phe Glu Leu Glu Asn Gly Arg Lys Arg Met Leu Ala Ser Ala Gly
    1205                1210                1215
Glu Leu Gln Lys Gly Asn Glu Leu Ala Leu Pro Ser Lys Tyr Val
    1220                1225                1230
Asn Phe Leu Tyr Leu Ala Ser His Tyr Glu Lys Leu Lys Gly Ser
    1235                1240                1245
Pro Glu Asp Asn Glu Gln Lys Gln Leu Phe Val Glu Gln His Lys
    1250                1255                1260
His Tyr Leu Asp Glu Ile Ile Glu Gln Ile Ser Glu Phe Ser Lys
    1265                1270                1275
Arg Val Ile Leu Ala Asp Ala Asn Leu Asp Lys Val Leu Ser Ala
    1280                1285                1290
Tyr Asn Lys His Arg Asp Lys Pro Ile Arg Glu Gln Ala Glu Asn
    1295                1300                1305
```

```
Ile Ile His Leu Phe Thr Leu Thr Asn Leu Gly Ala    Pro Ala Ala
    1310                1315                1320

Phe Lys Tyr Phe Asp Thr Thr Ile Asp Arg Lys Arg    Tyr Thr Ser
    1325                1330                1335

Thr Lys Glu Val Leu Asp Ala Thr Leu Ile His Gln    Ser Ile Thr
    1340                1345                1350

Gly Leu Tyr Glu Thr Arg Ile Asp Leu Ser Gln Leu    Gly Gly Asp
    1355                1360                1365

<210> SEQ ID NO 6
<211> LENGTH: 262
<212> TYPE: RNA
<213> ORGANISM: Artificial Sequence
<220> FEATURE:
<223> OTHER INFORMATION: Description of Artificial Sequence: Synthetic
      guide RNA polynucleotide
<220> FEATURE:
<221> NAME/KEY: modified_base
<222> LOCATION: (1)..(20)
<223> OTHER INFORMATION: a, c, u, g, unknown or other and this region
      may encompass 17-20 nucleotides
<220> FEATURE:
<221> NAME/KEY: modified_base
<222> LOCATION: (63)..(262)
<223> OTHER INFORMATION: a, c, u, g, unknown or other and this region
      may encompass 0-200 nucleotides

<400> SEQUENCE: 6
nnnnnnnnnn nnnnnnnnnn guuuuagagc uagaaauagc aaguuaaaau aaggcuaguc     60
cgnnnnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn nnnnnnnnnn nnnnnnnnnn nnnnnnnnnn nnnnnnnnnn    240
nnnnnnnnnn nnnnnnnnnn nn                                             262

<210> SEQ ID NO 7
<211> LENGTH: 275
<212> TYPE: RNA
<213> ORGANISM: Artificial Sequence
<220> FEATURE:
<223> OTHER INFORMATION: Description of Artificial Sequence: Synthetic
      guide RNA polynucleotide
<220> FEATURE:
<221> NAME/KEY: modified_base
<222> LOCATION: (1)..(20)
<223> OTHER INFORMATION: a, c, u, g, unknown or other and this region
      may encompass 17-20 nucleotides
<220> FEATURE:
<221> NAME/KEY: modified_base
<222> LOCATION: (76)..(275)
<223> OTHER INFORMATION: a, c, u, g, unknown or other and this region
      may encompass 0-200 nucleotides

<400> SEQUENCE: 7
nnnnnnnnnn nnnnnnnnnn guuuuagagc uaugcugaaa agcauagcaa guuaaaauaa     60
ggcuaguccg uuaucnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn nnnnnnnnnn nnnnnnnnnn nnnnnnnnnn nnnnnnnnnn    240
nnnnnnnnnn nnnnnnnnnn nnnnnnnnnn nnnnn                               275

<210> SEQ ID NO 8
<211> LENGTH: 287
<212> TYPE: RNA
<213> ORGANISM: Artificial Sequence
```

```
<220> FEATURE:
<223> OTHER INFORMATION: Description of Artificial Sequence: Synthetic
      guide RNA polynucleotide
<220> FEATURE:
<221> NAME/KEY: modified_base
<222> LOCATION: (1)..(20)
<223> OTHER INFORMATION: a, c, u, g, unknown or other and this region
      may encompass 17-20 nucleotides
<220> FEATURE:
<221> NAME/KEY: modified_base
<222> LOCATION: (88)..(287)
<223> OTHER INFORMATION: a, c, u, g, unknown or other and this region
      may encompass 0-200 nucleotides

<400> SEQUENCE: 8
nnnnnnnnnn nnnnnnnnnn guuuuagagc uaugcuguuu uggaaacaaa acagcauagc      60
aaguuaaaau aaggcuaguc cguuaucnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnn                   287

<210> SEQ ID NO 9
<211> LENGTH: 296
<212> TYPE: RNA
<213> ORGANISM: Artificial Sequence
<220> FEATURE:
<223> OTHER INFORMATION: Description of Artificial Sequence: Synthetic
      guide RNA polynucleotide
<220> FEATURE:
<221> NAME/KEY: modified_base
<222> LOCATION: (1)..(20)
<223> OTHER INFORMATION: a, c, u, g, unknown or other and this region
      may encompass 17-20 nucleotides
<220> FEATURE:
<221> NAME/KEY: modified_base
<222> LOCATION: (97)..(296)
<223> OTHER INFORMATION: a, c, u, g, unknown or other and this region
      may encompass 0-200 nucleotides

<400> SEQUENCE: 9
nnnnnnnnnn nnnnnnnnnn guuuuagagc uagaaauagc aaguuaaaau aaggcuaguc      60
cguuaucaac uugaaaaagu ggcaccgagu cggugcnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnn        296

<210> SEQ ID NO 10
<211> LENGTH: 96
<212> TYPE: RNA
<213> ORGANISM: Artificial Sequence
<220> FEATURE:
<223> OTHER INFORMATION: Description of Artificial Sequence: Synthetic
      guide RNA oligonucleotide
<220> FEATURE:
<221> NAME/KEY: modified_base
<222> LOCATION: (1)..(20)
<223> OTHER INFORMATION: a, c, u, g, unknown or other and this region
      may encompass 17-20 nucleotides

<400> SEQUENCE: 10
nnnnnnnnnn nnnnnnnnnn guuuaagagc uagaaauagc aaguuuaaau aaggcuaguc      60
cguuaucaac uugaaaaagu ggcaccgagu cggugc                                96

<210> SEQ ID NO 11
```

```
<211> LENGTH: 106
<212> TYPE: RNA
<213> ORGANISM: Artificial Sequence
<220> FEATURE:
<223> OTHER INFORMATION: Description of Artificial Sequence: Synthetic
      guide RNA polynucleotide
<220> FEATURE:
<221> NAME/KEY: modified_base
<222> LOCATION: (1)..(20)
<223> OTHER INFORMATION: a, c, u, g, unknown or other and this region
      may encompass 17-20 nucleotides

<400> SEQUENCE: 11
nnnnnnnnnn nnnnnnnnnn guuuuagagc uaugcuggaa acagcauagc aaguuuaaau    60
aaggcuaguc cguuaucaac uugaaaaagu ggcaccgagu cggugc                  106

<210> SEQ ID NO 12
<211> LENGTH: 106
<212> TYPE: RNA
<213> ORGANISM: Artificial Sequence
<220> FEATURE:
<223> OTHER INFORMATION: Description of Artificial Sequence: Synthetic
      guide RNA polynucleotide
<220> FEATURE:
<221> NAME/KEY: modified_base
<222> LOCATION: (1)..(20)
<223> OTHER INFORMATION: a, c, u, g, unknown or other and this region
      may encompass 17-20 nucleotides

<400> SEQUENCE: 12
nnnnnnnnnn nnnnnnnnnn guuuaagagc uaugcuggaa acagcauagc aaguuuaaau    60
aaggcuaguc cguuaucaac uugaaaaagu ggcaccgagu cggugc                  106

<210> SEQ ID NO 13
<211> LENGTH: 32
<212> TYPE: RNA
<213> ORGANISM: Artificial Sequence
<220> FEATURE:
<223> OTHER INFORMATION: Description of Artificial Sequence: Synthetic
      tracrRNA oligonucleotide
<220> FEATURE:
<221> NAME/KEY: modified_base
<222> LOCATION: (1)..(20)
<223> OTHER INFORMATION: a, c, u, g, unknown or other and this region
      may encompass 17-20 nucleotides

<400> SEQUENCE: 13
nnnnnnnnnn nnnnnnnnnn guuuuagagc ua                                  32

<210> SEQ ID NO 14
<211> LENGTH: 42
<212> TYPE: RNA
<213> ORGANISM: Artificial Sequence
<220> FEATURE:
<223> OTHER INFORMATION: Description of Artificial Sequence: Synthetic
      tracrRNA oligonucleotide
<220> FEATURE:
<221> NAME/KEY: modified_base
<222> LOCATION: (1)..(20)
<223> OTHER INFORMATION: a, c, u, g, unknown or other and this region
      may encompass 17-20 nucleotides

<400> SEQUENCE: 14
nnnnnnnnnn nnnnnnnnnn guuuuagagc uaugcuguuu ug                       42

<210> SEQ ID NO 15
<211> LENGTH: 36
<212> TYPE: RNA
<213> ORGANISM: Artificial Sequence
```

```
<220> FEATURE:
<223> OTHER INFORMATION: Description of Artificial Sequence: Synthetic
      tracrRNA oligonucleotide
<220> FEATURE:
<221> NAME/KEY: modified_base
<222> LOCATION: (1)..(20)
<223> OTHER INFORMATION: a, c, u, g, unknown or other and this region
      may encompass 17-20 nucleotides

<400> SEQUENCE: 15
nnnnnnnnnn nnnnnnnnnn guuuuagagc uaugcu                                 36

<210> SEQ ID NO 16
<211> LENGTH: 79
<212> TYPE: RNA
<213> ORGANISM: Artificial Sequence
<220> FEATURE:
<223> OTHER INFORMATION: Description of Artificial Sequence: Synthetic
      tracrRNA oligonucleotide

<400> SEQUENCE: 16
ggaaccauuc aaaacagcau agcaaguuaa aauaaggcua guccguuauc aacuugaaaa        60
aguggcaccg agucggugc                                                    79

<210> SEQ ID NO 17
<211> LENGTH: 60
<212> TYPE: RNA
<213> ORGANISM: Artificial Sequence
<220> FEATURE:
<223> OTHER INFORMATION: Description of Artificial Sequence: Synthetic
      tracrRNA oligonucleotide

<400> SEQUENCE: 17
uagcaaguua aaauaaggcu aguccguuau caacuugaaa aaguggcacc gagucggugc        60

<210> SEQ ID NO 18
<211> LENGTH: 64
<212> TYPE: RNA
<213> ORGANISM: Artificial Sequence
<220> FEATURE:
<223> OTHER INFORMATION: Description of Artificial Sequence: Synthetic
      tracrRNA oligonucleotide

<400> SEQUENCE: 18
agcauagcaa guuaaaauaa ggcuaguccg uuaucaacuu gaaaaagugg caccgagucg        60
gugc                                                                    64

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gtaaaacgac ggccag                                                       16

<210> SEQ ID NO 20
<211> LENGTH: 28
<212> TYPE: RNA
<213> ORGANISM: Artificial Sequence
<220> FEATURE:
<223> OTHER INFORMATION: Description of Artificial Sequence: Synthetic
      Csy4 RNA binding site oligonucleotide

<400> SEQUENCE: 20
```

```
guucacugcc guauaggcag cuaagaaa                                              28
```

<210> SEQ ID NO 21
<211> LENGTH: 252
<212> TYPE: RNA
<213> ORGANISM: Artificial Sequence
<220> FEATURE:
<223> OTHER INFORMATION: Description of Artificial Sequence: Synthetic
      multiplex guide RNA polynucleotide
<220> FEATURE:
<221> NAME/KEY: modified_base
<222> LOCATION: (21)..(40)
<223> OTHER INFORMATION: a, c, u, g, unknown or other
<220> FEATURE:
<221> NAME/KEY: modified_base
<222> LOCATION: (137)..(156)
<223> OTHER INFORMATION: a, c, u, g, unknown or other

<400> SEQUENCE: 21

```
guucacugcc guauaggcag nnnnnnnnnn nnnnnnnnnn guuuagagc uagaaauagc            60 aaguuaaaau aaggcuaguc cguuaucaac uugaaaaagu ggcaccgagu cggugcguuc          120
acugccguau aggcagnnnn nnnnnnnnnn nnnnnnguuu agagcuaga aauagcaagu          180 uaaaauaagg cuaguccguu aucaacuuga aaaguggca ccgagucggu gcuucacug           240 ccguauaggc ag                                                             252
```

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 22

Gly Gly Gly Ser
1

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 23

Gly Gly Gly Gly Ser
1               5

<210> SEQ ID NO 24
<211> LENGTH: 1602
<212> TYPE: PRT
<213> ORGANISM: Artificial Sequence
<220> FEATURE:
<223> OTHER INFORMATION: Description of Artificial Sequence: Synthetic
      FokI-dCas9 polypeptide

<400> SEQUENCE: 24

Met Gln Leu Val Lys Ser Glu Leu Glu Glu Lys Ser Glu Leu Arg
1               5                   10                  15

His Lys Leu Lys Tyr Val Pro His Glu Tyr Ile Glu Leu Ile Glu Ile
                20                  25                  30

Ala Arg Asn Ser Thr Gln Asp Arg Ile Leu Glu Met Lys Val Met Glu
            35                  40                  45

```
Phe Phe Met Lys Val Tyr Gly Tyr Arg Gly Lys His Leu Gly Gly Ser
 50                  55                  60

Arg Lys Pro Asp Gly Ala Ile Tyr Thr Val Gly Ser Pro Ile Asp Tyr
 65                  70                  75                  80

Gly Val Ile Val Asp Thr Lys Ala Tyr Ser Gly Gly Tyr Asn Leu Pro
                 85                  90                  95

Ile Gly Gln Ala Asp Glu Met Gln Arg Tyr Val Glu Glu Asn Gln Thr
            100                 105                 110

Arg Asn Lys His Ile Asn Pro Asn Glu Trp Trp Lys Val Tyr Pro Ser
        115                 120                 125

Ser Val Thr Glu Phe Lys Phe Leu Phe Val Ser Gly His Phe Lys Gly
    130                 135                 140

Asn Tyr Lys Ala Gln Leu Thr Arg Leu Asn His Ile Thr Asn Cys Asn
145                 150                 155                 160

Gly Ala Val Leu Ser Val Glu Glu Leu Leu Ile Gly Gly Glu Met Ile
                165                 170                 175

Lys Ala Gly Thr Leu Thr Leu Glu Glu Val Arg Arg Lys Phe Asn Asn
            180                 185                 190

Gly Glu Ile Asn Phe Gly Gly Gly Ser Asp Lys Lys Tyr Ser Ile
        195                 200                 205

Gly Leu Ala Ile Gly Thr Asn Ser Val Gly Trp Ala Val Ile Thr Asp
    210                 215                 220

Glu Tyr Lys Val Pro Ser Lys Lys Phe Lys Val Leu Gly Asn Thr Asp
225                 230                 235                 240

Arg His Ser Ile Lys Lys Asn Leu Ile Gly Ala Leu Leu Phe Asp Ser
                245                 250                 255

Gly Glu Thr Ala Glu Ala Thr Arg Leu Lys Arg Thr Ala Arg Arg Arg
            260                 265                 270

Tyr Thr Arg Arg Lys Asn Arg Ile Cys Tyr Leu Gln Glu Ile Phe Ser
        275                 280                 285

Asn Glu Met Ala Lys Val Asp Asp Ser Phe Phe His Arg Leu Glu Glu
    290                 295                 300

Ser Phe Leu Val Glu Glu Asp Lys Lys His Glu Arg His Pro Ile Phe
305                 310                 315                 320

Gly Asn Ile Val Asp Glu Val Ala Tyr His Glu Lys Tyr Pro Thr Ile
                325                 330                 335

Tyr His Leu Arg Lys Lys Leu Val Asp Ser Thr Asp Lys Ala Asp Leu
            340                 345                 350

Arg Leu Ile Tyr Leu Ala Leu Ala His Met Ile Lys Phe Arg Gly His
        355                 360                 365

Phe Leu Ile Glu Gly Asp Leu Asn Pro Asp Asn Ser Asp Val Asp Lys
    370                 375                 380

Leu Phe Ile Gln Leu Val Gln Thr Tyr Asn Gln Leu Phe Glu Glu Asn
385                 390                 395                 400

Pro Ile Asn Ala Ser Gly Val Asp Ala Lys Ala Ile Leu Ser Ala Arg
                405                 410                 415

Leu Ser Lys Ser Arg Arg Leu Glu Asn Leu Ile Ala Gln Leu Pro Gly
            420                 425                 430

Glu Lys Lys Asn Gly Leu Phe Gly Asn Leu Ile Ala Leu Ser Leu Gly
        435                 440                 445

Leu Thr Pro Asn Phe Lys Ser Asn Phe Asp Leu Ala Glu Asp Ala Lys
    450                 455                 460
```

```
Leu Gln Leu Ser Lys Asp Thr Tyr Asp Asp Asp Leu Asp Asn Leu Leu
465                 470                 475                 480

Ala Gln Ile Gly Asp Gln Tyr Ala Asp Leu Phe Leu Ala Ala Lys Asn
                485                 490                 495

Leu Ser Asp Ala Ile Leu Leu Ser Asp Ile Leu Arg Val Asn Thr Glu
            500                 505                 510

Ile Thr Lys Ala Pro Leu Ser Ala Ser Met Ile Lys Arg Tyr Asp Glu
        515                 520                 525

His His Gln Asp Leu Thr Leu Leu Lys Ala Leu Val Arg Gln Gln Leu
    530                 535                 540

Pro Glu Lys Tyr Lys Glu Ile Phe Phe Asp Gln Ser Lys Asn Gly Tyr
545                 550                 555                 560

Ala Gly Tyr Ile Asp Gly Gly Ala Ser Gln Glu Glu Phe Tyr Lys Phe
                565                 570                 575

Ile Lys Pro Ile Leu Glu Lys Met Asp Gly Thr Glu Glu Leu Leu Val
            580                 585                 590

Lys Leu Asn Arg Glu Asp Leu Leu Arg Lys Gln Arg Thr Phe Asp Asn
        595                 600                 605

Gly Ser Ile Pro His Gln Ile His Leu Gly Glu Leu His Ala Ile Leu
    610                 615                 620

Arg Arg Gln Glu Asp Phe Tyr Pro Phe Leu Lys Asp Asn Arg Glu Lys
625                 630                 635                 640

Ile Glu Lys Ile Leu Thr Phe Arg Ile Pro Tyr Tyr Val Gly Pro Leu
                645                 650                 655

Ala Arg Gly Asn Ser Arg Phe Ala Trp Met Thr Arg Lys Ser Glu Glu
            660                 665                 670

Thr Ile Thr Pro Trp Asn Phe Glu Glu Val Val Asp Lys Gly Ala Ser
        675                 680                 685

Ala Gln Ser Phe Ile Glu Arg Met Thr Asn Phe Asp Lys Asn Leu Pro
    690                 695                 700

Asn Glu Lys Val Leu Pro Lys His Ser Leu Leu Tyr Glu Tyr Phe Thr
705                 710                 715                 720

Val Tyr Asn Glu Leu Thr Lys Val Lys Tyr Val Thr Glu Gly Met Arg
                725                 730                 735

Lys Pro Ala Phe Leu Ser Gly Glu Gln Lys Lys Ala Ile Val Asp Leu
            740                 745                 750

Leu Phe Lys Thr Asn Arg Lys Val Thr Val Lys Gln Leu Lys Glu Asp
        755                 760                 765

Tyr Phe Lys Lys Ile Glu Cys Phe Asp Ser Val Glu Ile Ser Gly Val
    770                 775                 780

Glu Asp Arg Phe Asn Ala Ser Leu Gly Thr Tyr His Asp Leu Leu Lys
785                 790                 795                 800

Ile Ile Lys Asp Lys Asp Phe Leu Asp Asn Glu Glu Asn Glu Asp Ile
                805                 810                 815

Leu Glu Asp Ile Val Leu Thr Leu Thr Leu Phe Glu Asp Arg Glu Met
            820                 825                 830

Ile Glu Glu Arg Leu Lys Thr Tyr Ala His Leu Phe Asp Asp Lys Val
        835                 840                 845

Met Lys Gln Leu Lys Arg Arg Arg Tyr Thr Gly Trp Gly Arg Leu Ser
    850                 855                 860

Arg Lys Leu Ile Asn Gly Ile Arg Asp Lys Gln Ser Gly Lys Thr Ile
865                 870                 875                 880

Leu Asp Phe Leu Lys Ser Asp Gly Phe Ala Asn Arg Asn Phe Met Gln
```

```
                885                 890                 895
Leu Ile His Asp Asp Ser Leu Thr Phe Lys Glu Asp Ile Gln Lys Ala
                900                 905                 910

Gln Val Ser Gly Gln Gly Asp Ser Leu His Glu His Ile Ala Asn Leu
                915                 920                 925

Ala Gly Ser Pro Ala Ile Lys Lys Gly Ile Leu Gln Thr Val Lys Val
            930                 935                 940

Val Asp Glu Leu Val Lys Val Met Gly Arg His Lys Pro Glu Asn Ile
945                 950                 955                 960

Val Ile Glu Met Ala Arg Glu Asn Gln Thr Thr Gln Lys Gly Gln Lys
                965                 970                 975

Asn Ser Arg Glu Arg Met Lys Arg Ile Glu Glu Gly Ile Lys Glu Leu
            980                 985                 990

Gly Ser Gln Ile Leu Lys Glu His Pro Val Glu Asn Thr Gln Leu Gln
            995                 1000                1005

Asn Glu Lys Leu Tyr Leu Tyr Tyr Leu Gln Asn Gly Arg Asp Met
    1010                1015                1020

Tyr Val Asp Gln Glu Leu Asp Ile Asn Arg Leu Ser Asp Tyr Asp
    1025                1030                1035

Val Asp Ala Ile Val Pro Gln Ser Phe Leu Lys Asp Asp Ser Ile
    1040                1045                1050

Asp Asn Lys Val Leu Thr Arg Ser Asp Lys Asn Arg Gly Lys Ser
    1055                1060                1065

Asp Asn Val Pro Ser Glu Glu Val Val Lys Lys Met Lys Asn Tyr
    1070                1075                1080

Trp Arg Gln Leu Leu Asn Ala Lys Leu Ile Thr Gln Arg Lys Phe
    1085                1090                1095

Asp Asn Leu Thr Lys Ala Glu Arg Gly Gly Leu Ser Glu Leu Asp
    1100                1105                1110

Lys Ala Gly Phe Ile Lys Arg Gln Leu Val Glu Thr Arg Gln Ile
    1115                1120                1125

Thr Lys His Val Ala Gln Ile Leu Asp Ser Arg Met Asn Thr Lys
    1130                1135                1140

Tyr Asp Glu Asn Asp Lys Leu Ile Arg Glu Val Lys Val Ile Thr
    1145                1150                1155

Leu Lys Ser Lys Leu Val Ser Asp Phe Arg Lys Asp Phe Gln Phe
    1160                1165                1170

Tyr Lys Val Arg Glu Ile Asn Asn Tyr His His Ala His Asp Ala
    1175                1180                1185

Tyr Leu Asn Ala Val Val Gly Thr Ala Leu Ile Lys Lys Tyr Pro
    1190                1195                1200

Lys Leu Glu Ser Glu Phe Val Tyr Gly Asp Tyr Lys Val Tyr Asp
    1205                1210                1215

Val Arg Lys Met Ile Ala Lys Ser Glu Gln Glu Ile Gly Lys Ala
    1220                1225                1230

Thr Ala Lys Tyr Phe Phe Tyr Ser Asn Ile Met Asn Phe Phe Lys
    1235                1240                1245

Thr Glu Ile Thr Leu Ala Asn Gly Glu Ile Arg Lys Arg Pro Leu
    1250                1255                1260

Ile Glu Thr Asn Gly Glu Thr Gly Glu Ile Val Trp Asp Lys Gly
    1265                1270                1275

Arg Asp Phe Ala Thr Val Arg Lys Val Leu Ser Met Pro Gln Val
    1280                1285                1290
```

Asn Ile Val Lys Lys Thr Glu Val Gln Thr Gly Gly Phe Ser Lys
    1295               1300               1305

Glu Ser Ile Leu Pro Lys Arg Asn Ser Asp Lys Leu Ile Ala Arg
    1310               1315               1320

Lys Lys Asp Trp Asp Pro Lys Lys Tyr Gly Gly Phe Asp Ser Pro
    1325               1330               1335

Thr Val Ala Tyr Ser Val Leu Val Val Ala Lys Val Glu Lys Gly
    1340               1345               1350

Lys Ser Lys Lys Leu Lys Ser Val Lys Glu Leu Leu Gly Ile Thr
    1355               1360               1365

Ile Met Glu Arg Ser Ser Phe Glu Lys Asn Pro Ile Asp Phe Leu
    1370               1375               1380

Glu Ala Lys Gly Tyr Lys Glu Val Lys Lys Asp Leu Ile Ile Lys
    1385               1390               1395

Leu Pro Lys Tyr Ser Leu Phe Glu Leu Glu Asn Gly Arg Lys Arg
    1400               1405               1410

Met Leu Ala Ser Ala Gly Glu Leu Gln Lys Gly Asn Glu Leu Ala
    1415               1420               1425

Leu Pro Ser Lys Tyr Val Asn Phe Leu Tyr Leu Ala Ser His Tyr
    1430               1435               1440

Glu Lys Leu Lys Gly Ser Pro Glu Asp Asn Glu Gln Lys Gln Leu
    1445               1450               1455

Phe Val Glu Gln His Lys His Tyr Leu Asp Glu Ile Ile Glu Gln
    1460               1465               1470

Ile Ser Glu Phe Ser Lys Arg Val Ile Leu Ala Asp Ala Asn Leu
    1475               1480               1485

Asp Lys Val Leu Ser Ala Tyr Asn Lys His Arg Asp Lys Pro Ile
    1490               1495               1500

Arg Glu Gln Ala Glu Asn Ile Ile His Leu Phe Thr Leu Thr Asn
    1505               1510               1515

Leu Gly Ala Pro Ala Ala Phe Lys Tyr Phe Asp Thr Thr Ile Asp
    1520               1525               1530

Arg Lys Arg Tyr Thr Ser Thr Lys Glu Val Leu Asp Ala Thr Leu
    1535               1540               1545

Ile His Gln Ser Ile Thr Gly Leu Tyr Glu Thr Arg Ile Asp Leu
    1550               1555               1560

Ser Gln Leu Gly Gly Asp Gly Ser Pro Lys Lys Lys Arg Lys Val
    1565               1570               1575

Ser Ser Asp Tyr Lys Asp His Asp Gly Asp Tyr Lys Asp His Asp
    1580               1585               1590

Ile Asp Tyr Lys Asp Asp Asp Lys
    1595               1600

<210> SEQ ID NO 25
<211> LENGTH: 4809
<212> TYPE: DNA
<213> ORGANISM: Artificial Sequence
<220> FEATURE:
<223> OTHER INFORMATION: Description of Artificial Sequence: Synthetic
      FokI-dCas9 polynucleotide

<400> SEQUENCE: 25
atgcaactag tcaaaagtga actggaggag aagaaatctg aacttcgtca taaattgaaa        60
tatgtgcctc atgaatatat tgaattaatt gaaattgcca gaaattccac tcaggataga       120

| | |
|---|---|
| attcttgaaa tgaaggtaat ggaatttttt atgaaagttt atggatatag aggtaaacat | 180 |
| ttgggtggat caaggaaacc ggacggagca atttatactg tcggatctcc tattgattac | 240 |
| ggtgtgatcg tggatactaa agcttatagc ggaggttata atctgccaat tggccaagca | 300 |
| gatgaaatgc aacgatatgt cgaagaaaat caaacacgaa acaaacatat caaccctaat | 360 |
| gaatggtgga agtctatcc atcttctgta acggaattta agtttttatt tgtgagtggt | 420 |
| cactttaaag gaaactacaa agctcagctt acacgattaa atcatatcac taattgtaat | 480 |
| ggagctgttc ttagtgtaga gagcttttta attggtggag aaatgattaa agccggcaca | 540 |
| ttaaccttag aggaagtcag acggaaattt aataacggcg ataaaactt tggtggcggt | 600 |
| ggatccgata aaaagtattc tattggttta gccatcggca ctaattccgt tggatgggct | 660 |
| gtcataaccg atgaatacaa agtaccttca aagaaattta aggtgttggg aacacagac | 720 |
| cgtcattcga ttaaaaagaa tcttatcggt gccctcctat tcgatagtgg cgaaacggca | 780 |
| gaggcgactc gcctgaaacg aaccgctcgg agaaggtata cacgtcgcaa gaaccgaata | 840 |
| tgttacttac aagaaatttt tagcaatgag atggccaaag ttgacgattc tttctttcac | 900 |
| cgtttggaag agtccttcct tgtcgaagag acaagaaac atgaacggca ccccatcttt | 960 |
| ggaaacatag tagatgaggt ggcatatcat gaaaagtacc caacgattta tcacctcaga | 1020 |
| aaaaagctag ttgactcaac tgataaagcg gacctgaggt taatctactt ggctcttgcc | 1080 |
| catatgataa agttccgtgg gcactttctc attgagggtg atctaaatcc ggacaactcg | 1140 |
| gatgtcgaca aactgttcat ccagttagta caaacctata atcagttgtt tgaagagaac | 1200 |
| cctataaatg caagtggcgt ggatgcgaag gctattctta gcgcccgcct ctctaaatcc | 1260 |
| cgacggctag aaaacctgat cgcacaatta cccggagaga agaaaaatgg ttgttcggt | 1320 |
| aaccttatag cgctctcact aggcctgaca ccaaattta agtcgaactt cgacttagct | 1380 |
| gaagatgcca aattgcagct tagtaaggac acgtacgatg acgatctcga caatctactg | 1440 |
| gcacaaattg gagatcagta tgcggactta ttttggctg ccaaaaacct tagcgatgca | 1500 |
| atcctcctat ctgacatact gagagttaat actgagatta ccaaggcgcc gttatccgct | 1560 |
| tcaatgatca aaaggtacga tgaacatcac caagacttga cacttctcaa ggccctagtc | 1620 |
| cgtcagcaac tgcctgagaa atataaggaa atattctttg atcagtcgaa aaacgggtac | 1680 |
| gcaggttata ttgacggcgg agcgagtcaa gaggaattct acaagtttat caaacccata | 1740 |
| ttagagaaga tggatgggac ggaagagttg cttgtaaaac tcaatcgcga agatctactg | 1800 |
| cgaaagcagc ggactttcga caacggtagc attccacatc aaatccactt aggcgaattg | 1860 |
| catgctatac ttagaaggca ggaggatttt tatccgttcc tcaaagacaa tcgtgaaaag | 1920 |
| attgagaaaa tcctaacctt tcgcatacct tactatgtgg gacccctggc ccagggaac | 1980 |
| tctcggttcg catggatgac aagaaagtcc gaagaaacga ttactccatg gaattttgag | 2040 |
| gaagttgtcg ataaaggtgc gtcagctcaa tcgttcatcg agaggatgac aactttgac | 2100 |
| aagaatttac cgaacgaaaa agtattgcct aagcacagtt tactttacga gtatttcaca | 2160 |
| gtgtacaatg aactcacgaa agttaagtat gtcactgagg gcatgcgtaa acccgccttt | 2220 |
| ctaagcggag aacagaagaa agcaatagta gatctgttat tcaagaccaa ccgcaaagtg | 2280 |
| acagttaagc aattgaaaga ggactacttt aagaaaattg aatgcttcga ttctgtcgag | 2340 |
| atctccgggg tagaagatcg atttaatgcg tcacttggta cgtatcatga cctcctaaag | 2400 |
| ataattaaag ataaggactt cctggataac gaagagaatg aagatatctt agaagatata | 2460 |
| gtgttgactc ttaccctctt tgaagatcgg gaaatgattg aggaaagact aaaaacatac | 2520 |

```
gctcacctgt tcgacgataa ggttatgaaa cagttaaaga ggcgtcgcta tacgggctgg    2580
ggacgattgt cgcggaaact tatcaacggg ataagagaca agcaaagtgg taaaactatt    2640
ctcgattttc taaagagcga cggcttcgcc aataggaact ttatgcagct gatccatgat    2700
gactctttaa ccttcaaaga ggatatacaa aaggcacagg tttccggaca agggggactca   2760 ttgcacgaac atattgcgaa tcttgctggt cgccagcca tcaaaaaggg catactccag    2820
acagtcaaag tagtggatga gctagttaag gtcatgggac gtcacaaacc ggaaaacatt    2880
gtaatcgaga tggcacgcga aaatcaaacg actcagaagg ggcaaaaaaa cagtcgagag    2940
cggatgaaga gaatagaaga gggtattaaa gaactgggca gccagatctt aaaggagcat    3000
cctgtggaaa atacccaatt gcagaacgag aaactttacc tctattacct acaaaatgga    3060
agggacatgt atgttgatca ggaactggac ataaaccgtt tatctgatta cgacgtcgat    3120
gccattgtac cccaatcctt tttgaaggac gattcaatcg acaataaagt gcttacacgc    3180
tcggataaga accgagggaa aagtgacaat gttccaagcg aggaagtcgt aaagaaaatg    3240
aagaactatt ggcggcagct cctaaatgcg aaactgataa cgcaaagaaa gttcgataac    3300
ttaactaaag ctgagagggg tggcttgtct gaacttgaca aggccggatt tattaaacgt    3360
cagctcgtgg aaacccgcca aatcacaaag catgttgcac agatactaga ttcccgaatg    3420
aatacgaaat acgacgagaa cgataagctg attcggaag tcaaagtaat cacttttaaag   3480 tcaaaattgg tgtcggactt cagaaaggat tttcaattct ataaagttag ggagataaat    3540
aactaccacc atgcgcacga cgcttatctt aatgccgtcg tagggaccgc actcattaag    3600
aaatacccga agctagaaag tgagtttgtg tatggtgatt acaaagttta tgacgtccgt    3660
aagatgatcg cgaaaagcga acaggagata ggcaaggcta cagccaaata cttcttttat    3720
tctaacatta tgaatttctt taagacggaa atcactctgg caaacggaga gatacgcaaa    3780 cgaccttta ttgaaaccaa tggggagaca ggtgaaatcg tatgggataa gggccgggac    3840
ttcgcgacgg tgagaaaagt tttgtccatg ccccaagtca acatagtaaa gaaaactgag    3900
gtgcagaccg gagggttttc aaaggaatcg attcttccaa aaaggaatag tgataagctc    3960
atcgctcgta aaaaggactg ggacccgaaa aagtacggtg gcttcgatag ccctacagtt    4020
gcctattctg tcctagtagt ggcaaaagtt gagaagggaa atccaagaa actgaagtca    4080 gtcaaagaat tattggggat aacgattatg gagcgctcgt cttttgaaaa gaaccccatc    4140
gacttccttg aggcgaaagg ttacaaggaa gtaaaaaagg atctcataat taaactacca    4200
aagtatagtc tgtttgagtt agaaaatggc cgaaaacgga tgttggctag cgccggagag    4260
cttcaaaagg ggaacgaact cgcactaccg tctaaatacg tgaatttcct gtatttagcg    4320
tcccattacg agaagttgaa aggttcacct gaagataacg aacagaagca acttttttgtt   4380 gagcagcaca acattatct cgacgaaatc atagagcaaa tttcggaatt cagtaagaga    4440
gtcatcctag ctgatgccaa tctggacaaa gtattaagcg catacaacaa gcacagggat    4500
aaacccatac gtgagcaggc ggaaaatatt atccatttgt ttactcttac caacctcggc    4560
gctccagccg cattcaagta ttttgacaca acgatagatc gcaaacgata cacttctacc    4620
aaggaggtgc tagacgcgac actgattcac caatccatca cgggattata tgaaactcgg    4680
atagatttgt cacagcttgg gggtgacgga tcccccaaga agaagaggaa agtctcgagc    4740
gactacaaag accatgacgg tgattataaa gatcatgaca tcgattacaa ggatgacgat    4800
gacaagtga                                                           4809
```

<210> SEQ ID NO 26
<211> LENGTH: 1611
<212> TYPE: PRT
<213> ORGANISM: Artificial Sequence
<220> FEATURE:
<223> OTHER INFORMATION: Description of Artificial Sequence: Synthetic Nls-FokI-dCas9-nls polypeptide

<400> SEQUENCE: 26

```
Met Pro Lys Lys Arg Lys Val Ser Ser Gln Leu Val Lys Ser Glu
1               5                   10                  15

Leu Glu Glu Lys Lys Ser Glu Leu Arg His Lys Leu Lys Tyr Val Pro
            20                  25                  30

His Glu Tyr Ile Glu Leu Ile Glu Ile Ala Arg Asn Ser Thr Gln Asp
        35                  40                  45

Arg Ile Leu Glu Met Lys Val Met Glu Phe Phe Met Lys Val Tyr Gly
    50                  55                  60

Tyr Arg Gly Lys His Leu Gly Gly Ser Arg Lys Pro Asp Gly Ala Ile
65                  70                  75                  80

Tyr Thr Val Gly Ser Pro Ile Asp Tyr Gly Val Ile Val Asp Thr Lys
                85                  90                  95

Ala Tyr Ser Gly Gly Tyr Asn Leu Pro Ile Gly Gln Ala Asp Glu Met
            100                 105                 110

Gln Arg Tyr Val Glu Glu Asn Gln Thr Arg Asn Lys His Ile Asn Pro
        115                 120                 125

Asn Glu Trp Trp Lys Val Tyr Pro Ser Ser Val Thr Glu Phe Lys Phe
    130                 135                 140

Leu Phe Val Ser Gly His Phe Lys Gly Asn Tyr Lys Ala Gln Leu Thr
145                 150                 155                 160

Arg Leu Asn His Ile Thr Asn Cys Asn Gly Ala Val Leu Ser Val Glu
                165                 170                 175

Glu Leu Leu Ile Gly Gly Glu Met Ile Lys Ala Gly Thr Leu Thr Leu
            180                 185                 190

Glu Glu Val Arg Arg Lys Phe Asn Asn Gly Glu Ile Asn Phe Gly Gly
        195                 200                 205

Gly Gly Ser Asp Lys Lys Tyr Ser Ile Gly Leu Ala Ile Gly Thr Asn
    210                 215                 220

Ser Val Gly Trp Ala Val Ile Thr Asp Glu Tyr Lys Val Pro Ser Lys
225                 230                 235                 240

Lys Phe Lys Val Leu Gly Asn Thr Asp Arg His Ser Ile Lys Lys Asn
                245                 250                 255

Leu Ile Gly Ala Leu Leu Phe Asp Ser Gly Glu Thr Ala Glu Ala Thr
            260                 265                 270

Arg Leu Lys Arg Thr Ala Arg Arg Tyr Thr Arg Arg Lys Asn Arg
        275                 280                 285

Ile Cys Tyr Leu Gln Glu Ile Phe Ser Asn Glu Met Ala Lys Val Asp
    290                 295                 300

Asp Ser Phe Phe His Arg Leu Glu Glu Ser Phe Leu Val Glu Glu Asp
305                 310                 315                 320

Lys Lys His Glu Arg His Pro Ile Phe Gly Asn Ile Val Asp Glu Val
                325                 330                 335

Ala Tyr His Glu Lys Tyr Pro Thr Ile Tyr His Leu Arg Lys Lys Leu
            340                 345                 350

Val Asp Ser Thr Asp Lys Ala Asp Leu Arg Leu Ile Tyr Leu Ala Leu
        355                 360                 365
```

-continued

```
Ala His Met Ile Lys Phe Arg Gly His Phe Leu Ile Glu Gly Asp Leu
    370                 375                 380

Asn Pro Asp Asn Ser Asp Val Asp Lys Leu Phe Ile Gln Leu Val Gln
385                 390                 395                 400

Thr Tyr Asn Gln Leu Phe Glu Glu Asn Pro Ile Asn Ala Ser Gly Val
                    405                 410                 415

Asp Ala Lys Ala Ile Leu Ser Ala Arg Leu Ser Lys Ser Arg Arg Leu
                420                 425                 430

Glu Asn Leu Ile Ala Gln Leu Pro Gly Glu Lys Lys Asn Gly Leu Phe
            435                 440                 445

Gly Asn Leu Ile Ala Leu Ser Leu Gly Leu Thr Pro Asn Phe Lys Ser
    450                 455                 460

Asn Phe Asp Leu Ala Glu Asp Ala Lys Leu Gln Leu Ser Lys Asp Thr
465                 470                 475                 480

Tyr Asp Asp Asp Leu Asp Asn Leu Leu Ala Gln Ile Gly Asp Gln Tyr
                    485                 490                 495

Ala Asp Leu Phe Leu Ala Ala Lys Asn Leu Ser Asp Ala Ile Leu Leu
                500                 505                 510

Ser Asp Ile Leu Arg Val Asn Thr Glu Ile Thr Lys Ala Pro Leu Ser
            515                 520                 525

Ala Ser Met Ile Lys Arg Tyr Asp Glu His His Gln Asp Leu Thr Leu
    530                 535                 540

Leu Lys Ala Leu Val Arg Gln Gln Leu Pro Glu Lys Tyr Lys Glu Ile
545                 550                 555                 560

Phe Phe Asp Gln Ser Lys Asn Gly Tyr Ala Gly Tyr Ile Asp Gly Gly
                    565                 570                 575

Ala Ser Gln Glu Glu Phe Tyr Lys Phe Ile Lys Pro Ile Leu Glu Lys
                580                 585                 590

Met Asp Gly Thr Glu Glu Leu Leu Val Lys Leu Asn Arg Glu Asp Leu
            595                 600                 605

Leu Arg Lys Gln Arg Thr Phe Asp Asn Gly Ser Ile Pro His Gln Ile
    610                 615                 620

His Leu Gly Glu Leu His Ala Ile Leu Arg Arg Gln Glu Asp Phe Tyr
625                 630                 635                 640

Pro Phe Leu Lys Asp Asn Arg Glu Lys Ile Glu Lys Ile Leu Thr Phe
                    645                 650                 655

Arg Ile Pro Tyr Tyr Val Gly Pro Leu Ala Arg Gly Asn Ser Arg Phe
                660                 665                 670

Ala Trp Met Thr Arg Lys Ser Glu Glu Thr Ile Thr Pro Trp Asn Phe
            675                 680                 685

Glu Glu Val Val Asp Lys Gly Ala Ser Ala Gln Ser Phe Ile Glu Arg
    690                 695                 700

Met Thr Asn Phe Asp Lys Asn Leu Pro Asn Glu Lys Val Leu Pro Lys
705                 710                 715                 720

His Ser Leu Leu Tyr Glu Tyr Phe Thr Val Tyr Asn Glu Leu Thr Lys
                    725                 730                 735

Val Lys Tyr Val Thr Glu Gly Met Arg Lys Pro Ala Phe Leu Ser Gly
                740                 745                 750

Glu Gln Lys Lys Ala Ile Val Asp Leu Leu Phe Lys Thr Asn Arg Lys
            755                 760                 765

Val Thr Val Lys Gln Leu Lys Glu Asp Tyr Phe Lys Lys Ile Glu Cys
    770                 775                 780
```

```
Phe Asp Ser Val Glu Ile Ser Gly Val Glu Asp Arg Phe Asn Ala Ser
785                 790                 795                 800

Leu Gly Thr Tyr His Asp Leu Leu Lys Ile Ile Lys Asp Lys Asp Phe
            805                 810                 815

Leu Asp Asn Glu Glu Asn Glu Asp Ile Leu Glu Asp Ile Val Leu Thr
        820                 825                 830

Leu Thr Leu Phe Glu Asp Arg Glu Met Ile Glu Glu Arg Leu Lys Thr
    835                 840                 845

Tyr Ala His Leu Phe Asp Asp Lys Val Met Lys Gln Leu Lys Arg Arg
850                 855                 860

Arg Tyr Thr Gly Trp Gly Arg Leu Ser Arg Lys Leu Ile Asn Gly Ile
865                 870                 875                 880

Arg Asp Lys Gln Ser Gly Lys Thr Ile Leu Asp Phe Leu Lys Ser Asp
            885                 890                 895

Gly Phe Ala Asn Arg Asn Phe Met Gln Leu Ile His Asp Asp Ser Leu
        900                 905                 910

Thr Phe Lys Glu Asp Ile Gln Lys Ala Gln Val Ser Gly Gln Gly Asp
    915                 920                 925

Ser Leu His Glu His Ile Ala Asn Leu Ala Gly Ser Pro Ala Ile Lys
930                 935                 940

Lys Gly Ile Leu Gln Thr Val Lys Val Val Asp Glu Leu Val Lys Val
945                 950                 955                 960

Met Gly Arg His Lys Pro Glu Asn Ile Val Ile Glu Met Ala Arg Glu
            965                 970                 975

Asn Gln Thr Thr Gln Lys Gly Gln Lys Asn Ser Arg Glu Arg Met Lys
        980                 985                 990

Arg Ile Glu Glu Gly Ile Lys Glu Leu Gly Ser Gln Ile Leu Lys Glu
    995                 1000                1005

His Pro Val Glu Asn Thr Gln Leu Gln Asn Glu Lys Leu Tyr Leu Tyr
        1010                1015                1020

Tyr Leu Gln Asn Gly Arg Asp Met Tyr Val Asp Gln Glu Leu Asp Ile
1025                1030                1035                1040

Asn Arg Leu Ser Asp Tyr Asp Val Asp Ala Ile Val Pro Gln Ser Phe
            1045                1050                1055

Leu Lys Asp Asp Ser Ile Asp Asn Lys Val Leu Thr Arg Ser Asp Lys
        1060                1065                1070

Asn Arg Gly Lys Ser Asp Asn Val Pro Ser Glu Glu Val Val Lys Lys
    1075                1080                1085

Met Lys Asn Tyr Trp Arg Gln Leu Leu Asn Ala Lys Leu Ile Thr Gln
    1090                1095                1100

Arg Lys Phe Asp Asn Leu Thr Lys Ala Glu Arg Gly Gly Leu Ser Glu
1105                1110                1115                1120

Leu Asp Lys Ala Gly Phe Ile Lys Arg Gln Leu Val Glu Thr Arg Gln
            1125                1130                1135

Ile Thr Lys His Val Ala Gln Ile Leu Asp Ser Arg Met Asn Thr Lys
        1140                1145                1150

Tyr Asp Glu Asn Asp Lys Leu Ile Arg Glu Val Lys Val Ile Thr Leu
    1155                1160                1165

Lys Ser Lys Leu Val Ser Asp Phe Arg Lys Asp Phe Gln Phe Tyr Lys
    1170                1175                1180

Val Arg Glu Ile Asn Asn Tyr His His Ala His Asp Ala Tyr Leu Asn
1185                1190                1195                1200

Ala Val Val Gly Thr Ala Leu Ile Lys Lys Tyr Pro Lys Leu Glu Ser
```

Glu Phe Val Tyr Gly Asp Tyr Lys Val Tyr Asp Val Arg Lys Met Ile
                1220                1225                1230

Ala Lys Ser Glu Gln Glu Ile Gly Lys Ala Thr Ala Lys Tyr Phe Phe
            1235                1240                1245

Tyr Ser Asn Ile Met Asn Phe Phe Lys Thr Glu Ile Thr Leu Ala Asn
        1250                1255                1260

Gly Glu Ile Arg Lys Arg Pro Leu Ile Glu Thr Asn Gly Glu Thr Gly
1265                1270                1275                1280

Glu Ile Val Trp Asp Lys Gly Arg Asp Phe Ala Thr Val Arg Lys Val
                1285                1290                1295

Leu Ser Met Pro Gln Val Asn Ile Val Lys Lys Thr Glu Val Gln Thr
            1300                1305                1310

Gly Gly Phe Ser Lys Glu Ser Ile Leu Pro Lys Arg Asn Ser Asp Lys
        1315                1320                1325

Leu Ile Ala Arg Lys Lys Asp Trp Asp Pro Lys Lys Tyr Gly Gly Phe
1330                1335                1340

Asp Ser Pro Thr Val Ala Tyr Ser Val Leu Val Val Ala Lys Val Glu
1345                1350                1355                1360

Lys Gly Lys Ser Lys Lys Leu Lys Ser Val Lys Glu Leu Leu Gly Ile
                1365                1370                1375

Thr Ile Met Glu Arg Ser Ser Phe Glu Lys Asn Pro Ile Asp Phe Leu
            1380                1385                1390

Glu Ala Lys Gly Tyr Lys Glu Val Lys Lys Asp Leu Ile Ile Lys Leu
        1395                1400                1405

Pro Lys Tyr Ser Leu Phe Glu Leu Glu Asn Gly Arg Lys Arg Met Leu
1410                1415                1420

Ala Ser Ala Gly Glu Leu Gln Lys Gly Asn Glu Leu Ala Leu Pro Ser
1425                1430                1435                1440

Lys Tyr Val Asn Phe Leu Tyr Leu Ala Ser His Tyr Glu Lys Leu Lys
                1445                1450                1455

Gly Ser Pro Glu Asp Asn Glu Gln Lys Gln Leu Phe Val Glu Gln His
            1460                1465                1470

Lys His Tyr Leu Asp Glu Ile Ile Glu Gln Ile Ser Glu Phe Ser Lys
        1475                1480                1485

Arg Val Ile Leu Ala Asp Ala Asn Leu Asp Lys Val Leu Ser Ala Tyr
1490                1495                1500

Asn Lys His Arg Asp Lys Pro Ile Arg Glu Gln Ala Glu Asn Ile Ile
1505                1510                1515                1520

His Leu Phe Thr Leu Thr Asn Leu Gly Ala Pro Ala Ala Phe Lys Tyr
                1525                1530                1535

Phe Asp Thr Thr Ile Asp Arg Lys Arg Tyr Thr Ser Thr Lys Glu Val
            1540                1545                1550

Leu Asp Ala Thr Leu Ile His Gln Ser Ile Thr Gly Leu Tyr Glu Thr
        1555                1560                1565

Arg Ile Asp Leu Ser Gln Leu Gly Gly Asp Gly Ser Pro Lys Lys Lys
1570                1575                1580

Arg Lys Val Ser Ser Asp Tyr Lys Asp His Asp Gly Asp Tyr Lys Asp
1585                1590                1595                1600

His Asp Ile Asp Tyr Lys Asp Asp Asp Lys
                1605                1610

<210> SEQ ID NO 27

<211> LENGTH: 4836
<212> TYPE: DNA
<213> ORGANISM: Artificial Sequence
<220> FEATURE:
<223> OTHER INFORMATION: Description of Artificial Sequence: Synthetic
     Nls-FokI-dCas9-nls polynucleotide

<400> SEQUENCE: 27

| | | |
|---|---|---|
| atgcctaaga agaagcggaa ggtgagcagc caacttgtga agtctgaact cgaggagaaa | 60 |
| aaatcagagt tgagacacaa gttgaagtac gtgccacacg aatacatcga gcttatcgag | 120 |
| atcgccagaa acagtaccca ggataggatc cttgagatga agtcatgga gttctttatg | 180 |
| aaggtctacg gttatagagg aaagcacctt ggcggtagca gaaagcccga tggcgccatc | 240 |
| tatactgtcg gatctcctat cgattatggg gtgatcgtgg ataccaaagc ttactcaggc | 300 |
| gggtacaact tgcccatagg acaagccgac gagatgcagc ggtatgtcga agagaaccag | 360 |
| acgcgcaaca agcacatcaa ccccaatgaa tggtggaaag tgtacccaag tagtgtgact | 420 |
| gagttcaagt cctgttttgt ctccggccac tttaagggca attataaagc tcagctcact | 480 |
| agactcaatc acatcacaaa ctgcaacgga gctgtgttgt cagtggagga gctcctgatt | 540 |
| ggaggcgaga tgatcaaagc cggcacccct acactggagg aggtgcggcg aagttcaac | 600 |
| aatggagaga tcaacttcgg tggcggtgga tccgataaaa agtattctat ggtttagcc | 660 |
| atcggcacta ttccgttgg atgggctgtc ataaccgatg aatacaaagt accttcaaag | 720 |
| aaatttaagg tgttggggaa cacagaccgt cattcgatta aaagaatct tatcggtgcc | 780 |
| ctcctattcg atagtggcga aacggcagag gcgactcgcc tgaaacgaac cgctcggaga | 840 |
| aggtatacac gtcgcaagaa ccgaatatgt tacttacaag aaatttttag caatgagatg | 900 |
| gccaaagttg acgattcttt ctttcaccgt ttggaagagt ccttccttgt cgaagaggac | 960 |
| aagaaacatg aacggcaccc catctttgga aacatagtag atgaggtggc atatcatgaa | 1020 |
| aagtacccaa cgatttatca cctcagaaaa aagctagttg actcaactga taaagcggac | 1080 |
| ctgaggttaa tctacttggc tcttgcccat atgataaagt tccgtgggca ctttctcatt | 1140 |
| gagggtgatc taaatccgga caactcggat gtcgacaaac tgttcatcca gttagtacaa | 1200 |
| acctataatc agttgtttga agagaaccct ataaatgcaa gtggcgtgga tgcgaaggct | 1260 |
| attcttagcg cccgcctctc taaatcccga cggctagaaa acctgatcgc acaattaccc | 1320 |
| ggagagaaga aaatgggtt gttcggtaac cttatagcgc tctcactagg cctgacacca | 1380 |
| aattttaagt cgaacttcga cttagctgaa gatgccaaat tgcagcttag taaggacacg | 1440 |
| tacgatgacg atctcgacaa tctactggca caaattggag atcagtatgc ggacttattt | 1500 |
| ttggctgcca aaaaccttag cgatgcaatc ctcctatctg acatactgag agttaatact | 1560 |
| gagattacca aggcgccgtt atccgcttca atgatcaaaa ggtacgatga acatcaccaa | 1620 |
| gacttgacac ttctcaaggc cctagtccgt cagcaactgc ctgagaaata taggaaata | 1680 |
| ttctttgatc agtcgaaaaa cgggtacgca ggttatattg acggcggagc gagtcaagag | 1740 |
| gaattctaca gtttatcaa acccatatta gagaagatgg atgggacgga gagttgctt | 1800 |
| gtaaaactca atcgcgaaga tctactgcga aagcagcgga cttcgacaa cggtagcatt | 1860 |
| ccacatcaaa tccacttagg cgaattgcat gctatactta aaggcagga ggatttttat | 1920 |
| ccgttcctca agacaatcg tgaaagatt gagaaaatcc taaccttcg cataccttac | 1980 |
| tatgtgggac ccctggcccg agggaactct cggttcgcat ggatgacaag aaagtccgaa | 2040 |
| gaaacgatta ctccatggaa ttttgaggaa gttgtcgata aggtgcgtc agctcaatcg | 2100 |

```
ttcatcgaga ggatgaccaa ctttgacaag aatttaccga acgaaaaagt attgcctaag    2160
cacagtttac tttacgagta tttcacagtg tacaatgaac tcacgaaagt taagtatgtc    2220
actgagggca tgcgtaaacc cgcctttcta agcggagaac agaagaaagc aatagtagat    2280
ctgttattca agaccaaccg caaagtgaca gttaagcaat tgaaagagga ctactttaag    2340
aaaattgaat gcttcgattc tgtcgagatc tccggggtag aagatcgatt taatgcgtca    2400
cttggtacgt atcatgacct cctaaagata attaaagata aggacttcct ggataacgaa    2460
gagaatgaag atatcttaga agatatagtg ttgactctta ccctctttga agatcgggaa    2520
atgattgagg aaagactaaa aacatacgct cacctgttcg acgataaggt tatgaaacag    2580
ttaaagaggc gtcgctatac gggctgggga cgattgtcgc ggaaacttat caacgggata    2640
agagacaagc aaagtggtaa aactattctc gattttctaa agagcgacgg cttcgccaat    2700
aggaacttta tgcagctgat ccatgatgac tctttaacct tcaaagagga tatacaaaag    2760
gcacaggttt ccggacaagg ggactcattg cacgaacata ttgcgaatct tgctggttcg    2820
ccagccatca aaaagggcat actccagaca gtcaaagtag tggatgagct agttaaggtc    2880
atgggacgtc acaaaccgga aaacattgta atcgagatgg cacgcgaaaa tcaaacgact    2940
cagaaggggc aaaaaaacag tcgagagcgg atgaagagaa tagaagaggg tattaaagaa    3000
ctgggcagcc agatcttaaa ggagcatcct gtggaaaata cccaattgca gaacgagaaa    3060
cttacctct attacctaca aaatggaagg gacatgtatg ttgatcagga actggacata    3120
aaccgtttat ctgattacga cgtcgatgcc attgtacccc aatcctttt gaaggacgat    3180
tcaatcgaca ataaagtgct tacacgctcg gataagaacc gagggaaaag tgacaatgtt    3240
ccaagcgagg aagtcgtaaa gaaaatgaag aactattggc ggcagctcct aaatgcgaaa    3300
ctgataacgc aaagaaagtt cgataactta actaaagctg agaggggtgg cttgtctgaa    3360
cttgacaagg ccggatttat taaacgtcag ctcgtggaaa cccgccaaat cacaaagcat    3420
gttgcacaga tactagattc ccgaatgaat acgaaatacg acgagaacga taagctgatt    3480
cgggaagtca agtaatcac tttaaagtca aaattggtgt cggacttcag aaaggatttt    3540
caattctata aagttaggga gataaataac taccaccatg cgcacgacgc ttatcttaat    3600
gccgtcgtag ggaccgcact cattaagaaa tacccgaagc tagaaagtga gtttgtgtat    3660
ggtgattaca agtttatga cgtccgtaag atgatcgcga aaagcgaaca ggagataggc    3720
aaggctacag ccaaatactt cttttattct aacattatga atttctttaa gacggaaatc    3780
actctggcaa acgagagat acgcaaacga cctttaattg aaaccaatgg ggagacaggt    3840
gaaatcgtat gggataaggg ccgggacttc gcgacggtga gaaaagtttt gtccatgccc    3900
caagtcaaca tagtaaagaa aactgaggtg cagaccggag ggttttcaaa ggaatcgatt    3960
cttccaaaaa ggaatagtga taagctcatc gctcgtaaaa aggactggga cccgaaaaag    4020
tacggtggct tcgatagccc tacagttgcc tattctgtcc tagtagtggc aaaagttgag    4080
aagggaaaat ccaagaaact gaagtcagtc aaagaattat tggggataac gattatggag    4140
cgctcgtctt ttgaaaagaa ccccatcgac ttccttgagg cgaaaggtta caggaagta    4200
aaaaggatc tcataattaa actaccaaag tatagtctgt ttgagttaga aaatggccga    4260
aaacggatgt tggctagcgc cggagagctt caaaagggga acgaactcgc actaccgtct    4320
aaatacgtga atttcctgta tttagcgtcc cattacgaga agttgaaagg ttcacctgaa    4380
gataacgaac agaagcaact ttttgttgag cagcacaaac attatctcga cgaaatcata    4440
gagcaaattt cggaattcag taagagagtc atcctagctg atgccaatct ggacaaagta    4500
```
ttaagcgcat acaacaagca cagggataaa cccatacgtg agcaggcgga aaatattatc    4560
catttgttta ctcttaccaa cctcggcgct ccagccgcat tcaagtattt tgacacaacg    4620
atagatcgca aacgatacac ttctaccaag gaggtgctag acgcgacact gattcaccaa    4680
tccatcacgg gattatatga aactcggata gatttgtcac agcttggggg tgacggatcc    4740
cccaagaaga agaggaaagt ctcgagcgac tacaaagacc atgacggtga ttataaagat    4800
catgacatcg attacaagga tgacgatgac aagtga                              4836

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gagctggacg gcgacgtaaa cgg                                              23

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cgccggacac gctgaacttg tgg                                              23

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ccggcaagct gcccgtgccc tgg                                              23

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ggtcagggtg gtcacgaggg tgg                                              23

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cgaggagctg ttcaccgggg tgg                                              23

```
<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ccgtccagct cgaccaggat ggg                                              23

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cgaggagctg ttcaccgggg tgg                                              23

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gccgtccagc tcgaccagga tgg                                              23

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ccggcaagct gcccgtgccc tgg                                              23

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gtaggtcagg gtggtcacga ggg                                              23

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gggcgaggag ctgttcaccg ggg                                              23

<210> SEQ ID NO 39
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ccgtccagct cgaccaggat ggg                                           23

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
agggcgagga gctgttcacc ggg                                           23

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ccgtccagct cgaccaggat ggg                                           23

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
aagggcgagg agctgttcac cgg                                           23

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ccgtccagct cgaccaggat ggg                                           23

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
aagggcgagg agctgttcac cgg                                           23

<210> SEQ ID NO 45
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gccgtccagc tcgaccagga tgg                                              23

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cagcgtgtcc ggcgagggcg agg                                              23

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cttcagggtc agcttgccgt agg                                              23

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gggcgaggag ctgttcaccg ggg                                              23

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cgtcgccgtc cagctcgacc agg                                              23

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
agggcgagga gctgttcacc ggg                                              23

<210> SEQ ID NO 51
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 51
cgtcgccgtc cagctcgacc agg                                              23

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
aagggcgagg agctgttcac cgg                                              23

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
cgtcgccgtc cagctcgacc agg                                              23

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ctgaagttca tctgcaccac cgg                                              23

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gtggtcacga gggtgggcca ggg                                              23

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
aagttcagcg tgtccggcga ggg                                              23

<210> SEQ ID NO 57
<211> LENGTH: 23
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 57
cttcagggtc agcttgccgt agg                                                23

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
caagttcagc gtgtccggcg agg                                                23

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cttcagggtc agcttgccgt agg                                                23

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ggtgcccatc ctggtcgagc tgg                                                23

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
cgccggacac gctgaacttg tgg                                                23

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gagctggacg gcgacgtaaa cgg                                                23

<210> SEQ ID NO 63
<211> LENGTH: 23
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 63
ggcatcgccc tcgccctcgc cgg                                              23

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ggagcgcacc atcttcttca agg                                              23

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ctcgaacttc acctcggcgc ggg                                              23

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ctgaagttca tctgcaccac cgg                                              23

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gtcagggtgg tcacgagggt ggg                                              23

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ggccacaagt tcagcgtgtc cgg                                              23

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic

```
                          primer

<400> SEQUENCE: 69
cttcagggtc agcttgccgt agg                                            23

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ctcgtgacca ccctgaccta cgg                                            23

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cgtgctgctt catgtggtcg ggg                                            23

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ccggcaagct gcccgtgccc tgg                                            23

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gctgaagcac tgcacgccgt agg                                            23

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
agcgtgtccg gcgagggcga ggg                                            23

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 75
ggtggtgcag atgaacttca ggg                                              23

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
cagcgtgtcc ggcgagggcg agg                                              23

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ggtggtgcag atgaacttca ggg                                              23

<210> SEQ ID NO 78
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
caccggggtg gtgcccatcc tgg                                              23

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
cgccggacac gctgaacttg tgg                                              23

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ggcgagggcg atgccaccta cgg                                              23

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 81
gggcacgggc agcttgccgg tgg                                          23

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ctcgtgacca ccctgaccta cgg                                          23

<210> SEQ ID NO 83
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
agaagtcgtg ctgcttcatg tgg                                          23

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
caactacaag acccgcgccg agg                                          23

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
cgatgccctt cagctcgatg cgg                                          23

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
cccatcctgg tcgagctgga cgg                                          23

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ggcatcgccc tcgccctcgc cgg                                              23

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
caagttcagc gtgtccggcg agg                                              23

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
ggtggtgcag atgaacttca ggg                                              23

<210> SEQ ID NO 90
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gagctggacg gcgacgtaaa cgg                                              23

<210> SEQ ID NO 91
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gaccaggatg ggcaccaccc cgg                                              23

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
accatcttct tcaaggacga cgg                                              23

<210> SEQ ID NO 93
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
cgctcctgga cgtagccttc ggg                                                23

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
ggcgagggcg atgccaccta cgg                                                23

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
cgccggacac gctgaacttg tgg                                                23

<210> SEQ ID NO 96
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
ttcaagtccg ccatgcccga agg                                                23

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
gtcgtgctgc ttcatgtggt cgg                                                23

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ttcaagtccg ccatgcccga agg                                                23

<210> SEQ ID NO 99
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
tcgtgctgct tcatgtggtc ggg                                                23

<210> SEQ ID NO 100
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
ggccacaagt tcagcgtgtc cgg                                          23

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
cgtcgccgtc cagctcgacc agg                                          23

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
ctcgtgacca ccctgaccta cgg                                          23

<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
ccagggcacg ggcagcttgc cgg                                          23

<210> SEQ ID NO 104
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
cagccacaac gtctatatca tgg                                          23

<210> SEQ ID NO 105
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
tgtactccag cttgtgcccc agg                                          23

```
<210> SEQ ID NO 106
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
ggccacaagt tcagcgtgtc cgg                                               23

<210> SEQ ID NO 107
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
gccgtccagc tcgaccagga tgg                                               23

<210> SEQ ID NO 108
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
ggccacaagt tcagcgtgtc cgg                                               23

<210> SEQ ID NO 109
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
ccgtccagct cgaccaggat ggg                                               23

<210> SEQ ID NO 110
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
aagttcagcg tgtccggcga ggg                                               23

<210> SEQ ID NO 111
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
cgtcgccgtc cagctcgacc agg                                               23
```

<210> SEQ ID NO 112
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 112
cgcgccgagg tgaagttcga ggg                                        23

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 113
gccgtcgtcc ttgaagaaga tgg                                        23

<210> SEQ ID NO 114
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 114
ccggcaagct gcccgtgccc tgg                                        23

<210> SEQ ID NO 115
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 115
cttcagggtc agcttgccgt agg                                        23

<210> SEQ ID NO 116
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 116
caagttcagc gtgtccggcg agg                                        23

<210> SEQ ID NO 117
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 117
gccgtccagc tcgaccagga tgg                                        23

<210> SEQ ID NO 118

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
caagttcagc gtgtccggcg agg                                             23

<210> SEQ ID NO 119
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
ccgtccagct cgaccaggat ggg                                             23

<210> SEQ ID NO 120
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
aagttcagcg tgtccggcga ggg                                             23

<210> SEQ ID NO 121
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
ccgtccagct cgaccaggat ggg                                             23

<210> SEQ ID NO 122
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
agcgtgtccg gcgagggcga ggg                                             23

<210> SEQ ID NO 123
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
cgtcgccgtc cagctcgacc agg                                             23

<210> SEQ ID NO 124
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
ctgaagttca tctgcaccac cgg                                              23

<210> SEQ ID NO 125
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
ggcatcgccc tcgccctcgc cgg                                              23

<210> SEQ ID NO 126
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
cagcgtgtcc ggcgagggcg agg                                              23

<210> SEQ ID NO 127
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
gccgtccagc tcgaccagga tgg                                              23

<210> SEQ ID NO 128
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
ggccacaagt tcagcgtgtc cgg                                              23

<210> SEQ ID NO 129
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
gaccaggatg ggcaccaccc cgg                                              23

<210> SEQ ID NO 130
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 130
agcgtgtccg gcgagggcga ggg                                              23

<210> SEQ ID NO 131
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
ccgtccagct cgaccaggat ggg                                              23

<210> SEQ ID NO 132
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
caactacaag acccgcgccg agg                                              23

<210> SEQ ID NO 133
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
gcgctcctgg acgtagcctt cgg                                              23

<210> SEQ ID NO 134
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
caactacaag acccgcgccg agg                                              23

<210> SEQ ID NO 135
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
cgctcctgga cgtagccttc ggg                                              23

<210> SEQ ID NO 136
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 136
gctgaagggc atcgacttca agg                                            23

<210> SEQ ID NO 137
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
cctcgaactt cacctcggcg cgg                                            23

<210> SEQ ID NO 138
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
caagttcagc gtgtccggcg agg                                            23

<210> SEQ ID NO 139
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
gaccaggatg ggcaccaccc cgg                                            23

<210> SEQ ID NO 140
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
aagttcagcg tgtccggcga ggg                                            23

<210> SEQ ID NO 141
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
gaccaggatg ggcaccaccc cgg                                            23

<210> SEQ ID NO 142
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 142
gaagggcatc gacttcaagg agg                                              23

<210> SEQ ID NO 143
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
cctcgaactt cacctcggcg cgg                                              23

<210> SEQ ID NO 144
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
caactacaag acccgcgccg agg                                              23

<210> SEQ ID NO 145
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
ctggacgtag ccttcgggca tgg                                              23

<210> SEQ ID NO 146
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
ggagcgcacc atcttcttca agg                                              23

<210> SEQ ID NO 147
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
agaagtcgtg ctgcttcatg tgg                                              23

<210> SEQ ID NO 148
<211> LENGTH: 23
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 148
caagttcagc gtgtccggcg agg                                    23

<210> SEQ ID NO 149
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
cgtcgccgtc cagctcgacc agg                                    23

<210> SEQ ID NO 150
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
catgcccgaa ggctacgtcc agg                                    23

<210> SEQ ID NO 151
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
agaagtcgtg ctgcttcatg tgg                                    23

<210> SEQ ID NO 152
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
caactacaag acccgcgccg agg                                    23

<210> SEQ ID NO 153
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
tgaagaagat ggtgcgctcc tgg                                    23

<210> SEQ ID NO 154
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
ggtgaaccgc atcgagctga agg         23

<210> SEQ ID NO 155
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
cctcgaactt cacctcggcg cgg         23

<210> SEQ ID NO 156
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
ttcaagtccg ccatgcccga agg         23

<210> SEQ ID NO 157
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
gcttcatgtg gtcggggtag cgg         23

<210> SEQ ID NO 158
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
ccgcgccgag gtgaagttcg agg         23

<210> SEQ ID NO 159
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
gccgtcgtcc ttgaagaaga tgg         23

<210> SEQ ID NO 160
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 160
ggtgaaccgc atcgagctga agg                                          23

<210> SEQ ID NO 161
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
ctcgaacttc acctcggcgc ggg                                          23

<210> SEQ ID NO 162
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
gtgaaccgca tcgagctgaa ggg                                          23

<210> SEQ ID NO 163
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
cctcgaactt cacctcggcg cgg                                          23

<210> SEQ ID NO 164
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
caagatccgc cacaacatcg agg                                          23

<210> SEQ ID NO 165
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
gatgccgttc ttctgcttgt cgg                                          23

<210> SEQ ID NO 166
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
```
gtgaaccgca tcgagctgaa ggg                                              23

<210> SEQ ID NO 167
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
ctcgaacttc acctcggcgc ggg                                              23

<210> SEQ ID NO 168
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
caaggaggac ggcaacatcc tgg                                              23

<210> SEQ ID NO 169
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
tcagctcgat gcggttcacc agg                                              23

<210> SEQ ID NO 170
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
catgcccgaa ggctacgtcc agg                                              23

<210> SEQ ID NO 171
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
gtcgtgctgc ttcatgtggt cgg                                              23

<210> SEQ ID NO 172
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
caaggaggac ggcaacatcc tgg                                    23

<210> SEQ ID NO 173
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
cagctcgatg cggttcacca ggg                                    23

<210> SEQ ID NO 174
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
aaggaggacg gcaacatcct ggg                                    23

<210> SEQ ID NO 175
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
tcagctcgat gcggttcacc agg                                    23

<210> SEQ ID NO 176
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
aagttcagcg tgtccggcga ggg                                    23

<210> SEQ ID NO 177
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
gccgtccagc tcgaccagga tgg                                    23

<210> SEQ ID NO 178
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
catgcccgaa ggctacgtcc agg                                    23

<210> SEQ ID NO 179
<211> LENGTH: 23
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 179
tcgtgctgct tcatgtggtc ggg                                              23

<210> SEQ ID NO 180
<211> LENGTH: 23
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 180
aaggaggacg gcaacatcct ggg                                              23

<210> SEQ ID NO 181
<211> LENGTH: 23
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 181
cagctcgatg cggttcacca ggg                                              23

<210> SEQ ID NO 182
<211> LENGTH: 23
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 182
aggaggacgg caacatcctg ggg                                              23

<210> SEQ ID NO 183
<211> LENGTH: 23
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 183
tcagctcgat gcggttcacc agg                                              23

<210> SEQ ID NO 184
<211> LENGTH: 23
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 184
atccgccaca acatcgagga cgg                                              23

<210> SEQ ID NO 185
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
gatgccgttc ttctgcttgt cgg                                             23

<210> SEQ ID NO 186
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
cagcgtgtcc ggcgagggcg agg                                             23

<210> SEQ ID NO 187
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
cgtcgccgtc cagctcgacc agg                                             23

<210> SEQ ID NO 188
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
ccggcaagct gcccgtgccc tgg                                             23

<210> SEQ ID NO 189
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
cagggtcagc ttgccgtagg tgg                                             23

<210> SEQ ID NO 190
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
catgcccgaa ggctacgtcc agg                                             23

-continued

<210> SEQ ID NO 191
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
cgtgctgctt catgtggtcg ggg                                              23

<210> SEQ ID NO 192
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
aggaggacgg caacatcctg ggg                                              23

<210> SEQ ID NO 193
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
cagctcgatg cggttcacca ggg                                              23

<210> SEQ ID NO 194
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
caacatcctg gggcacaagc tgg                                              23

<210> SEQ ID NO 195
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
cgatgccctt cagctcgatg cgg                                              23

<210> SEQ ID NO 196
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
gctgaagggc atcgacttca agg                                              23

<210> SEQ ID NO 197

-continued

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
gtcgccctcg aacttcacct cgg                                          23

<210> SEQ ID NO 198
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
ccagaagtac gagcgccgcc cgg                                          23

<210> SEQ ID NO 199
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
tggcaggtga gtgaggctgc agg                                          23

<210> SEQ ID NO 200
<211> LENGTH: 62
<212> TYPE: DNA
<213> ORGANISM: Artificial Sequence
<220> FEATURE:
<223> OTHER INFORMATION: Description of Artificial Sequence: Synthetic
      RFN target site oligonucleotide

<400> SEQUENCE: 200
ccgggcggcg ctcgtacttc tggccactgg gcgagcgtct ggcaggtgag tgaggctgca    60
gg                                                                  62

<210> SEQ ID NO 201
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
gaatacccat ctgtcagctt cgg                                          23

<210> SEQ ID NO 202
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
ggcggaacct gagaggcgta agg                                          23
```

```
<210> SEQ ID NO 203
<211> LENGTH: 62
<212> TYPE: DNA
<213> ORGANISM: Artificial Sequence
<220> FEATURE:
<223> OTHER INFORMATION: Description of Artificial Sequence: Synthetic
      RFN target site oligonucleotide

<400> SEQUENCE: 203
ccgaagctga cagatgggta ttctttgacg gggggtaggg gcggaacctg agaggcgtaa      60
gg                                                                    62

<210> SEQ ID NO 204
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
aatattcaag cagcaggcac agg                                             23

<210> SEQ ID NO 205
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
ctcgcgcagg aggctgcagc ggg                                             23

<210> SEQ ID NO 206
<211> LENGTH: 62
<212> TYPE: DNA
<213> ORGANISM: Artificial Sequence
<220> FEATURE:
<223> OTHER INFORMATION: Description of Artificial Sequence: Synthetic
      RFN target site oligonucleotide

<400> SEQUENCE: 206
cctgtgcctg ctgcttgaat atttccgcct tttagggtgc tcgcgcagga ggctgcagcg      60
gg                                                                    62

<210> SEQ ID NO 207
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
cccaaagcct ggccagggag tgg                                             23

<210> SEQ ID NO 208
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
```
gccccacagg gcttgaagcc cgg                                                23

<210> SEQ ID NO 209
<211> LENGTH: 62
<212> TYPE: DNA
<213> ORGANISM: Artificial Sequence
<220> FEATURE:
<223> OTHER INFORMATION: Description of Artificial Sequence: Synthetic
      RFN target site oligonucleotide

<400> SEQUENCE: 209
ccactccctg gccaggcttt ggggaggcct ggagtcatgg ccccacaggg cttgaagccc    60
gg                                                                   62

<210> SEQ ID NO 210
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
ccctacttcc gctttcacct tgg                                                23

<210> SEQ ID NO 211
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
ggaatccctt ctgcagcacc tgg                                                23

<210> SEQ ID NO 212
<211> LENGTH: 62
<212> TYPE: DNA
<213> ORGANISM: Artificial Sequence
<220> FEATURE:
<223> OTHER INFORMATION: Description of Artificial Sequence: Synthetic
      RFN target site oligonucleotide

<400> SEQUENCE: 212
ccaaggtgaa agcggaagta gggccttcgc gcacctcatg gaatcccttc tgcagcacct    60
gg                                                                   62

<210> SEQ ID NO 213
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
cgctccagag ccgtgcgaat ggg                                                23

<210> SEQ ID NO 214
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
tggaggcaag agggcggctt tgg                                      23

<210> SEQ ID NO 215
<211> LENGTH: 62
<212> TYPE: DNA
<213> ORGANISM: Artificial Sequence
<220> FEATURE:
<223> OTHER INFORMATION: Description of Artificial Sequence: Synthetic
      RFN target site oligonucleotide

<400> SEQUENCE: 215
cccattcgca cggctctgga gcggcggctg cacaaccagt ggaggcaaga gggcggcttt    60
gg                                                                  62

<210> SEQ ID NO 216
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
cgaggagact ggggactgta ggg                                      23

<210> SEQ ID NO 217
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
ccagctgctg ccttgcctcc agg                                      23

<210> SEQ ID NO 218
<211> LENGTH: 62
<212> TYPE: DNA
<213> ORGANISM: Artificial Sequence
<220> FEATURE:
<223> OTHER INFORMATION: Description of Artificial Sequence: Synthetic
      RFN target site oligonucleotide

<400> SEQUENCE: 218
ccctacagtc cccagcctcc tcgtcccatg cctccgtctc cagctgctgc cttgcctcca    60
gg                                                                  62

<210> SEQ ID NO 219
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
catagctact gattggtggt ggg                                      23

<210> SEQ ID NO 220
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
ccggcccctc cccagtcagg ggg                                            23

<210> SEQ ID NO 221
<211> LENGTH: 62
<212> TYPE: DNA
<213> ORGANISM: Artificial Sequence
<220> FEATURE:
<223> OTHER INFORMATION: Description of Artificial Sequence: Synthetic
      RFN target site oligonucleotide

<400> SEQUENCE: 221
cccaccacca atcagtagct atggcgagcc ctgctgtctc cggcccctcc ccagtcaggg    60
gg                                                                   62

<210> SEQ ID NO 222
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
ggaaacgtct agatgctcaa cgg                                            23

<210> SEQ ID NO 223
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
caaaatgtcg ttcgtggcag tgg                                            23

<210> SEQ ID NO 224
<211> LENGTH: 62
<212> TYPE: DNA
<213> ORGANISM: Artificial Sequence
<220> FEATURE:
<223> OTHER INFORMATION: Description of Artificial Sequence: Synthetic
      RFN target site oligonucleotide

<400> SEQUENCE: 224
ccgttgagca tctagacgtt tccttggctc ttctggcgcc aaaatgtcgt tcgtggcagg    60
gg                                                                   62

<210> SEQ ID NO 225
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
ctgttgctgg ccatgccaag cgg                                            23

<210> SEQ ID NO 226

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
cctgggggcg ggcacctcaa tgg                                              23

<210> SEQ ID NO 227
<211> LENGTH: 62
<212> TYPE: DNA
<213> ORGANISM: Artificial Sequence
<220> FEATURE:
<223> OTHER INFORMATION: Description of Artificial Sequence: Synthetic
      RFN target site oligonucleotide

<400> SEQUENCE: 227
ccgcttggca tggccagcaa cagcagctcc tgcccgacac ctgggggcgg gcacctcaat      60
gg                                                                     62

<210> SEQ ID NO 228
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
ttcggagcga aaaccaagac agg                                              23

<210> SEQ ID NO 229
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
gagtcccccg ccttcagaag agg                                              23

<210> SEQ ID NO 230
<211> LENGTH: 62
<212> TYPE: DNA
<213> ORGANISM: Artificial Sequence
<220> FEATURE:
<223> OTHER INFORMATION: Description of Artificial Sequence: Synthetic
      RFN target site oligonucleotide

<400> SEQUENCE: 230
cctgtcttgg ttttcgctcc gaaggtaaaa gaaatcattg agtcccccgc cttcagaaga      60
gg                                                                     62

<210> SEQ ID NO 231
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
ggcccggtcg actccgggcc cgg                                              23
```

<210> SEQ ID NO 232
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
tgctgggaat cagcagtgtt tgg                                            23

<210> SEQ ID NO 233
<211> LENGTH: 62
<212> TYPE: DNA
<213> ORGANISM: Artificial Sequence
<220> FEATURE:
<223> OTHER INFORMATION: Description of Artificial Sequence: Synthetic
      RFN target site oligonucleotide

<400> SEQUENCE: 233
ccgggcccgg agtcgaccgg gccgaggcgg aggcgggcct gctgggaatc agcagtgttt    60
gg                                                                   62

<210> SEQ ID NO 234
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
gggtgggggg agtttgctcc tgg                                            23

<210> SEQ ID NO 235
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235 tccctctttacc gccagagccg ggg                                          23

<210> SEQ ID NO 236
<211> LENGTH: 62
<212> TYPE: DNA
<213> ORGANISM: Artificial Sequence
<220> FEATURE:
<223> OTHER INFORMATION: Description of Artificial Sequence: Synthetic
      RFN target site oligonucleotide

<400> SEQUENCE: 236
ccaggagcaa actcccccca ccccctttcc aaagcccatt ccctctttag ccagagccgg    60
gg                                                                   62

<210> SEQ ID NO 237
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 237
gccgccggcc ggggaggagg tgg                                             23

<210> SEQ ID NO 238
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
ggcgagccgc gggcaggggc cgg                                             23

<210> SEQ ID NO 239
<211> LENGTH: 62
<212> TYPE: DNA
<213> ORGANISM: Artificial Sequence
<220> FEATURE:
<223> OTHER INFORMATION: Description of Artificial Sequence: Synthetic
      RFN target site oligonucleotide

<400> SEQUENCE: 239
ccacctcctc cccggccggc ggcggacagt ggacgcggcg gcgagccgcg ggcaggggcc     60
gg                                                                    62

<210> SEQ ID NO 240
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
ccgtctgcac accccggctc tgg                                             23

<210> SEQ ID NO 241
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
ctcggccacc acagggaagc tgg                                             23

<210> SEQ ID NO 242
<211> LENGTH: 62
<212> TYPE: DNA
<213> ORGANISM: Artificial Sequence
<220> FEATURE:
<223> OTHER INFORMATION: Description of Artificial Sequence: Synthetic
      RFN target site oligonucleotide

<400> SEQUENCE: 242
ccagagccgg ggtgtgcaga cggcagtcac taggggcgc tcggccacca cagggaagct     60
gg                                                                    62

<210> SEQ ID NO 243
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 243
ggctgtggga agccagcaac                                                    20

<210> SEQ ID NO 244
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
aagccagggg ccaactggag                                                    20

<210> SEQ ID NO 245
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
gcgcgggaat tacagataaa ttaaaa                                             26

<210> SEQ ID NO 246
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
aggtcccatc ctctcataca tacca                                              25

<210> SEQ ID NO 247
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
accgcccctt ggcaccac                                                      18

<210> SEQ ID NO 248
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
cggagctcat ctgcttcctg t                                                  21

<210> SEQ ID NO 249
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 249
ggagcagctg gtcagagggg                                           20

<210> SEQ ID NO 250
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
gggaaggggg acactgggga                                           20

<210> SEQ ID NO 251
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
gccctacatc tgctctccct cca                                       23

<210> SEQ ID NO 252
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
gggccgggaa agagttgctg                                           20

<210> SEQ ID NO 253
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
gccctacatc tgctctccct cca                                       23

<210> SEQ ID NO 254
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
gggccgggaa agagttgctg                                           20

<210> SEQ ID NO 255
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 255
ggggagggag gctccaggtt                                               20

<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
ggcacaatgg ctcccaagca                                               20

<210> SEQ ID NO 257
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
ccttacccct cccctcactc a                                             21

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
agaagggcgg gccagacagt                                               20

<210> SEQ ID NO 259
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
atatccttct aggtagcggg cagtagcc                                      28

<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
tctcggggga gagcggtaaa                                               20

<210> SEQ ID NO 261
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 261
cccaggaaaa gtgccagctc a                                              21

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
tgatggtcac cccaactgga                                                20

<210> SEQ ID NO 263
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
aaggcggcgc tggcttttt                                                 19

<210> SEQ ID NO 264
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
ccagcacaac ttactcgcac ttga                                           24

<210> SEQ ID NO 265
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
gggatgcagg gacggtcaag                                                20

<210> SEQ ID NO 266
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
gccgccccat ccctagagaa a                                              21

<210> SEQ ID NO 267
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
```
tccagatggc acattgtcag                                               20

<210> SEQ ID NO 268
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
agggagcagg aaagtgaggt                                               20

<210> SEQ ID NO 269
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
agagaagtcg aggaagagag ag                                            22

<210> SEQ ID NO 270
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
cagcagaaag ttcatggttt cg                                            22

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
tccagatggc acattgtcag                                               20

<210> SEQ ID NO 272
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
agggagcagg aaagtgaggt                                               20

<210> SEQ ID NO 273
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
cgatggctcc caagaaacgc                                              20

<210> SEQ ID NO 274
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
gcaggtagaa tgcacagccg                                              20

<210> SEQ ID NO 275
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
gcccagagtc aaggaacacg                                              20

<210> SEQ ID NO 276
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
aggtagtgct tgagaccgcc                                              20

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
catccatcgg cgctttggtc                                              20

<210> SEQ ID NO 278
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
ccgggaaaga gttgctgcac                                              20

<210> SEQ ID NO 279
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
ctccccgtct gcagtccatc                                              20

<210> SEQ ID NO 280
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
cctgcaggga catgtggtga                                              20

<210> SEQ ID NO 281
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
tagggctaga ggggtgaggc                                              20

<210> SEQ ID NO 282
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
ccgaggtgaa acaagctgcc                                              20

<210> SEQ ID NO 283
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
atgagggctc cagatggcac                                              20

<210> SEQ ID NO 284
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
ttcacccagc ttccctgtgg                                              20

<210> SEQ ID NO 285
<211> LENGTH: 1752
<212> TYPE: DNA
<213> ORGANISM: Planomicrobium okeanokoites

<400> SEQUENCE: 285 atgttttga gtatggtttc taaaataaga actttcggtt gggttcaaaa tccaggtaaa    60
tttgagaatt taaacgagt agttcaagta tttgatagaa attctaaagt acataatgaa   120
gtgaaaaata taaagatacc aaccctagtc aaagaaagta gatccaaaaa agaactagtt   180

```
gctattatga atcaacatga tttgatttat acatataaag agttagtagg aacaggaact      240
tcaatacgtt cagaagcacc atgcgatgca attattcaag caacaatagc agatcaagga      300
aataaaaaag gctatatcga taattggtca tctgacggtt ttttgcgttg ggcacatgct      360
ttaggattta ttgaatatat aaataaaagt gattcttttg taataactga tgttggactt      420
gcttactcta aatcagctga cggcagcgcc attgaaaaag atttttgat tgaagcgata       480 tcatcttatc ctccagcgat tcgtatttta actttgctag aagatggaca acatttgaca      540
aagtttgatc ttggcaagaa tttaggtttt agtggagaaa gtggatttac ttctctaccg      600
gaaggaattc ttttagatac tctagctaat gctatgccta aagataaagg cgaaattcgt      660
aataattggg aaggatcttc agataagtac gcaagaatga taggtggttg gctggataaa      720
ctaggattag taaagcaagg aaaaaaagaa tttatcattc ctactttggg taagccggac      780
aataaagagt ttatatccca cgcttttaaa attactggag aaggtttgaa agtactgcgt      840
cgagcaaaag gctctacaaa atttacacgt gtacctaaaa gagtatattg ggaaatgctt      900
gctacaaacc taaccgataa agagtatgta agaacaagaa gagctttgat tttagaaata      960
ttaatcaaag ctggatcatt aaaaatagaa caaatacaag acaacttgaa gaaattagga     1020
tttgatgaag ttatagaaac tattgaaaat gatatcaaag gcttaattaa cacaggtata     1080
tttatagaaa tcaaagggcg attttatcaa ttgaaagacc atattcttca atttgtaata     1140
cctaatcgtg gtgtgactaa gcaactagtc aaaagtgaac tggaggagaa gaaatctgaa     1200
cttcgtcata aattgaaata tgtgcctcat gaatatattg aattaattga aattgccaga     1260
aattccactc aggatagaat tcttgaaatg aaggtaatgg aatttttat gaaagtttat      1320 ggatatagag gtaaacattt gggtggatca aggaaaccgg acggagcaat ttatactgtc     1380
ggatctccta ttgattacgg tgtgatcgtg gatactaaag cttatagcgg aggttataat     1440
ctgccaattg gccaagcaga tgaaatgcaa cgatatgtcg aagaaaatca aacacgaaac     1500
aaacatatca accctaatga atggtggaaa gtctatccat cttctgtaac ggaatttaag     1560
tttttatttg tgagtggtca ctttaaagga aactacaaag ctcagcttac acgattaaat     1620
catatcacta attgtaatgg agctgttctt agtgtagaag agcttttaat tggtggagaa     1680
atgattaaag ccggcacatt aaccttagag gaagtgagac ggaaatttaa taacggcgag     1740
ataaactttt aa                                                         1752
```

<210> SEQ ID NO 286
<211> LENGTH: 23
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 286
ggtgagtgag tgtgtgcgtg tgg                                              23

<210> SEQ ID NO 287
<211> LENGTH: 18
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 287

```
gggcgatgcc acctacgg                                                 18
```

<210> SEQ ID NO 288
<211> LENGTH: 20
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 288

```
gagggcgatg ccacctacgg                                               20
```

<210> SEQ ID NO 289
<211> LENGTH: 22
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 289

```
gcgagggcga tgccacctac gg                                            22
```

<210> SEQ ID NO 290
<211> LENGTH: 23
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 290

```
ggcgagggcg atgccaccta cgg                                           23
```

<210> SEQ ID NO 291
<211> LENGTH: 24
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 291

```
gggcgagggc gatgccacct acgg                                          24
```

<210> SEQ ID NO 292
<211> LENGTH: 26
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 292

```
gagggcgagg gcgatgccac ctacgg                                        26
```

<210> SEQ ID NO 293
<211> LENGTH: 28
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 293

```
gcgcgggcga gggcgatgcc acctacgg                                      28
```

<210> SEQ ID NO 294
<211> LENGTH: 21
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 294
gcacgggcag cttgccggtg g                                           21

<210> SEQ ID NO 295
<211> LENGTH: 23
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 295
gggcacgggc agcttgccgg tgg                                         23

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 296
gccgttcttc tgcttgtcgg                                             20

<210> SEQ ID NO 297
<211> LENGTH: 23
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 297
gatgccgttc ttctgcttgt cgg                                         23

<210> SEQ ID NO 298
<211> LENGTH: 19
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 298
gtgcagatga acttcaggg                                              19

<210> SEQ ID NO 299
<211> LENGTH: 20
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 299
ggtgcagatg aacttcaggg                                             20

<210> SEQ ID NO 300
<211> LENGTH: 23
<212> TYPE: DNA
<213> ORGANISM: Artificial Sequence
<220> FEATURE:
<223> OTHER INFORMATION: Description of Artificial Sequence: Synthetic
target binding site oligonucleotide

<400> SEQUENCE: 300
ggtggtgcag atgaacttca ggg                                              23

<210> SEQ ID NO 301
<211> LENGTH: 19
<212> TYPE: DNA
<213> ORGANISM: Artificial Sequence
<220> FEATURE:
<223> OTHER INFORMATION: Description of Artificial Sequence: Synthetic
target binding site oligonucleotide

<400> SEQUENCE: 301
gaggagctgt tcaccgggg                                                   19

<210> SEQ ID NO 302
<211> LENGTH: 21
<212> TYPE: DNA
<213> ORGANISM: Artificial Sequence
<220> FEATURE:
<223> OTHER INFORMATION: Description of Artificial Sequence: Synthetic
target binding site oligonucleotide

<400> SEQUENCE: 302
gcgaggagct gttcaccggg g                                                21

<210> SEQ ID NO 303
<211> LENGTH: 23
<212> TYPE: DNA
<213> ORGANISM: Artificial Sequence
<220> FEATURE:
<223> OTHER INFORMATION: Description of Artificial Sequence: Synthetic
target binding site oligonucleotide

<400> SEQUENCE: 303
gggcgaggag ctgttcaccg ggg                                              23

<210> SEQ ID NO 304
<211> LENGTH: 21
<212> TYPE: DNA
<213> ORGANISM: Artificial Sequence
<220> FEATURE:
<223> OTHER INFORMATION: Description of Artificial Sequence: Synthetic
target binding site oligonucleotide

<400> SEQUENCE: 304 gtgggggag tttgctcctg g                                                 21

<210> SEQ ID NO 305
<211> LENGTH: 23
<212> TYPE: DNA
<213> ORGANISM: Artificial Sequence
<220> FEATURE:
<223> OTHER INFORMATION: Description of Artificial Sequence: Synthetic
target binding site oligonucleotide

<400> SEQUENCE: 305
gggtgggggg agtttgctcc tgg                                              23

```
<210> SEQ ID NO 306
<211> LENGTH: 20
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 306
gagtgagtgt gtgcgtgtgg                                                   20

<210> SEQ ID NO 307
<211> LENGTH: 23
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 307
ggtgagtgag tgtgtgcgtg tgg                                               23

<210> SEQ ID NO 308
<211> LENGTH: 21
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 308
gtccgagcag aagaagaagg g                                                 21

<210> SEQ ID NO 309
<211> LENGTH: 23
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 309
gagtccgagc agaagaagaa ggg                                               23

<210> SEQ ID NO 310
<211> LENGTH: 20
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 310
gatgtagtgt ttccacaggg                                                   20

<210> SEQ ID NO 311
<211> LENGTH: 23
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 311
gcagatgtag tgtttccaca ggg                                               23

<210> SEQ ID NO 312
```

```
<211> LENGTH: 67
<212> TYPE: DNA
<213> ORGANISM: Homo sapiens

<400> SEQUENCE: 312
gaagctggag gaggaagggc ctgagtccga gcagaagaag aagggctccc atcacatcaa    60
ccggtgg                                                              67

<210> SEQ ID NO 313
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
gaagctggag gagga                                                     15

<210> SEQ ID NO 314
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
tcaaccggtg g                                                         11

<210> SEQ ID NO 315
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
gaagctggag gaggaagg                                                  18

<210> SEQ ID NO 316
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
gggctcccat cacatcaacc ggtgg                                          25

<210> SEQ ID NO 317
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
gaagctggag gaggaagggc ctga                                           24

<210> SEQ ID NO 318
<211> LENGTH: 14
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 318
gaagctggag gagg                                                        14

<210> SEQ ID NO 319
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
gaagctggag gaggaagggc ccatcacatc aaccggtgg                             39

<210> SEQ ID NO 320
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
gaagctggag gaggaagggc tcgcacacat caaccggtgg                            40

<210> SEQ ID NO 321
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
gaagctggag gaggaagggc cttccatcac atcaaccggt gg                         42

<210> SEQ ID NO 322
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
gaagctggag gaggaagggc ctgagtccca tcacatcaac cggtgg                     46

<210> SEQ ID NO 323
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
gaagctggag gaggaagggc ctgagtccga gtcccatcac atcaaccggt gg              52

<210> SEQ ID NO 324
<211> LENGTH: 58
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 324
gaagctggag gaggaagggc ctgagtccga gcagaagtcc catcacatca accggtgg         58

<210> SEQ ID NO 325
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
gaagctggag gaggaagggc ctgagtcctg ccgtttgtag ccatcacatc aaccggtgg        59

<210> SEQ ID NO 326
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
gaagctggag gaggaagggc ctgagtccga gcagaagagc tcccatcaca tcaaccggtg       60
g                                                                      61

<210> SEQ ID NO 327
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
gaagctggag gaggaagggc ctgagtccga gcagaagaac tcccatcaca tcaaccggtg       60
g                                                                      61

<210> SEQ ID NO 328
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
gaagctggag gaggaagggc ctgagtccga gcagaagaag ggctcccatc acatcaaccg       60
gtgg                                                                   64

<210> SEQ ID NO 329
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
gaagctggag gaggaagggc ctgagtccga gcagaagaaa gggctcccat cacatcaacc       60
```

<210> SEQ ID NO 330
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
gaagctggag gaggaagggc ctgagtccga gcagaagaac agaagggctc ccatcacatc    60
aaccggt                                                               67

<210> SEQ ID NO 331
<211> LENGTH: 67
<212> TYPE: DNA
<213> ORGANISM: Homo sapiens

<400> SEQUENCE: 331
gaagctggag gaggaagggc ctgagtccga gcagaagaag aagggctccc atcacatcaa    60
ccggtgg                                                               67

<210> SEQ ID NO 332
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
gaagctggag gaggaagggc ctgagtccga g                                    31

<210> SEQ ID NO 333
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
gaagctggag g                                                          11

<210> SEQ ID NO 334
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
gaagctggag g                                                          11

<210> SEQ ID NO 335
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335

```
gaagctggag gaggaagggc ctgagtgg                                        28
```

<210> SEQ ID NO 336
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336

```
gaagctggag gaggaagggc tcccatcaca tcaaccggtg g                         41
```

<210> SEQ ID NO 337
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337

```
gaagctggag gaggaagggc ctgagtccat cacatcaacc ggtgg                     45
```

<210> SEQ ID NO 338
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338

```
gaagctggag gaggaagggc ctgagtccca tcacatcaac cggtgg                    46
```

<210> SEQ ID NO 339
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339

```
gaagctggag gaggaagggc ctgagtccga gcatcacatc aaccggtgg                 49
```

<210> SEQ ID NO 340
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340

```
gaagctggag gaggaagggc ctgagtccga gctcccatca catcaaccgg tgg            53
```

<210> SEQ ID NO 341
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341

```
gaagctggag gaggaagggc ctgagtccga gcagaagggc tcccatcaca tcaaccggtg     60
```

```
g                                                              61

<210> SEQ ID NO 342
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
gaagctggag gaggaagggc ctgagtccga gcagaagaag ggctcccatc acatcaaccg    60
gtgg                                                                64

<210> SEQ ID NO 343
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
gaagctggag gaggaagggc ctgagtccga gcagaaagaa gggctcccat cacatcaacc    60
ggtgg                                                                65

<210> SEQ ID NO 344
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
gaagctggag gaggaagggc ctgagtccga gcagaagaac agaagggctc ccatcacatc    60
aaccggt                                                              67

<210> SEQ ID NO 345
<211> LENGTH: 187
<212> TYPE: DNA
<213> ORGANISM: Aequorea victoria

<400> SEQUENCE: 345
tcgtgaccac cctgacctac ggcgtgcagt gcttcagccg ctaccccgac cacatgaagc    60
agcacgactt cttcaagtcc gccatgcccg aaggctacgt ccaggagcgc accatcttct   120
tcaaggagac ggcaactaca agacccgcgc cgaggtgaag ttcgagggcg acaccctggt   180
gaaccgc                                                             187

<210> SEQ ID NO 346
<211> LENGTH: 184
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 346
tcgtgaccac cctgacctac gtgcagtgct tcagccgcta ccccgaccac atgaagcagc    60
acgacttctt caagtccgcc atgcccgaag gctacgtcca ggagcgcacc atcttcttca   120
```
aggacgacgg caactacaag acccgcgcga ggtgaagttc gagggcgaca ccctggtgaa    180
ccgc    184

<210> SEQ ID NO 347
<211> LENGTH: 159
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 347
tcgtgaccac cctgacctca gccgctaccc cgaccacatg aagcagcacg acttcttcaa    60
gtccgccatg cccgaaggct acgtccagga gcgcaccatc ttcttcaagg acgacggcaa    120
ctacaagacc cgcgccgagg cgacaccctg gtgaaccgc    159

<210> SEQ ID NO 348
<211> LENGTH: 154
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 348
tcgtgaccac cctgacctac ggcgtgcagt gcttcagccg ctaccccgac cacatgaagc    60
agcacgactt cttcaagtcc gccatgcccg aaggctacgt ccaggagcgc accatcttct    120
tcaaggagac ggcaactaca ccctggtgaa ccgc    154

<210> SEQ ID NO 349
<211> LENGTH: 181
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 349
tcgtgaccac cctgaccgtg cagtgcttca gccgctaccc cgaccacatg aagcagcacg    60
acttcttcaa gtccgccatg cccgaaggct acgtccagga gcgcaccatc ttcttcaagg    120
acgacggcaa ctacaagacc cgcgcgaggg tcttgttcga gggcgacacc ctggtgaacc    180
g    181

<210> SEQ ID NO 350
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
tcgtgaccac cctgacctac gtgaagttcg agggcgacac cctggtgaac cgc    53

<210> SEQ ID NO 351
<211> LENGTH: 187
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 351
tcgtgaccac cctgacctac gcctcggcgc gggtcttgta gttgccgtcg tcctt gaaga      60 agatggtgcg ctcctggacg tagccttcgg gcatggcgga cttgaagaag tcgtgctgct     120
tcatgtgtcg gggtagcggc tgaagcactg cacgctgaag ttcgagggcg acaccctggt     180
gaaccgc                                                                187

<210> SEQ ID NO 352
<211> LENGTH: 146
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 352
tcggcgcggg tcttgtagtt gccgtcgtcc ttgaagaaga tggtgcgctc ctggacgtag       60
ccttcgggca tgcggactt gaagaagtcg tgctgcttca tgtggtcggg gtagcggctg      120
aagcactgca caccctggtg aaccgc                                           146

<210> SEQ ID NO 353
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
tcgtgaccac cctgttcgag ggcgacaccc tggtgaaccg c                           41

<210> SEQ ID NO 354
<211> LENGTH: 92
<212> TYPE: DNA
<213> ORGANISM: Homo sapiens

<400> SEQUENCE: 354
caggagacga agagcccggg cggcgctcgt acttctggcc actgggcgag cgtctggcag       60
gtgagtgagg ctgcaggcat tgacgtctcc tc                                     92

<210> SEQ ID NO 355
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
caggagacga agagcccggg cggcgctcgt acttctggcc actggcgaag cgtctggcag       60
gtgagtgagg ctgcaggcat tgacgtctcc tc                                     92

<210> SEQ ID NO 356
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
caggagacga agagcccggg cggcgctcgt acttctggcc tctggcaggt gagtgaggct       60
```
gcaggcattg acgtctcctc                                                80

<210> SEQ ID NO 357
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
caggagacga agagcccggg cggcgctcgt acttctagcg tctggcaggt gagtgaggct    60
gcaggcattg acgtctcctc                                                80

<210> SEQ ID NO 358
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
caggagacga agagcccggg cggcgctcgt acttcgtctg gcaggtgagt gaggctgcag    60
gcattgacgt ctcctc                                                    76

<210> SEQ ID NO 359
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
caggagacga agagcccggg cggcgctcgt acttctggcc actgtgagtg aggctgcagg    60
cattgacgtc tcctc                                                     75

<210> SEQ ID NO 360
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
caggagacga agagcccggg cggcgctcgt acttctggca ggtgagtgag gctgcaggca    60
ttgacgtctc ctc                                                       73

<210> SEQ ID NO 361
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
caggagacga agagcccggg cggcgctcgt ctggcaggtg agtgaggctg caggcattga    60
cgtctcctc                                                            69

```
<210> SEQ ID NO 362
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
caggagacga agagcccgtc tggcaggtga gtgaggctgc aggcattgac gtctcctc         58

<210> SEQ ID NO 363
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
accggcggca gcaggtgagt gaggctgcag gcattgacgt ctcctc                      46

<210> SEQ ID NO 364
<211> LENGTH: 92
<212> TYPE: DNA
<213> ORGANISM: Homo sapiens

<400> SEQUENCE: 364
tgggagagtg gatttccgaa gctgacagat gggtattctt tgagggggggg taggggcgga     60 acctgagagg cgtaaggcgt tgtgaaccct gg                                     92

<210> SEQ ID NO 365
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
tgggagagtg gatttccgaa gctgacagat gggtattctt tgagtagggg cggaacctga      60
gaggcgtaag gcgttgtgaa ccctgg                                            86

<210> SEQ ID NO 366
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
tgggagagtg gatttccgaa gctgacagat gggtatgggg ggtaggggcg gaacctgaga      60
ggcgtaaggc gttgtgaacc ctgg                                              84

<210> SEQ ID NO 367
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
tgggagagtg gatttccgaa gctgacagat gggtattctt ggtaggggcg gaacctgaga      60
```

```
ggcgtaaggc gttgtgaacc ctgg                                          84

<210> SEQ ID NO 368
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
tgggagagtg gatttccgaa gctgacagat gggtattctt tgagggggga acctgagagg   60
cgtaaggcgt tgtgaaccct gg                                            82

<210> SEQ ID NO 369
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
tgggagagtg gatttccgaa gctgacagat gggtattctt tgggcggaac ctgagaggcg   60
taaggcgttg tgaaccctgg                                               80

<210> SEQ ID NO 370
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
tgggagagtg gatttccgaa gctgacagat ggggcggaac ctgagaggcg taaggcgttg   60
tgaaccctgg                                                          70

<210> SEQ ID NO 371
<211> LENGTH: 92
<212> TYPE: DNA
<213> ORGANISM: Homo sapiens

<400> SEQUENCE: 371
caagctggac tctggccact ccctggccag gctttgggga ggcctggagt catggcccca   60
cagggcttga agcccggggg gccgccattg ac                                 92

<210> SEQ ID NO 372
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
caagctggac tctggccact ccctggccag gctttatggc cccacagggc ttgaagcccg   60 ggggccgcc attgac                                                    76

<210> SEQ ID NO 373
<211> LENGTH: 92
<212> TYPE: DNA
```

<213> ORGANISM: Homo sapiens

<400> SEQUENCE: 373
agagagtcgc cgtctccaag gtgaaagcgg aagtagggcc ttcgcgcacc tcatggaatc    60
ccttctgcag cacctggatc gcttttccga gc                                  92

<210> SEQ ID NO 374
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
agagagtcgc cgtctccaag gtgaaagcgg aagtagcgca cctcatggaa tcccttctgc    60
agcacctgga tcgcttttcc gagc                                           84

<210> SEQ ID NO 375
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
agagagtcgc cgtctccaag gtgaaagcgg aagtagggcc ctcatggaat cccttctgca    60
gcacctggat cgcttttccg agc                                            83

<210> SEQ ID NO 376
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
agagagtcgc cgtctccaag gtgaaagcgg aagtaggccc tcatggaatc ccttctgcag    60
cacctggatc gcttttccga gc                                             82

<210> SEQ ID NO 377
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
agagagtcgc cgtctccaag gtgaaagcgg aagtagggcc tcatggaatc ccttctgcag    60
cacctggatc gcttttccga gc                                             82

<210> SEQ ID NO 378
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
agagagtcgc cgtctccaag gtgaaagcgg aagtagcacc tcatggaatc ccttctgcag    60
cacctggatc gcttttccga gc    82

<210> SEQ ID NO 379
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
agagagtcgc cgtctccaag gtgaaagcgg aaacgcacct catggaatcc cttctgcagc    60
acctggatcg cttttccgag c    81

<210> SEQ ID NO 380
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
agagagtcgc cgtctccaag gtgaaagcgg aagtagggcc ttcgcgcatt ctgcagcacc    60
tggatcgctt ttccgagc    78

<210> SEQ ID NO 381
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
agagagtcgc cgtctccaag gtgaaagcgg aagcctcatg gaatcccttc tgcagcacct    60
ggatcgcttt tccgagc    77

<210> SEQ ID NO 382
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
agagagtcgc cgtctccaag catggaatcc cttctgcagc acctggatcg cttttccgag    60
c    61

<210> SEQ ID NO 383
<211> LENGTH: 92
<212> TYPE: DNA
<213> ORGANISM: Homo sapiens

<400> SEQUENCE: 383
tttggtcggc atggccccat tcgcacggct ctggagcggc ggctgcacaa ccagtggagg    60
caagagggcg gctttgggcg gggtccagtt cc    92

<210> SEQ ID NO 384
<211> LENGTH: 89

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
tttggtcggc atggccccat tcgcacggct ctggagcggc ggcgcaacca gtggaggcaa      60
gagggcggct ttgggcgggg tccagttcc                                        89

<210> SEQ ID NO 385
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
tttggtcggc atggccccat tcgcacggct ctggagcggc ggctaaccag tggaggcaag      60
agggcggctt tgggcggggt ccagttcc                                         88

<210> SEQ ID NO 386
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
tttggtcggc atggccccat tcgcacggct ctggagcggc ggccagtgga ggcaagaggg      60
cggctttggg cggggtccag ttcc                                             84

<210> SEQ ID NO 387
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
tttggtcggc atggccccat tcgcacggct ctggagcggc ggctgtggag gcaagagggc      60
ggctttgggc ggggtccagt tcc                                              83

<210> SEQ ID NO 388
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
tttggtcggc atggccccat tcgcacggct ctggagcggc ggctggaggc aagagggcgg      60
ctttgggcgg ggtccagttc c                                                81

<210> SEQ ID NO 389
<211> LENGTH: 80
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 389
tttggtcggc atggccccat tcgcacggct ctggagcggc gggagaggca agagggcggc    60
tttgggcggg gtccagttcc                                                80

<210> SEQ ID NO 390
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
tttggtcggc atggccccat tcgcacggct ctggagcggc ggcgaggcaa gagggcggct    60 tgggcgggg tccagttcc                                                  79

<210> SEQ ID NO 391
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
tttggtcggc atggccccat tcgcacggct ctggagcggc ggctggcaag agggcggctt    60
tgggcggggt ccagttcc                                                  78

<210> SEQ ID NO 392
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
tttggtcggc atggccccat tcgcacggct ctggagcggc ggcggcaaga gggcggcttt    60
gggcggggtc cagttcc                                                   77

<210> SEQ ID NO 393
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
tttggtcggc atggccccat tcgcacggct ctggagtgga ggcaagaggg cggctttggg    60
cggggtccag ttcc                                                      74

<210> SEQ ID NO 394
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394

```
tttggtcggc atggccccat tcgcacggct ctggaggcaa agggcggct ttgggcgggg    60 tccagttcc                                                           69
```

<210> SEQ ID NO 395
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395

```
tttggtcggc atggccccgt cactgt                                        26
```

<210> SEQ ID NO 396
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 396

```
tttggtcggc atggccccat tcgcacggct ctggagcggc ggcacactat tgcaatgaaa    60
ataaatttcc tttattagct agaagtgaga tctgaagggg cttcatgatg tccccataat   120
ttttggcaga gggaaaaaga tctcagtggt atttgtgagc cagggcattg ccacaccag    180 ccaccacctt tgataggca gcctgcacct gaggagtgcg agtggaggca agagggcggc    240
tttgggcggg gtccagttcc                                              260
```

<210> SEQ ID NO 397
<211> LENGTH: 92
<212> TYPE: DNA
<213> ORGANISM: Homo sapiens

<400> SEQUENCE: 397

```
gttcaactcg atgaccccac caccaatcag tagctatggc gagccctgct gtctccggcc    60
cctccccagt cagggggccc ccagtgtggg ga                                 92
```

<210> SEQ ID NO 398
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398

```
gttcaactcg atgaccccac caccaatcag tagctatcct gctgtctccg gcccctcccc    60
agtcaggggg cccccagtgt gggga                                         85
```

<210> SEQ ID NO 399
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399

```
gttcaactcg atgaccccac caccaatcag tagctatgtc tccggcccct ccccagtcag    60
ggggccccca gtgtgggga                                                79
```

<210> SEQ ID NO 400
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
gttcaactcg atgacccccac caccaatcag tagctatggc gagcccccccc agtcagggggg    60 cccccagtgt gggga                                                        75

<210> SEQ ID NO 401
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
gttcaactcg atgacccccac caccaacctg ctgtctccgg ccctccccca gtcaggggc       60 ccccagtgtg ggga                                                         74

<210> SEQ ID NO 402
<211> LENGTH: 92
<212> TYPE: DNA
<213> ORGANISM: Homo sapiens

<400> SEQUENCE: 402
tggctgaagg cacttccgtt gagcatctag acgtttcctt ggctcttctg gcgccaaaat       60
gtcgttcgtg gcagggggtta ttcggcggct gg                                    92

<210> SEQ ID NO 403
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
tggctgaagg cacttccgtt gagcatctag acgtttcctt ggcgccaaaa tgtcgttcgt       60 ggcagggggtt attcggcggc tgg                                              83

<210> SEQ ID NO 404
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
tggctgaagg cacttccgtt gagcatctat tctggcgcca aaatgtcgtt cgtggcaggg       60
gttattcggc ggctgg                                                       76

<210> SEQ ID NO 405
<211> LENGTH: 76
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 405
tggctgaagg cacttccgtt gagcatctag acgtttcctt ggatgtcgtt cgtggcaggg    60
gttattcggc ggctgg                                                   76

<210> SEQ ID NO 406
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
tggctgaagg cacttccgtt gagcatctag acgtttgtcg ttcgtggcag gggttattcg    60
gcggctgg                                                            68

<210> SEQ ID NO 407
<211> LENGTH: 92
<212> TYPE: DNA
<213> ORGANISM: Homo sapiens

<400> SEQUENCE: 407
cccttctgac tgtggccgct tggcatggcc agcaacagca gctcctgccc gacacctggg    60
ggcgggcacc tcaatgggta cccggtgcct cc                                  92

<210> SEQ ID NO 408
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
cccttctgac tgtggccgct tggcatggcc agcaacacct gcccgacacc tggggcggg    60 cacctcaatg ggtacccggt gcctcc                                        86

<210> SEQ ID NO 409
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
cccttctgac tgtggccgct tggcatggcc agcaacactg cccgacacct ggggcgggc    60 acctcaatgg gtacccggtg cctcc                                         85

<210> SEQ ID NO 410
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410
cccttctgac tgtggccgct tggcatggcc agcagcccga cacctggggg cgggcacctc    60

```
aatgggtacc cggtgcctcc                                                  80

<210> SEQ ID NO 411
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
cccttctgac tgtggccgct tggcatggcc aggcccgaca cctgggggcg ggcacctcaa      60
tgggtacccg gtgcctcc                                                    78

<210> SEQ ID NO 412
<211> LENGTH: 92
<212> TYPE: DNA
<213> ORGANISM: Homo sapiens

<400> SEQUENCE: 412
tcagaaatag ggggtccagg agcaaactcc ccccaccccc tttccaaagc ccattccctc      60
tttagccaga gccggggtgt gcagacggca gt                                    92

<210> SEQ ID NO 413
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
tcagaaatag ggggtccagg agcaaactcc ccccaccccc tttccaaaaa gcccattccc      60
tctttagcca gagccggggt gtgcagacgg ca                                    92

<210> SEQ ID NO 414
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414
tcagaaatag ggggtccagg agcaaactcc ccccaccccc tttccgccca ttccctcttt      60
agccagagcc ggggtgtgca gacggcagt                                        89

<210> SEQ ID NO 415
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
tcagaaatag ggggtccagg agcaaactcc ccccaccccc ttagcccatt ccctctttag      60
ccagagccgg ggtgtgcaga cggcagt                                          87

<210> SEQ ID NO 416
<211> LENGTH: 87
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 416
tcagaaatag ggggtccagg agcaaactcc ccccaccccc aaagcccatt ccctctttag      60
ccagagccgg ggtgtgcaga cggcagt                                         87

<210> SEQ ID NO 417
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
tcagaaatag ggggtccagg agcaaactcc ccccacccca agcccattc cctctttagc      60 cagagccggg gtgtgcagac ggcagt                                          86

<210> SEQ ID NO 418
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
tcagaaatag ggggtccagg agcaaactcc ccccaccccc tttccattcc ctctttagcc      60
agagccgggg tgtgcagacg gcagt                                           85

<210> SEQ ID NO 419
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
tcagaaatag ggggtccagg agcaaactcc ccccaccccc tttcattccc tctttagcca     60
gagccggggt gtgcagacgg cagt                                            84

<210> SEQ ID NO 420
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 420
tcagaaatag ggggtccagg agcaaactcc ccccacaaag cccattccct ctttagccag     60
agccggggtg tgcagacggc agt                                             83

<210> SEQ ID NO 421
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 421
tcagaaatag ggggtccagg agcaaactcc ccccacccat tccctcttta gccagagccg      60
gggtgtgcag acggcagt                                                    78

<210> SEQ ID NO 422
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
tcagaaatag ggggtccagg agcaaaccaa agcccattcc ctctttagcc agagccgggg      60
tgtgcagacg gcagt                                                       75

<210> SEQ ID NO 423
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
tcagaaatag ggggtccagg agcaaactcc ccccaccccc tctttagcca gagccggggt      60
gtgcagacgg cagt                                                        74

<210> SEQ ID NO 424
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424
tcagaaatag ggggtccagg agcaaactcc ccccaccccc tttagccaga gccggggtgt      60
gcagacggca gt                                                          72

<210> SEQ ID NO 425
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
tcagaaatag ggggtccagg caaagcccat tccctcttta gccagagccg ggtgtgcag       60 acggcagt                                                               68

<210> SEQ ID NO 426
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 426
tcagaaatag ggggtccagg agctctttag ccagagccgg ggtgtgcaga cggcagt         57
```

<210> SEQ ID NO 427
<211> LENGTH: 92
<212> TYPE: DNA
<213> ORGANISM: Homo sapiens

<400> SEQUENCE: 427
ccccagcccc agctaccacc tcctccccgg ccggcggcgg acagtggacg cggcggcgag      60
ccgcgggcag gggccggagc ccgcgcccgg ag                                   92

<210> SEQ ID NO 428
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 428
ccccagcccc agctaccacc tcctccccgg ccggcgtgga cgcggcggcg agccgcgggc      60
aggggccgga gcccgcgccc ggag                                            84

<210> SEQ ID NO 429
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 429
ccccagcccc agctaccacc tcctccccgg ccggacgcgg cggcgagccg cgggcagggg      60
ccggagcccg cgcccggag                                                  79

<210> SEQ ID NO 430
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 430
ccccagcccc agctaccacc tcctccccgg ctggacgcgg cggcgagccg cgggcagggg      60
ccggagcccg cgcccggag                                                  79

<210> SEQ ID NO 431
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431
ccccagcccc agctaccacc tcctccccgg ccggcggcgg acagccgcgg gcaggggccg      60
gagcccgcgc ccggag                                                     76

<210> SEQ ID NO 432
<211> LENGTH: 75
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 432
ccccagcccc agctaccacc tcctccccgg acgcggcggc gagccgcggg caggggccgg    60
agcccgcgcc cggag                                                   75

<210> SEQ ID NO 433
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 433
ccccagcccc agctaccacc tcctccccgg ccggagcccg cgcccgaag              49

<210> SEQ ID NO 434
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 434
ccccagcccc agctaccacc tcctccccgg ccggcggcgg acagtggagg gggtcggggc   60
tcg                                                                63

<210> SEQ ID NO 435
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 435
ccccagcccc agctaccacc tcctccccgg ccggag                            36

<210> SEQ ID NO 436
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 436
ccccagcccc agctaccacc tcctccccgg ccggcggcgg ggtggagggg gtcgg        55

<210> SEQ ID NO 437
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 437
ccccagcccc agctaccacc tcctccccgg ccggcggcgg acacacacgc ggcgtcgcac   60

<210> SEQ ID NO 438
<211> LENGTH: 53
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 438
ccccagcccc agctaccacc tcctccccgg ccggcggcct gaaactttc gtc              53

<210> SEQ ID NO 439
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 439
ccggagcgcg gcgtggaggg ggtcggggct                                       30

<210> SEQ ID NO 440
<211> LENGTH: 92
<212> TYPE: DNA
<213> ORGANISM: Homo sapiens

<400> SEQUENCE: 440
ccattccctc tttagccaga gccggggtgt gcagacggca gtcactaggg ggcgctcggc      60
caccacaggg aagctgggtg aatggagcga gc                                    92

<210> SEQ ID NO 441
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 441
ccattccctc tttagccaga gccggggtgt gcagacggca cttaggggc gctcggccac       60 cacagggaag ctgggtgaat ggagcgagc                                        89

<210> SEQ ID NO 442
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 442
ccattccctc tttagccaga gccggggtgt gcagacggca ctaggggcg ctcggccacc       60 acagggaagc tgggtgaatg gagcgagc                                         88

<210> SEQ ID NO 443
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 443
ccattccctc tttagccaga gccggggtgt gcagacggca gtcagggcgc tcggccacca      60
cagggaagct gggtgaatgg agcgagc                                          87
```

<210> SEQ ID NO 444
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 444
ccattccctc tttagccaga gccggggtgt gcagacggca taggggggcgc tcggccacca    60 cagggaagct gggtgaatgg agcgagc                                         87

<210> SEQ ID NO 445
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 445
ccattccctc tttagccaga gccggggtgt gcagacctag ggggcgctcg gccaccacag    60
ggaagctggg tgaatggagc gagc                                            84

<210> SEQ ID NO 446
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 446
ccattccctc tttagccaga gccggggtgt gcagacggca gggcgctcgg ccaccacagg    60
gaagctgggt gaatggagcg agc                                             83

<210> SEQ ID NO 447
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 447
ccattccctc tttagccaga gccggggtgt gcagactagg gggcgctcgg ccaccacagg    60
gaagctgggt gaatggagcg agc                                             83

<210> SEQ ID NO 448
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 448
ccattccctc tttagccaga gccggggtgt gcagctaggg ggcgctcggc caccacaggg    60
aagctgggtg aatggagcga gc                                              82

<210> SEQ ID NO 449
<211> LENGTH: 81
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 449
ccattccctc tttagccaga gccggggtgt gcagaagggg gcgctcggcc accacaggga        60
agctgggtga atggagcgag c                                                  81

<210> SEQ ID NO 450
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 450
ccattccctc tttagccaga gccggggtgt gcactagggg gcgctcggcc accacaggga        60
agctgggtga atggagcgag c                                                  81

<210> SEQ ID NO 451
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 451
ccattccctc tttagccaga gccggggtgt gcagacggca gttcggccac cacagggaag        60
ctgggtgaat ggagcgagc                                                     79

<210> SEQ ID NO 452
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 452
ccattccctc tttagccaga gccggggtgt ctaggggggcg ctcggccacc acagggaagc       60
tgggtgaatg gagcgagc                                                      78

<210> SEQ ID NO 453
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453
ccattccctc tttagccaga gccggggtgt gcagggggcgc tcggccacca cagggaagct       60
gggtgaatgg agcgagc                                                       77

<210> SEQ ID NO 454
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 454
ccattccctc tttagccaga gccggggtgt gcagggcgct cggccaccac agggaagctg    60
ggtgaatgga gcgagc    76

<210> SEQ ID NO 455
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 455
ccattccctc tttagccaga gccggggtgt gcagacggca gtcactacac agggaagctg    60
ggtgaatgga gcgagc    76

<210> SEQ ID NO 456
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 456
ccattccctc tttagccaga gccggggtgt gcagacggct cggccaccac agggaagctg    60
ggtgaatgga gcgagc    76

<210> SEQ ID NO 457
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
ccattccctc tttagccaga gccggggtgt gcagacgctc ggccaccaca gggaagctgg    60
gtgaatggag cgagc    75

<210> SEQ ID NO 458
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 458
ccattccctc tttagccaga gccggggtgg gggcgctcgg ccaccacagg gaagctgggt    60
gaatggagcg agc    73

<210> SEQ ID NO 459
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 459
ccattccctc tttagccaga gccggggtgt gcgctcggcc accacaggga agctgggtga    60
atggagcgag c                                                          71

<210> SEQ ID NO 460
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 460
ccattccctc tttagccaga gccggggtgt gcagacggca gtcacaggga agctgggtga    60
atggagcgag c                                                          71

<210> SEQ ID NO 461
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 461
ccattccctc tttagccaga gccggggtgt gcagacggcc accacaggga agctgggtga    60
atggagcgag c                                                          71

<210> SEQ ID NO 462
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 462
ccattccctc tttagccaga gccggggtgt gcagacggca gtcagggaag ctgggtgaat    60
ggagcgagc                                                             69

<210> SEQ ID NO 463
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 463
ccattccctc tttagccaga gccggggtgt gcaggccacc acagggaagc tgggtgaatg    60
gagcgagc                                                              68

<210> SEQ ID NO 464
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 464
ccattccctc tttagccaga gccggggtgt gcagaccacc acagggaagc tgggtgaatg    60
gagcgagc                                                              68

```
<210> SEQ ID NO 465
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 465
ccattccctc tttagccaga gccggggtgt gcagaccaca gggaagctgg gtgaatggag      60
cgagc                                                                 65

<210> SEQ ID NO 466
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 466
ccattccctc ttagtgactg ctcggccacc acagggaagc tgggtgaatg gagcgagc       58
```

UNITED STATES PATENT AND TRADEMARK OFFICE
CERTIFICATE OF CORRECTION

PATENT NO. : 10,544,433 B2
APPLICATION NO. : 16/003973
DATED : January 28, 2020
INVENTOR(S) : J. Keith Joung and Shengdar Tsai Page 1 of 1

It is certified that error appears in the above-identified patent and that said Letters Patent is hereby corrected as shown below:

In the Specification

In Column 1, Line 17, delete "DP1 GM105378" and insert -- AR063070; GM088040; GM105189; GM105378; and HG005550 --

In Column 1, Line 18, after "Health" insert -- , and under Grant No. W911NF-11-2-0056 awarded by the Army Research Laboratory – Army Research Office --

Signed and Sealed this
Eleventh Day of February, 2025

Coke Morgan Stewart
*Acting Director of the United States Patent and Trademark Office*